(12) United States Patent
Kajihara et al.

(10) Patent No.: US 7,135,566 B2
(45) Date of Patent: Nov. 14, 2006

(54) PROCESS FOR PRODUCING SUGAR CHAIN ASPARAGINE DERIVATIVE

(75) Inventors: Yasuhiro Kajihara, c/o Graduate School of Integrated Science, Yokohama City University, 22-2, Seto, Kanazawa-ku, Yokohama-shi, Kanagawa 236-0027 (JP); Ken Sasaki, Yokkaichi (JP)

(73) Assignees: Otsuka Chemical Co., Ltd., Osaka (JP); Yasuhiro Kajihara, Kanagawa (JP)

( * ) Notice: Subject to any disclaimer, the term of this patent is extended or adjusted under 35 U.S.C. 154(b) by 88 days.

(21) Appl. No.: 10/481,246

(22) PCT Filed: Jun. 19, 2002

(86) PCT No.: PCT/JP02/06091

§ 371 (c)(1),
(2), (4) Date: Dec. 18, 2003

(87) PCT Pub. No.: WO03/008431

PCT Pub. Date: Jan. 30, 2003

(65) Prior Publication Data

US 2004/0181054 A1  Sep. 16, 2004

(30) Foreign Application Priority Data

Jun. 19, 2001 (JP) .............................. 2001-185685

(51) Int. Cl.
*C07H 1/06* (2006.01)
*C07H 5/06* (2006.01)
(52) U.S. Cl. .................................. 536/123.1; 536/124
(58) Field of Classification Search ........... 536/123.13, 536/124
See application file for complete search history.

(56) References Cited

FOREIGN PATENT DOCUMENTS

| JP | 7-224082 | * | 8/1995 |
| JP | 7-224082 | A | 8/1995 |
| JP | 11-255807 | A | 9/1999 |

OTHER PUBLICATIONS

Nomoto, H. et al Carbohydrate Research, 1982, 107, 91-101.*
Shin Seikagaku Jiken Koza3, May 21, 1990, 163-165.*
Haneda et al Carbohyrate Research, 1996, 292, 61-70.*
Watt, G.M. et al Carbohydrate Research, 1998, 305, 533-541.*
Unverzagt, C. Tetrahedron Letters, 1997, 38(32), 5627-5630.*
McGuire, J.M., Carbohydrate Research, 1996, 292, 1-9.*
Haneda et al., Carbohydrate Research, vol. 292, pp. 61-70 (1996).
The Japanese Biochemical Society, pp. 163-165 (1990).
Nomoto et al., Carbohydrate Research, vol. 107, pp. 91-101 (1982).
Unverzagt et al., Tetrahedron Letters, vol. 38, No. 32, pp. 5627-5630 (1997).

(Continued)

*Primary Examiner*—Shaojia A. Jiang
*Assistant Examiner*—Ganapathy Krishnan
(74) *Attorney, Agent, or Firm*—Birch, Stewart, Kolasch & Birch, LLP

(57) ABSTRACT

The present invention provides a process for preparing a sugar chain asparagine derivative. According to the process, various isolated sugar chain asparagine derivatives useful in the field of the development of pharmaceuticals and the like can be conveniently obtained in a large amount as compared to that of the prior art. The present invention also provides a process for preparing a sugar chain asparagine and a process for preparing a sugar chain via a step for preparing a sugar chain asparagine derivative. The present invention further provides a novel sugar chain asparagine derivative, a sugar chain asparagine and a sugar chain.

19 Claims, 115 Drawing Sheets

1

OTHER PUBLICATIONS

Chiesa et al., Eur. J. Org. Chem., pp. 3541-3554 (2000).
Unverzagt, Carbohydrate Research, vol. 305, pp. 423-431 (1998).
Watt et al., Carbohydrate Research, vol. 305, pp. 533-541 (1998).
McGuire et al., Carbohydrate Research, vol. 292, pp. 1-9 (1996).
Brockhausen et al., Biochem. Cell Biol., vol. 66, pp. 1134-1151 (1988).
Hokke et al., Carbohydrate Research, vol. 305, pp. 463-468 (1997).
Koketsu et al., J. Carbohydrate Chemistry, vol. 14, No. 6, pp. 833-841 (1995).
Lin et al., Bioorganic & Medicinal Chemistry, vol. 3, No. 12, pp. 1625-1630 (1995).
Meinjohanns et al., J. Chem. Soc., Perkin Trans., vol. 1, pp. 549-560 (1998).
Mizuno et al., J. Am. Chem. Soc., vol. 121, pp. 284-290 (1999).
Rice et al., Biochemistry, vol. 32, pp. 7264-7270 (1993).
Sears et al., Science, vol. 291, pp. 2344-2350 (2001).
Seifert et al., Angew. Chem Int. Ed., vol. 39, No. 3, pp. 531-534 (2000).
Seko et al., Biochimica et Biophysica Acta, vol 1335, pp. 23-32 (1997).
Tamura et al., Analytical Biochemistry, vol. 216, pp. 335-344 (1994).
Thomas et al., Carbohydrate Research, vol. 306, pp. 387-400 (1998).
Unverzagt, Angew. Chem. Int. Ed. Engl., vol. 35, No. 20, pp. 2350-2353 (1996).

* cited by examiner

63

33

1) Hydrazine
2) Ac$_2$O/NaHCO$_3$/H$_2$O

PROCESS FOR PRODUCING SUGAR CHAIN ASPARAGINE DERIVATIVE

TECHNICAL FIELD

The present invention relates to a process for preparing a sugar chain asparagine derivative and a sugar chain asparagine derivative.

BACKGROUND ART

Conventionally, a technique for degrading a sugar chain by a glycosidase to derivatize the sugar chain has been utilized in the analytical studies on a several milligram scale such as structural analysis of a sugar chain. However, since derivatives of individual sugar chains could not be obtained in a large amount, development of the studies on a gram scale has been retarded. Therefore, it has been difficult to apply a sugar chain derivative in the synthesis studies such as the manufacture of pharmaceuticals.

On the other hand, it has been known that a glycopeptide is obtained in a large amount from an egg yolk (*Biochimica et Biophysica Acta* 1335 (1997) p 23–32). However, there has not been reported a case where a fluorenylmethoxycarbonylated (Fmoc-)sugar chain derivative of a compound 1 shown in FIG. 1, or a series of compounds having deletions of several sugar residues such as sialic acid or galactose on one of non-reducing terminals of a branched sugar chain in the compound 1, are obtained in a large amount. In addition, there are some cases where several sugar chains are isolated in a small amount from a protein or the like in human blood. However, when the sugar chain is employed in the manufacture of a pharmaceutical, there is a risk of allowing the pharmaceutical to contaminate AIDS virus, hepatitis viruses or the like. Therefore, there has been a controversy over the technique of applying the sugar chain to a pharmaceutical.

Meanwhile, there are numerous examples of processes for preparing sugar chains of which branched moieties have the same structure for a branched sugar chain. As conventional techniques, there are three kinds of processes. A first is a process for isolating and purifying an asparagine type sugar chain complex from a naturally occurring glycoprotein. Representative examples of this type are those reported in T. Tamura, et al., *Anal. Biochem.*, 1994, 216, p 335–344, V. H. Thomas, et al., *Carbohydr. Res.*, 1998, 306, p 387–400, K. G. Rice, et al., *Biochemistry*, 1993, 32, p 7264–7270 and the like. The advantage of these processes is that the synthesis of the sugar chain is not necessary. However, there are several defects. For instance, the sugar chain derived from the above glycoprotein is obtained as a mixture of the sugar chains having random deletions of several sugar residues in non-reducing terminal moieties, and the sugar chains contained in the above mixture are similar to each other in their physical and chemical characteristics, so that it is very difficult to separate into individual sugar chains, thereby making it substantially impossible to obtain a single sugar chain in a large amount. Also, there is a case where a sugar chain has been isolated from a protein in human blood (isolation from Fibrinogen: C. H. Hokke, et al., *Carbohydr. Res.*, 305 (1997), p 463–468, isolation from Human Serum Transferrin: M. Mizuno et. al., *J. Am. Chem. Soc.*, 1999, 121, p 284–290) in order to obtain the sugar chain in a relatively large amount. As mentioned above, a protein in human blood must be handled carefully because the protein may be contaminated with an AIDS virus or hepatitis viruses. Therefore, it is difficult to utilize the resulting sugar chains and derivatives thereof in the development of pharmaceuticals.

Even if the sugar chains were obtained in a large amount, their structures are limited, and any cases where sugar chains and derivatives thereof having many kinds of structures are obtained do not substantially exist.

In K. G. Rice, et al., *Biochemistry*, 1993, 32, p 7264–7270, or Rice, et al., *Neoglycoconjugate*, Academic Press, 1994, ISBN 0-12-440585-1 p 286–321, a sugar residue is removed from a non-reducing terminal of a sugar chain with a glycosidase. However, since a sugar chain having a single structure used as a raw material cannot be obtained in a large amount, the process can only be carried out on an analytical scale. E. Meinjohanns (*J. Chem. Soc. Perkin Trans* 1, 1998, p 549–560) et al. have obtained a compound 56 shown in FIG. 5 from a bovine fetuin (bovine-derived glycoprotein) and then synthesized a compound 10 shown in FIG. 1 via a compound 33 shown in FIG. 3. In order to obtain the compound 56, which is a first raw material, a hydrazine degradation reaction has been utilized. This hydrazine is highly toxic, so that there is a problem in safety when the resulting sugar chain derivative is applied to a pharmaceutical, due to the contamination of a trace amount of the hydrazine. In addition, the sugar chain derivatives of the compounds 56, 33 and 10 to which sialic acid is not bound can be obtained only in a small amount.

A second process is a process of synthesizing a sugar chain chemically. Currently, a construction of about 10 sugars prepared by combining monosaccharides according to a chemical synthesis process can be made as shown in a reported case of J. Seifert et al., *Angew Chem Int. Ed.* 2000, 39, p 531–534. The advantage of this process is that all of the sugar chain derivatives can be theoretically obtained. However, since its preparation steps are enormous, there is a defect that a synthesis in a large amount is difficult. In addition, even in case where a sugar chain in which about 10 sugar residues are bound is synthesized in an amount of several milligrams, a time period of as long as about one year is required. While there have been so far some cases where several sugar chains are synthesized chemically, most of the cases actually could synthesize the intended sugar chain only in an amount as small as several milligrams.

A third process is a process of synthesizing a sugar chain by combining an enzymatic reaction and a chemical reaction. As a representative example, there is a process as reported by Carlo Unverzagt, *Angew Chem Int. Ed.* 1996, 35, p 2350–2353. This process employs a technique in which a sugar chain is constructed to a certain length by chemical synthesis, and thereafter a sugar residue is added to the sugar chain by an enzymatic reaction, thereby extending the sugar chain. However, since the enzyme used in the chain extension has substrate specificity, the kinds of sugar which can be introduced into the sugar chain are limited. In addition, since the preparation steps are enormous in the chemical synthesis, a large-scale synthesis is difficult, so that the final product can be obtained only in a small amount. Alternatively, in C. H. Lin et al. (*Bioorganic & Medicinal Chemistry*, 1995, p 1625–1630), a sialyloligoglycopeptide is obtained from an egg yolk by employing a process reported by M. Koketsu et al. (*J. Carbohydrate Chemistry*, 1995, 14(6), p 833–841), and the structure of the non-reducing terminal moieties of the sugar chain is modified with a glycosidase and a sugar transferase. A sugar chain having only one asparagine (Asn) residue bound to its non-reducing terminal moiety is shown in a drawing of this article. However, according to the process reported in *J. Carbohy-* drate Chemistry, 1995, 14(6), p 833–841, a mixture of sugar chains each having on average about 2.5 amino acids other than asparagine, such as lysine, which are bound to a non-reducing terminal of the sugar chain. Therefore, a sugar chain derivative cannot be obtained as a single compound. Also, there is not suggested obtainment of individual derivatives of the compounds having arbitrary deletions of the sugar residues in the branched sugar chain of the branching sugar chains in a large amount. An article by C. H. Lin et al. does not give any evidence that a sugar chain is obtained as a single product. Y. Ichikawa mentions in *Glycopeptide and Related Compounds* (Marcel Dekker, Inc., 1997, ISBN 0-8247-9531-8, p. 79–205) that if the trifurcated sugar chain complex is sequentially treated from a terminal with a glycosidase, sugar chains can be sequentially removed from a non-reducing terminal of the sugar chain, thereby giving various sugar chain derivatives. However, how the individual sugar chains are separated after the enzymatic treatment is not described, and the synthesis is limited only to those having uniform branching. Therefore, even with this process, it is thought that the individual derivatives of the compounds having arbitrary deletions of sugar residues in the branched sugar chain of the branching sugar chains cannot be obtained in a large amount.

the present invention is to provide a novel sugar chain asparagine derivative, a sugar chain asparagine and a sugar chain.

Concretely, the present invention relates to:

(1) a process for preparing a sugar chain aspargine derivative derived from a sugar chain asparagine, comprising the steps of:

(a) introducing a fat-soluble protecting group into the sugar chain asparagine contained in a mixture of one or more sugar chain asparagines, to give a mixture of sugar chain asparagine derivatives; and (b) subjecting the mixture of sugar chain asparagine derivatives or a mixture obtainable by hydrolyzing a sugar chain asparagine derivative contained in the mixture of sugar chain asparagine derivatives to chromatography, to separate each of the sugar chain asparagine derivatives therefrom;

(2) the process according to the above (1), further comprising the step of (b'): hydrolyzing the sugar chain asparagine derivative separated in step (b) with a glycosidase;

(3) the process according to the above (1) or (2), wherein the mixture of one or more sugar chain asparagines comprises:

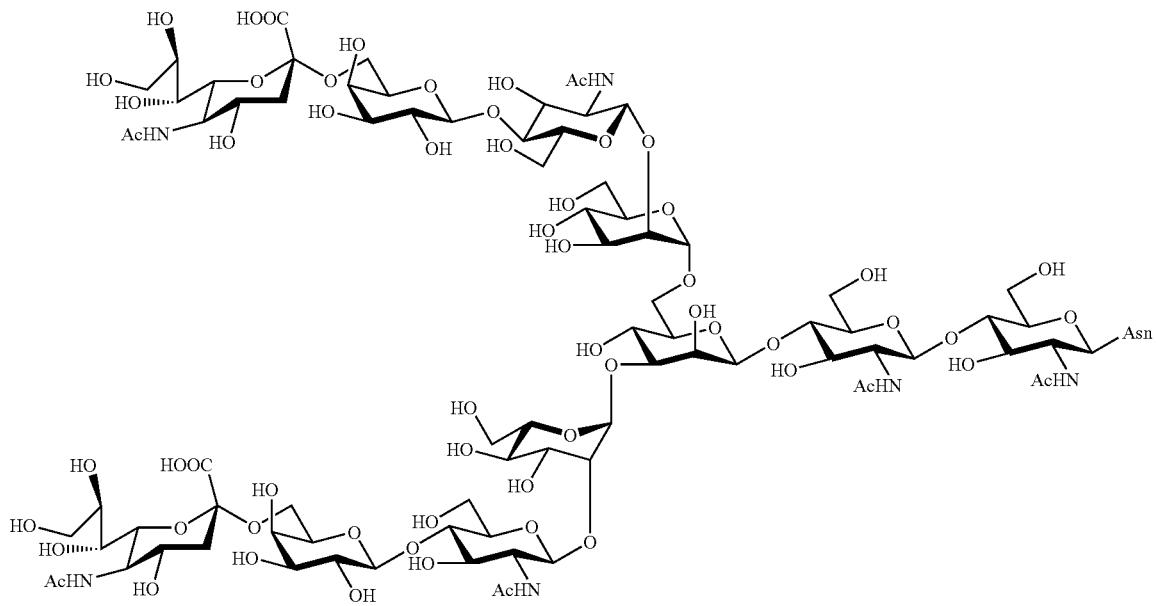

DISCLOSURE OF INVENTION

An object of the present invention is to provide a process for preparing a sugar chain asparagine derivative, whereby various isolated sugar chain asparagine derivatives useful in the field of the development of pharmaceuticals and the like can be conveniently obtained in a large amount as compared to those of the prior art. Another object of the present invention is to provide a process for preparing a sugar chain asparagine and a process for preparing a sugar chain via a step for preparing a sugar chain asparagine derivative, whereby various isolated sugar chain asparagines and sugar chains, which are useful as much as sugar chain asparagine derivatives, can be conveniently obtained in a large amount as compared to those of the prior art. Still another object of and/or a compound having one or more deletions of sugar residues in the above compound;

(4) the process according to any one of the above (1) to (3), wherein the fat-soluble protecting group is fluorenylmethoxycarbonyl (Fmoc) group;

(5) the process according to any one of the above (1) to (3), wherein the step (a) is a step of introducing Fmoc group into the sugar chain aspargine contained in a mixture of one or more sugar chain asparagines having a sialic acid residue at a non-reducing terminal, and introducing benzyl group into the sialic acid residue, to give a mixture of sugar chain asparagine derivatives;

(6) a process for preparing a sugar chain aspargine, comprising the steps of:
(a) introducing a fat-soluble protecting group into a sugar chain aspargine contained in a mixture of one or more sugar chain asparagines, to give a mixture of sugar chain asparagine derivatives;
(b) subjecting the mixture of sugar chain asparagine derivatives or a mixture obtainable by hydrolyzing a sugar chain asparagine derivative contained in the mixture of sugar chain asparagine derivatives to chromatography, to separate each of the sugar chain asparagine derivatives therefrom; and
(c) removing the protecting group from the sugar chain asparagine derivative separated in the step (b), to give the sugar chain asparagine;

(7) the process according to the above (6), further comprising the step of:
(b') hydrolyzing the sugar chain asparagine derivative separated in step (b) with a glycosidase; and/or
(c') hydrolyzing the sugar chain asparagine obtained in step (c) with a glycosidase;

(8) The process according to the above (6) or (7), wherein the mixture of one or more sugar chain asparagines comprises:

a non-reducing terminal, and introducing benzyl group into the sialic acid residue, to give a mixture of sugar chain asparagine derivatives;

(11) a process for preparing a sugar chain, comprising the steps of:
(a) introducing a fat-soluble protecting group into a sugar chain aspargine contained in a mixture of one or more sugar chain asparagines, to give a mixture of sugar chain asparagine derivatives;
(b) subjecting the mixture of sugar chain asparagine derivatives or a mixture obtainable by hydrolyzing a sugar chain asparagine derivative contained in the mixture of sugar chain asparagine derivatives to chromatography, to separate each of the sugar chain asparagine derivatives therefrom;
(c) removing the protecting group from the sugar chain asparagine derivative separated in the step (b), to give a sugar chain asparagine; and
(d) removing an asparagine residue from the sugar chain asparagine obtained in the step (c), to give the sugar chain;

(12) the process the above (11), further comprising the step of:

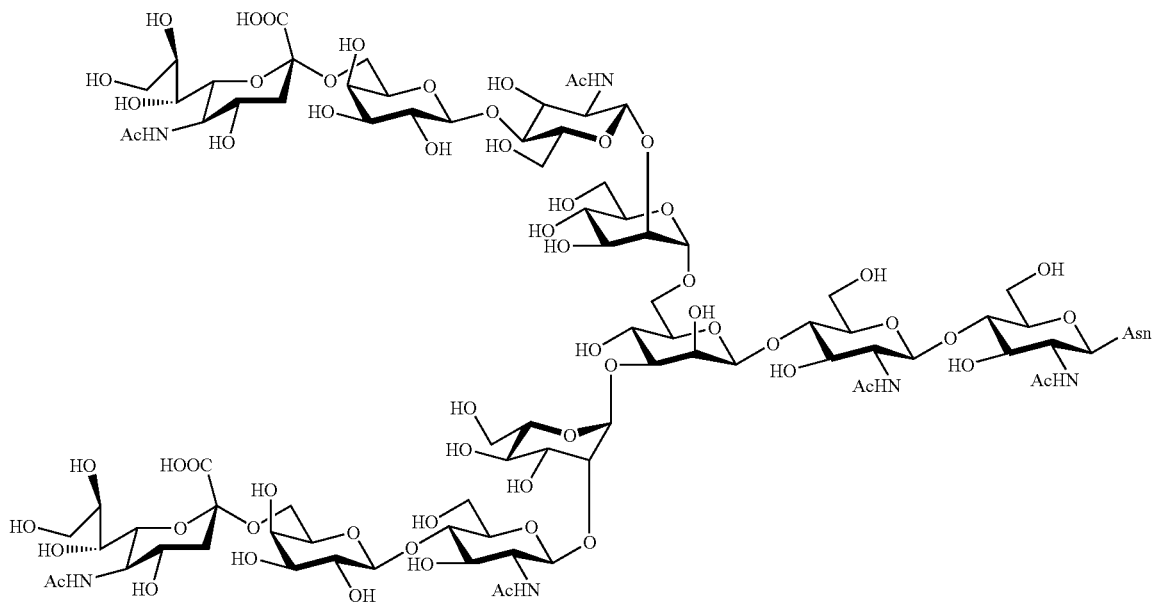

and/or a compound having one or more deletions of sugar residues in the above compound;

(9) the process according to any one of the above (6) to (8), wherein the fat-soluble protecting group is Fmoc group;

(10) the process according to any one of the above (6) to (8), wherein the step (a) is a step of introducing Fmoc group into the sugar chain aspargine contained in a mixture of one or more sugar chain asparagines having a sialic acid residue at (b') hydrolyzing the sugar chain asparagine derivative separated in step (b) with a glycosidase; and/or
(c') hydrolyzing the sugar chain asparagine obtained in step (c) with a glycosidase; and/or
(d') hydrolyzing the sugar chain obtained in step (d) with a glycosidase;

(13) the process according to the above (11) or (12), wherein the mixture of one or more sugar chain asparagines comprises:

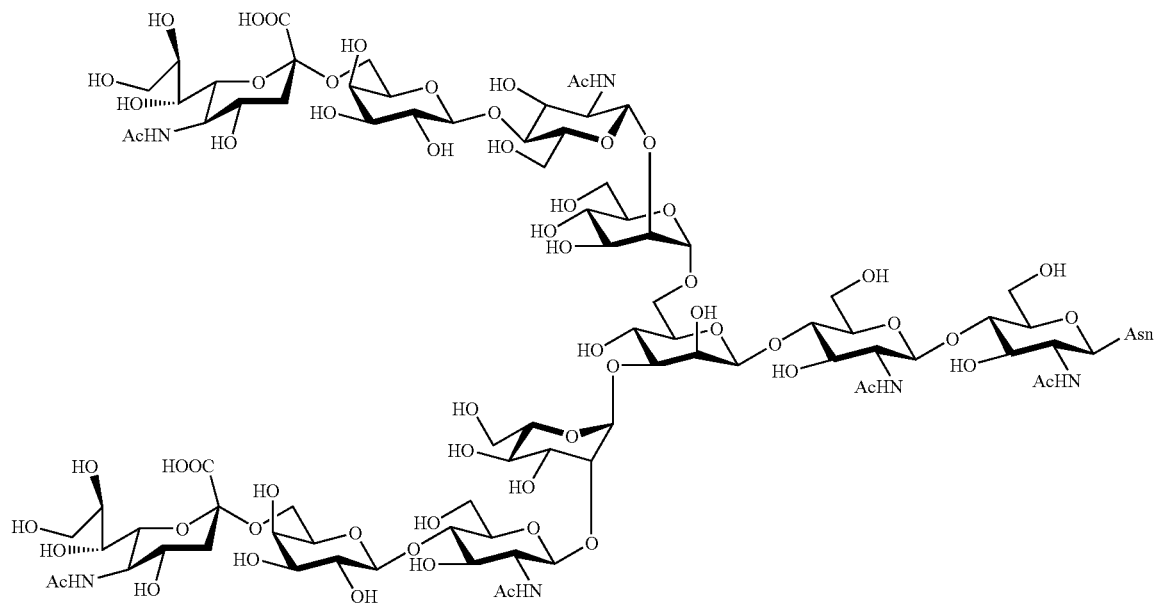

and/or a compound having one or more deletions of sugar residues in the above compound;

(14) the process according to any one of the above (11) to (13), wherein the fat-soluble protecting group is Fmoc group;

(15) the process according to any one of the above (11) to (13), wherein the step (a) is a step of introducing Fmoc group into the sugar chain aspargine contained in a mixture of one or more sugar chain asparagines having a sialic acid residue at a non-reducing terminal, and introducing benzyl group into the sialic acid residue, to give a mixture of sugar chain asparagine derivatives;

(16) a sugar chain asparagine derivative having the general formula:

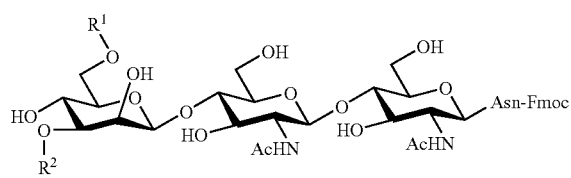

wherein $R^1$ and $R^2$, which may be identical or different, are H,

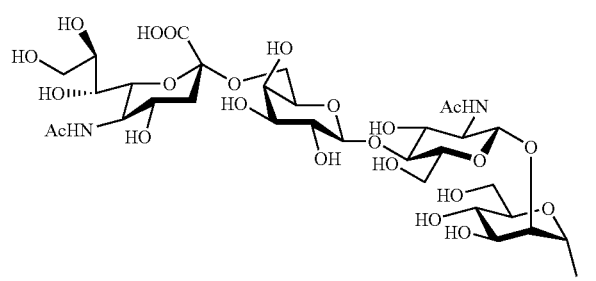

-continued

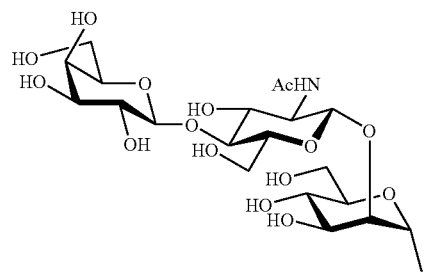

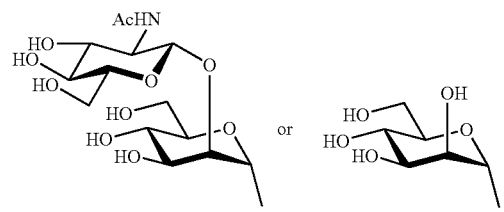

with proviso that a case where $R^1$ and $R^2$ are both

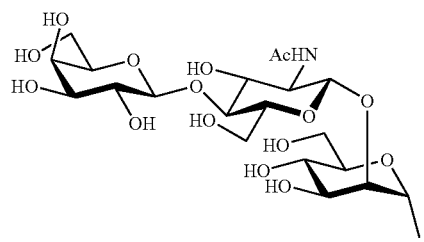

is excluded;

(17) a sugar chain asparagine derivative having the general formula:
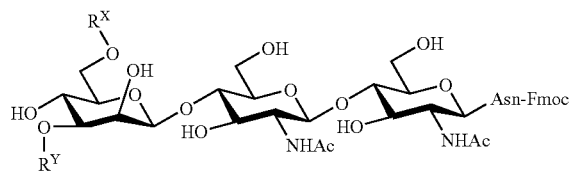
wherein one of $R^x$ and $R^y$ is
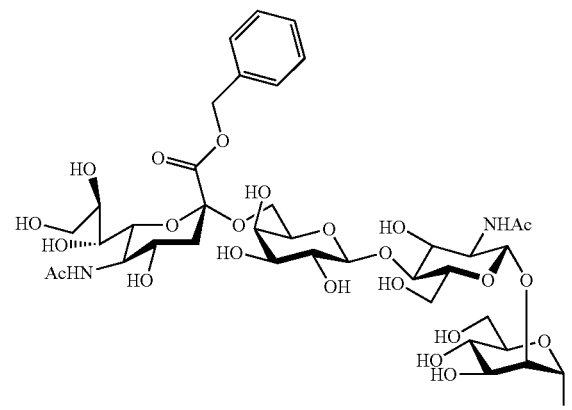
and the other is H,
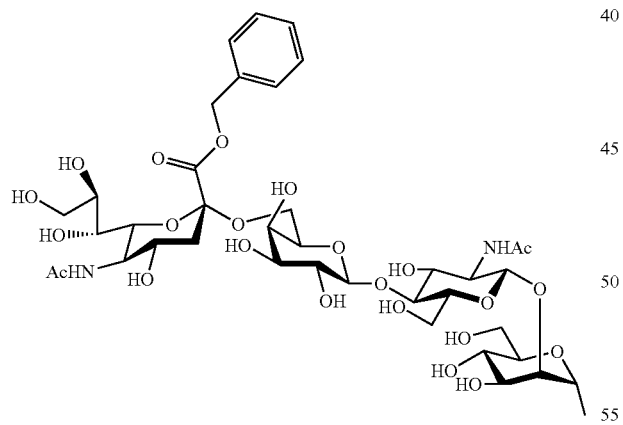
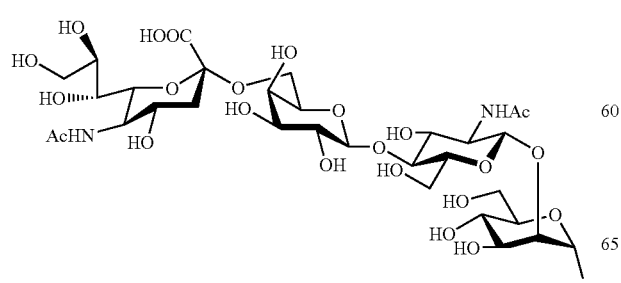
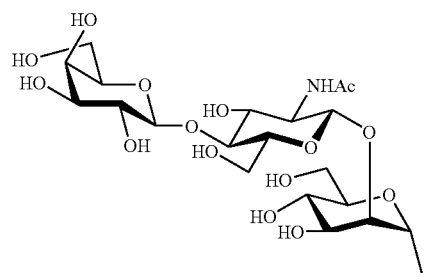
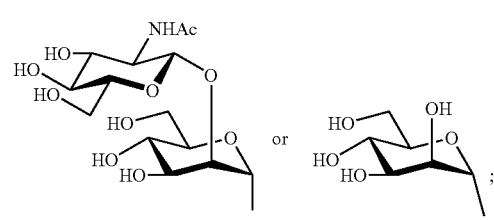
(18) a sugar chain asparagine having the general formula:
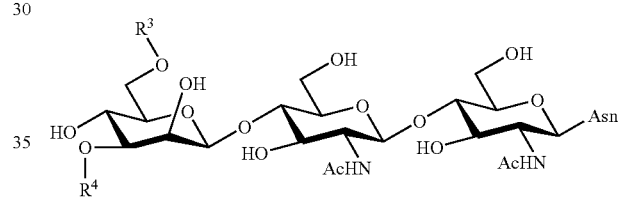
wherein $R^3$ and $R^4$, which may be identical or different, are H,
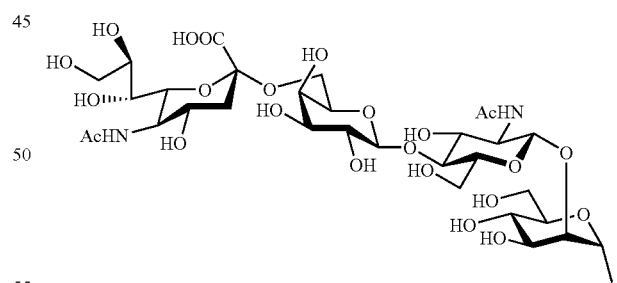
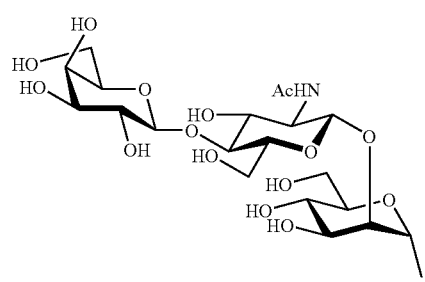

-continued
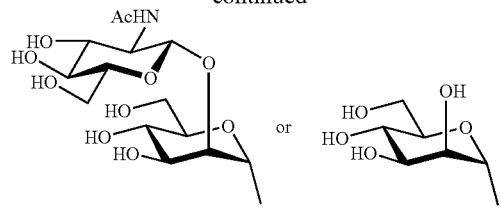
with proviso that a case where $R^3$ and $R^4$ are both
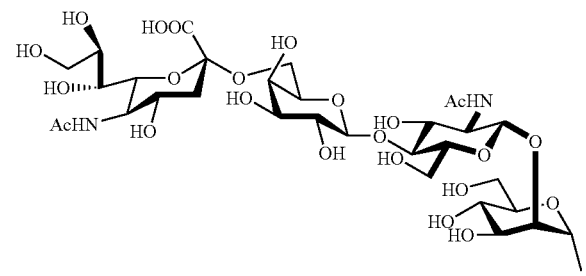
or
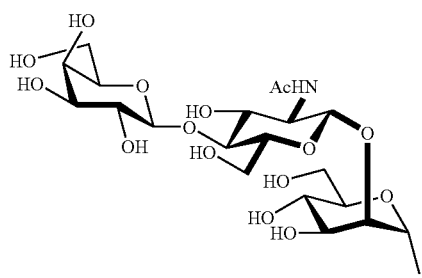
is excluded; and
(19) a sugar chain having the general formula:
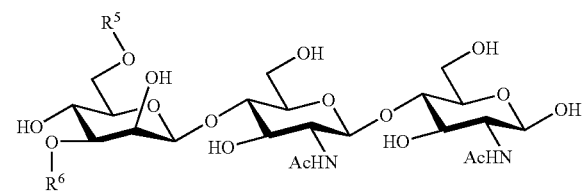
wherein $R^5$ and $R^6$, which may be identical or different, are H,
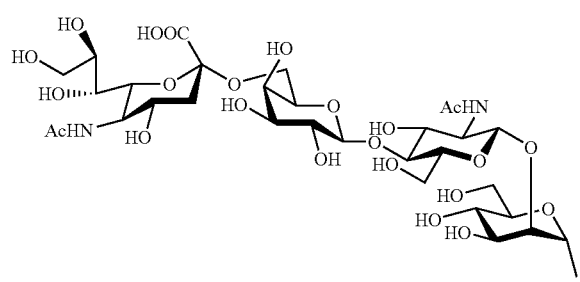
-continued
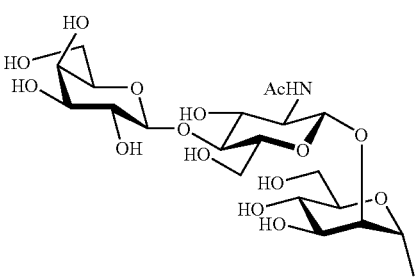
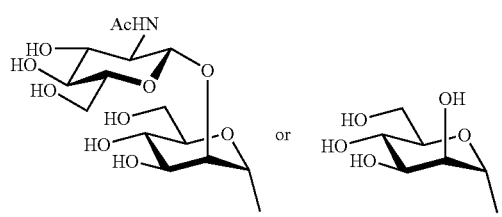
with proviso that a case where $R^5$ and $R^6$ are both
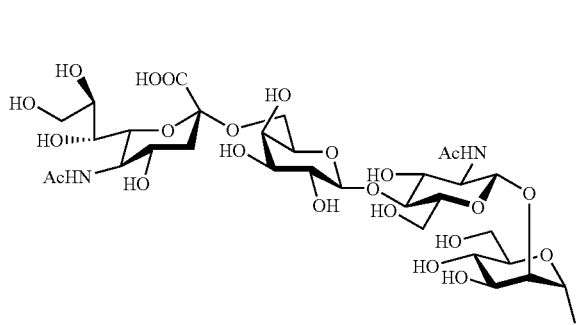
or one of $R^5$ or $R^6$ is H and the other is
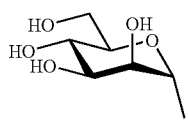
is excluded.

BEST MODE FOR CARRYING OUT THE INVENTION

Figure 1A:
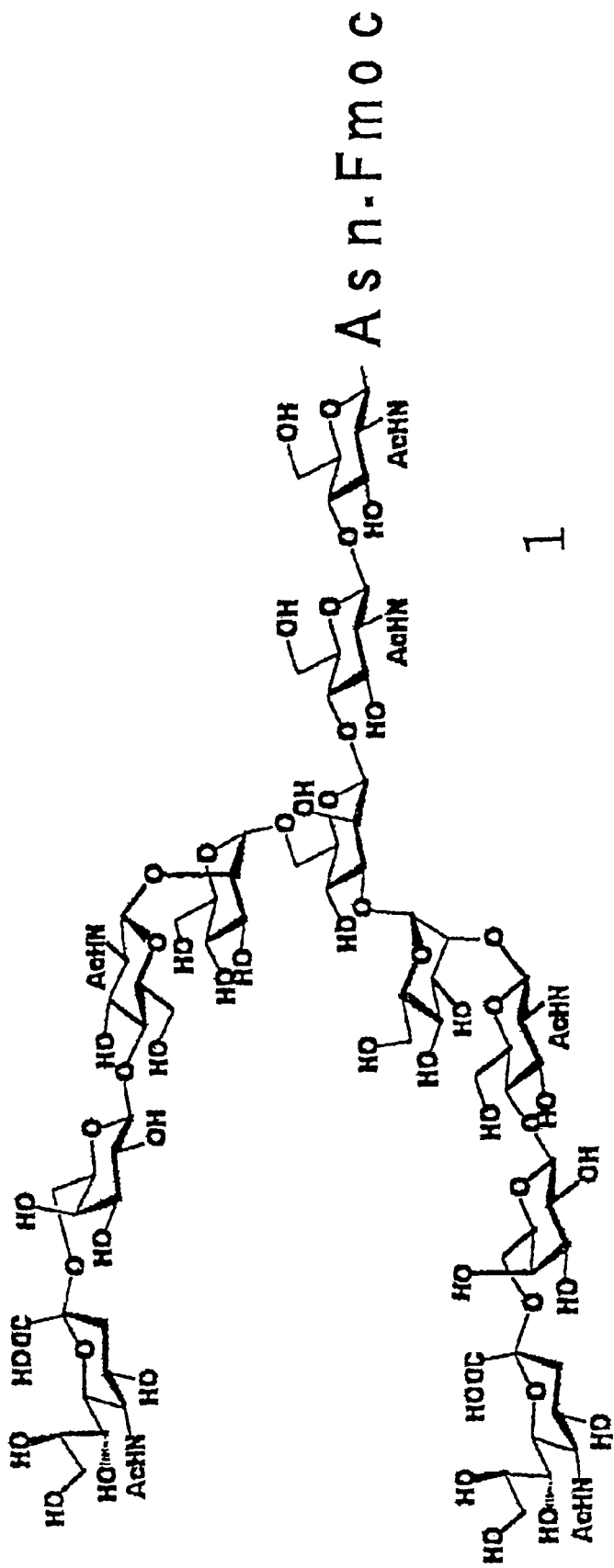
FIG. 1 shows a group of structures of sugar chain asparagine derivatives obtainable according to the present invention.
Figure 1B:
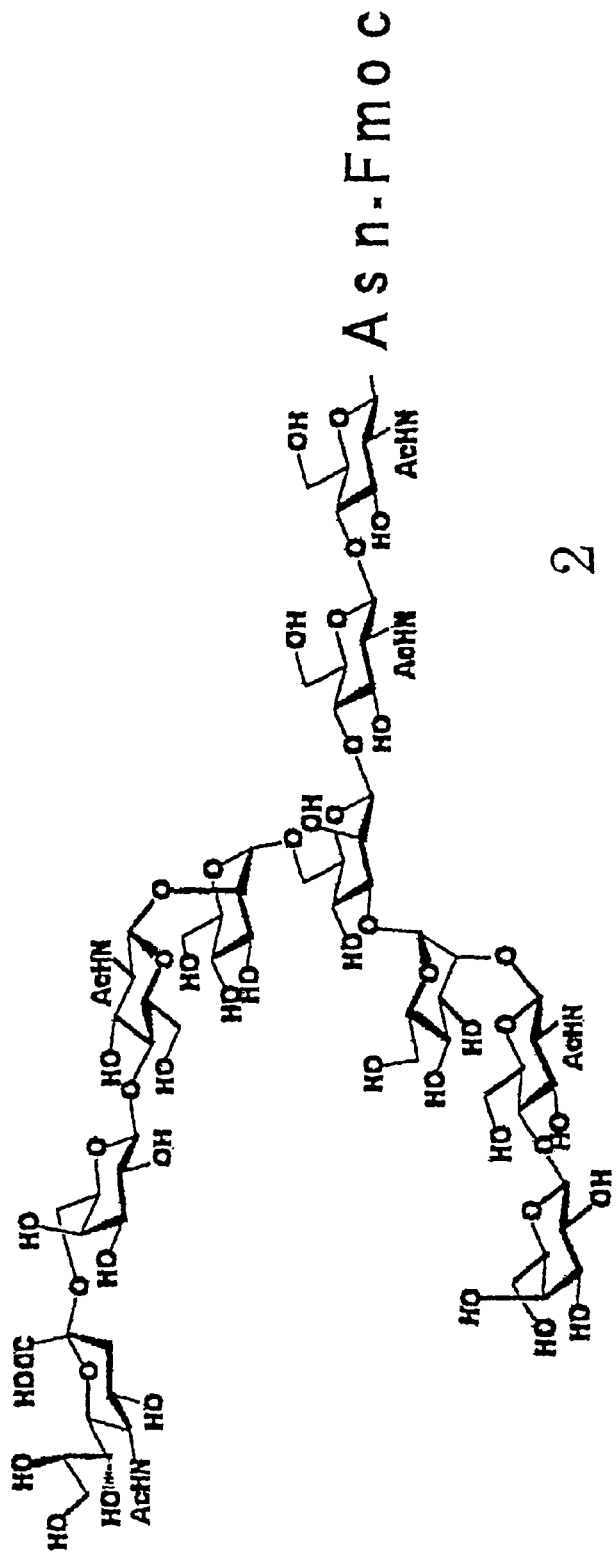
Figure 1C:
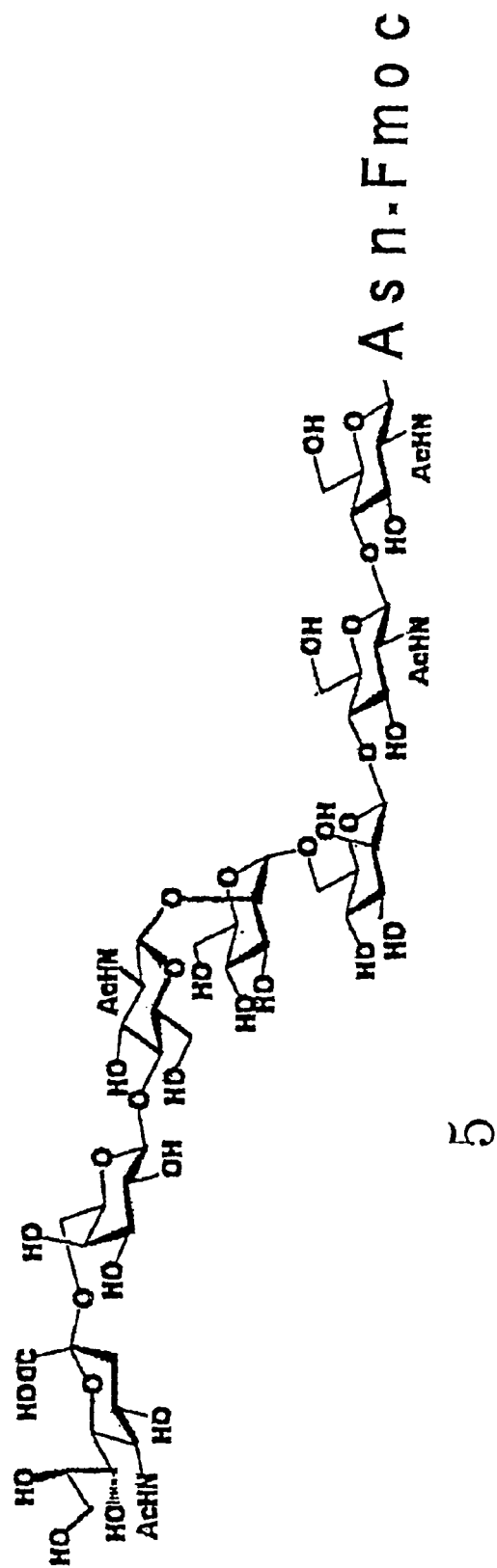
Figure 1D:
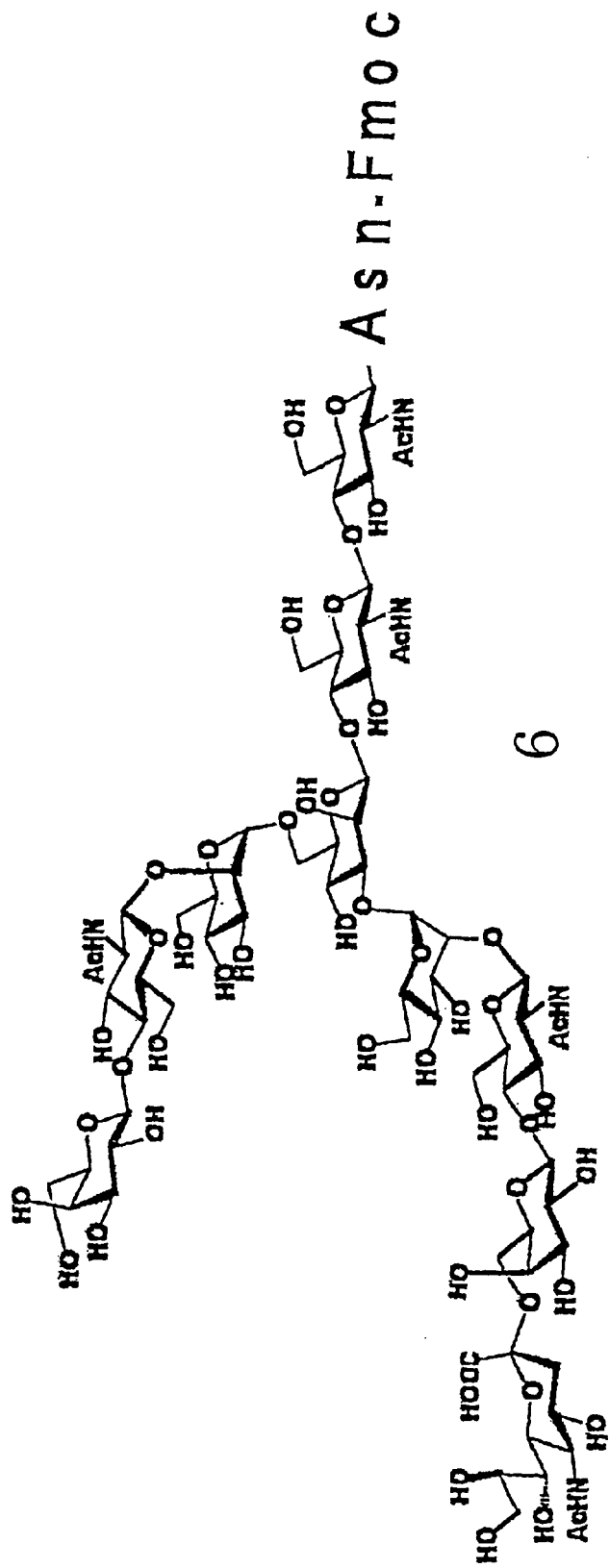
Figure 1E:
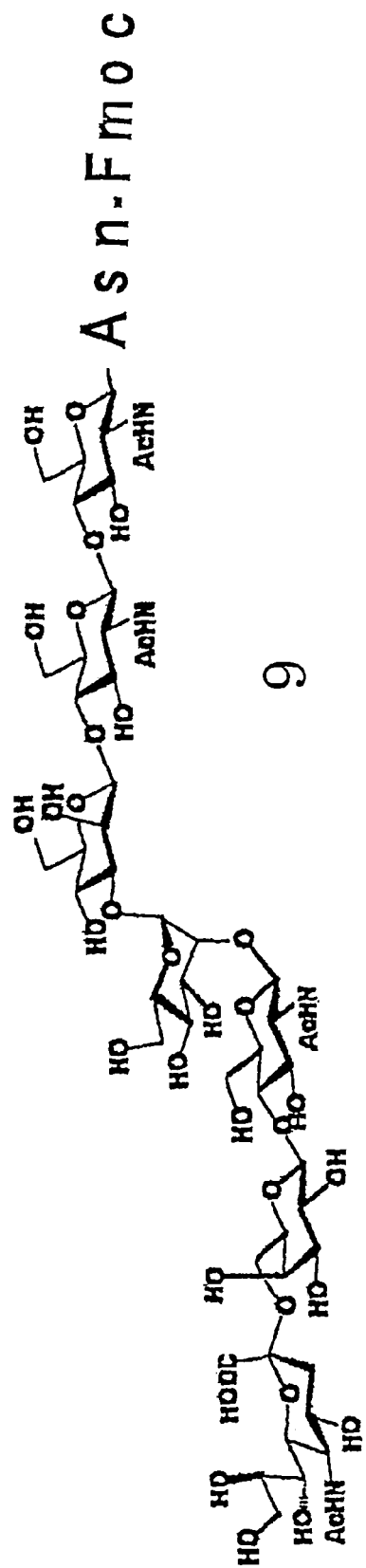
Figure 1F:
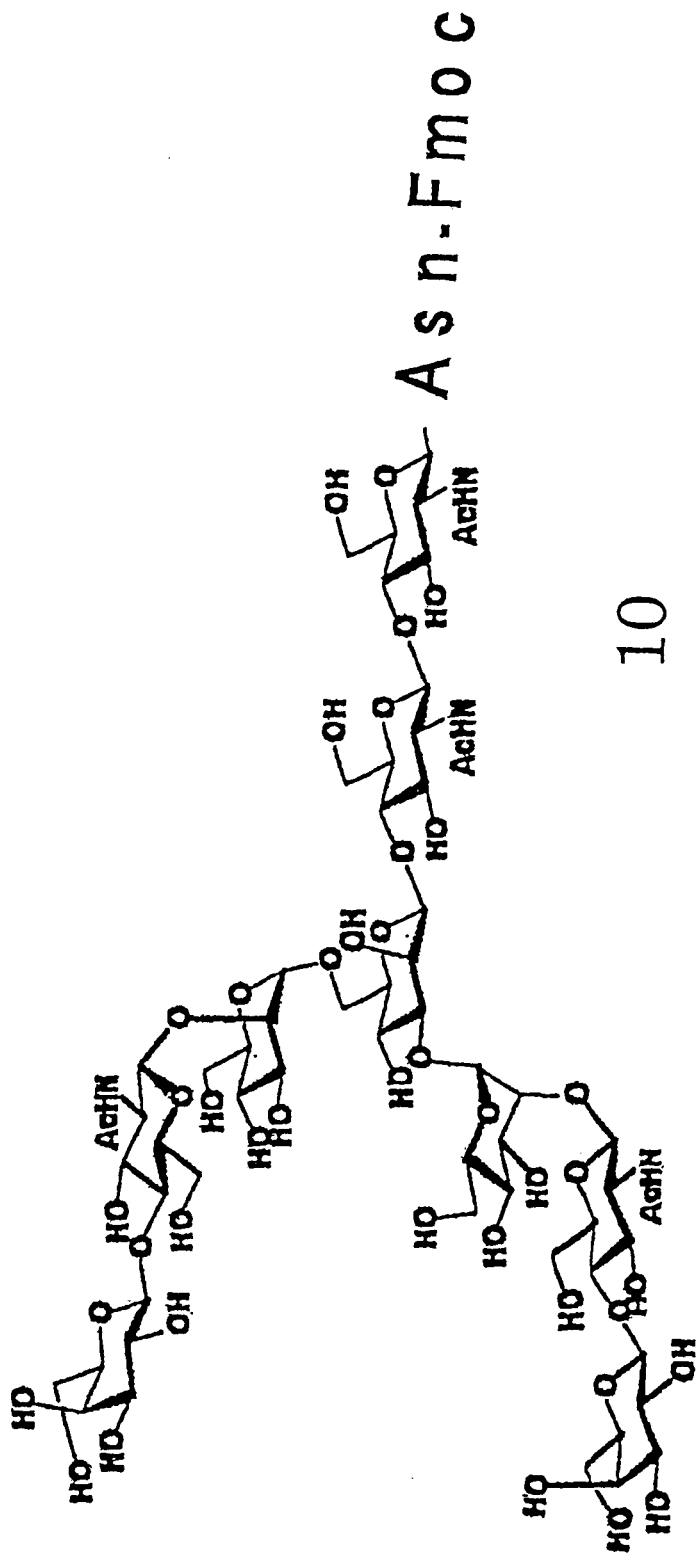
Figure 1G:
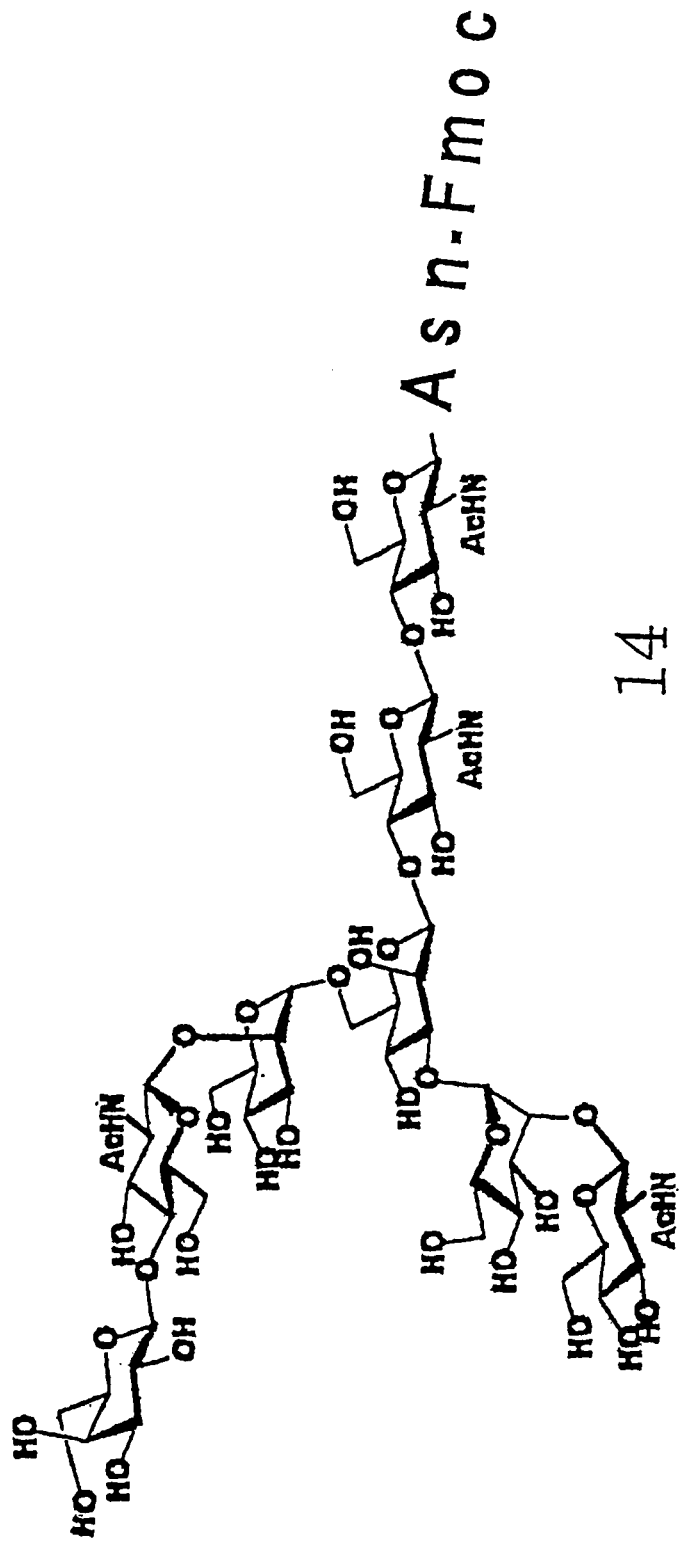
Figure 1H:
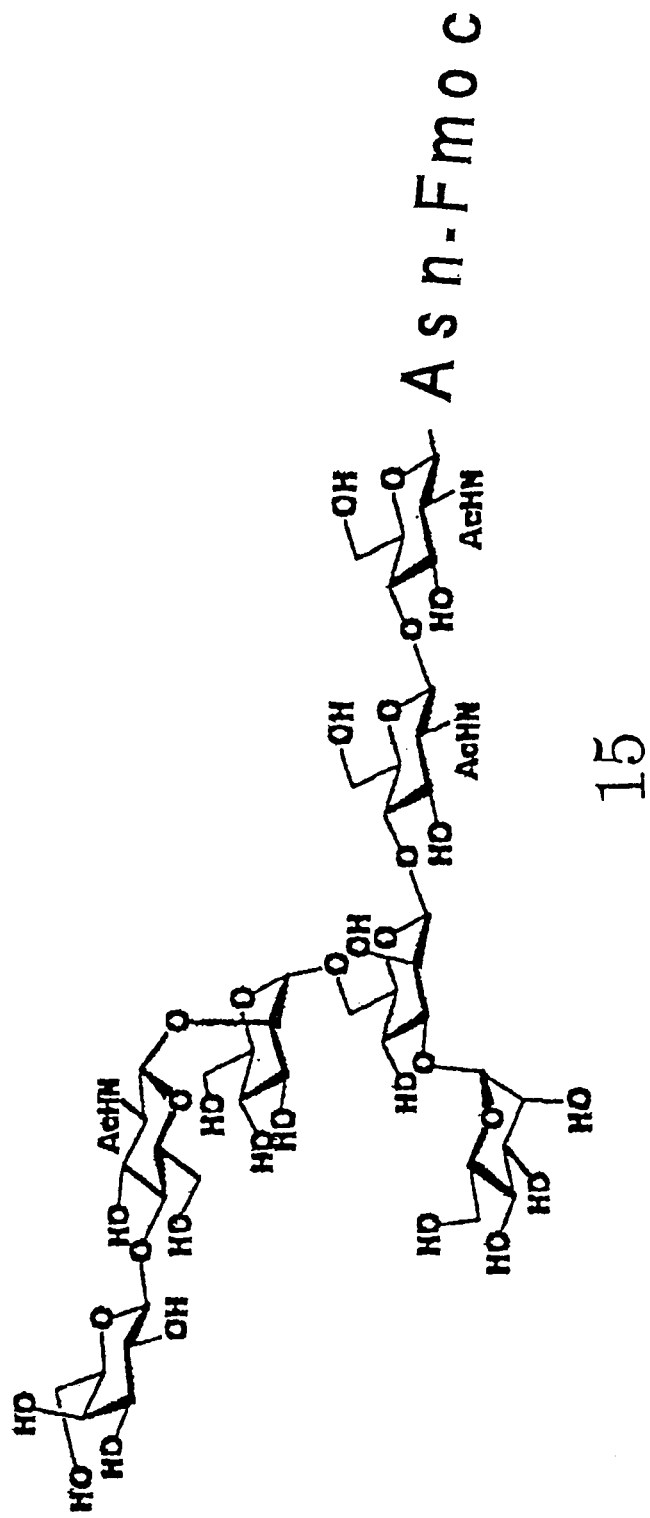
Figure 1I:
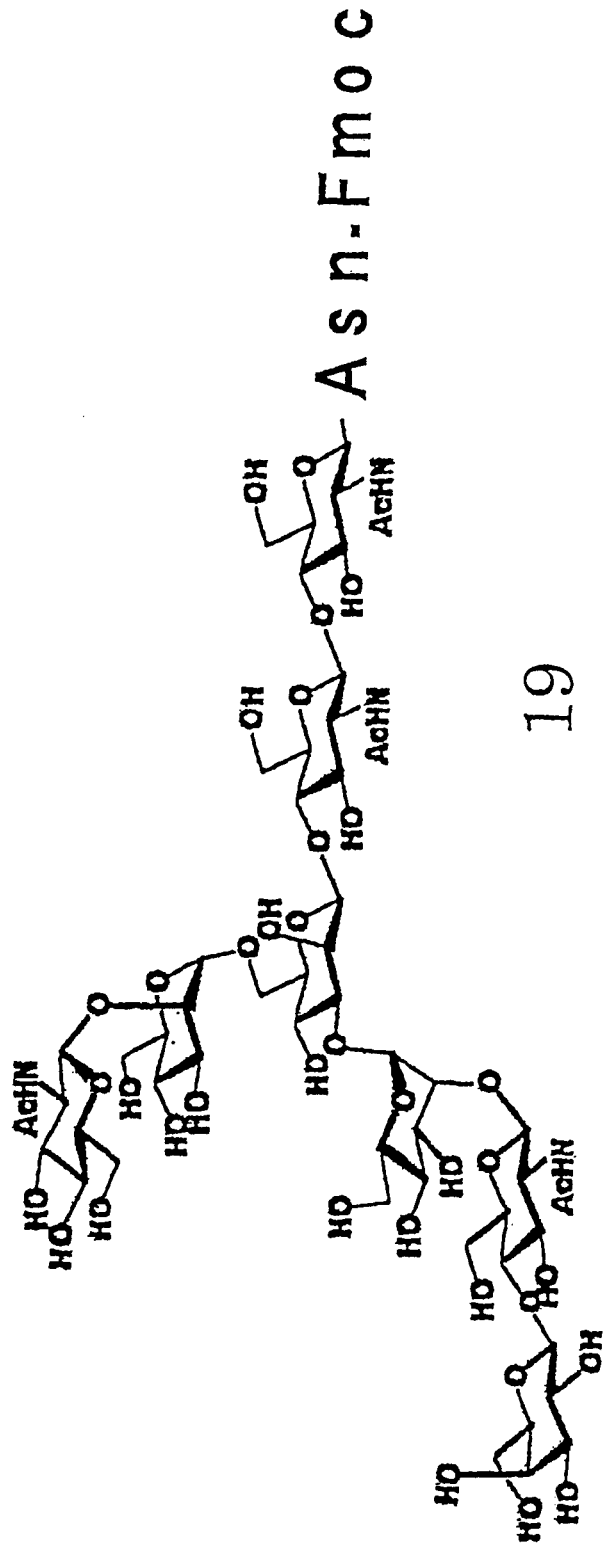
Figure 1J:
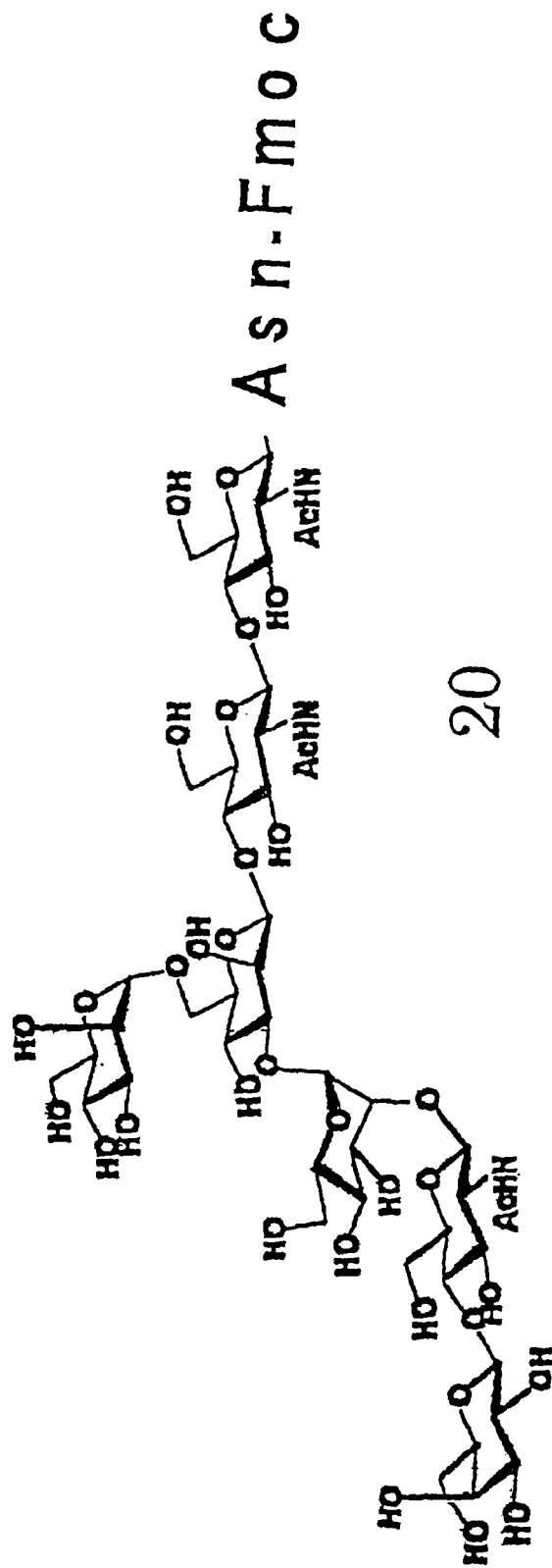
Figure 1K:
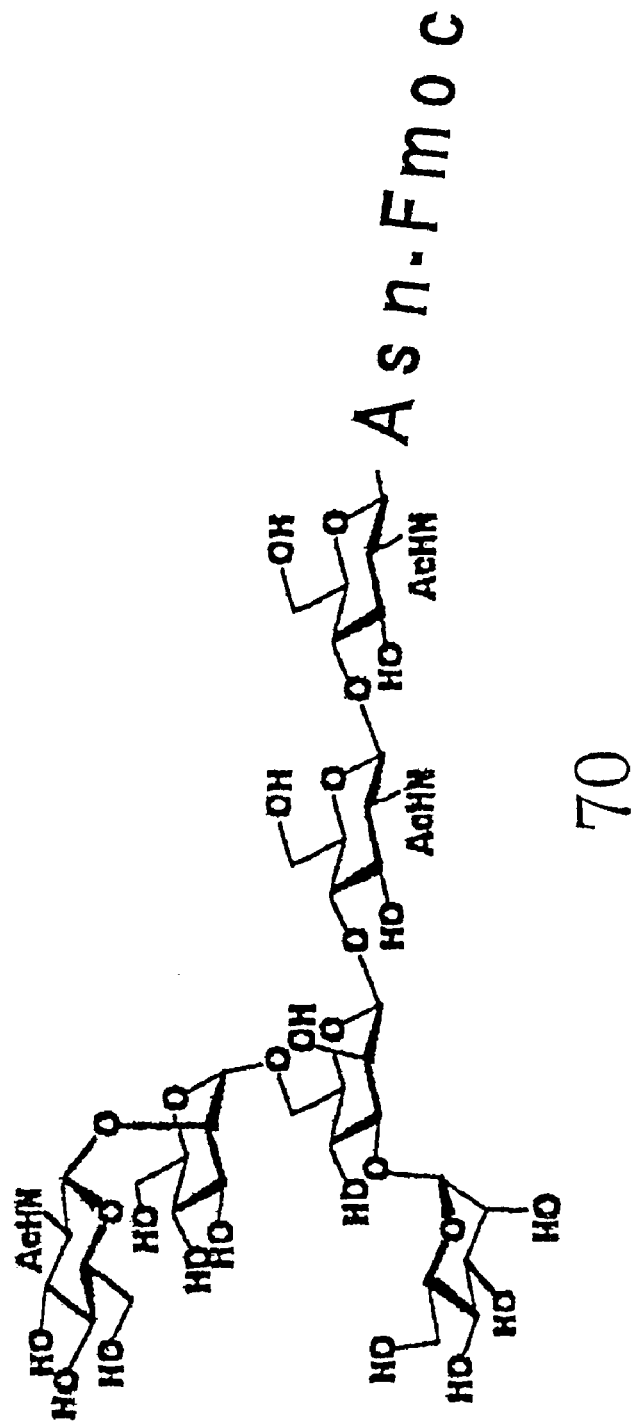
Figure 1L:
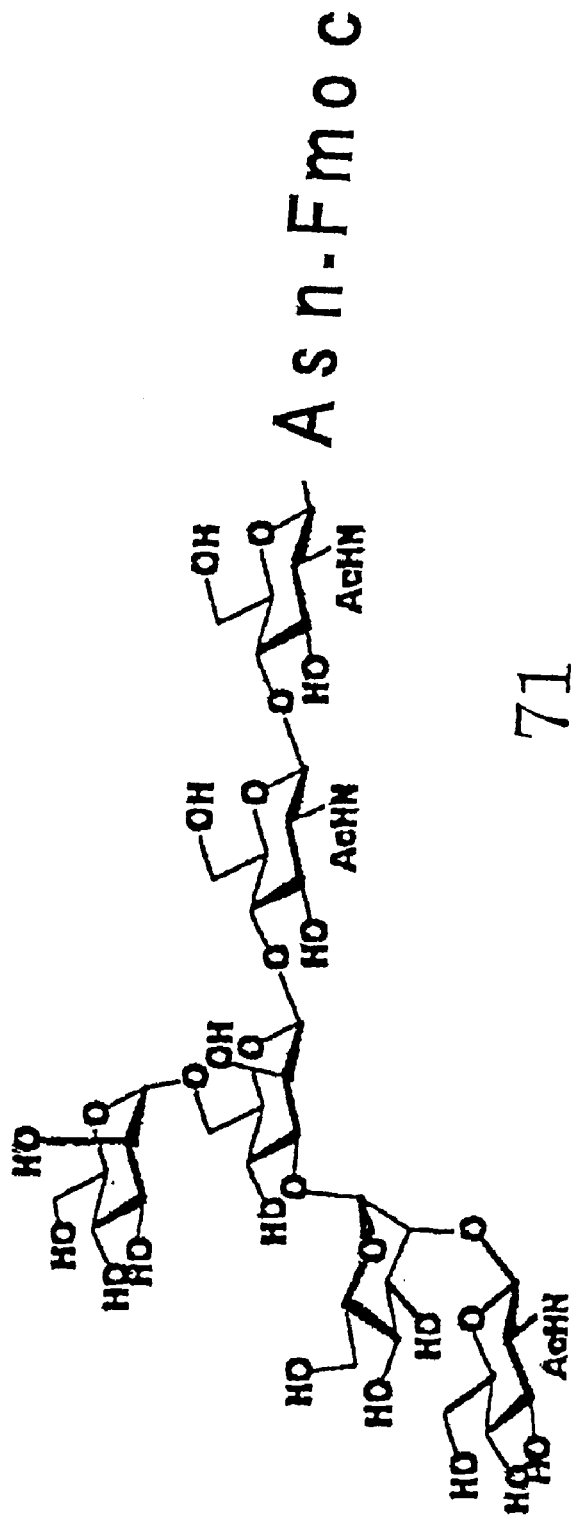
Figure 2A:
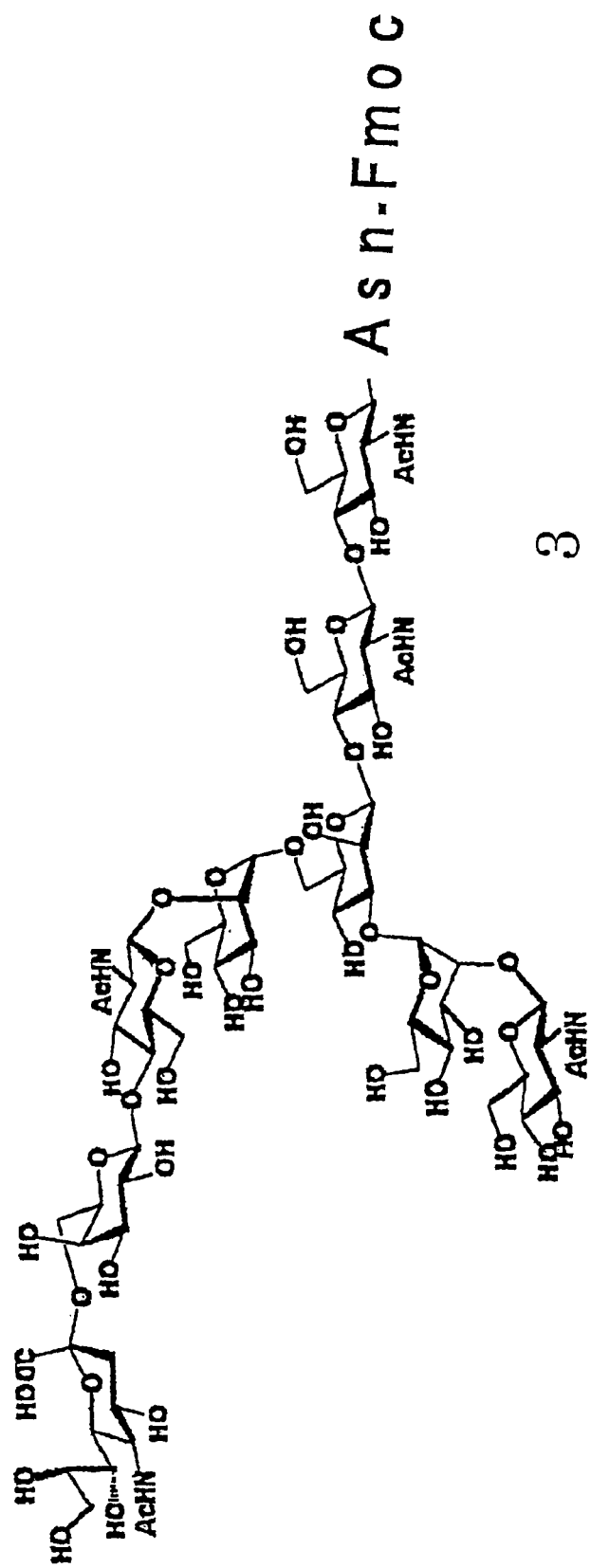
FIG. 2 shows a group of structures of sugar chain asparagine derivatives obtainable according to the present invention.
Figure 2B:
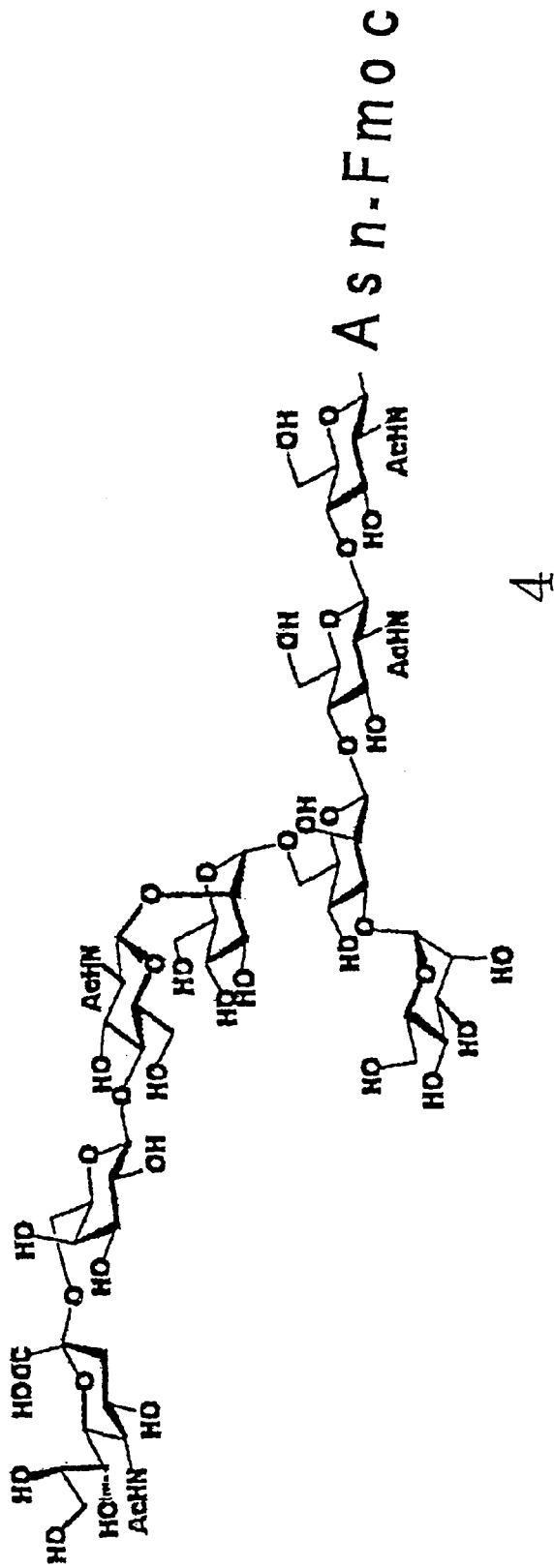
Figure 2C:
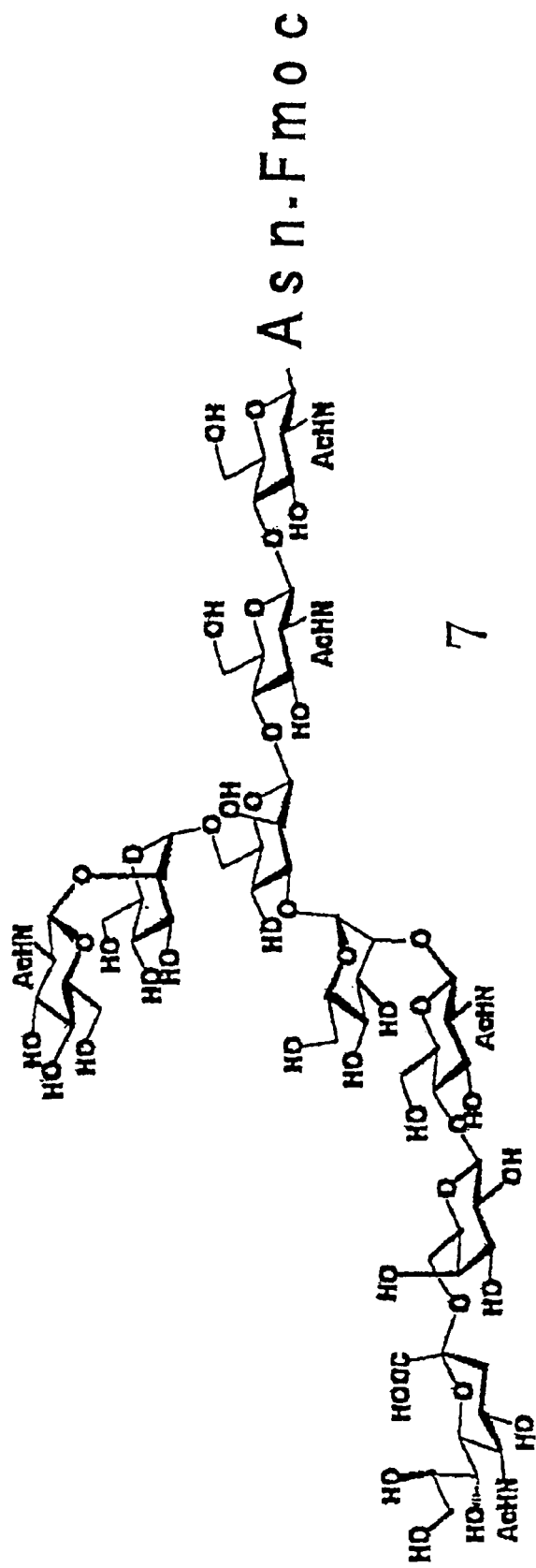
Figure 2D:
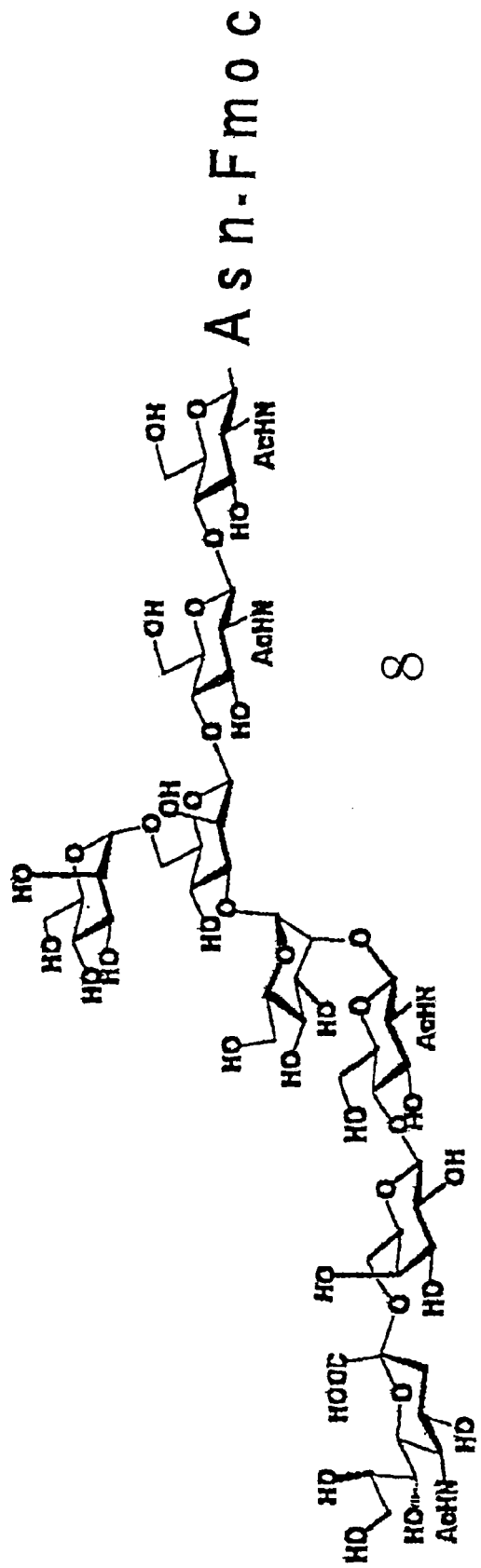
Figure 2E:
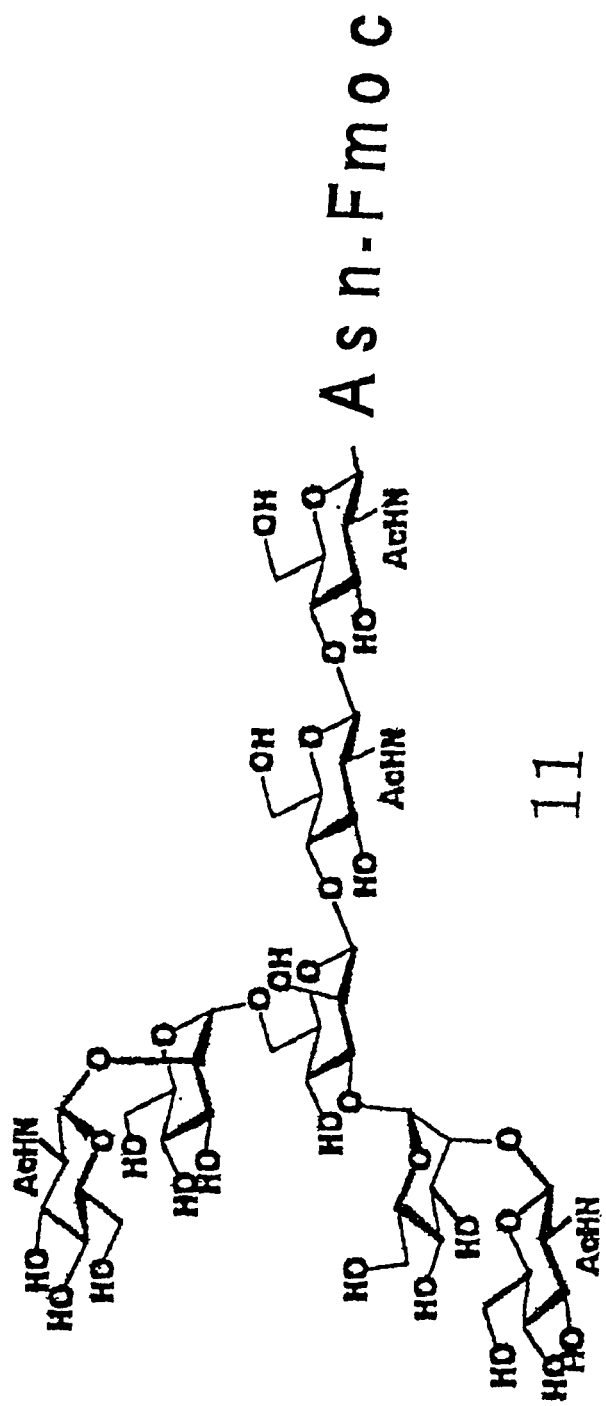
Figure 2F:
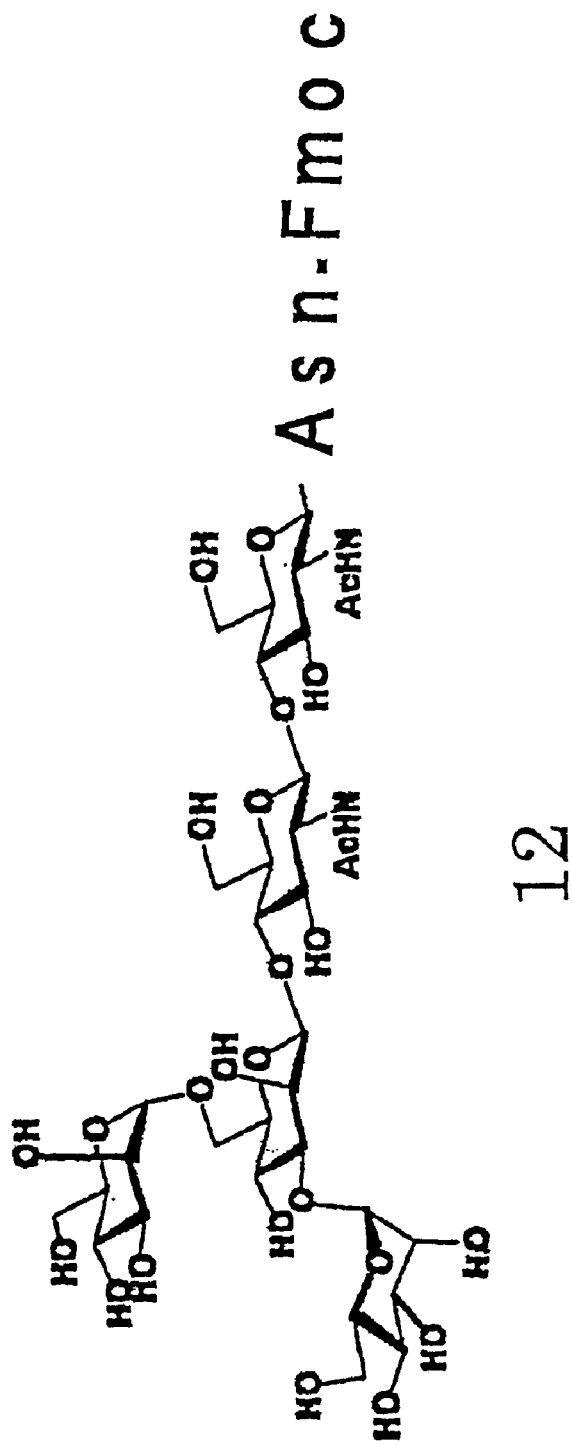
Figure 2G:
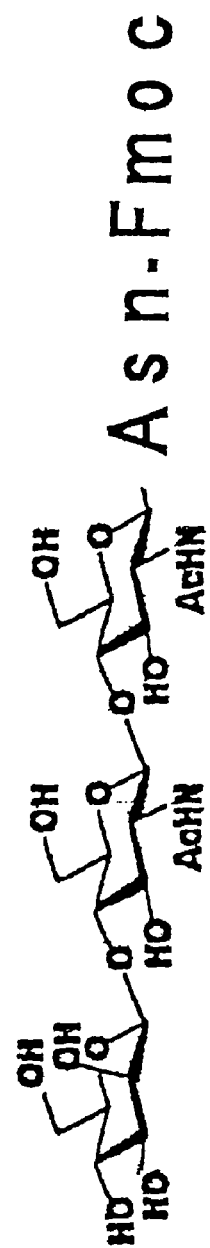
Figure 2H:
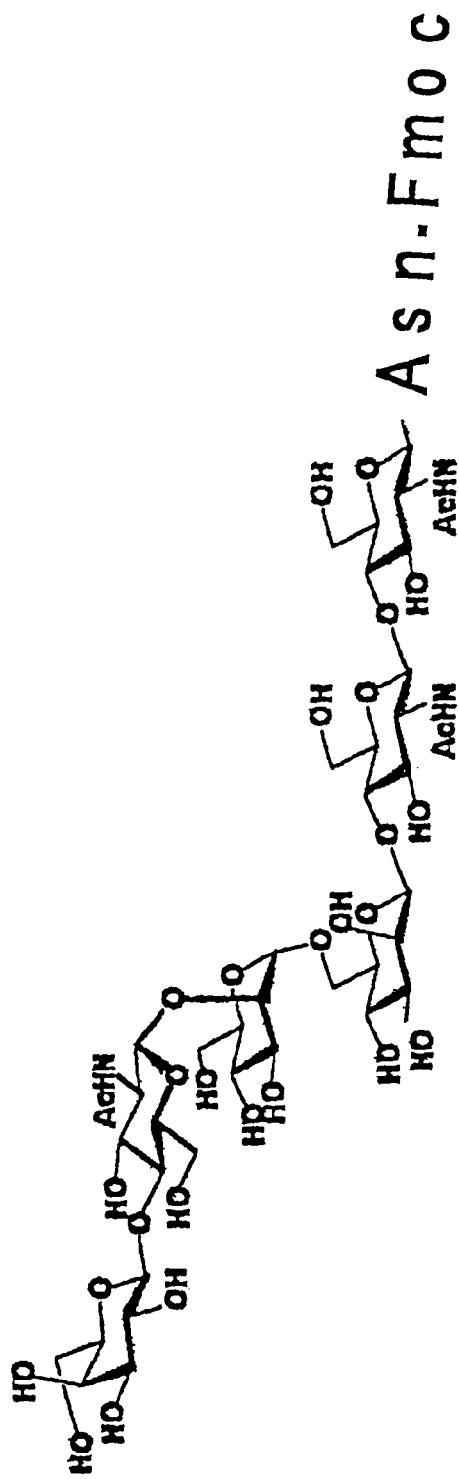
Figure 2I:
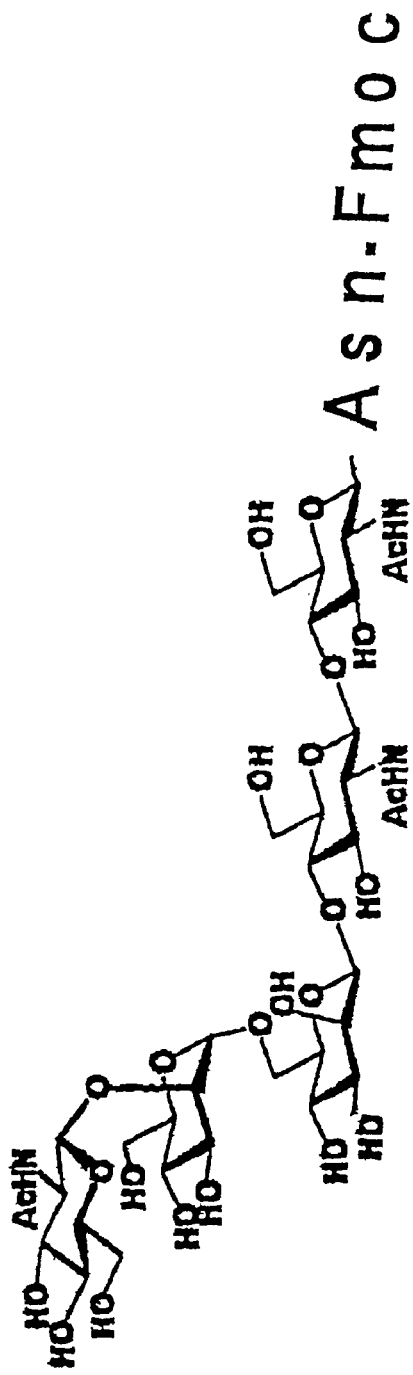
Figure 2J:
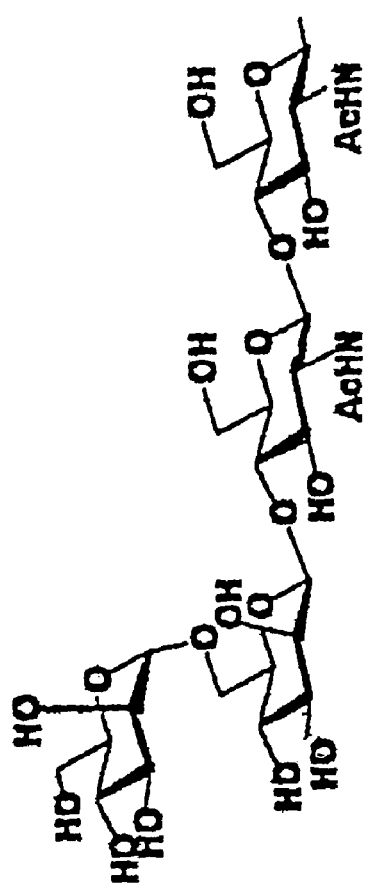
Figure 2K:
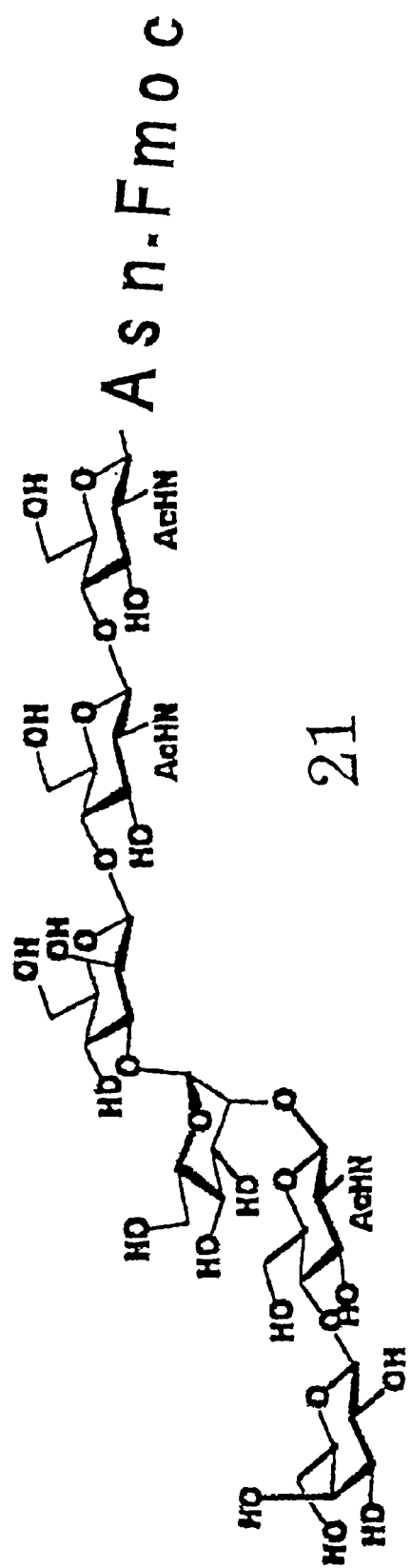
Figure 2L:
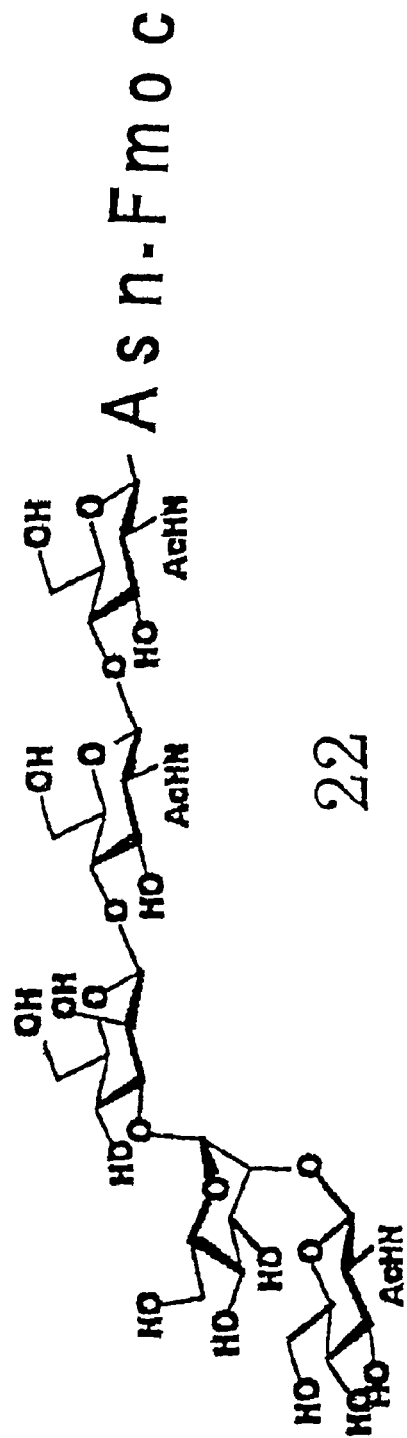
Figure 2M:
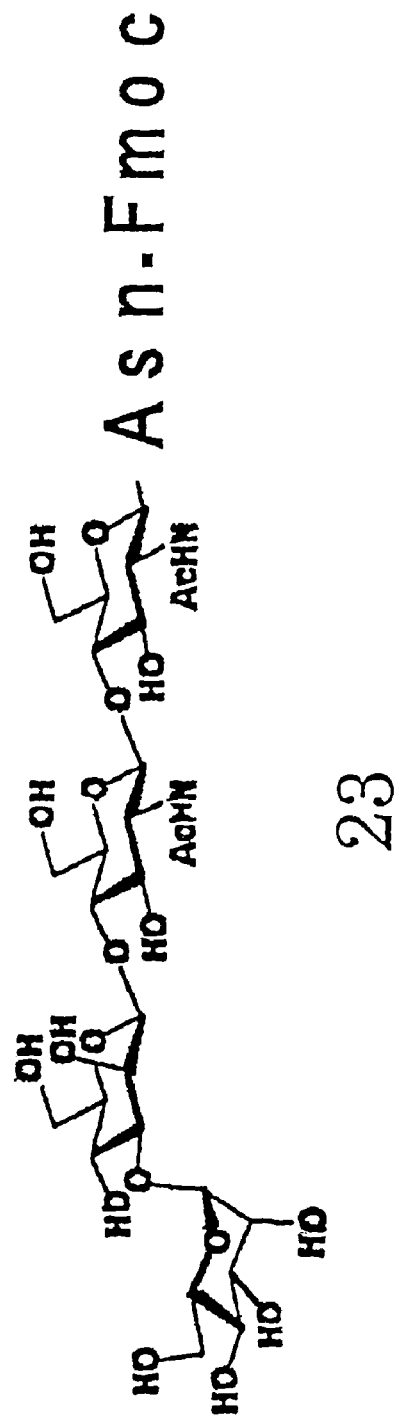
Figure 3A:
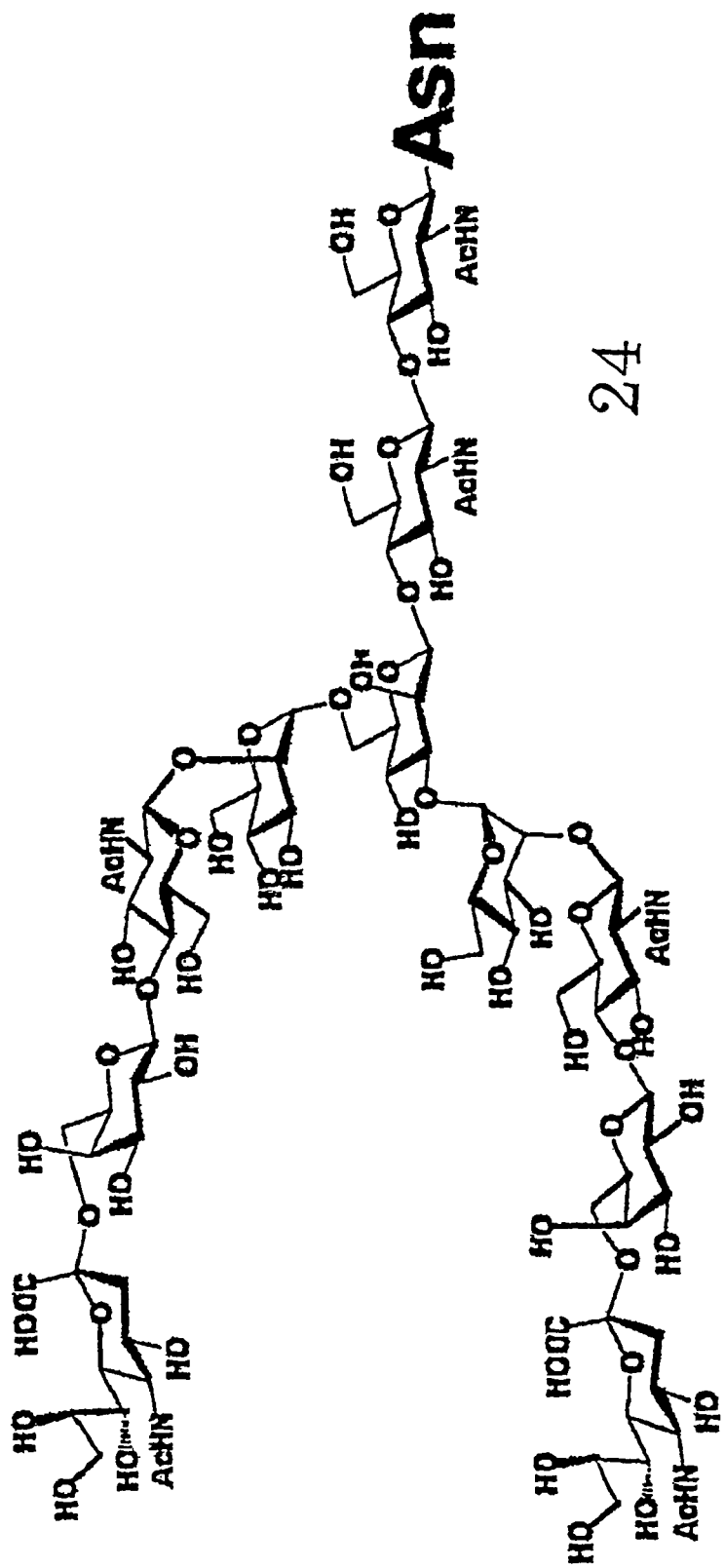
FIG. 3 shows a group of structures of sugar chain asparagines obtainable according to the present invention.
Figure 3B:
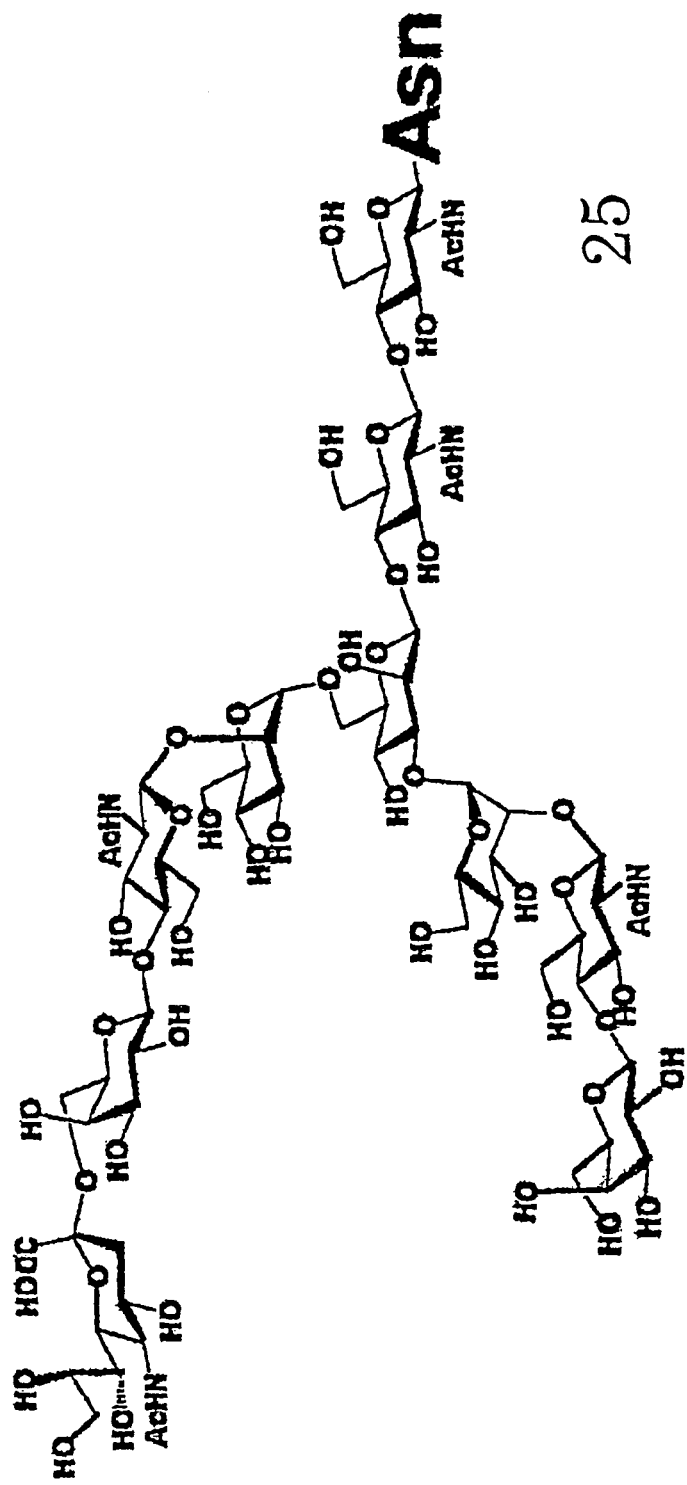
Figure 3C:
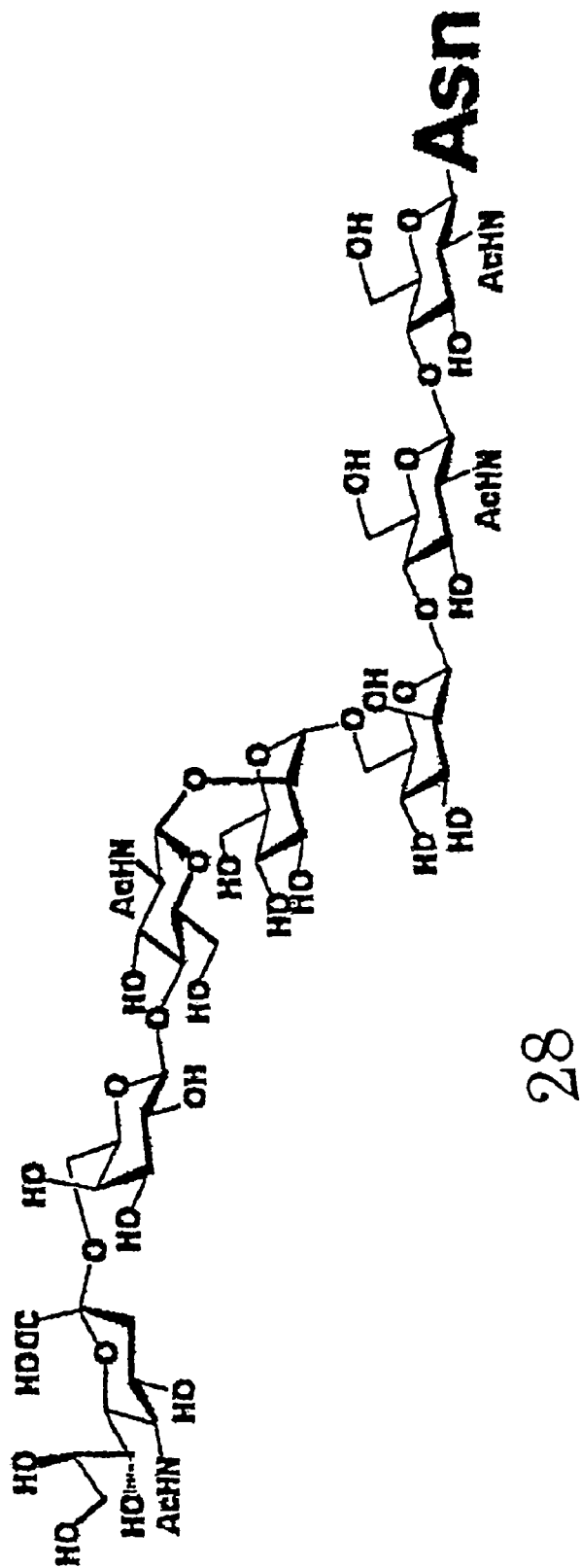
Figure 3D:
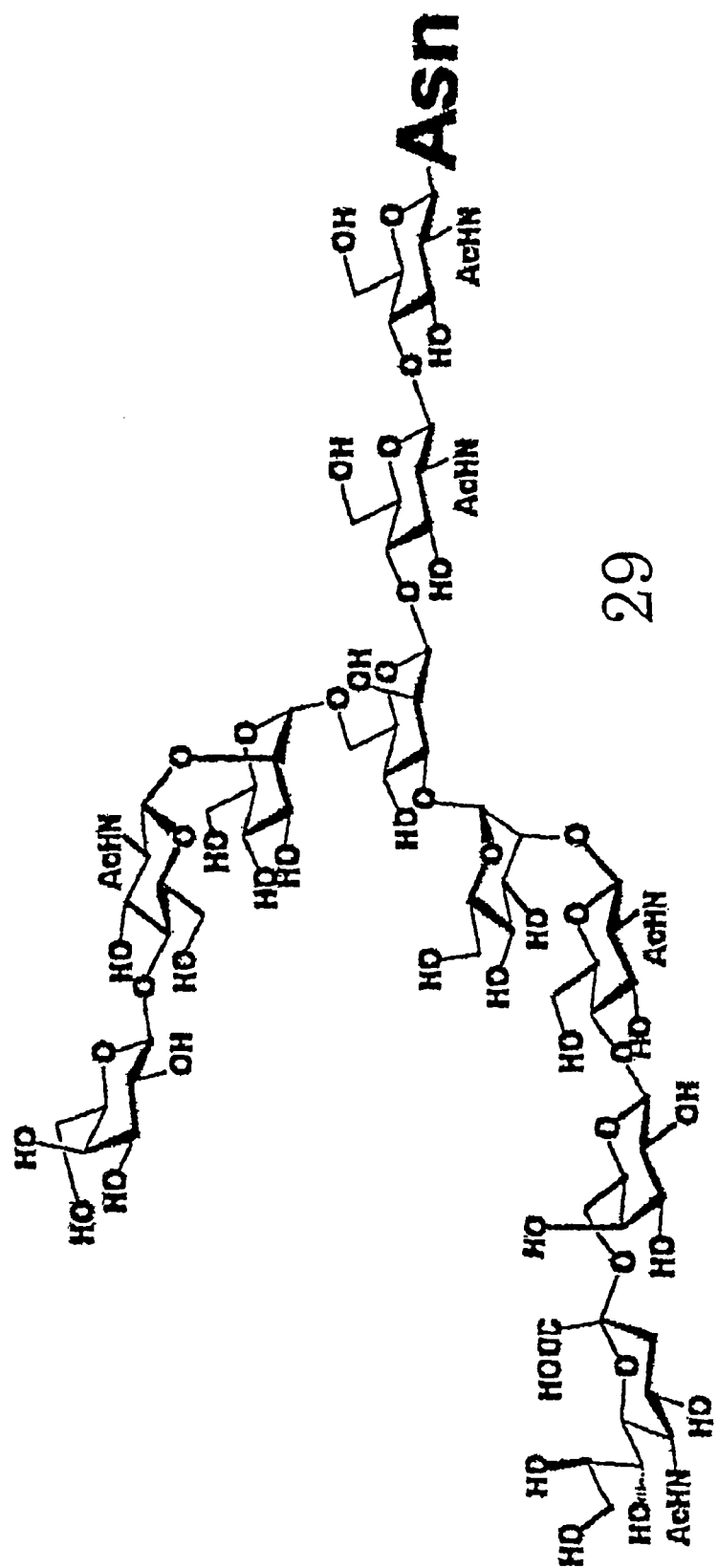
Figure 3E:
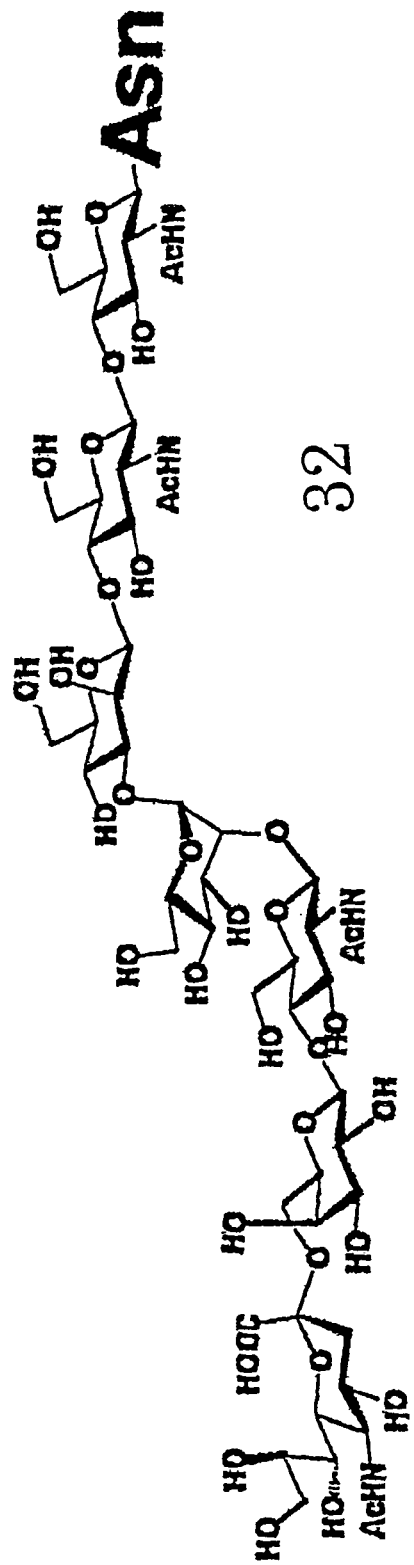
Figure 3F:
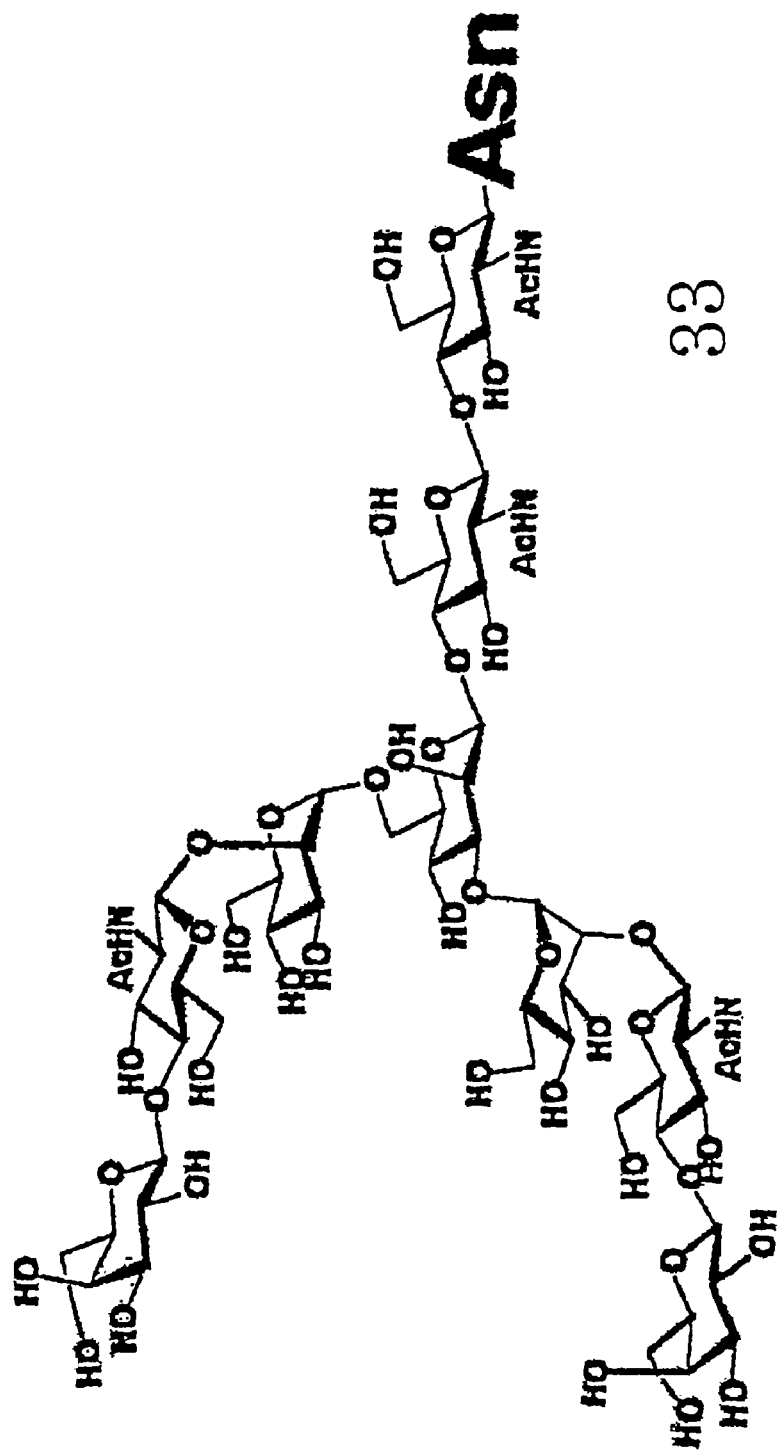
Figure 3G:
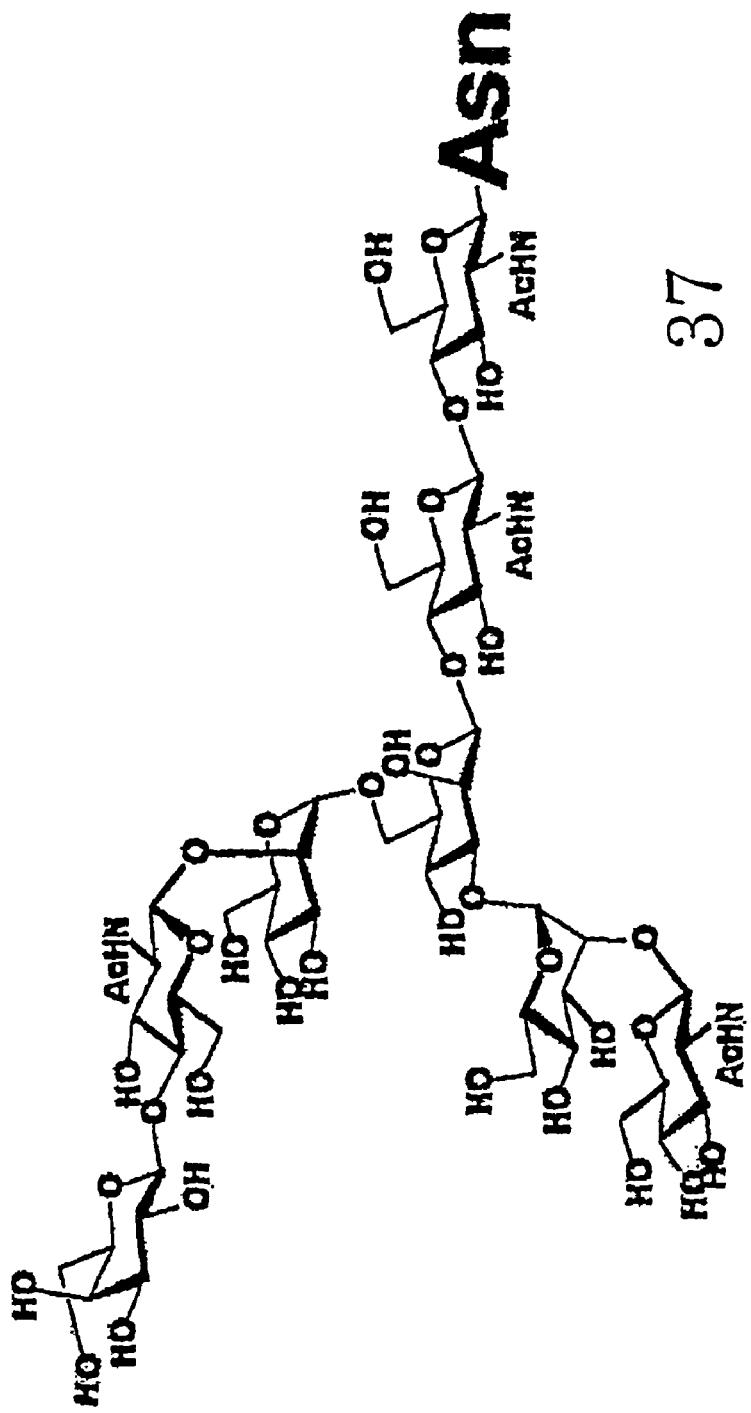
Figure 3H:
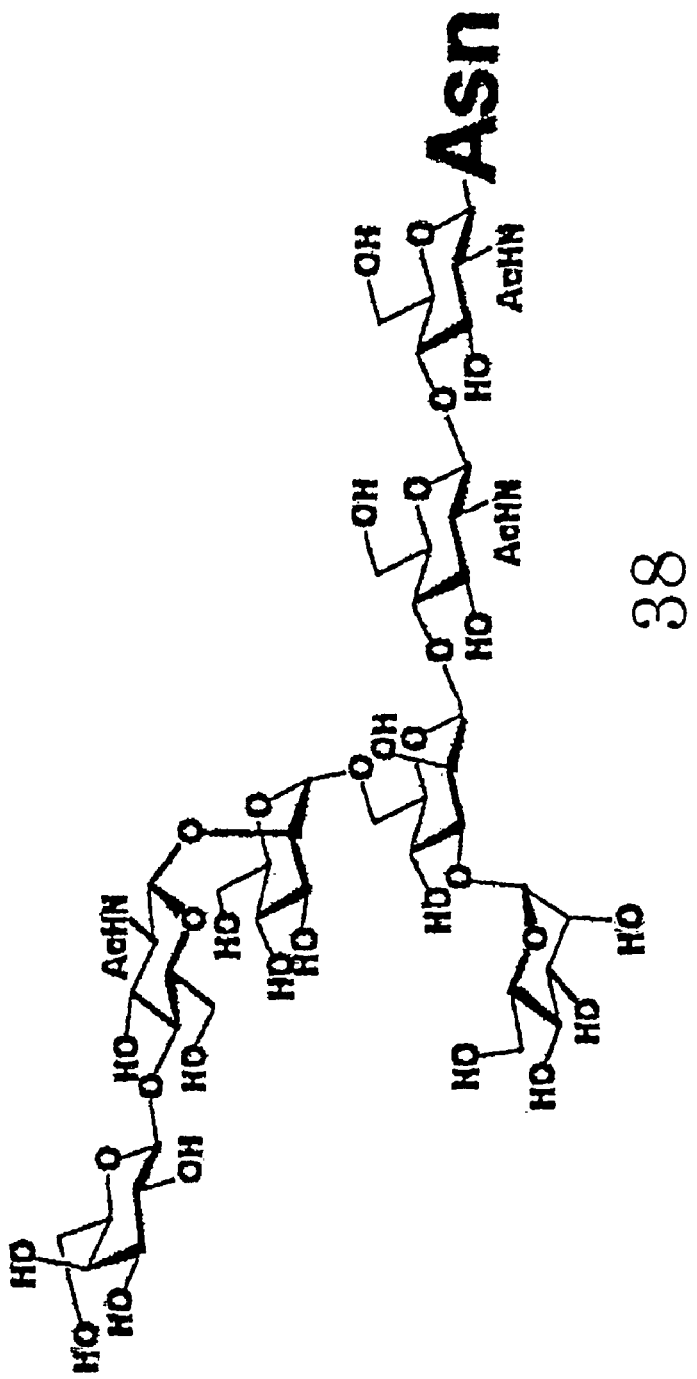
Figure 3I:
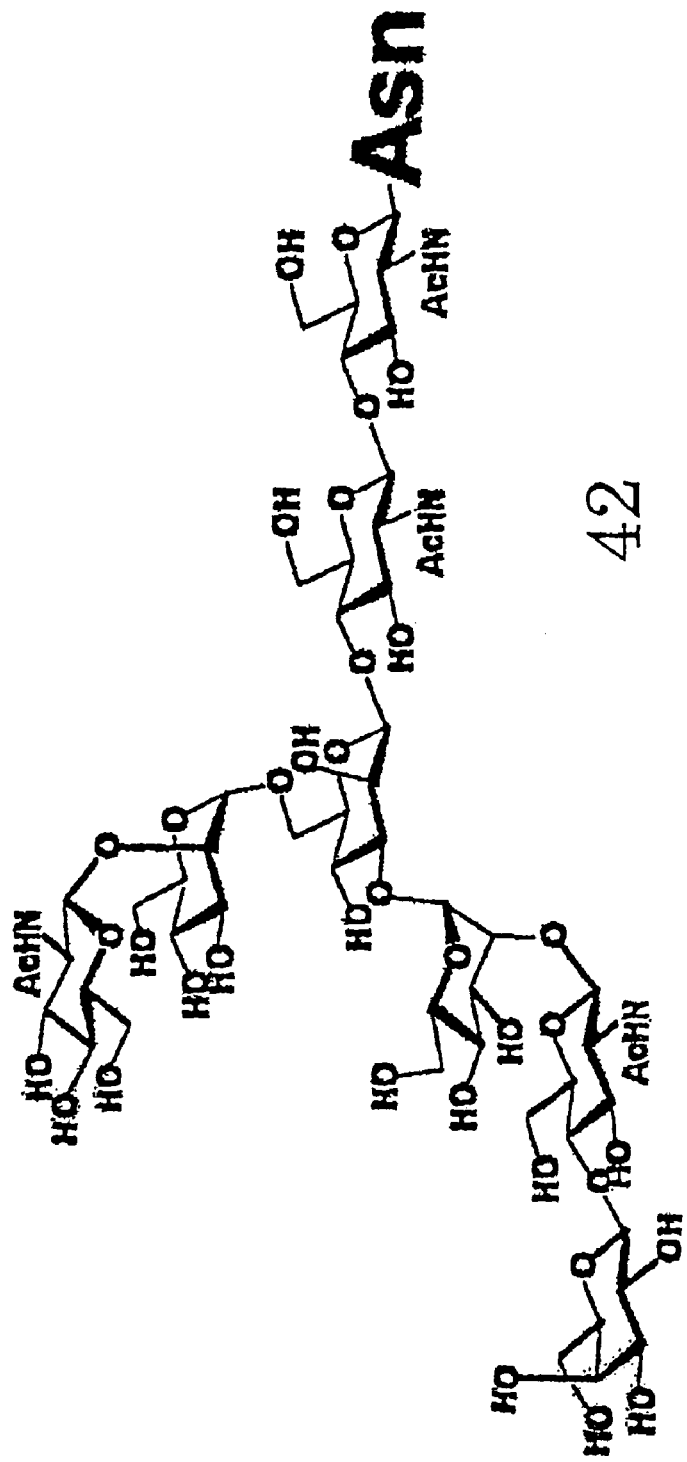
Figure 3J:
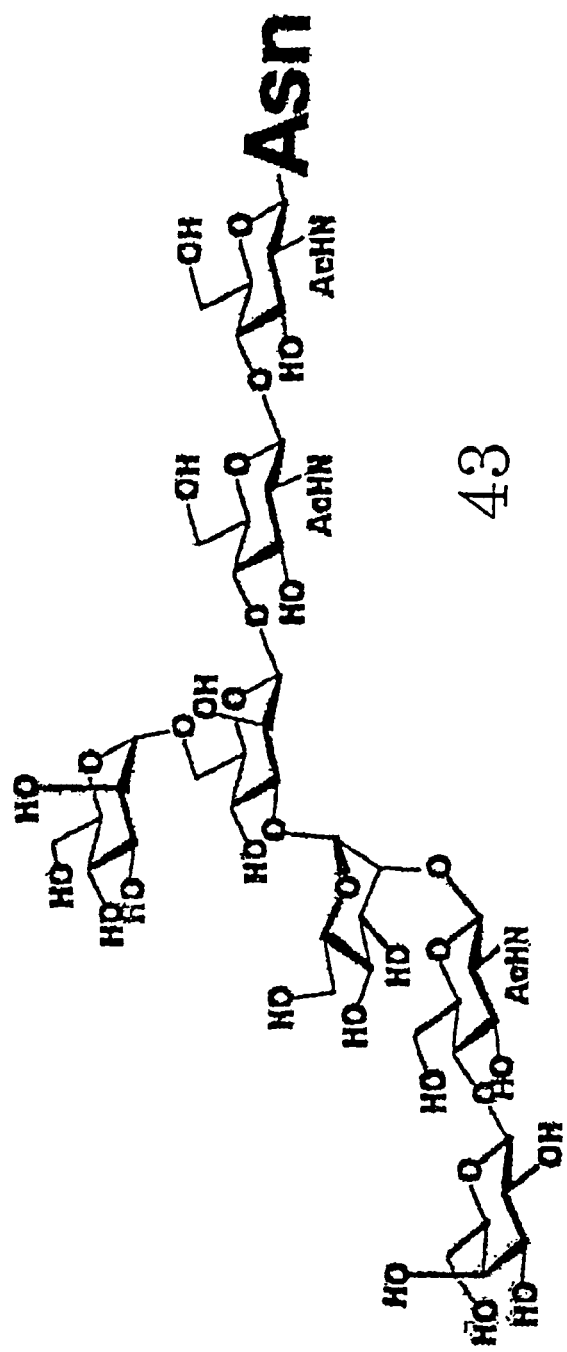
Figure 3K:
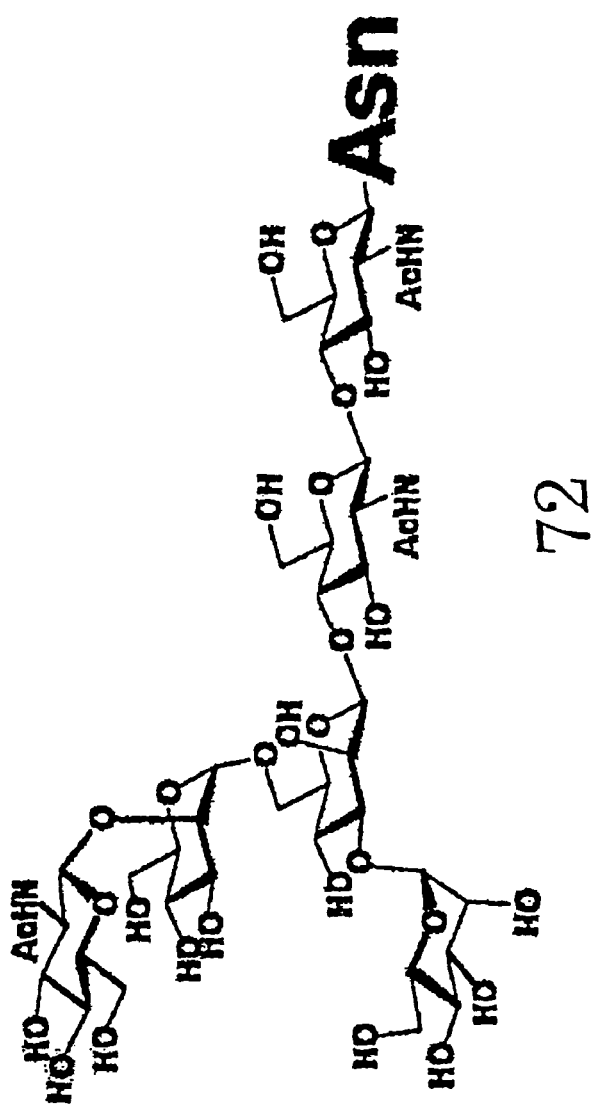
Figure 3L:
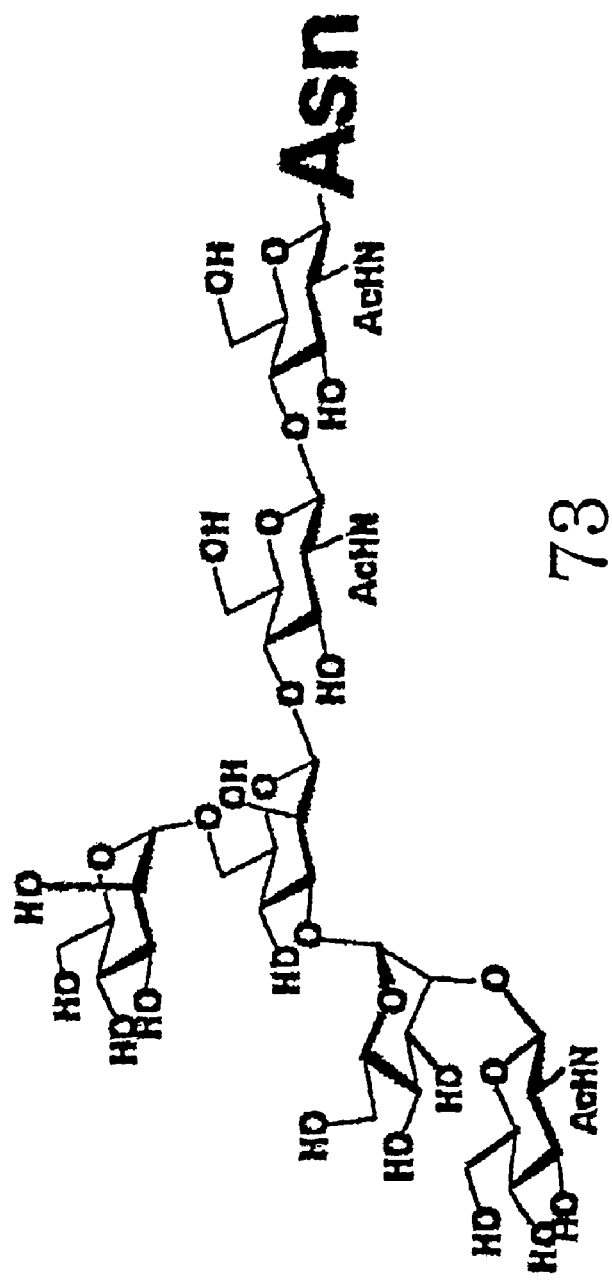
Figure 4A:
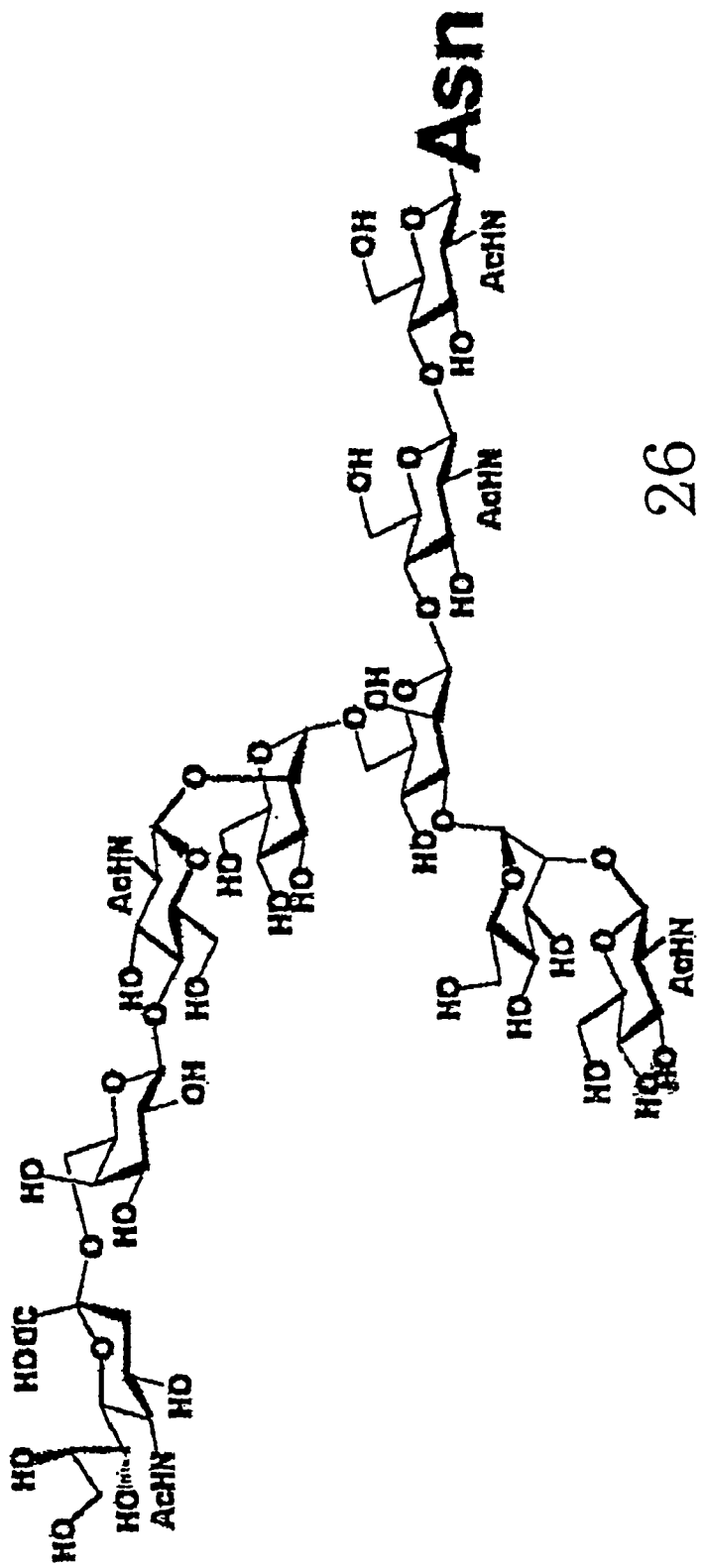
FIG. 4 shows a group of structures of sugar chain asparagines obtainable according to the present invention.
Figure 4B:
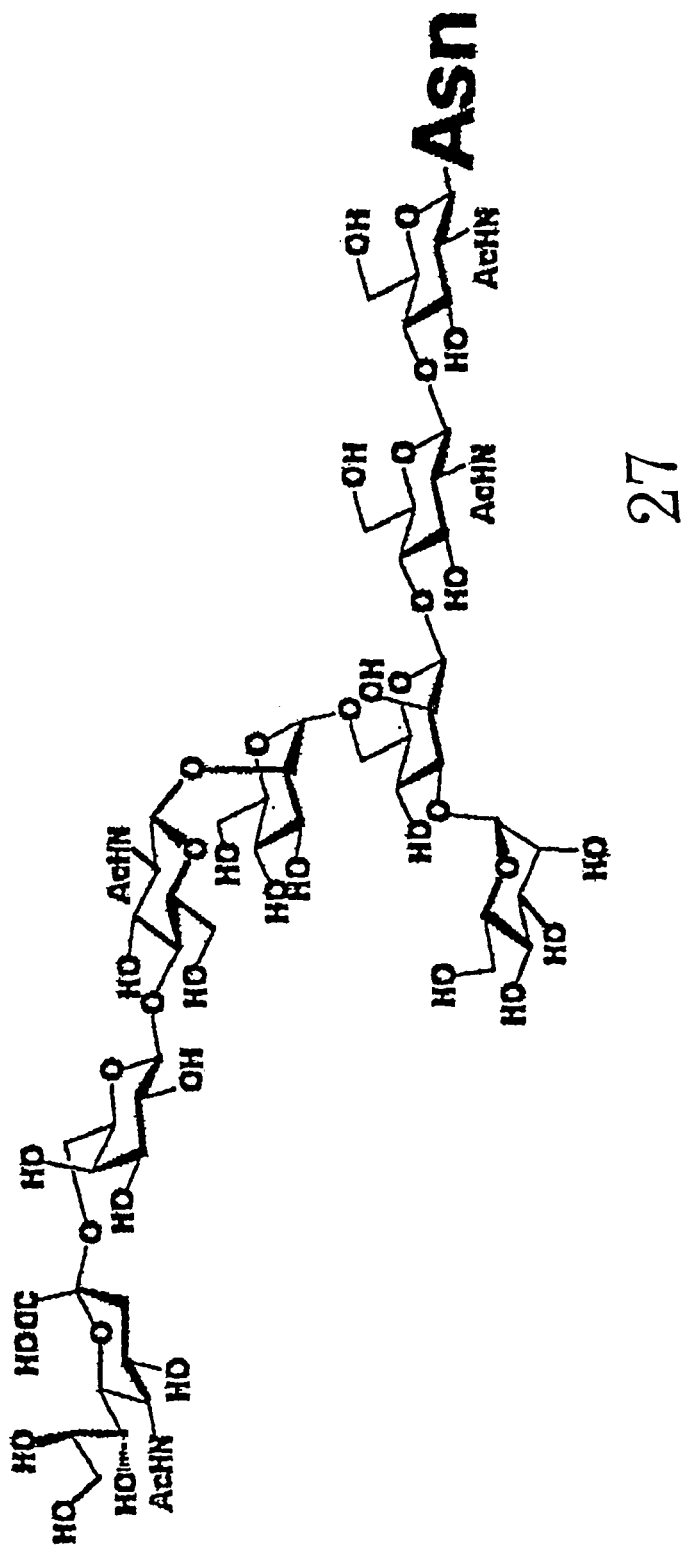
Figure 4C:
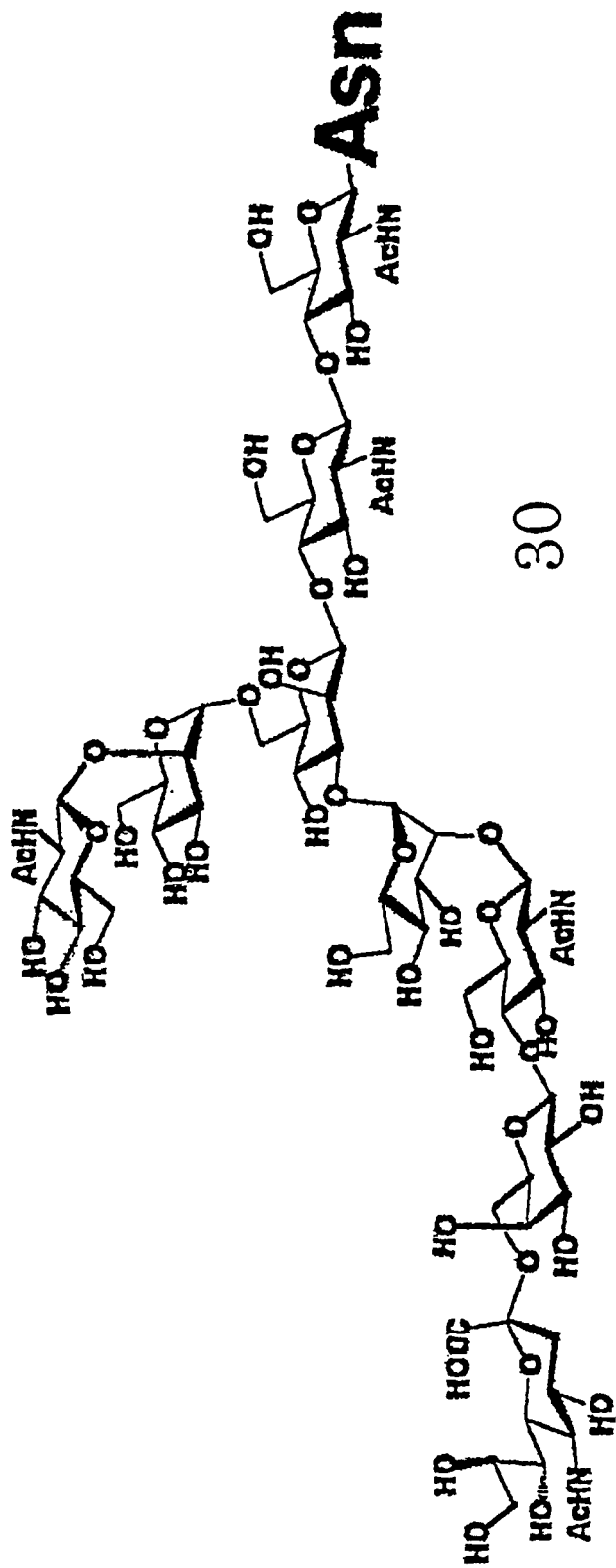
Figure 4D:
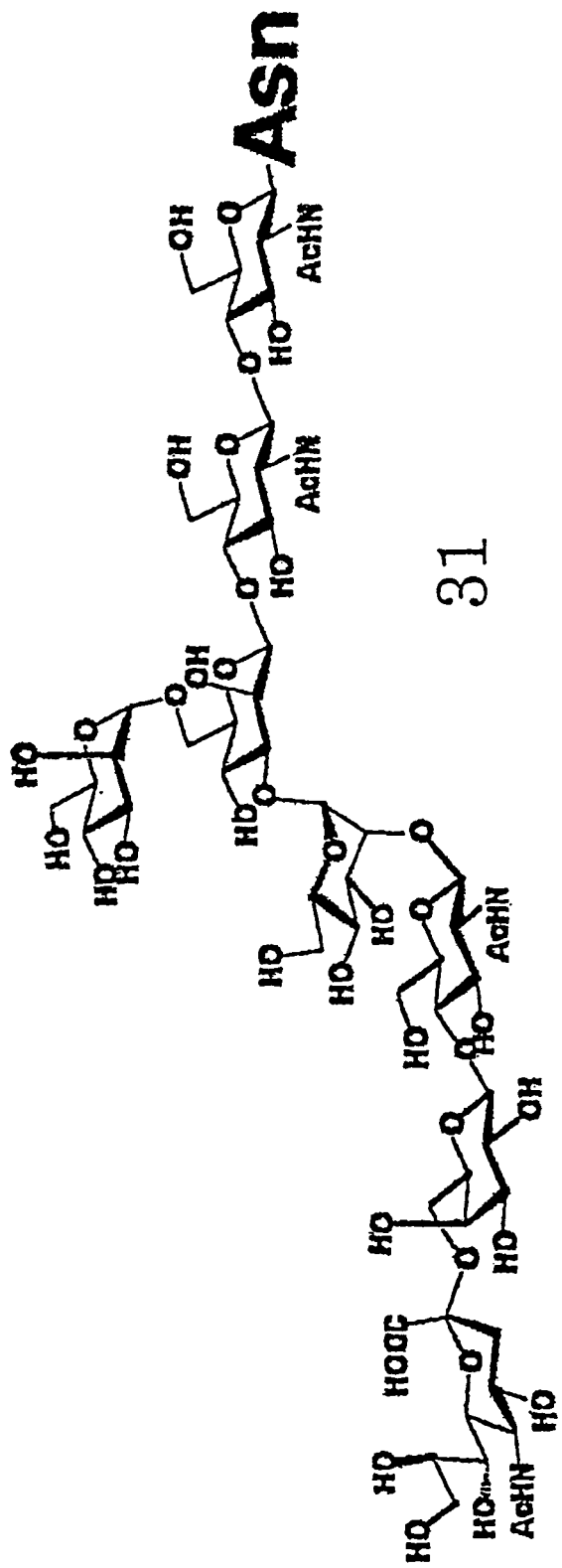
Figure 4E:
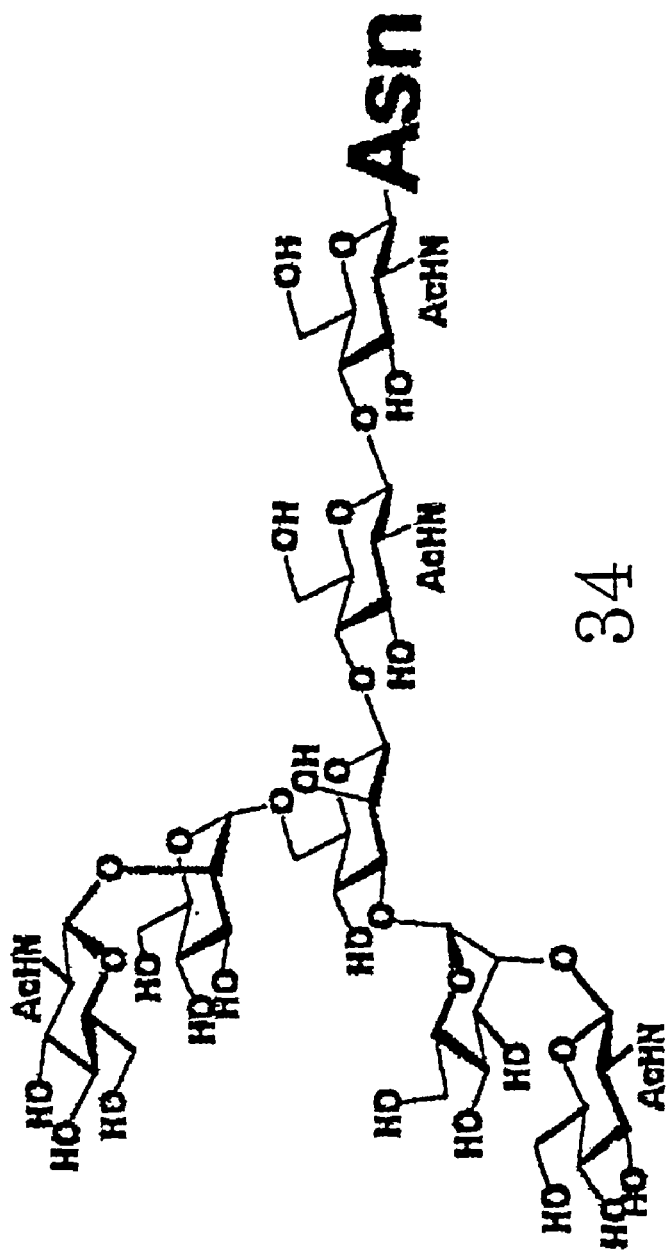
Figure 4F:
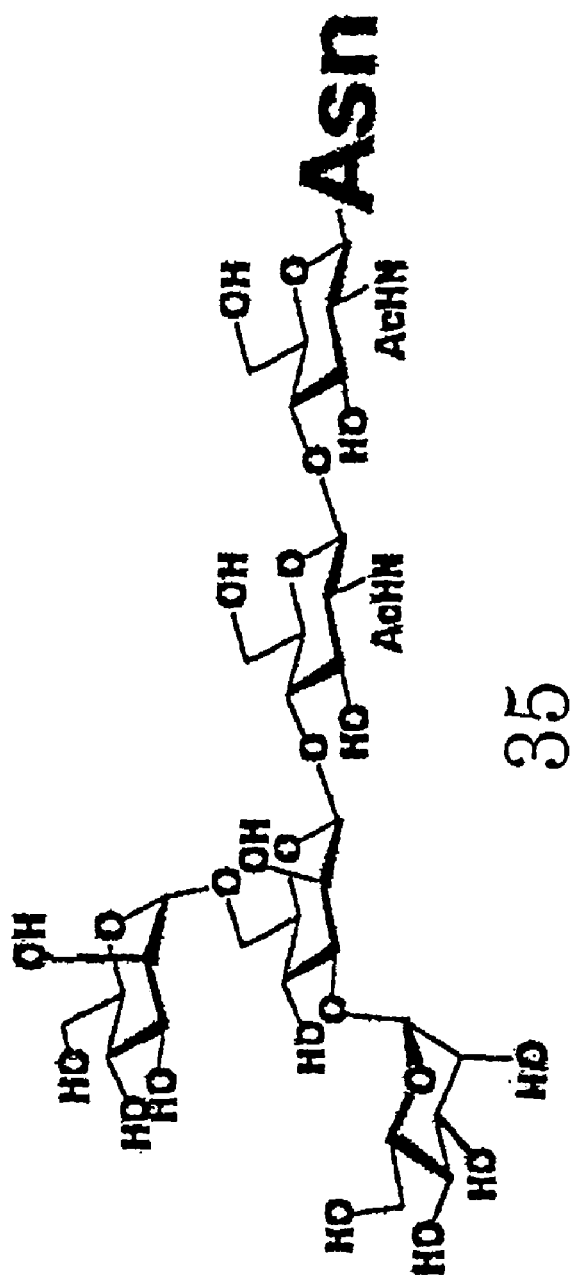
Figure 4G:
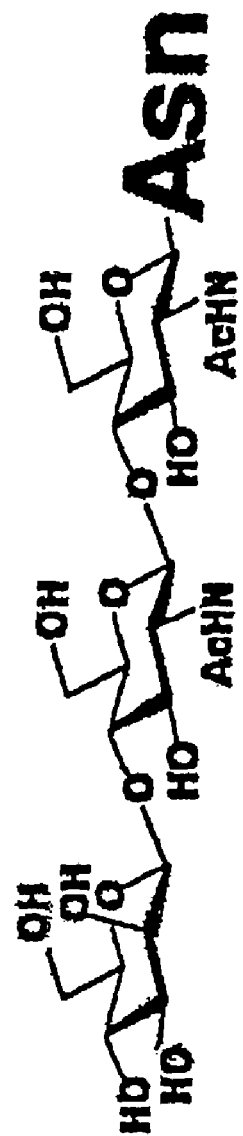
Figure 4H:
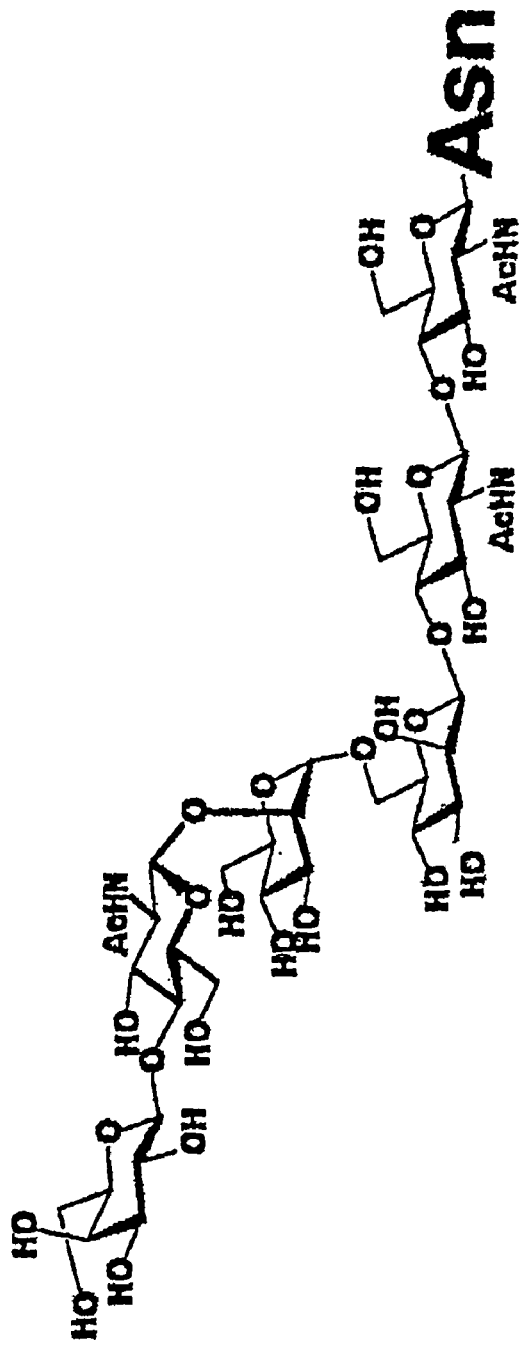
Figure 4I:
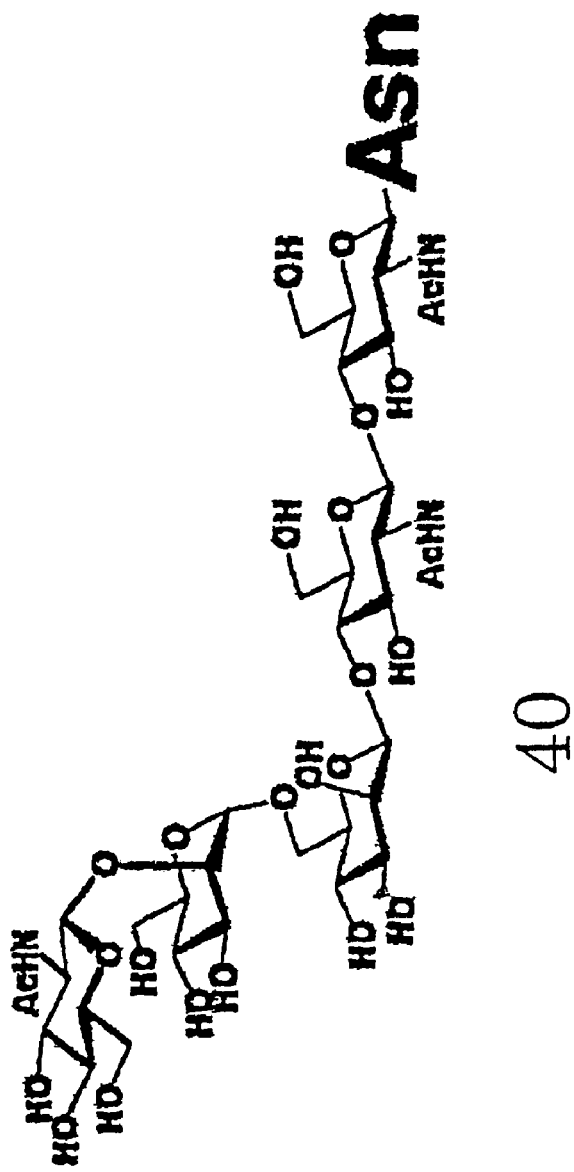
Figure 4J:
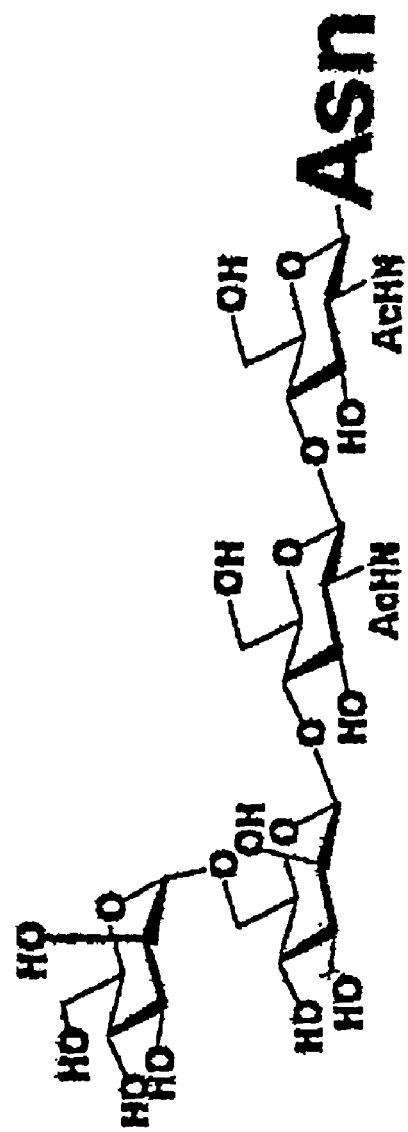
Figure 4K:
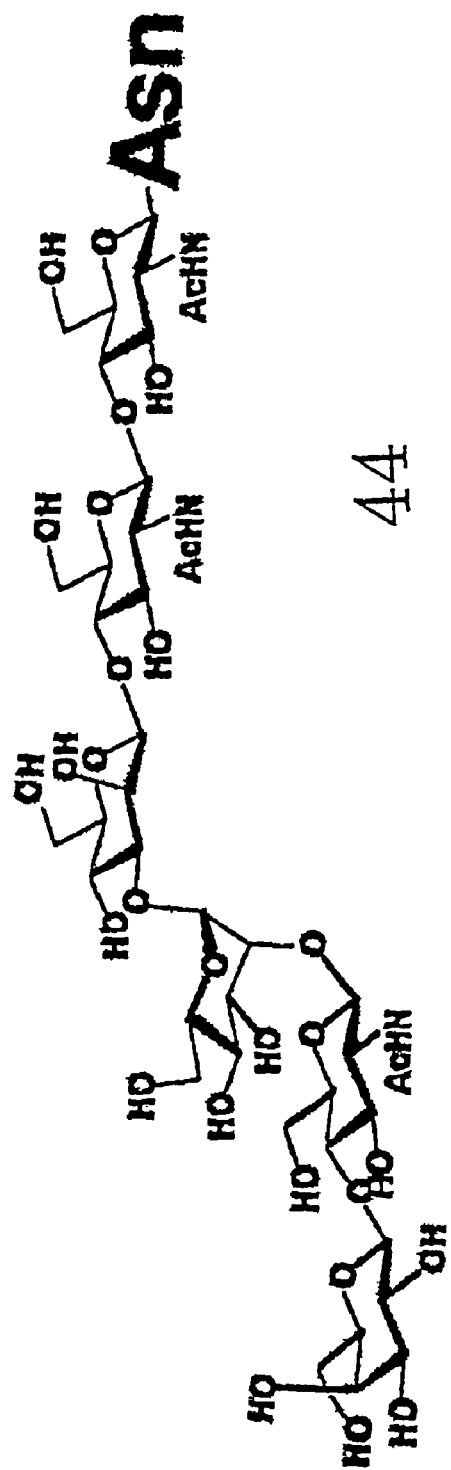
Figure 4L:
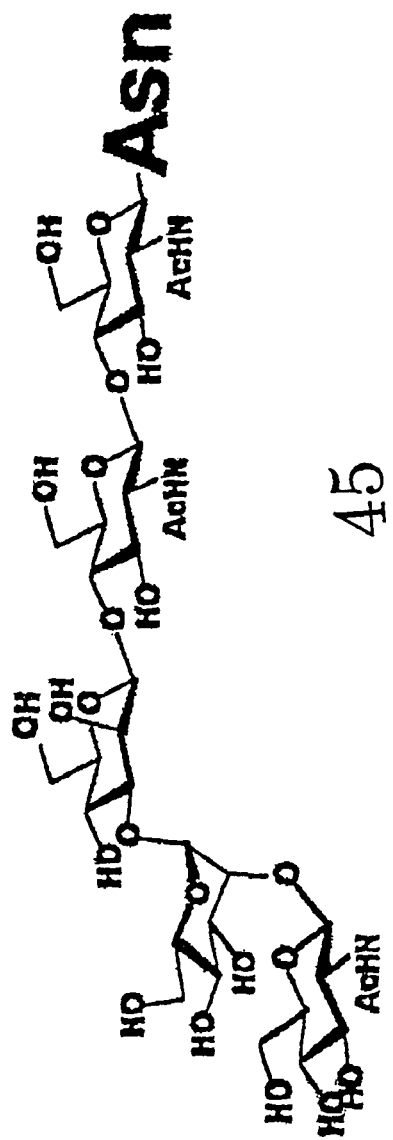
Figure 4M:
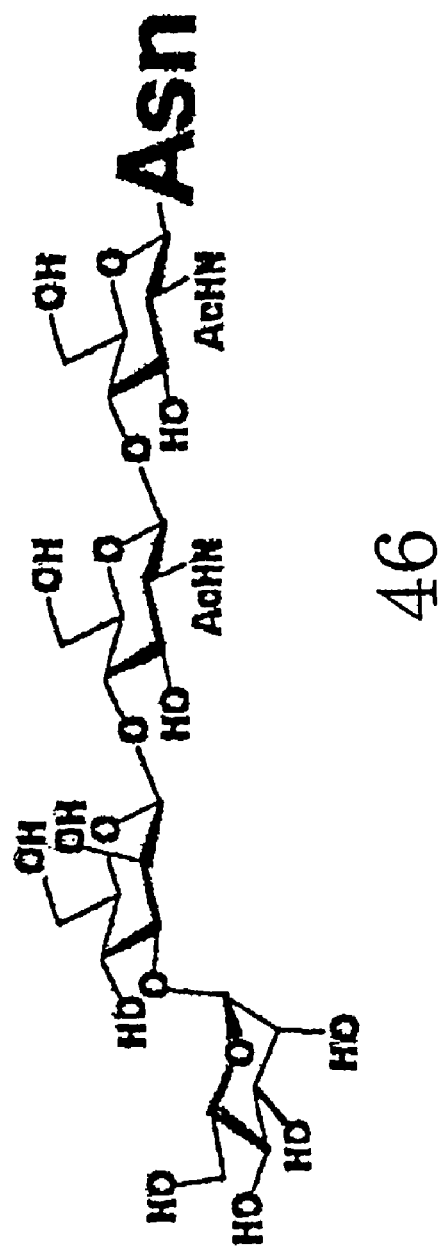
Figure 5A:
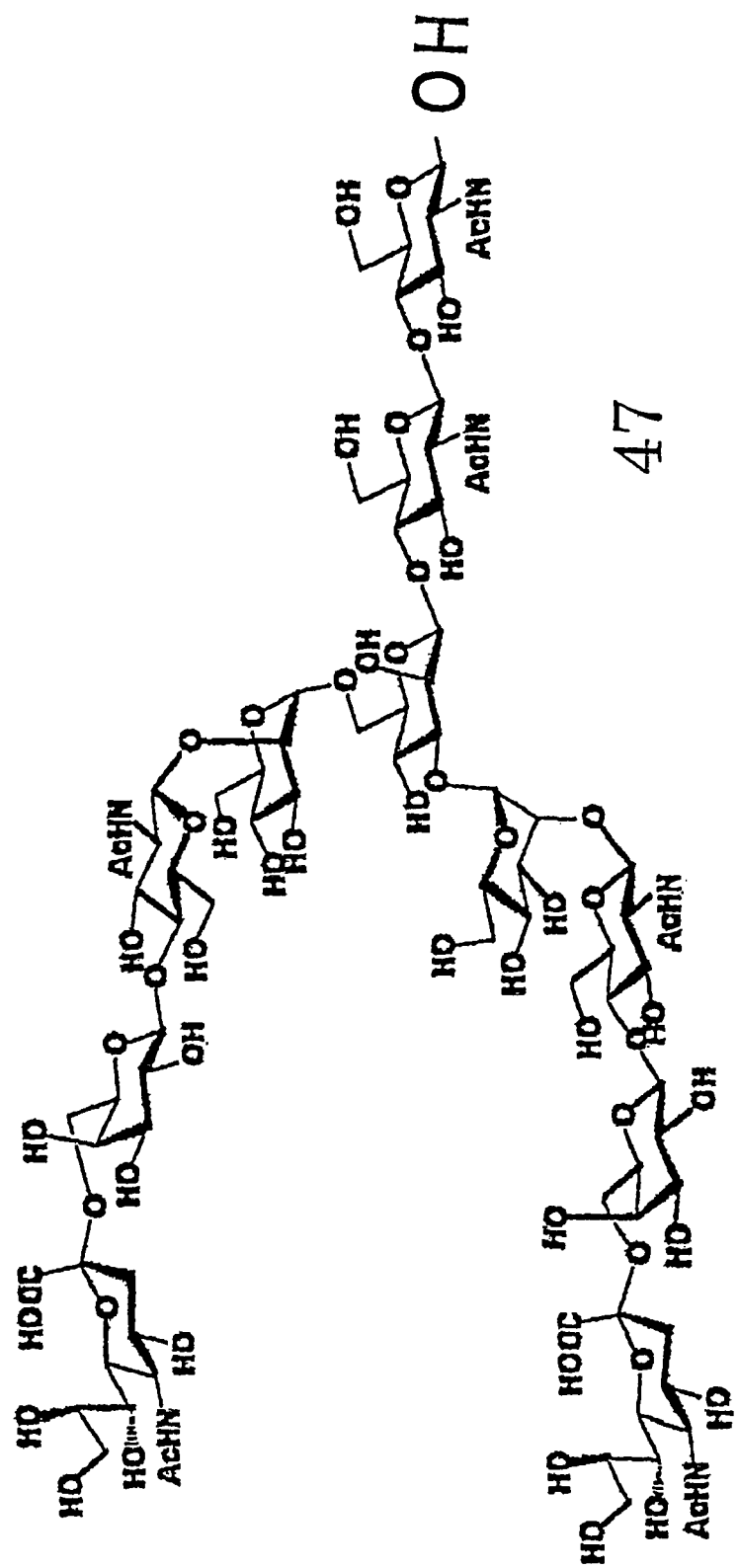
FIG. 5 shows a group of structures of sugar chains obtainable according to the present invention.
Figure 5B:
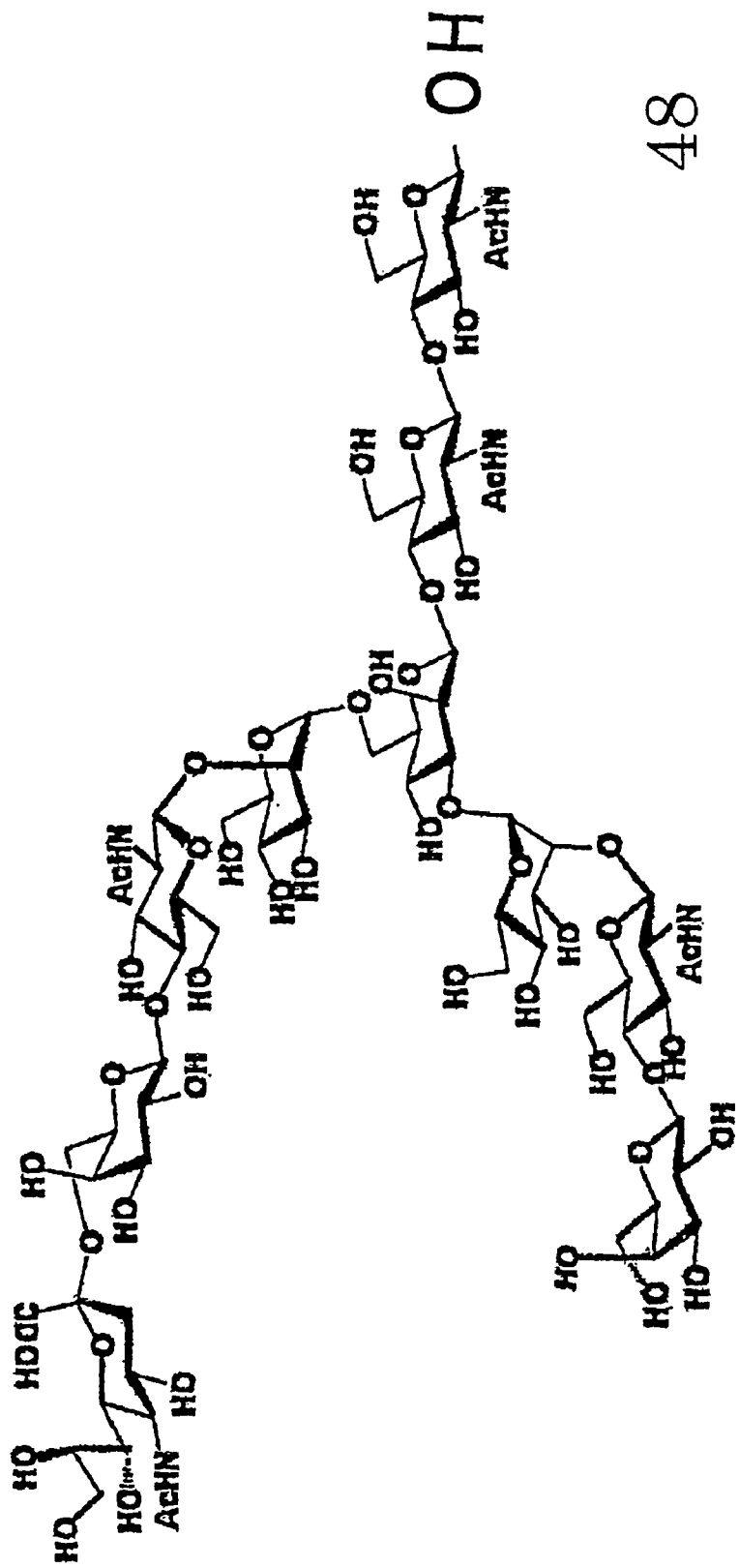
Figure 5C:
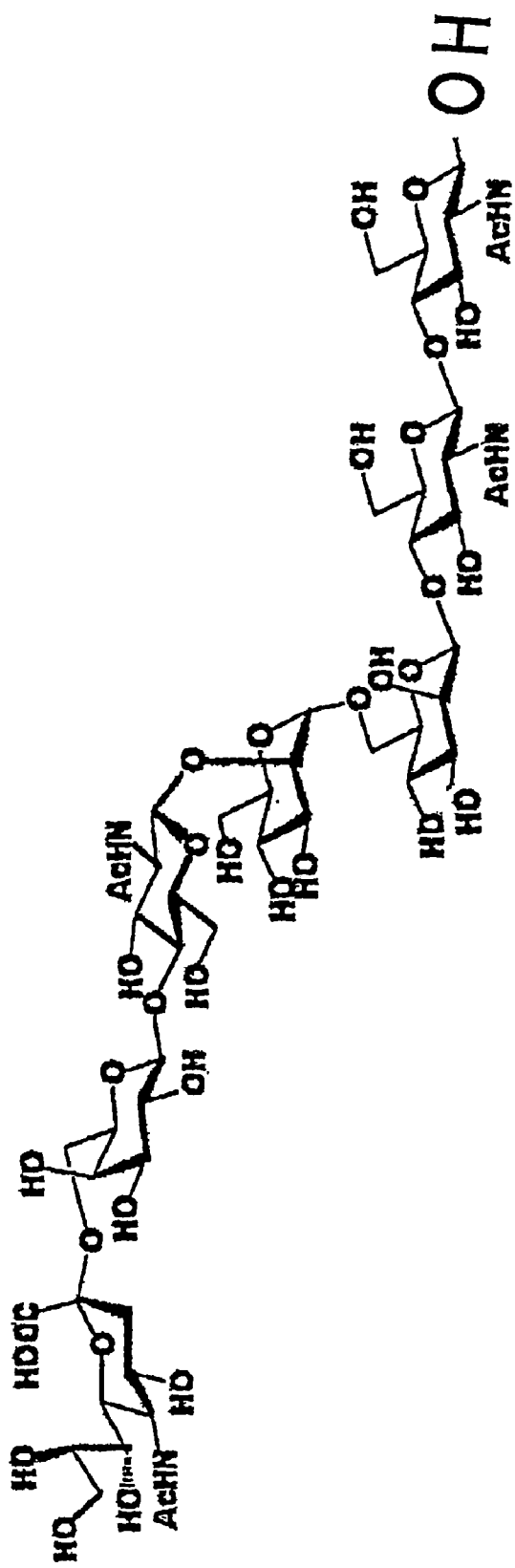
Figure 5D:
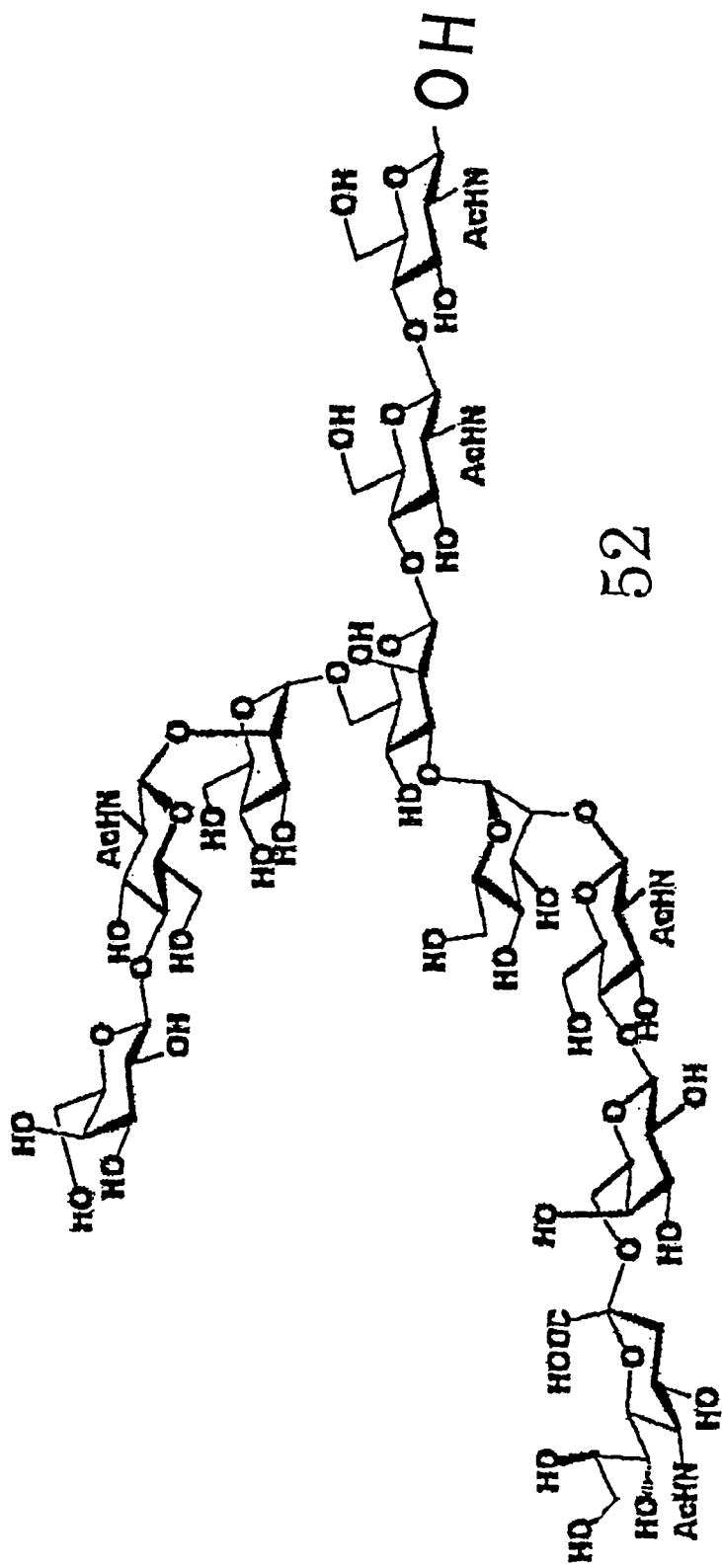
Figure 5E:
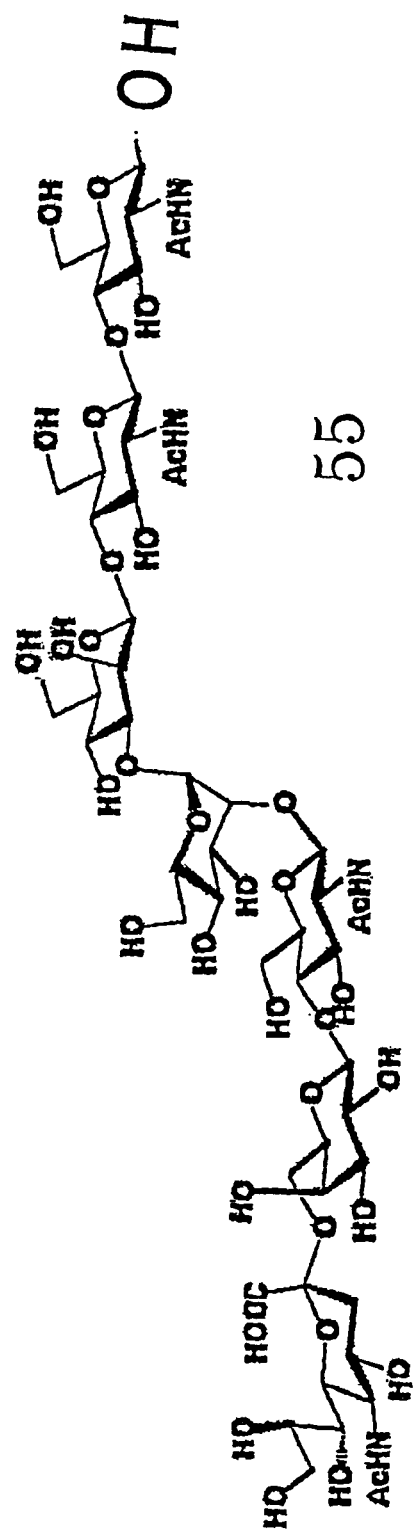
Figure 5F:
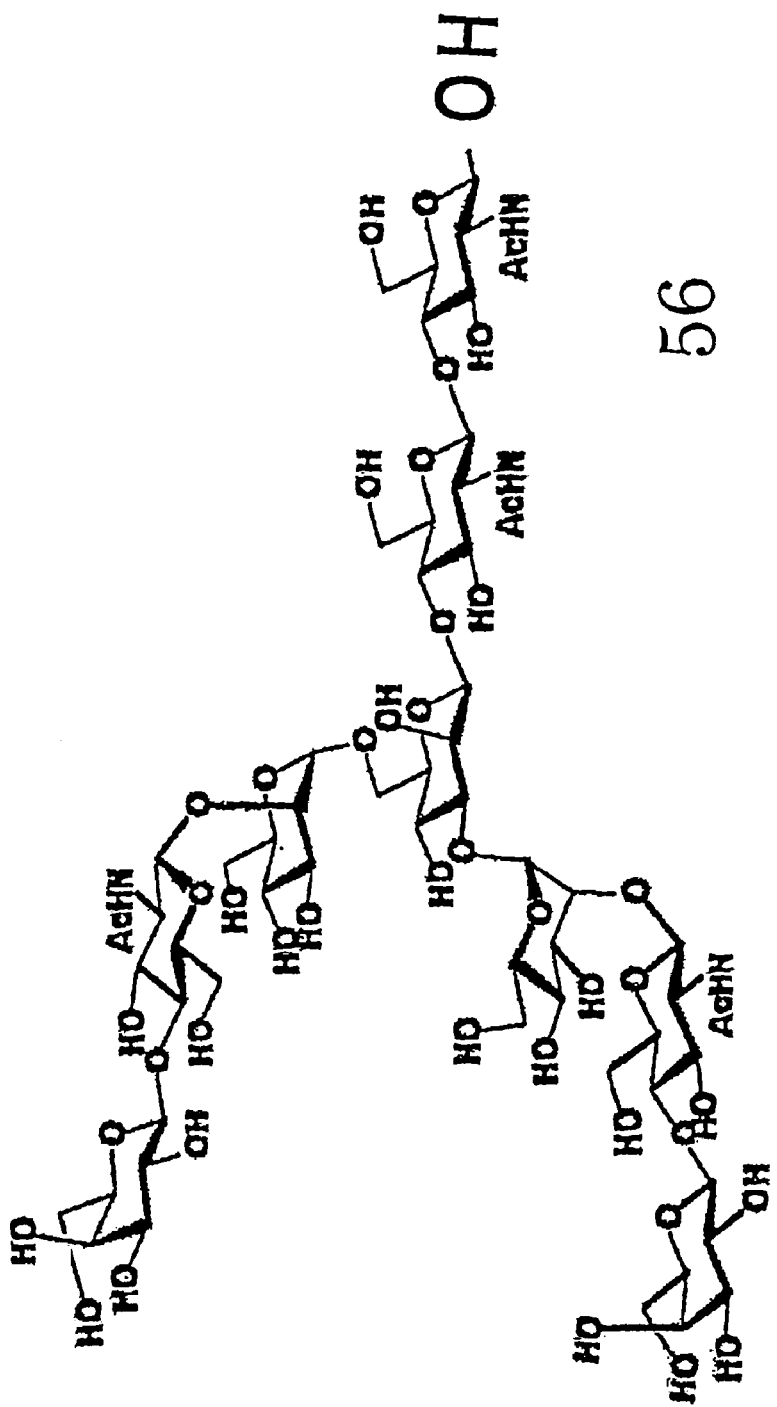
Figure 5G:
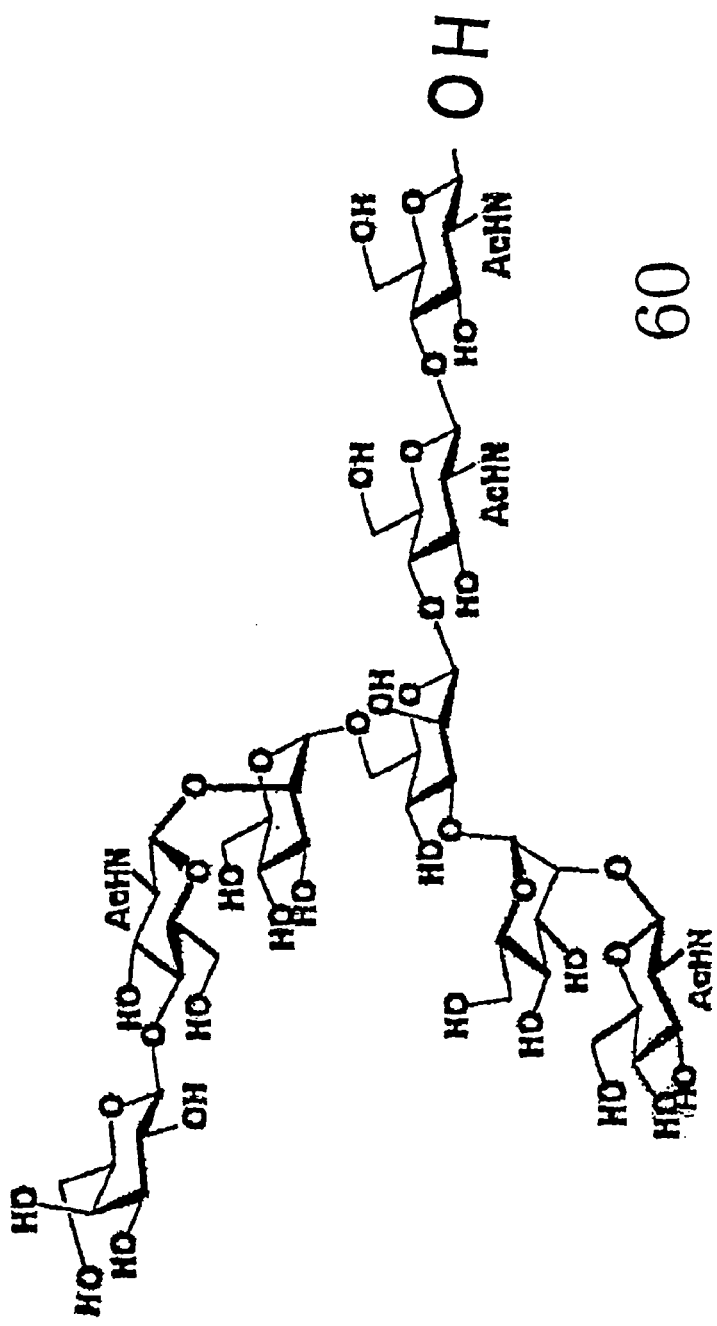
Figure 5H:
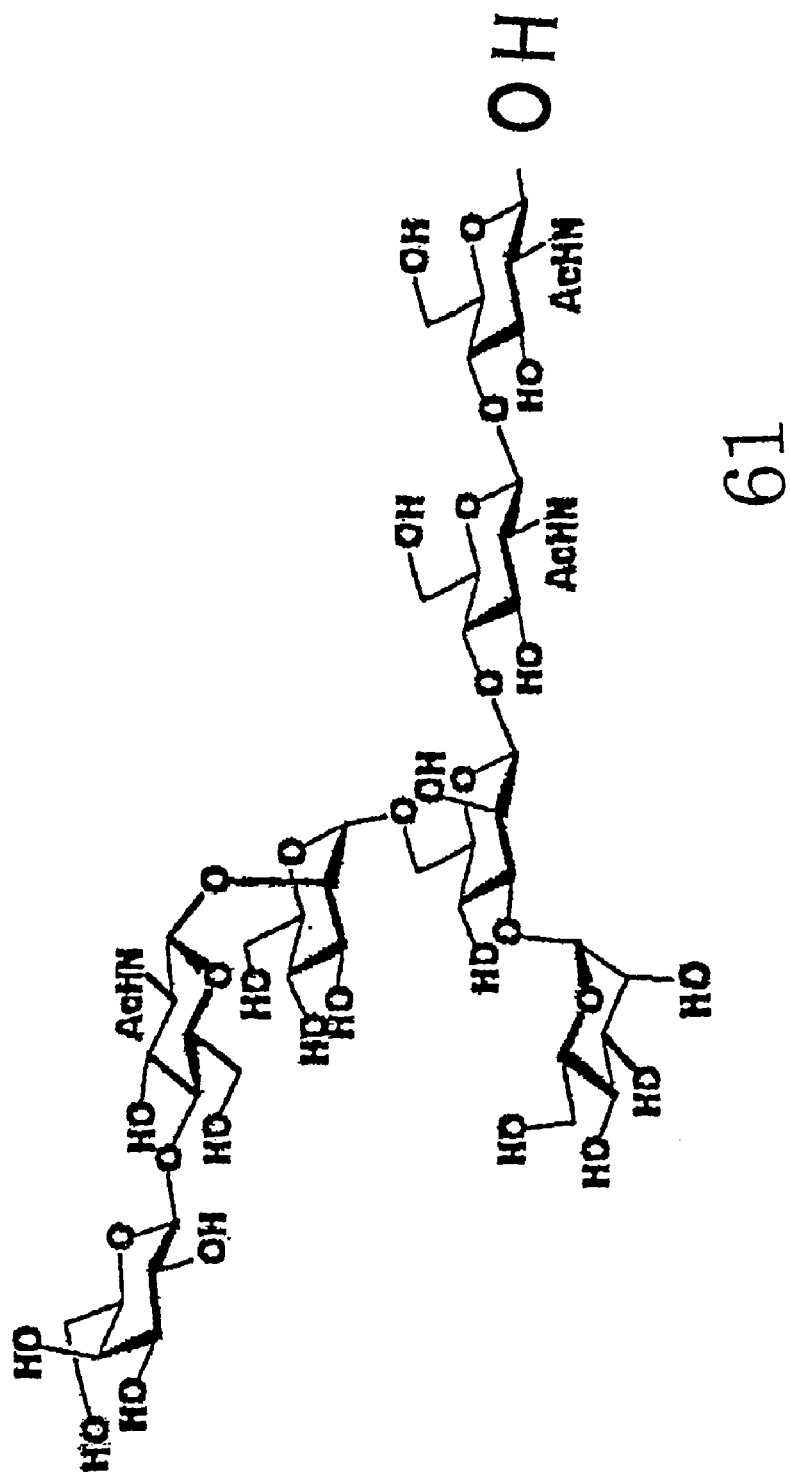
Figure 5I:
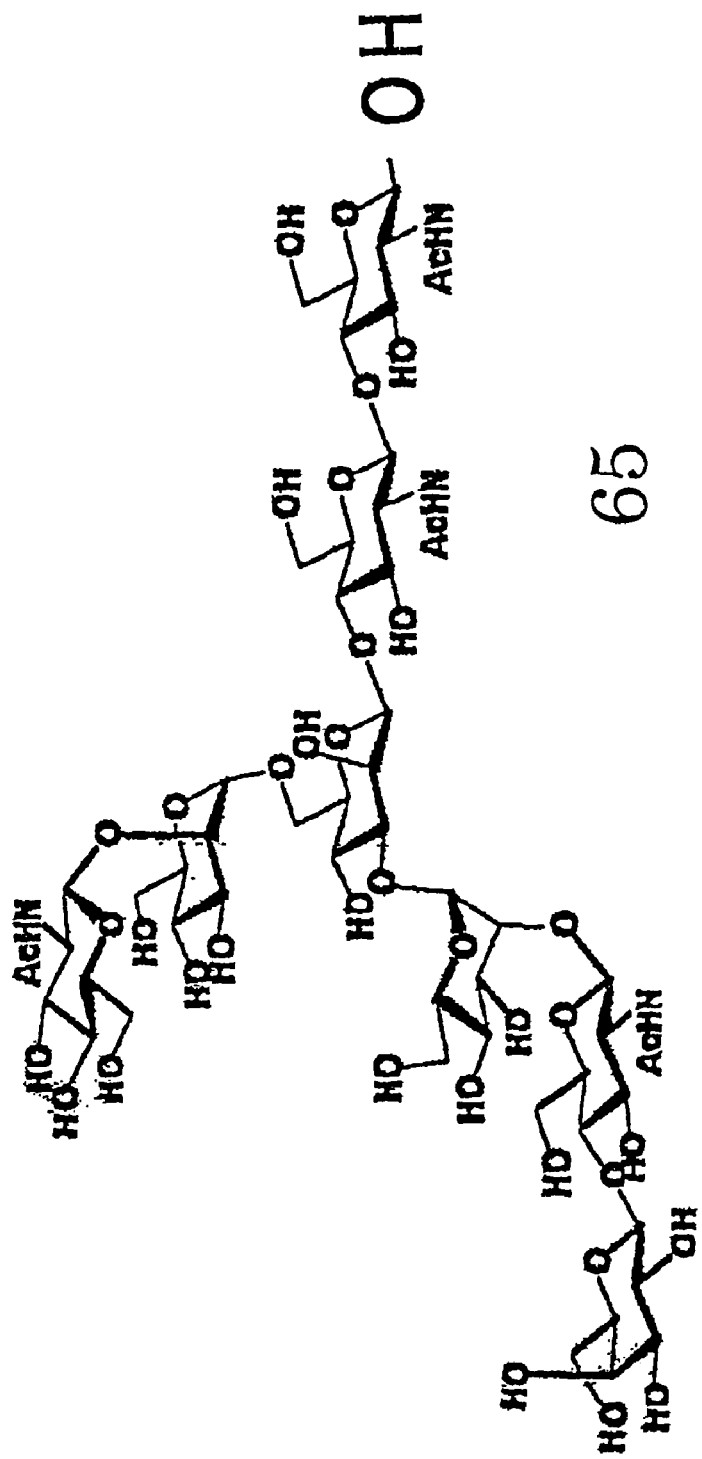
Figure 5J:
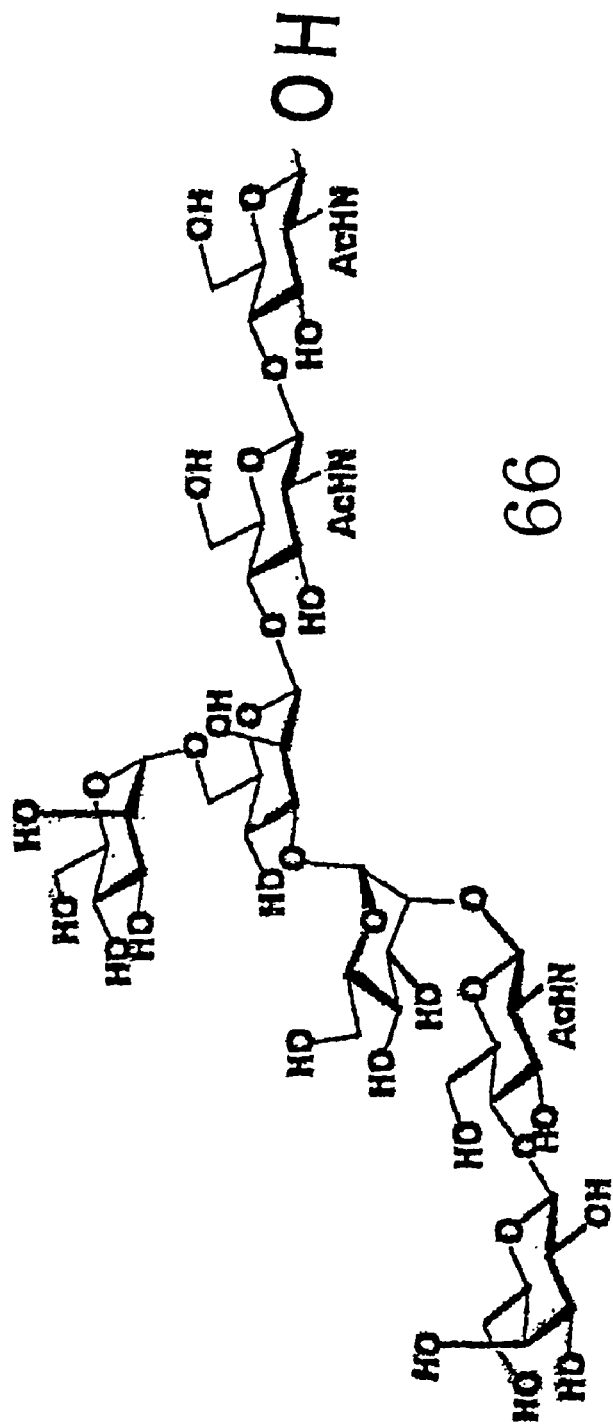
Figure 5K:
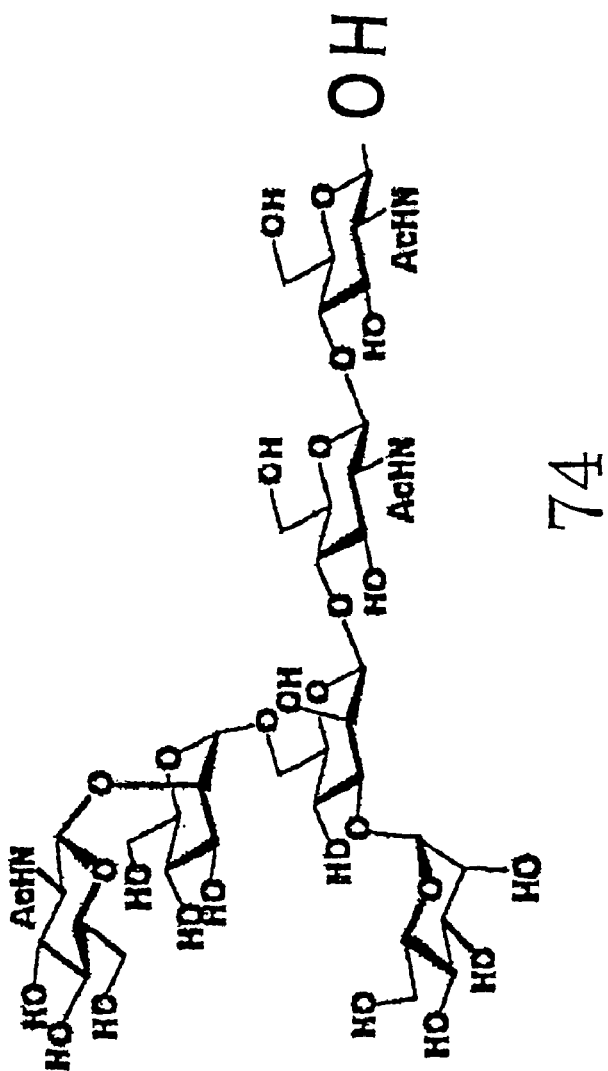
Figure 5L:
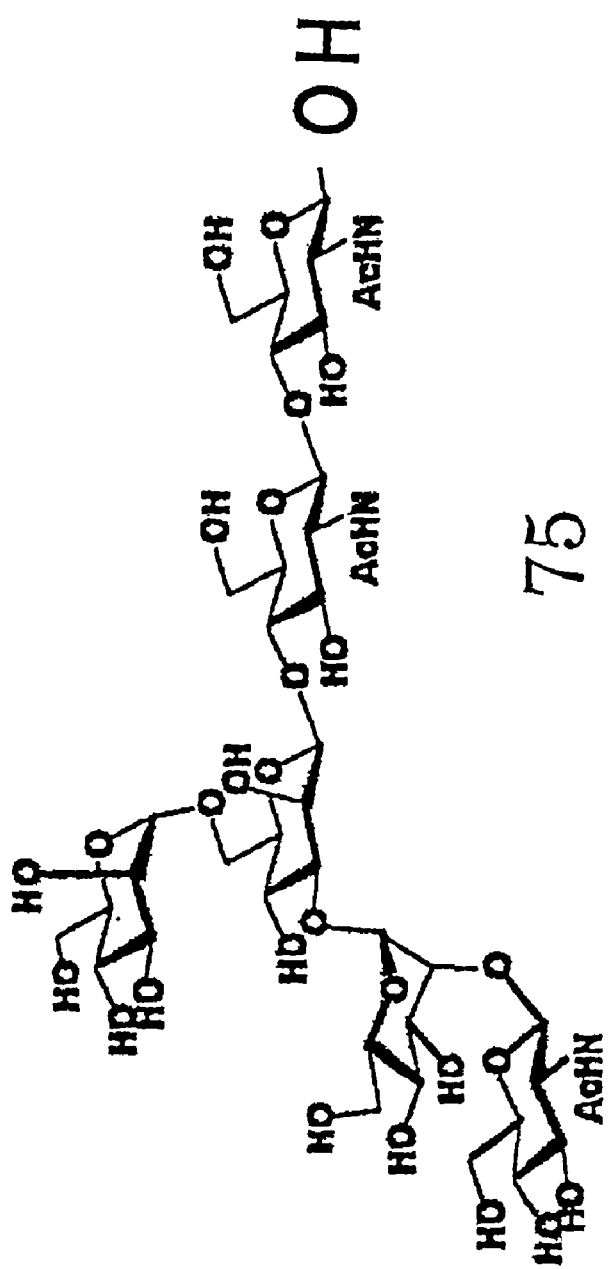
Figure 6A:
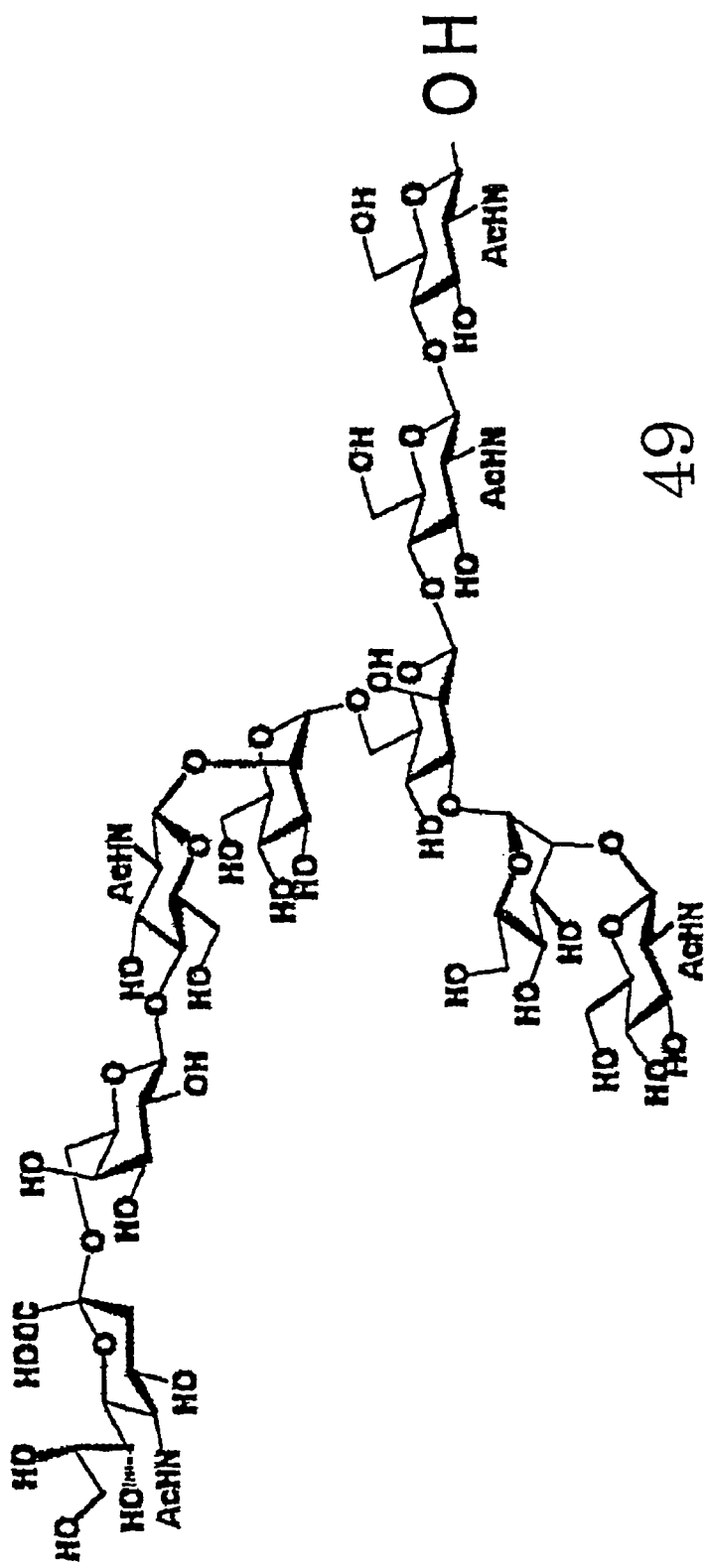
FIG. 6 shows a group of structures of sugar chains obtainable according to the present invention.
Figure 6B:
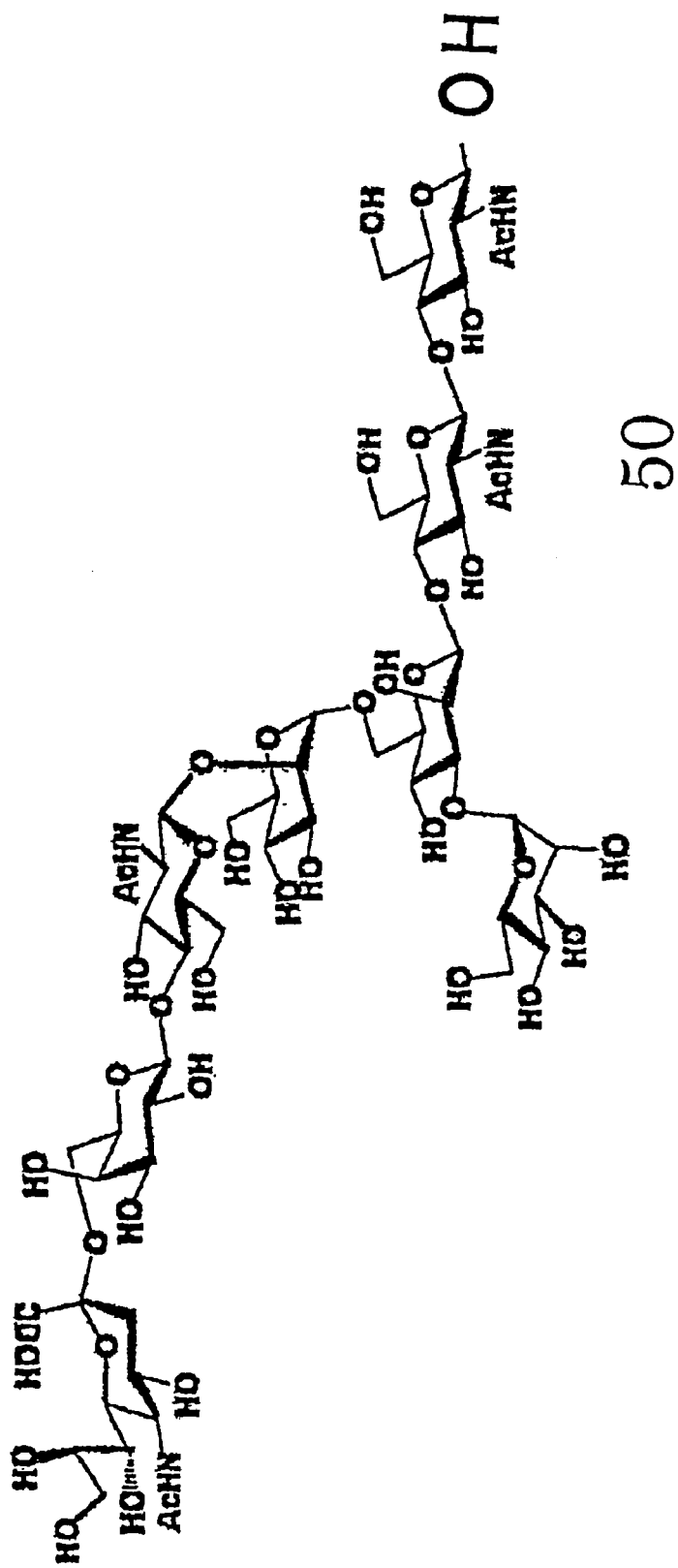
Figure 6C:
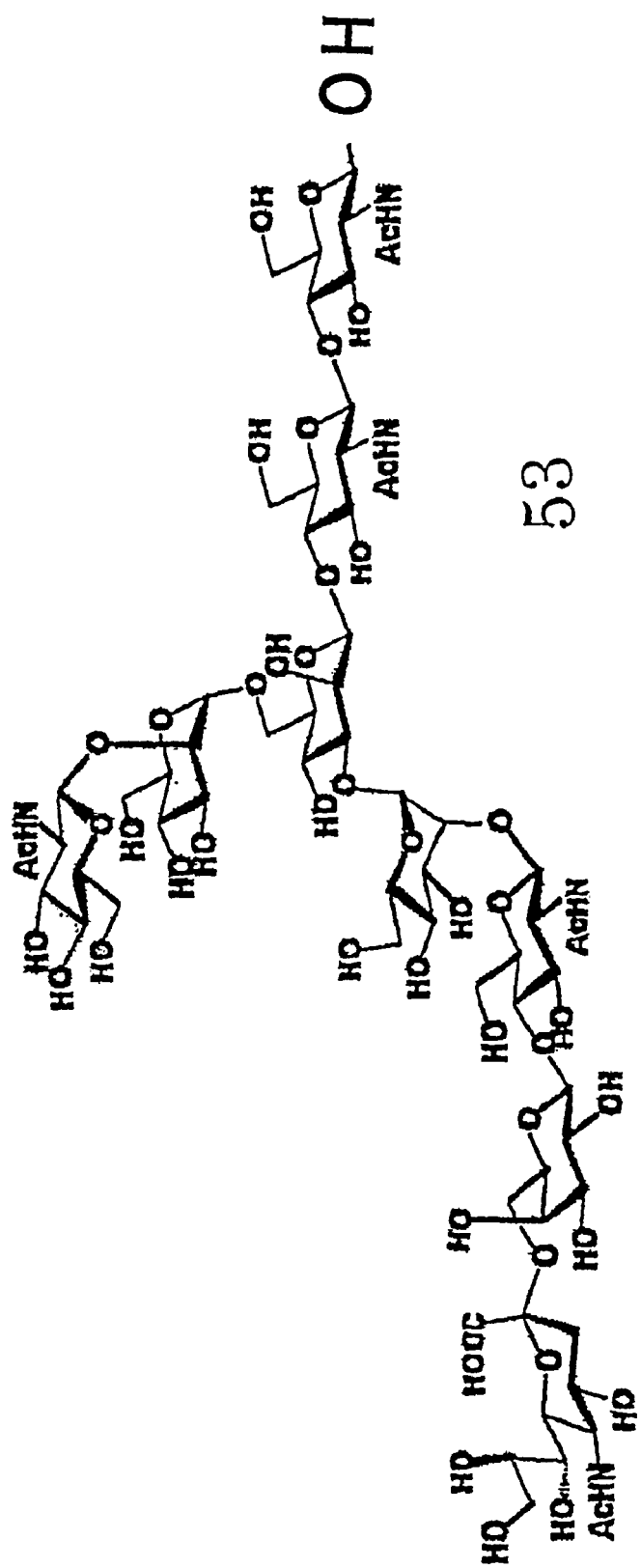
Figure 6D:
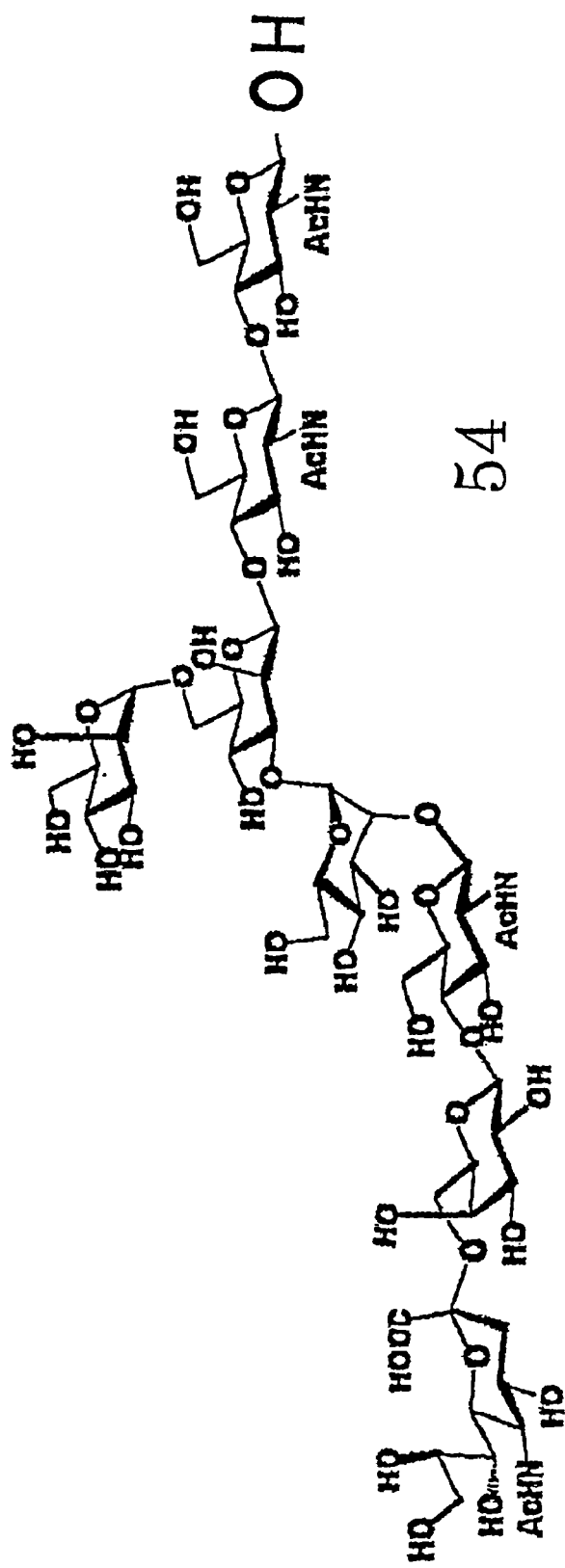
Figure 6E:
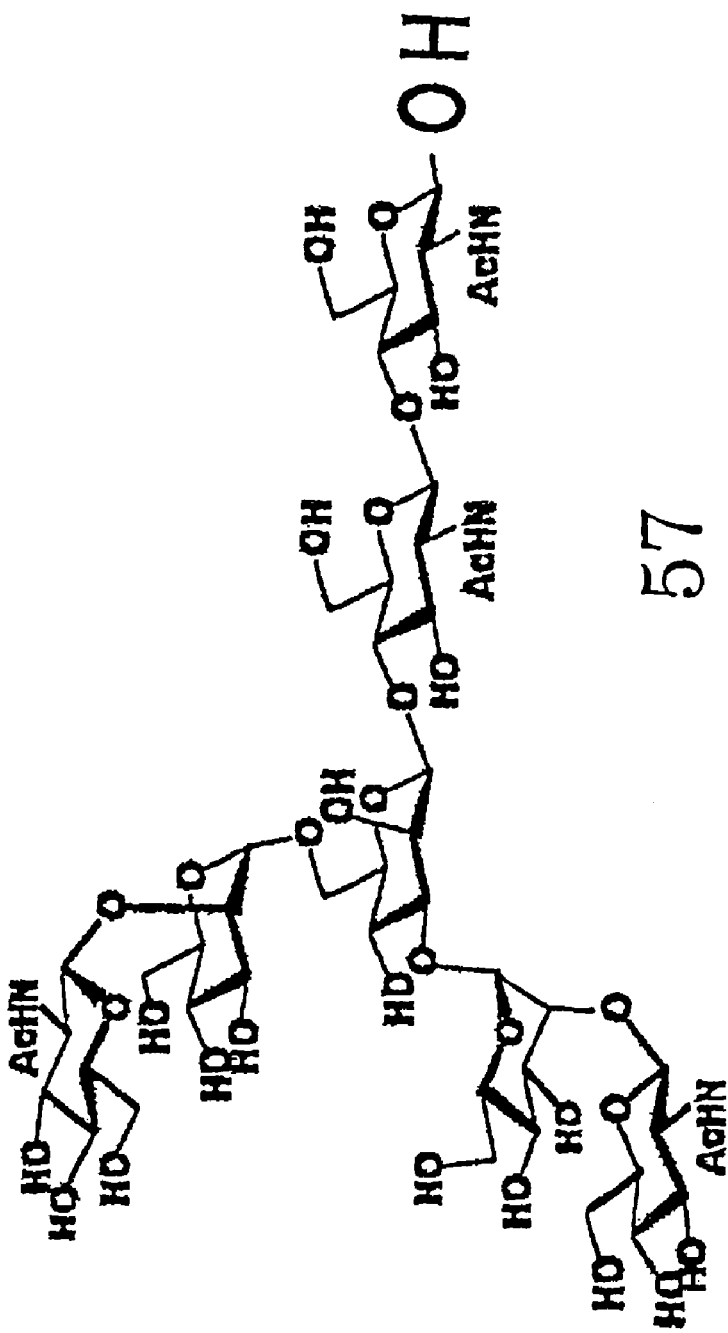
Figure 6F:
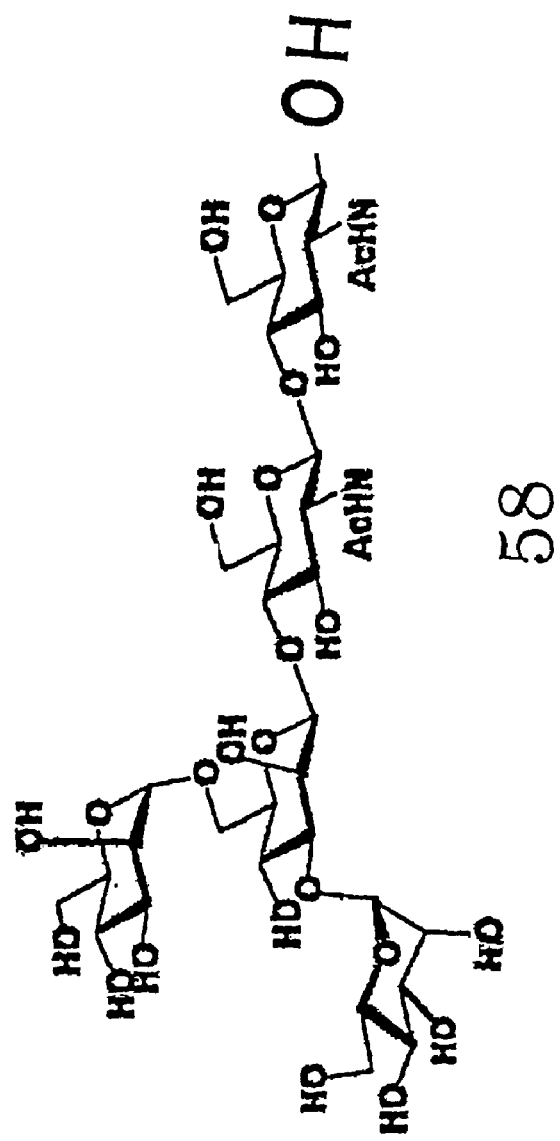
Figure 6G:
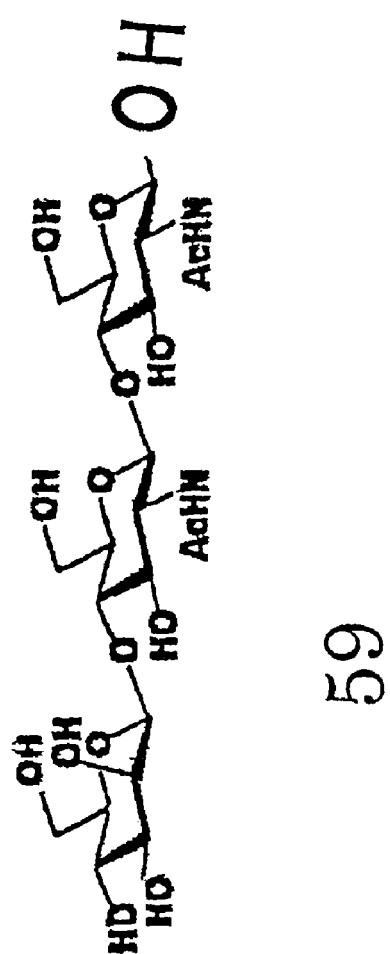
Figure 6H:
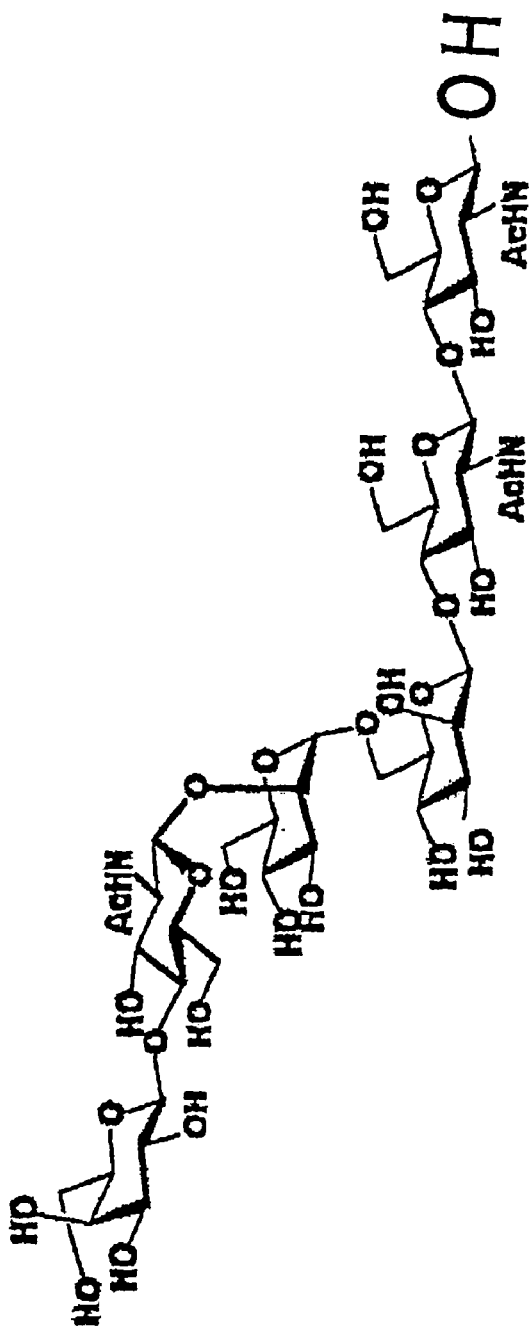
Figure 6I:
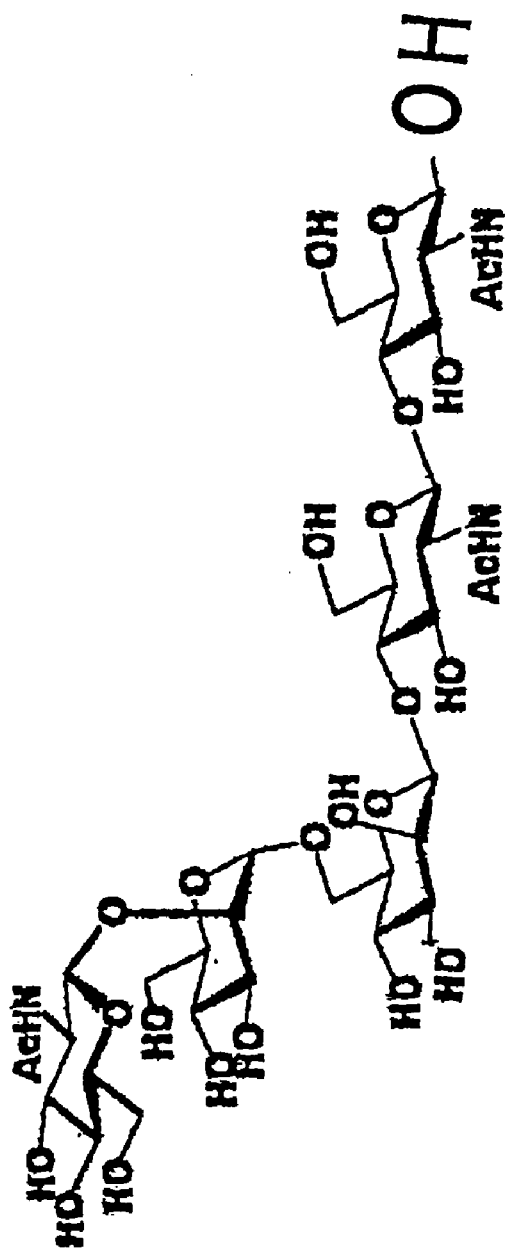
Figure 6J:
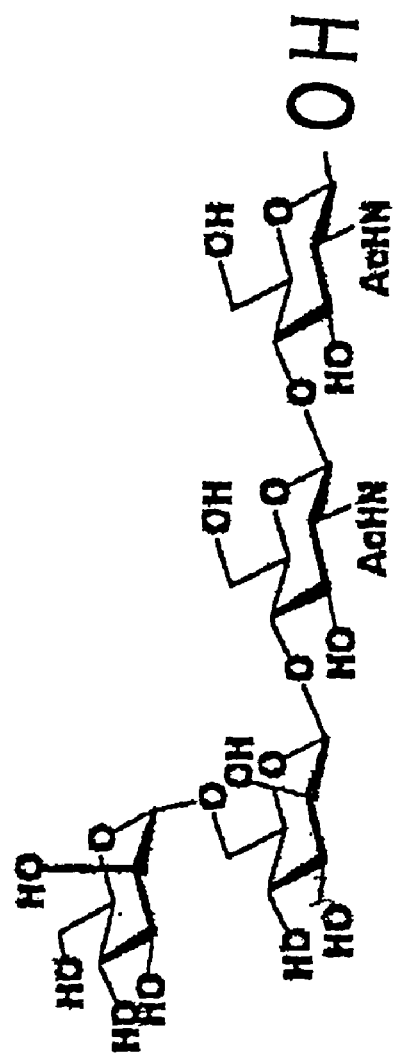
Figure 6K:
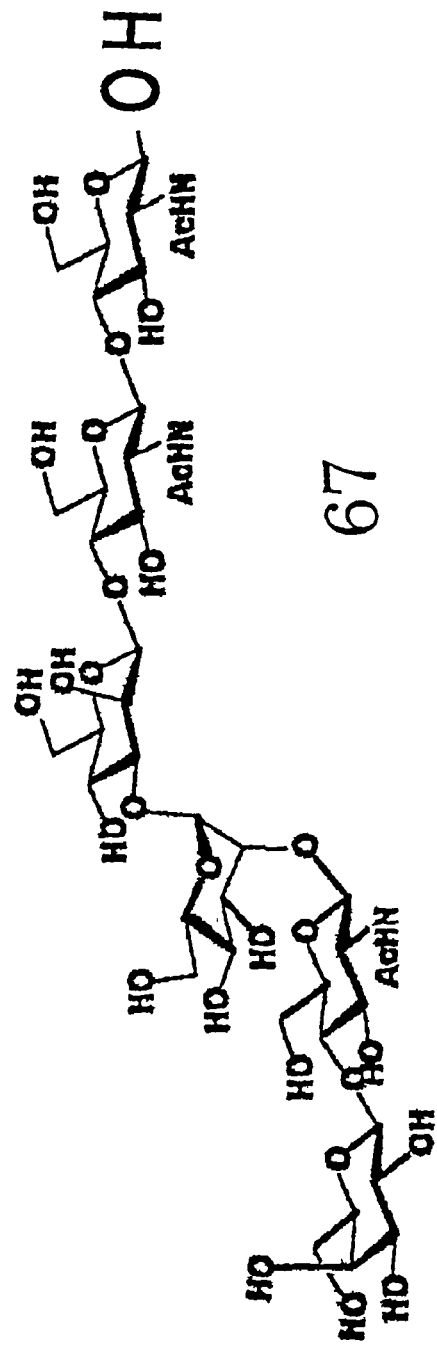
Figure 6L:
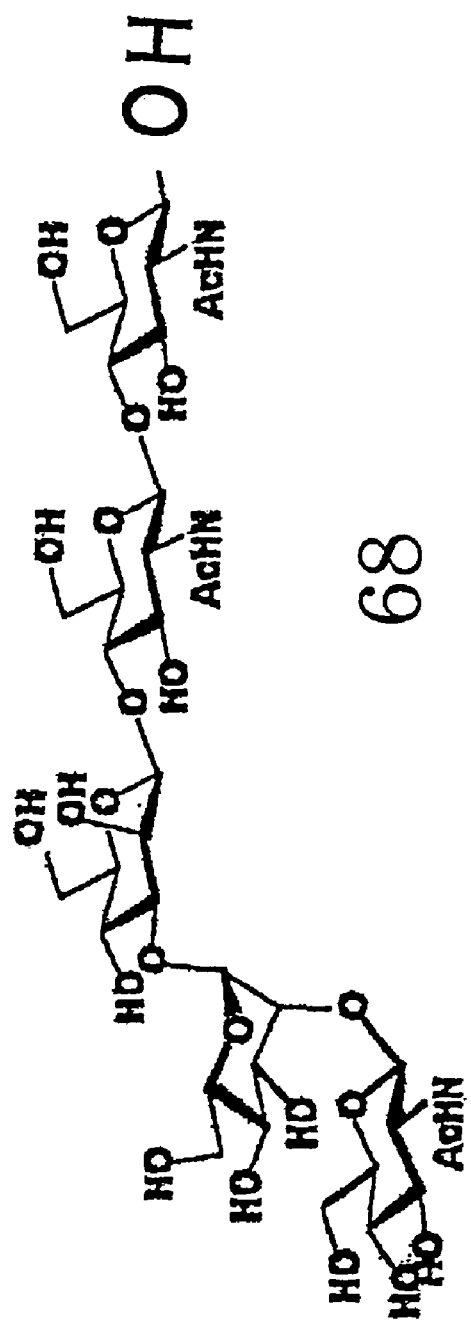
Figure 6M:
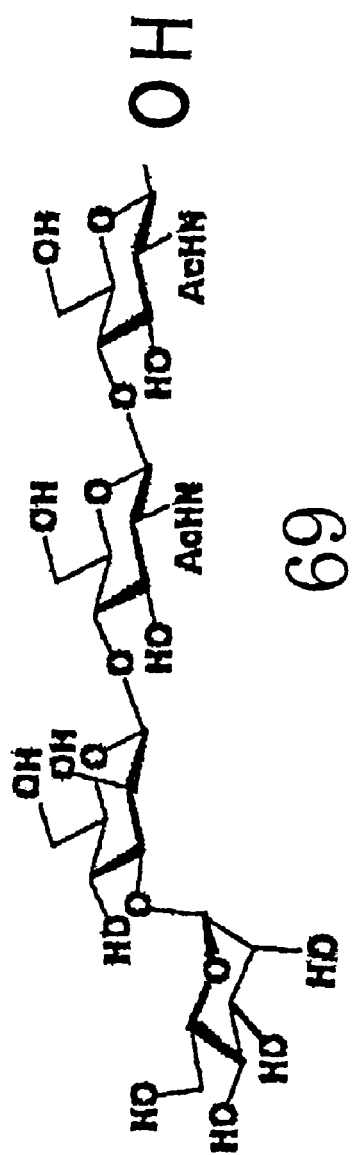
Figure 7A:
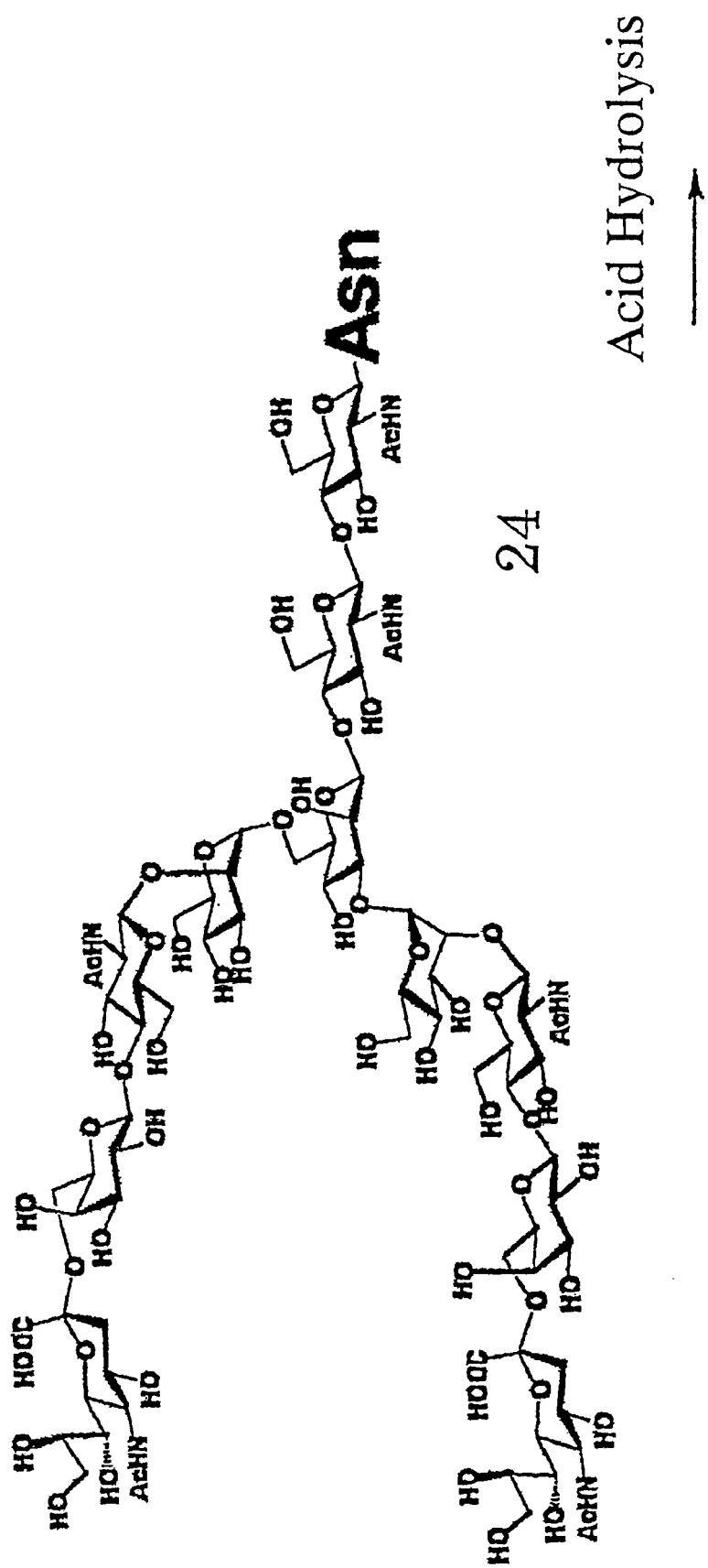
FIG. 7 shows an example of a step in the process for preparing a sugar chain asparagine derivative according to the present invention.
Figure 7B:
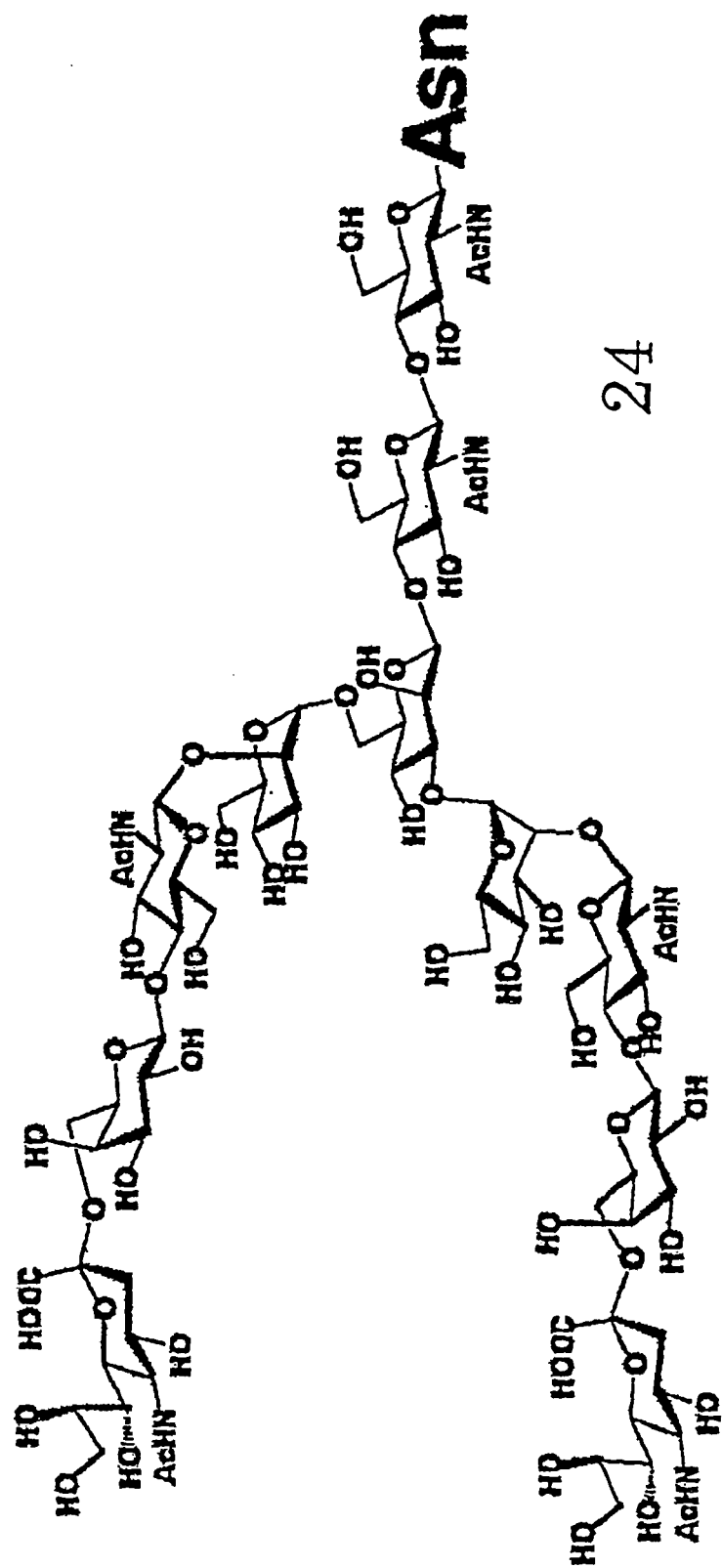
Figure 7C:
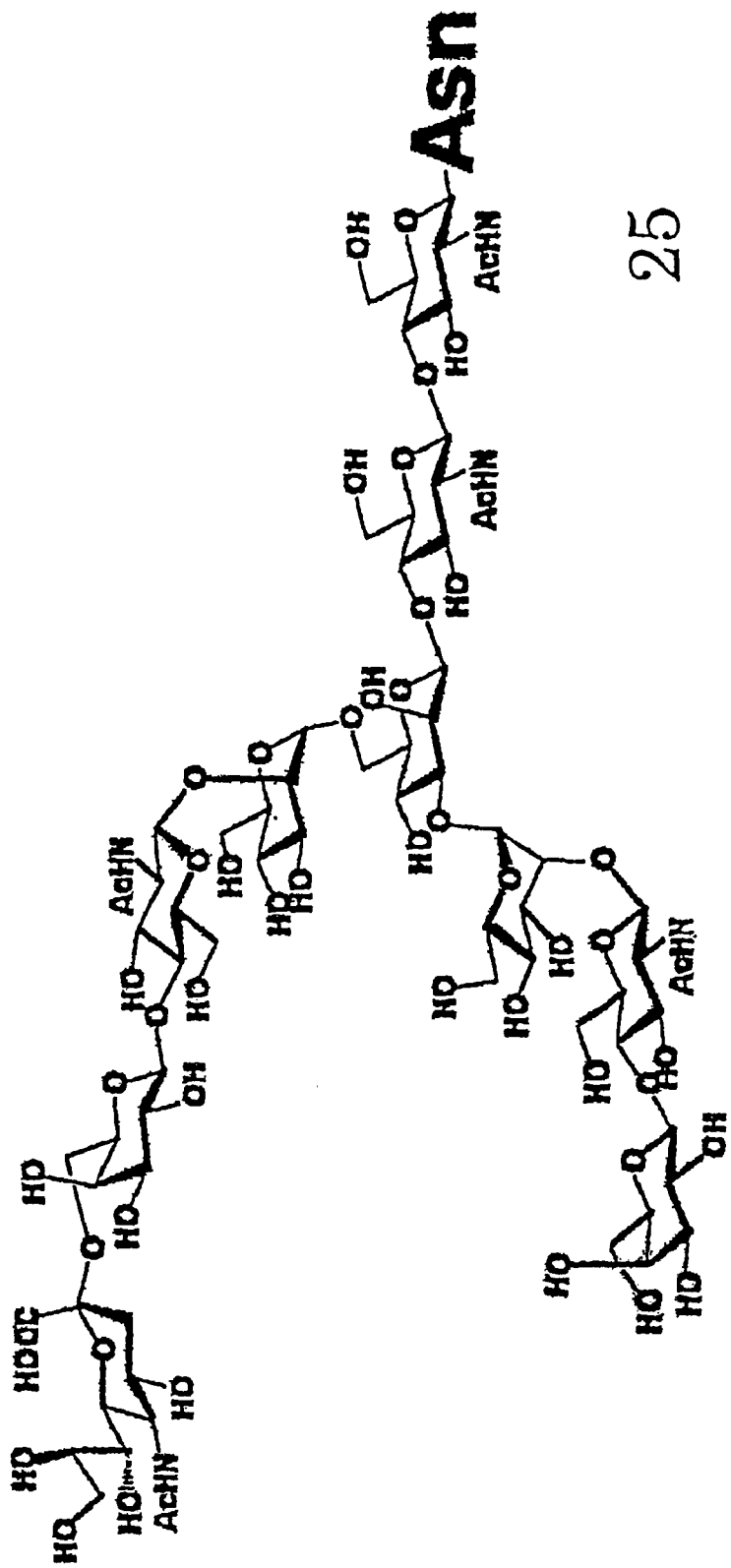
Figure 7D:
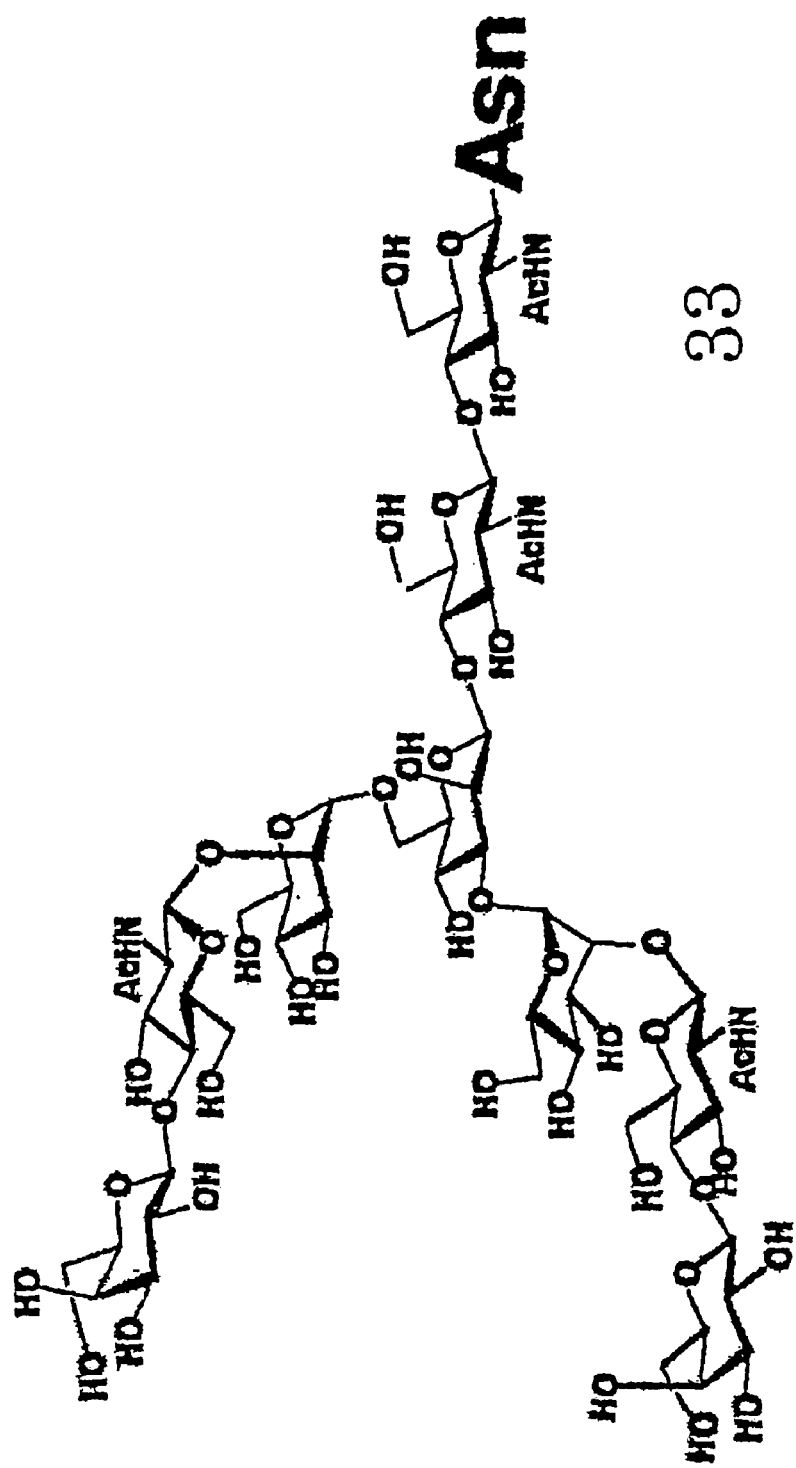
Figure 7E:
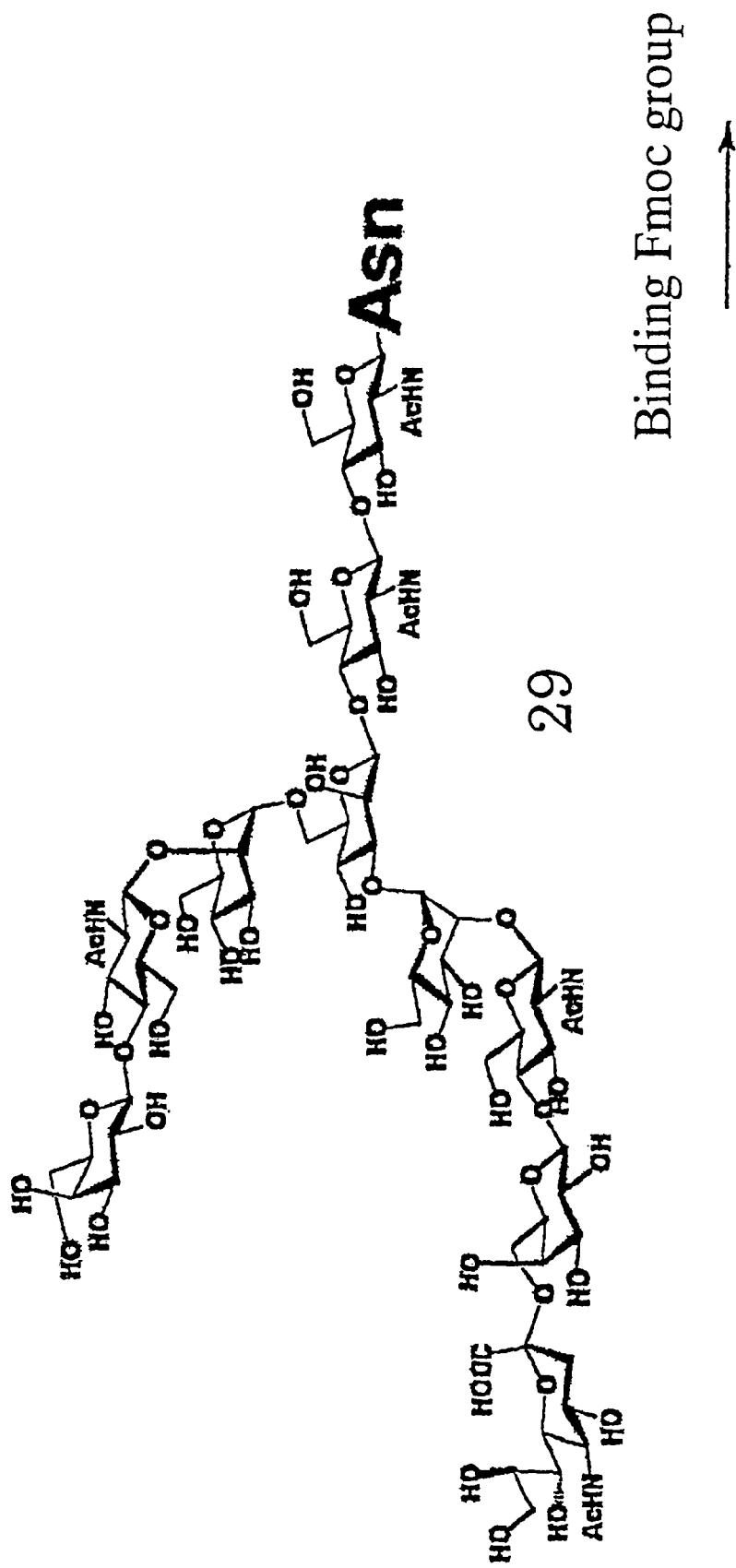
Figure 7F:
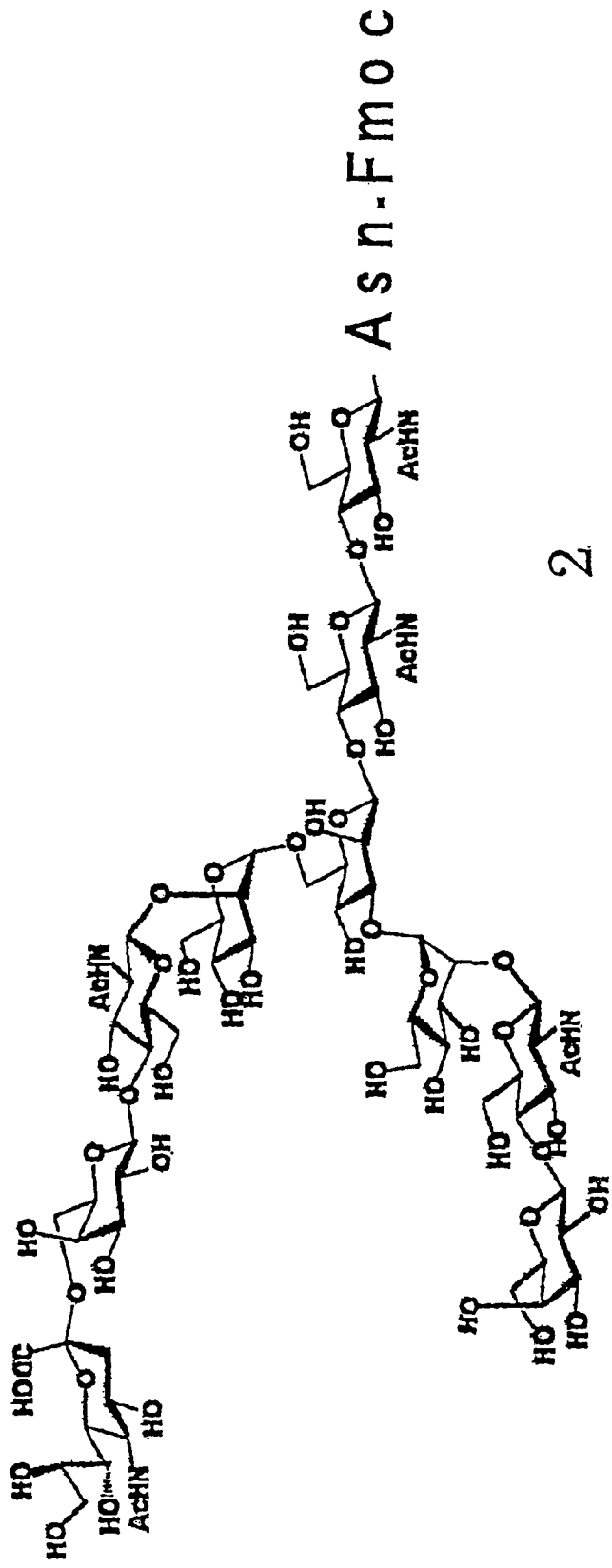
Figure 7G:
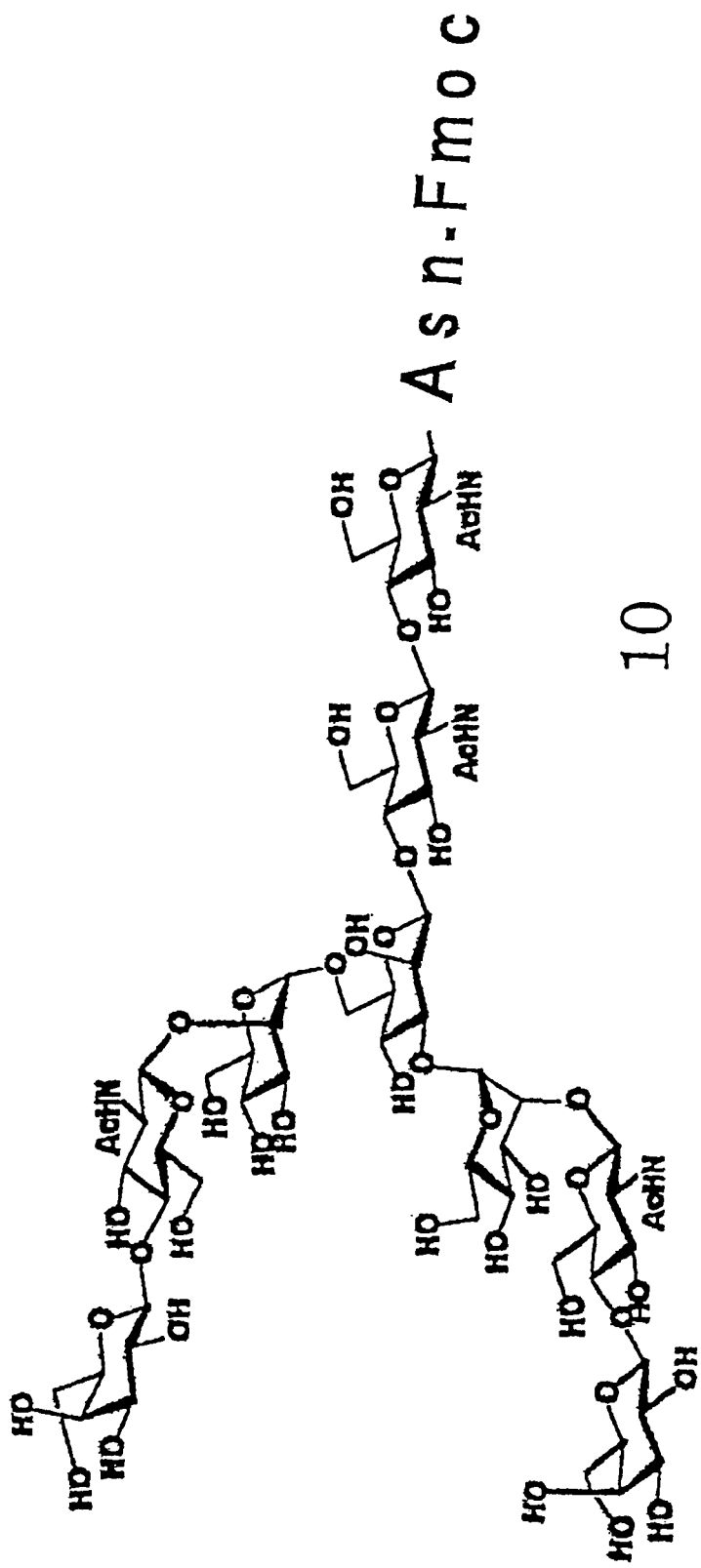
Figure 7H:
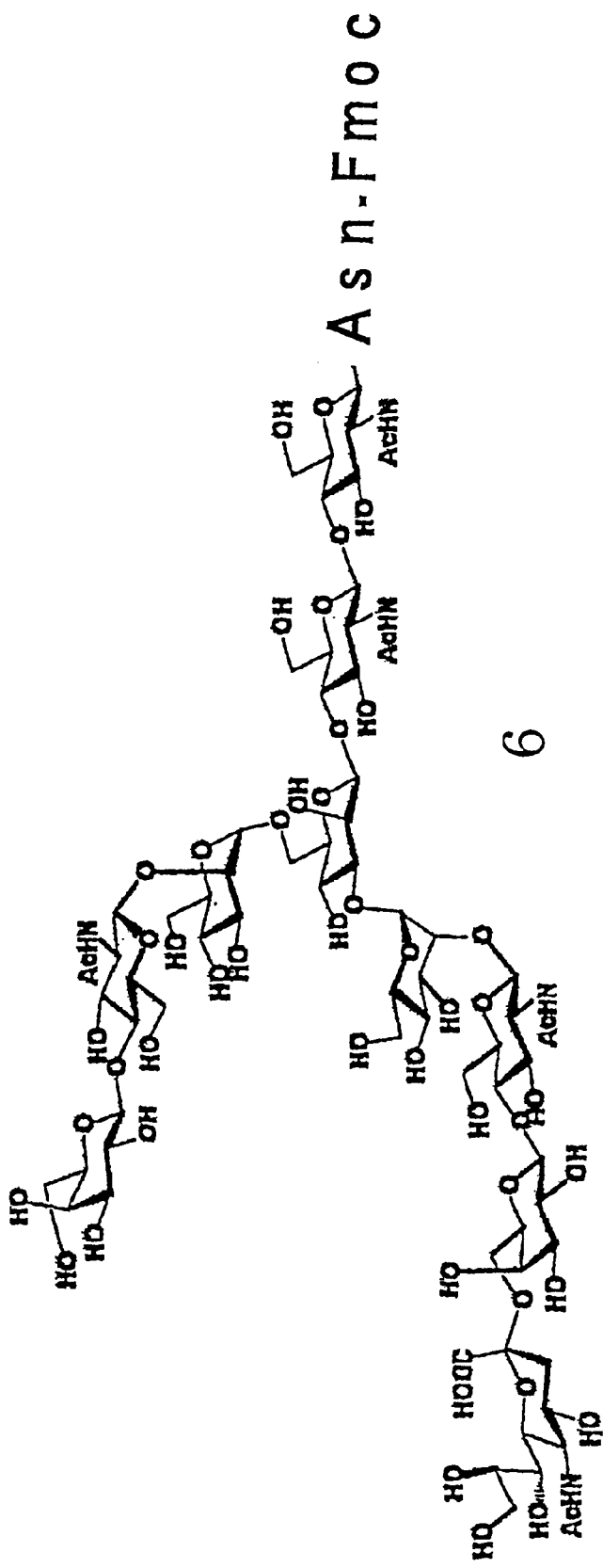
Figure 7I:
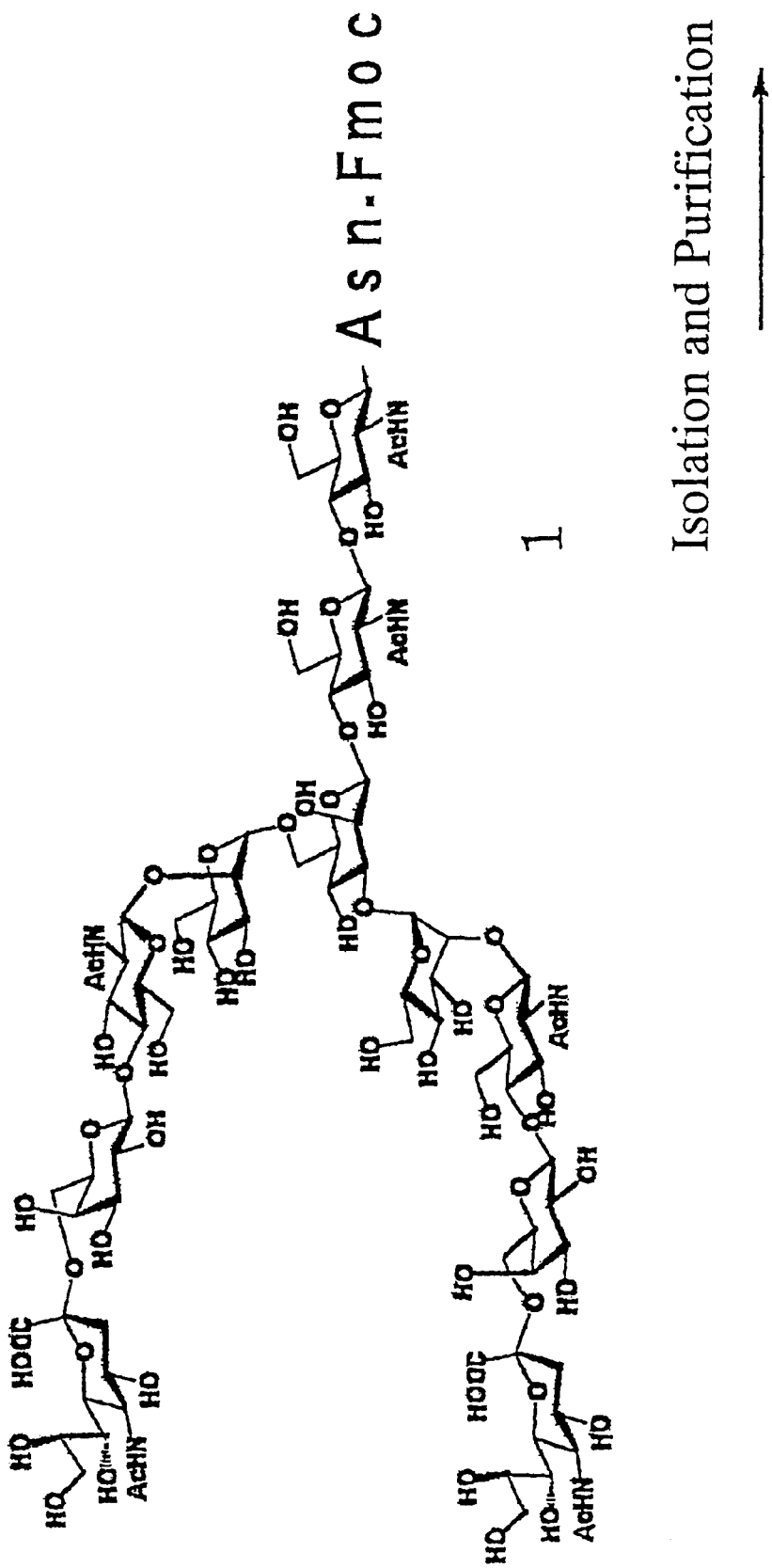
Figure 7J:
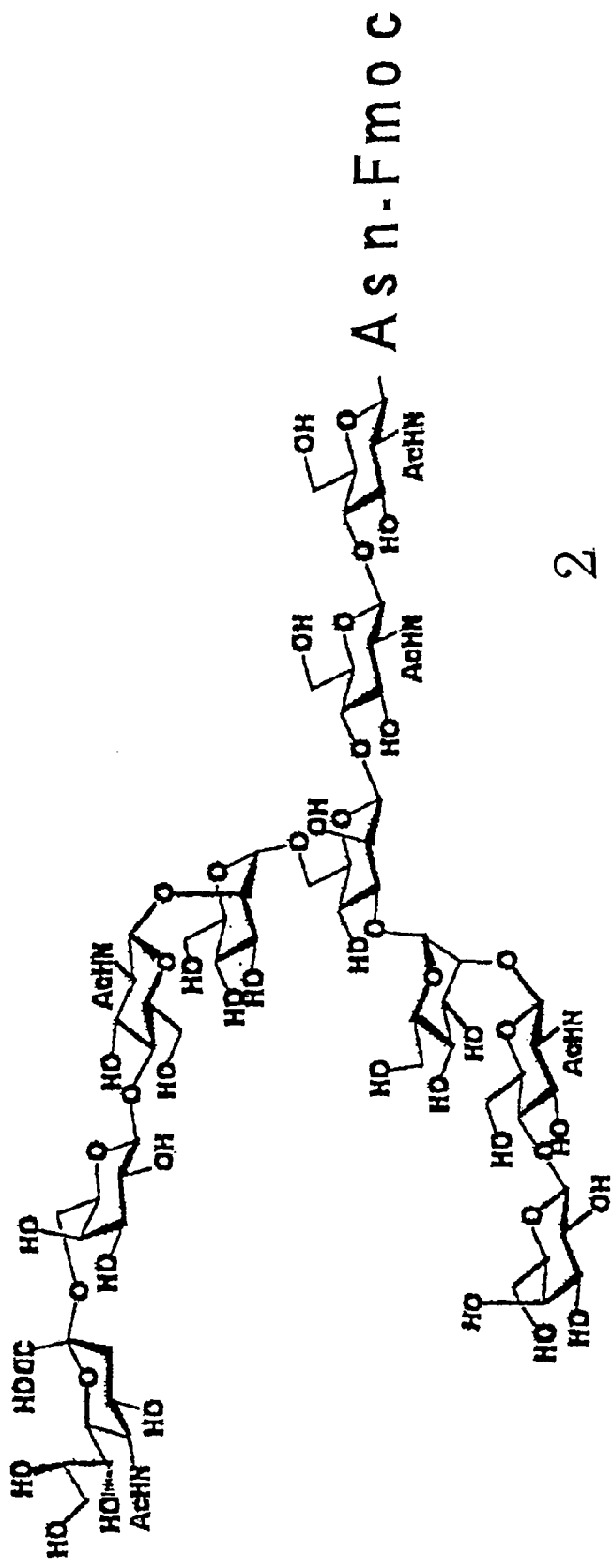
Figure 7K:
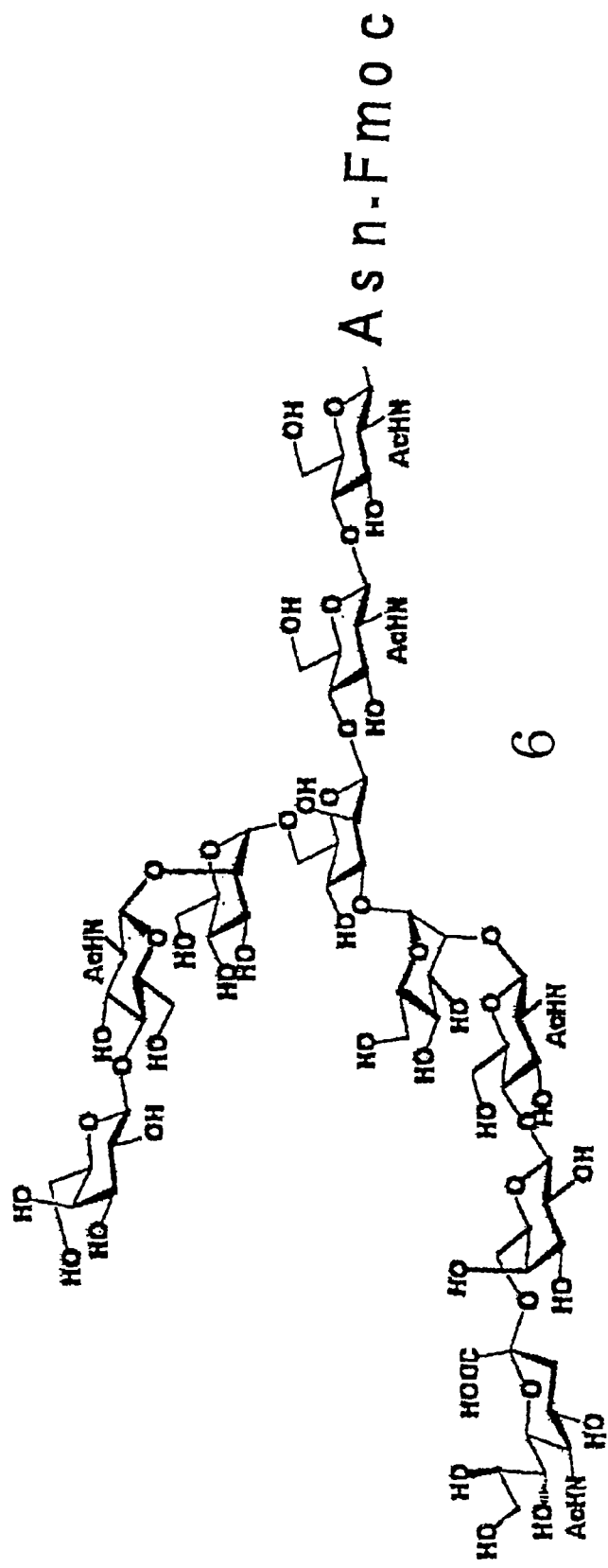
Figure 8A:
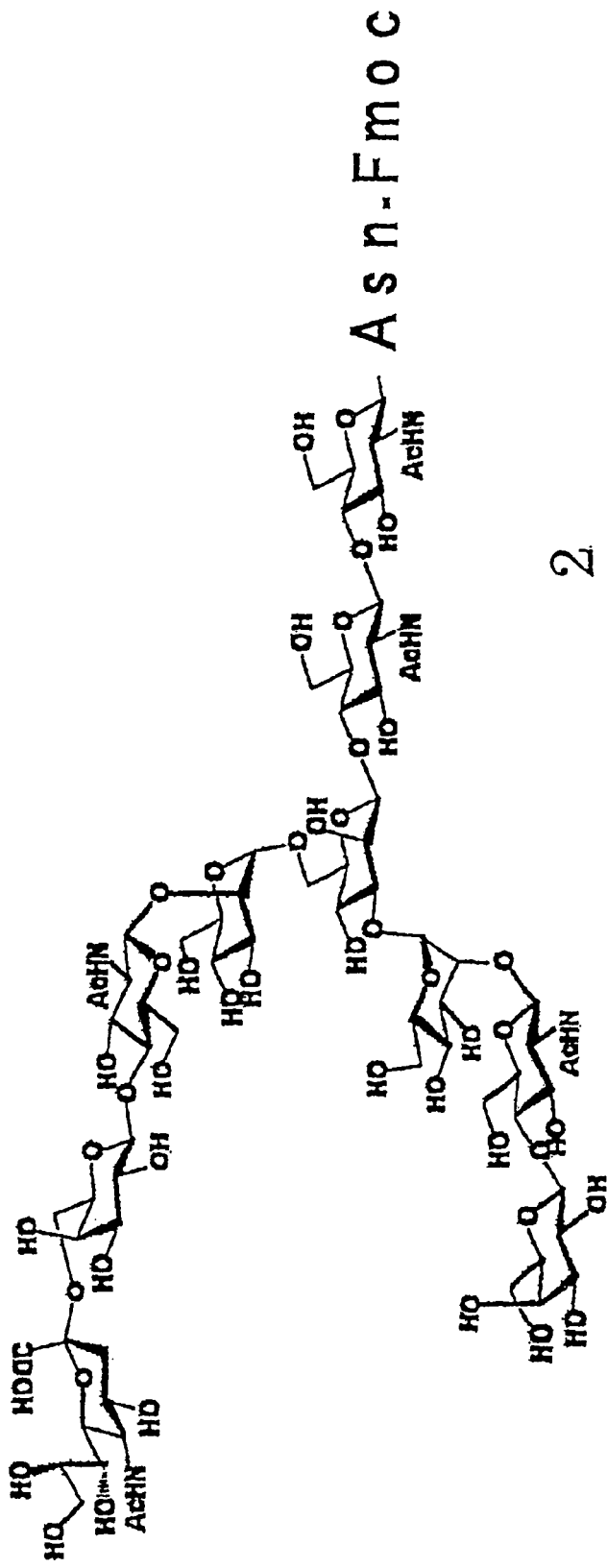
FIG. 8 shows an example of a conversion step of a sugar chain asparagine derivative with various glycosidases.
Figure 8B:
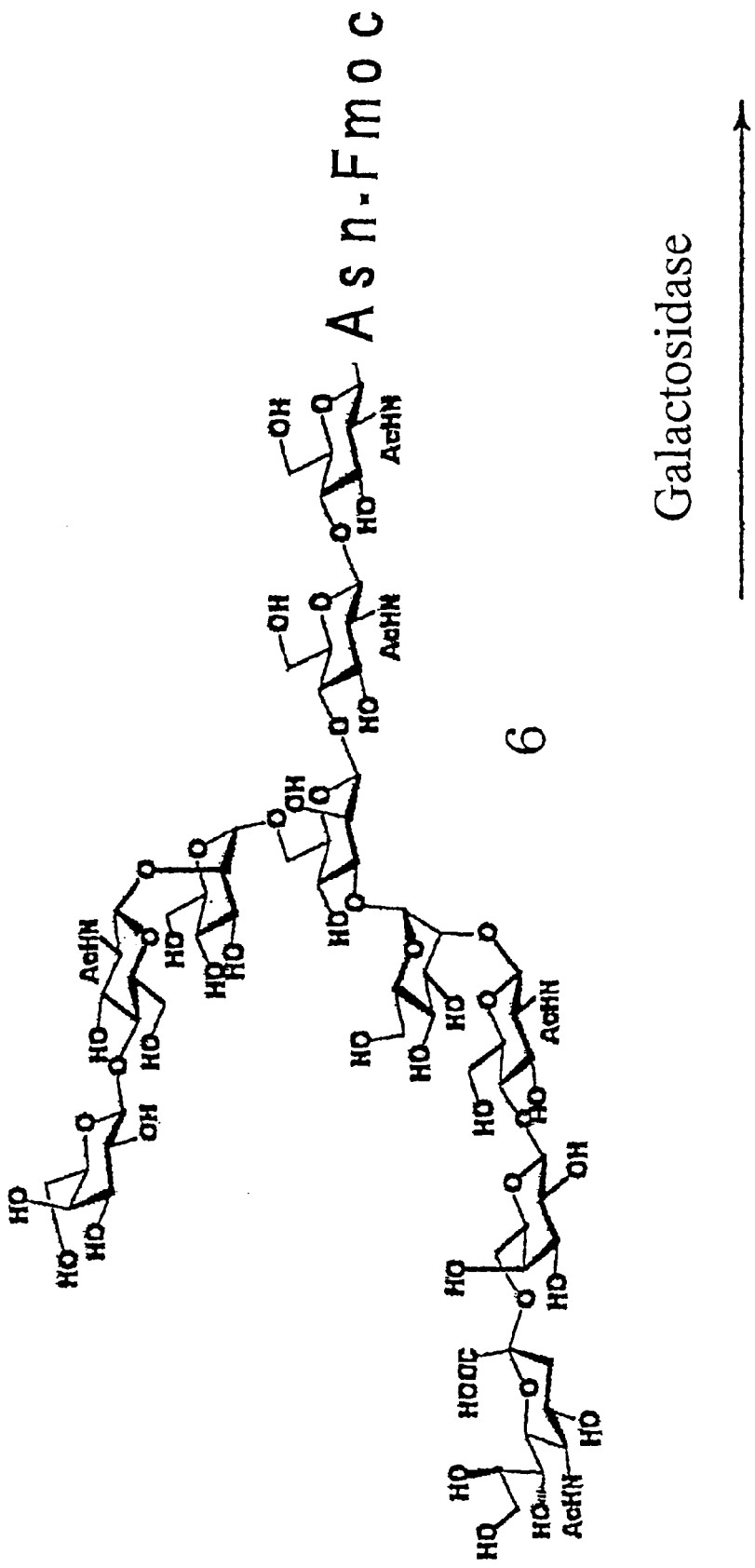
Figure 8C:
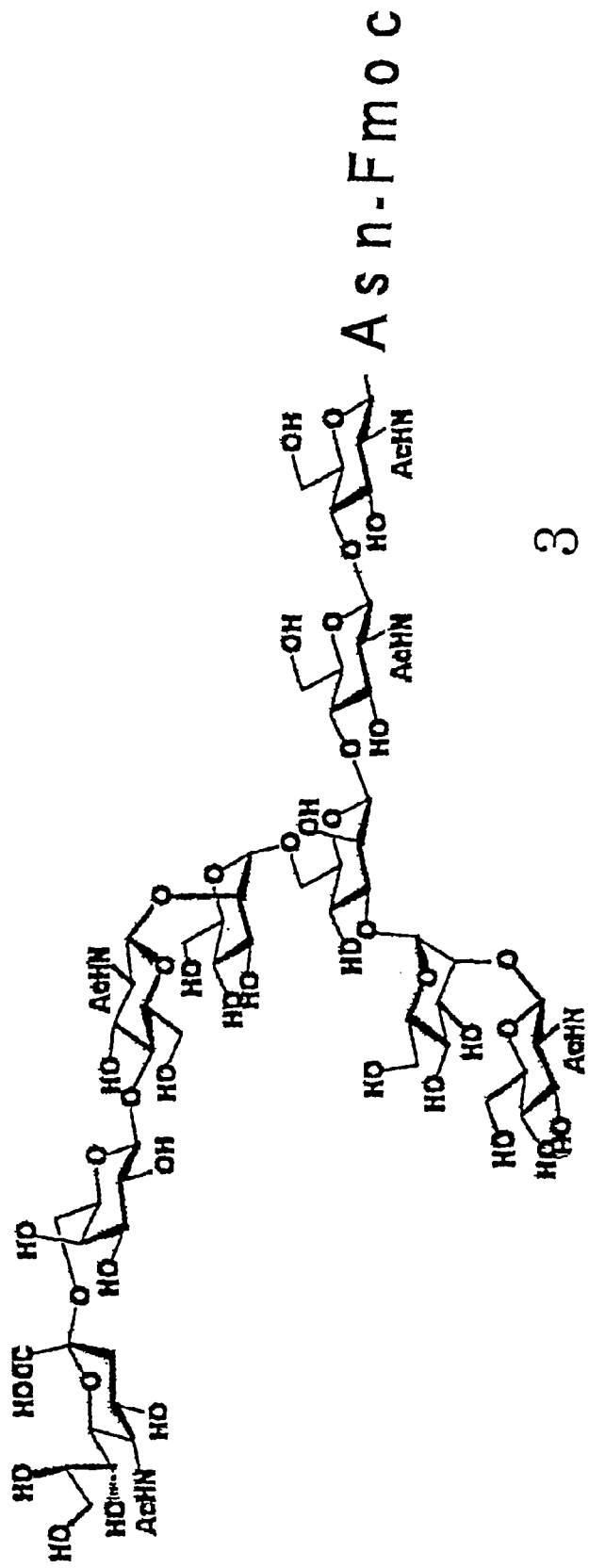
Figure 8D:
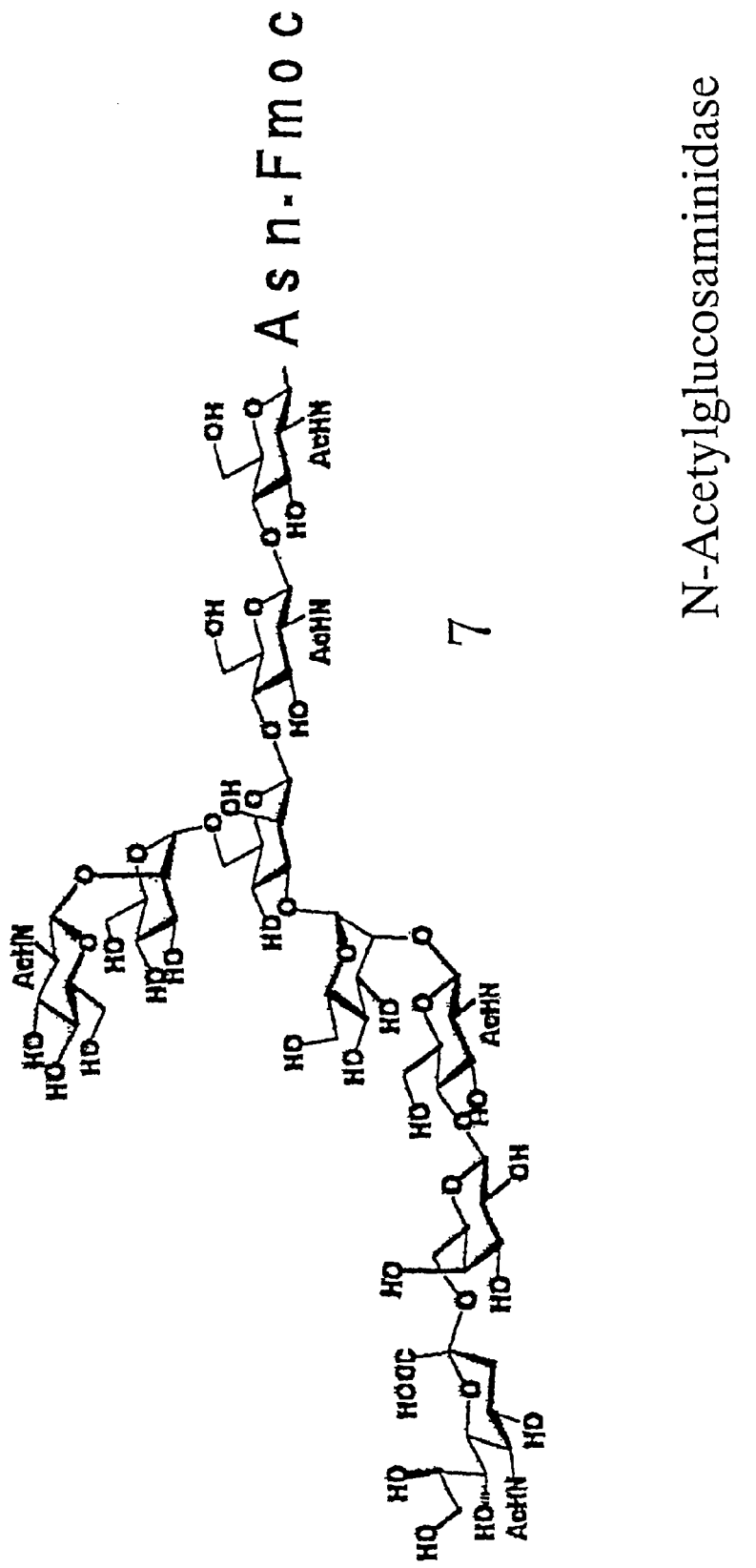
Figure 8E:
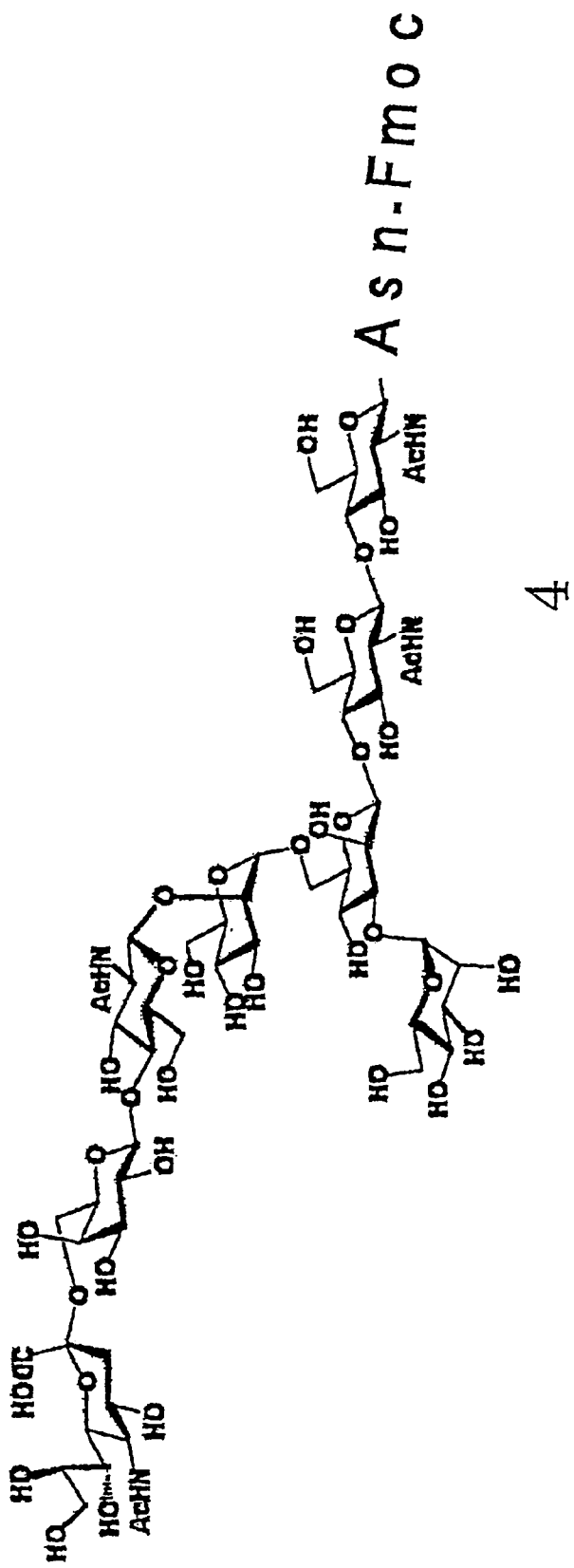
Figure 8F:
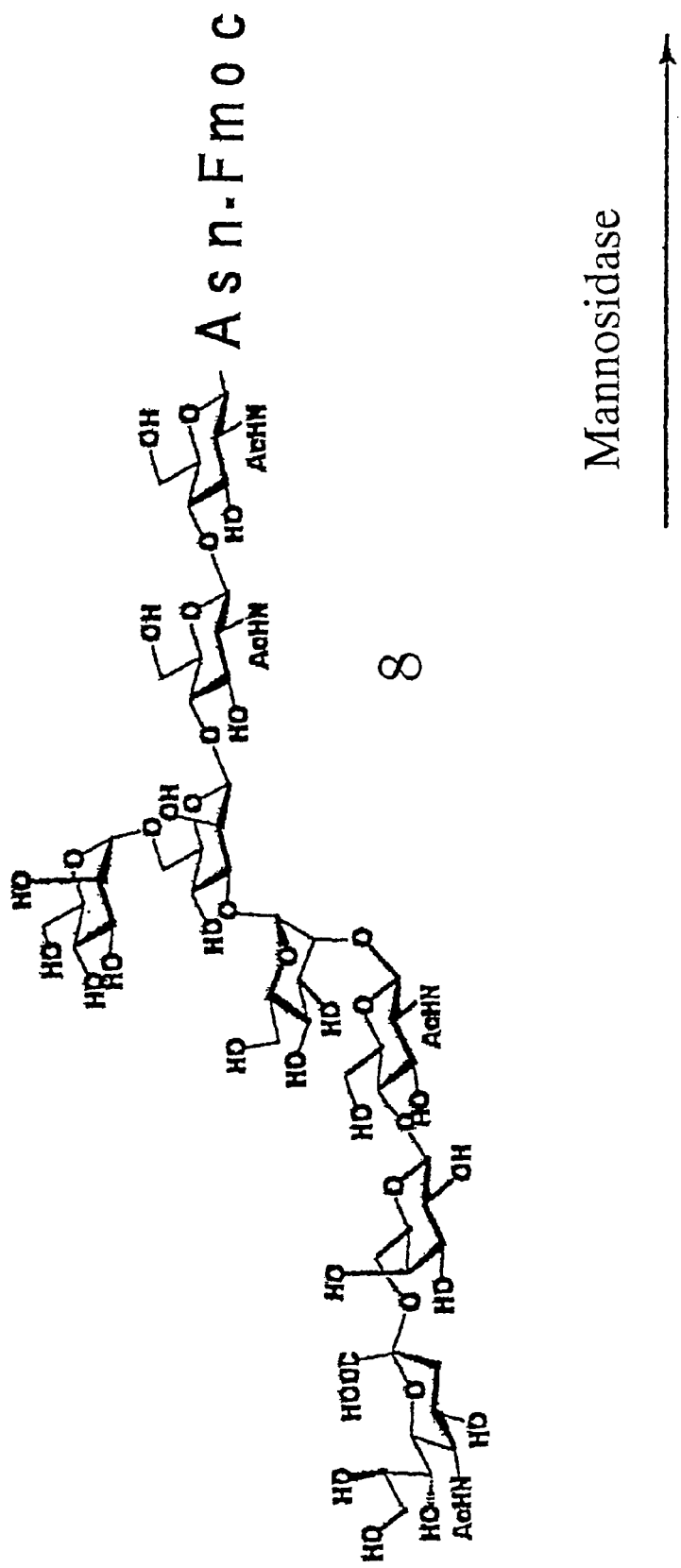
Figure 8G:
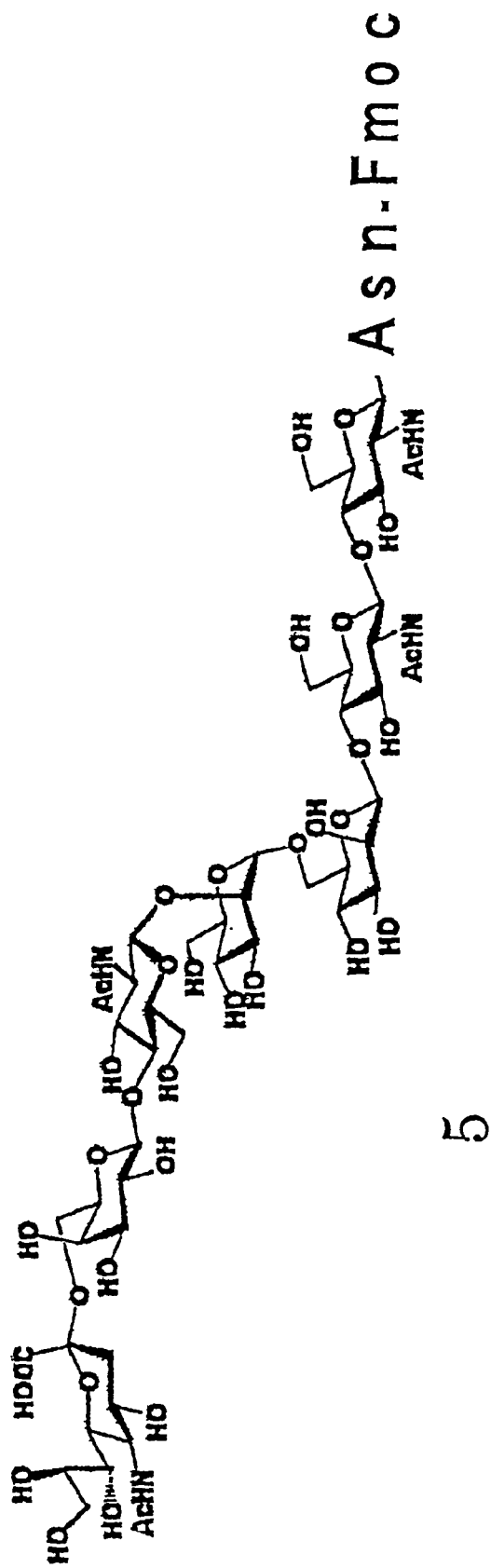
Figure 8H:
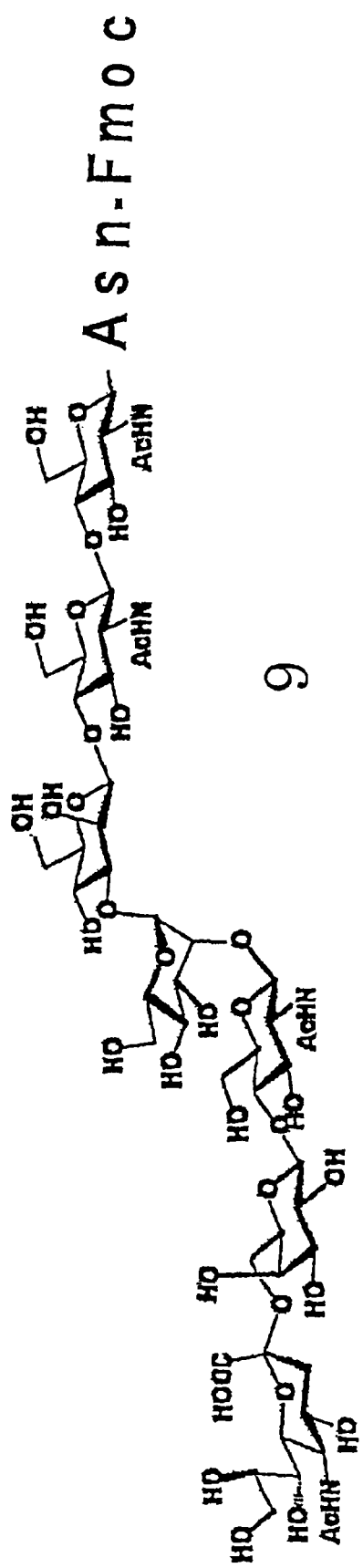
Figure 9A:
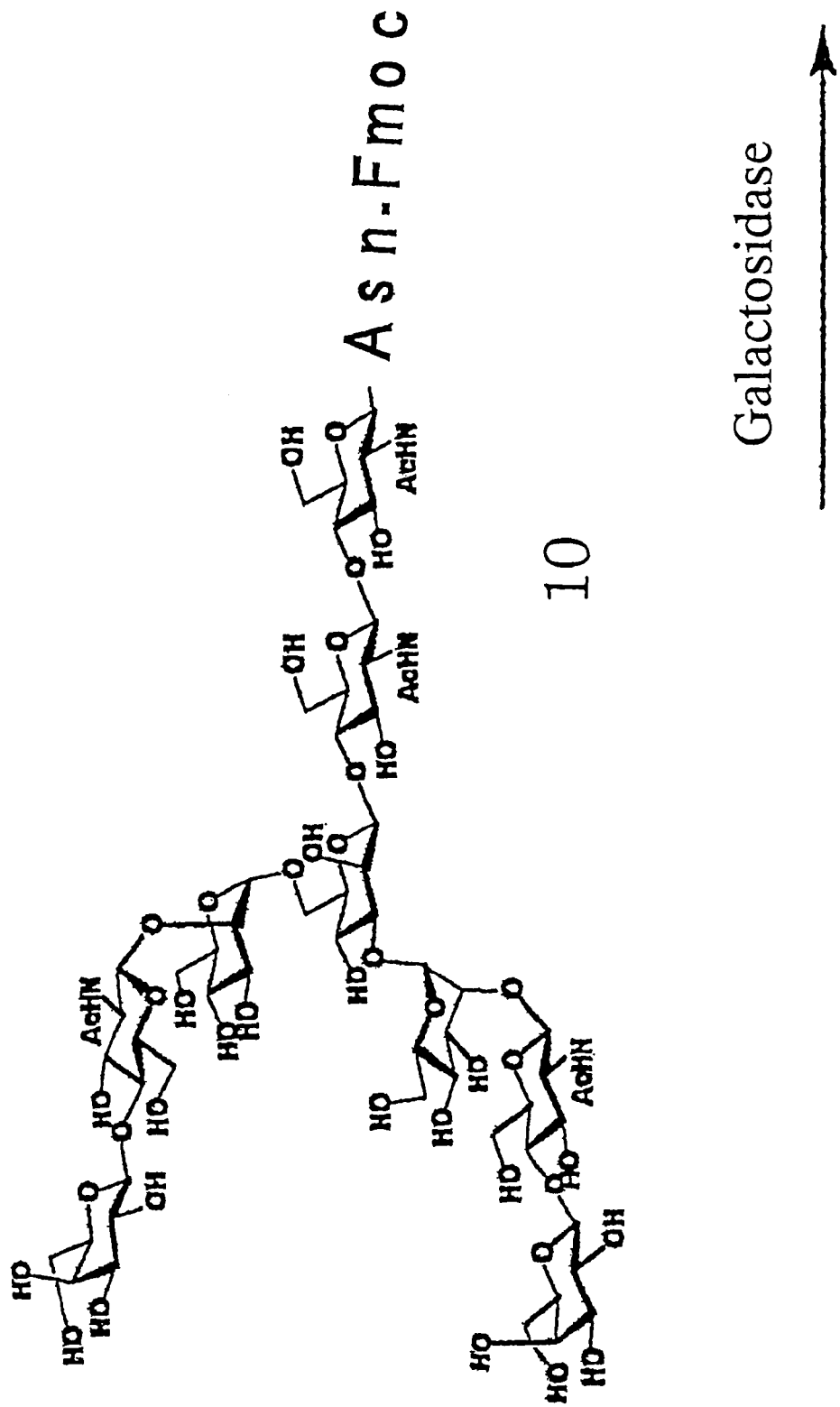
FIG. 9 shows an example of a conversion step of a sugar chain asparagine derivative with various glycosidases.
Figure 9B:
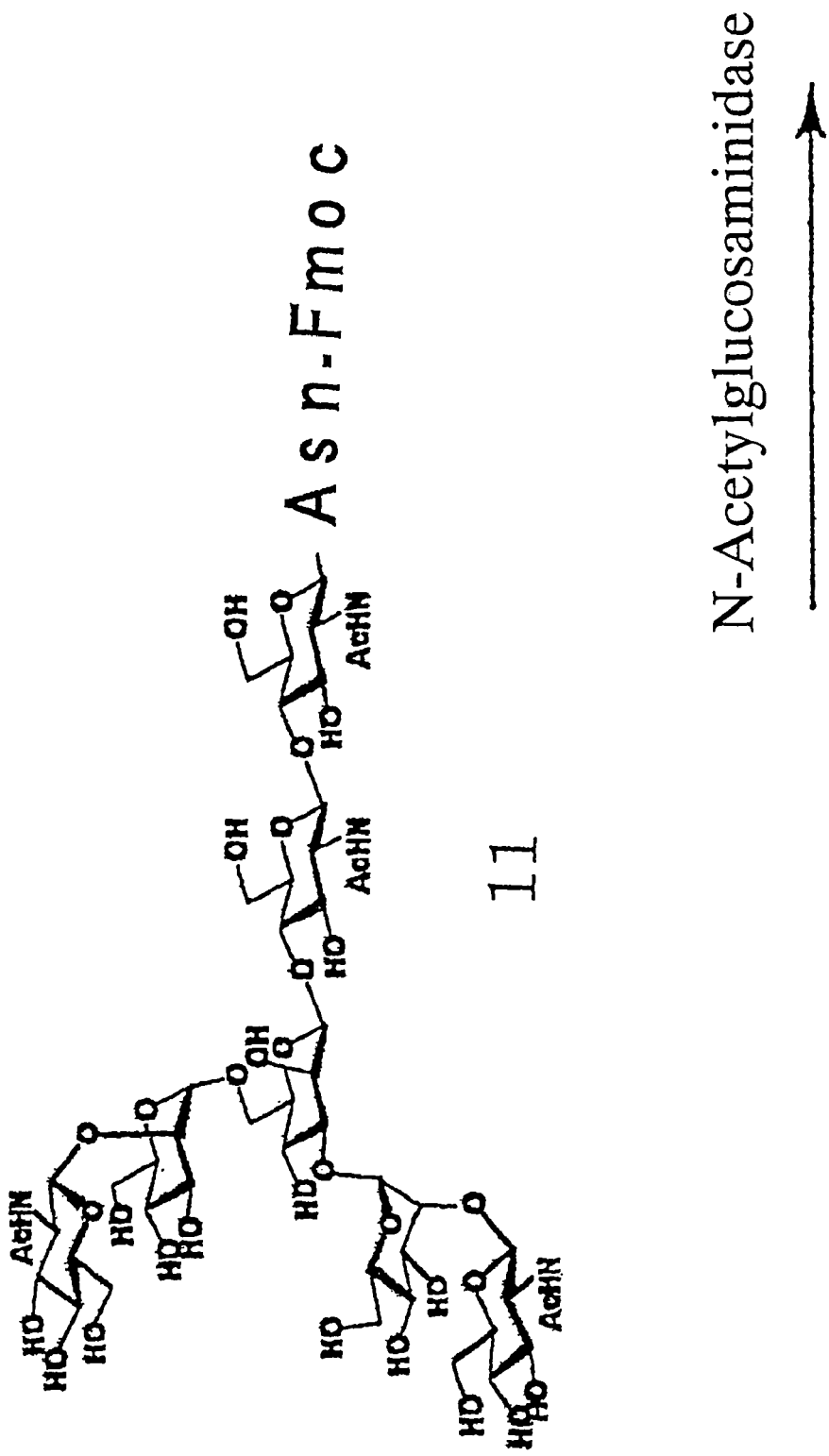
Figure 9C:
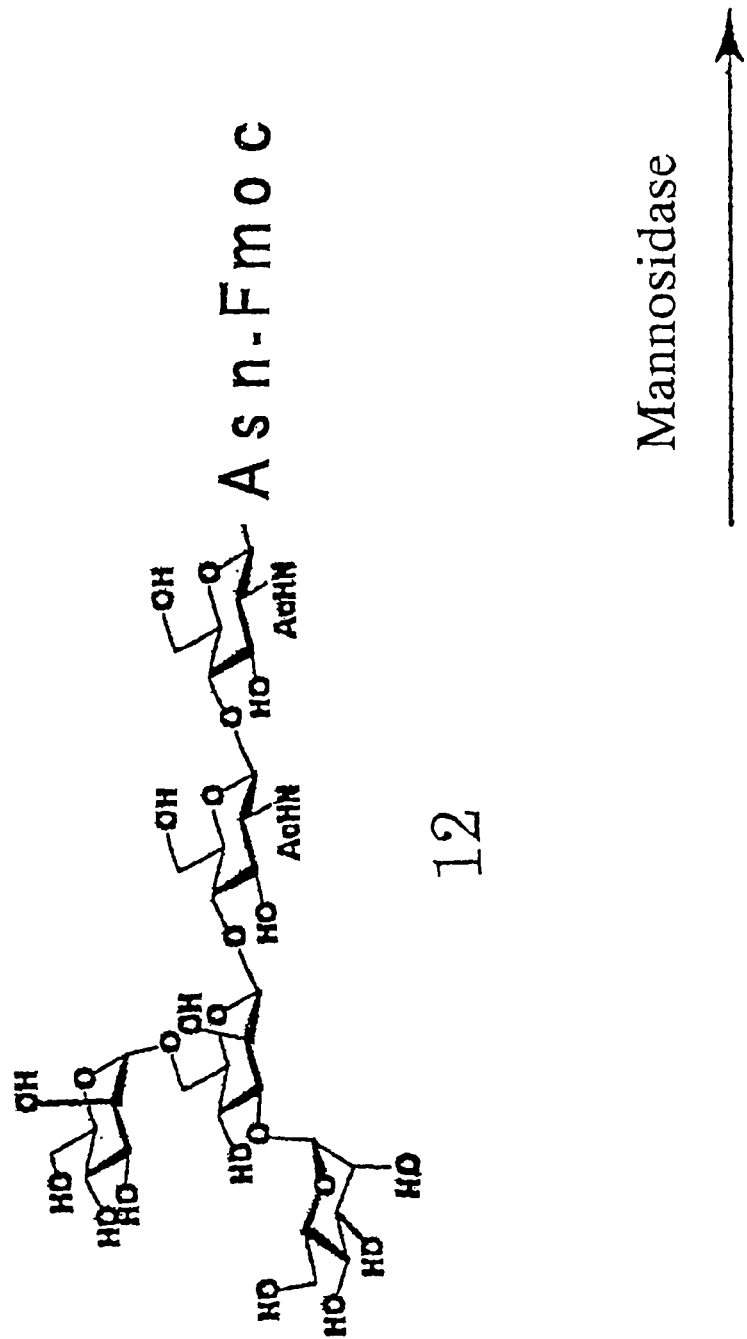
Figure 9D:
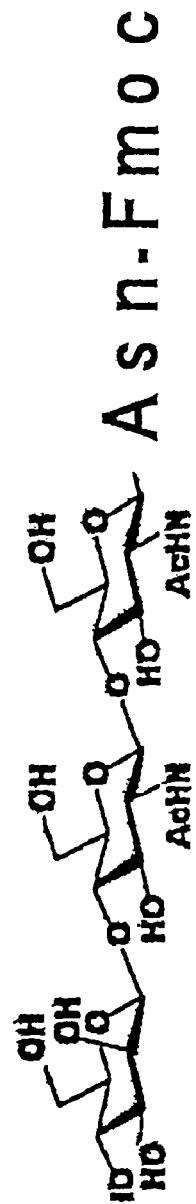
Figure 10A:
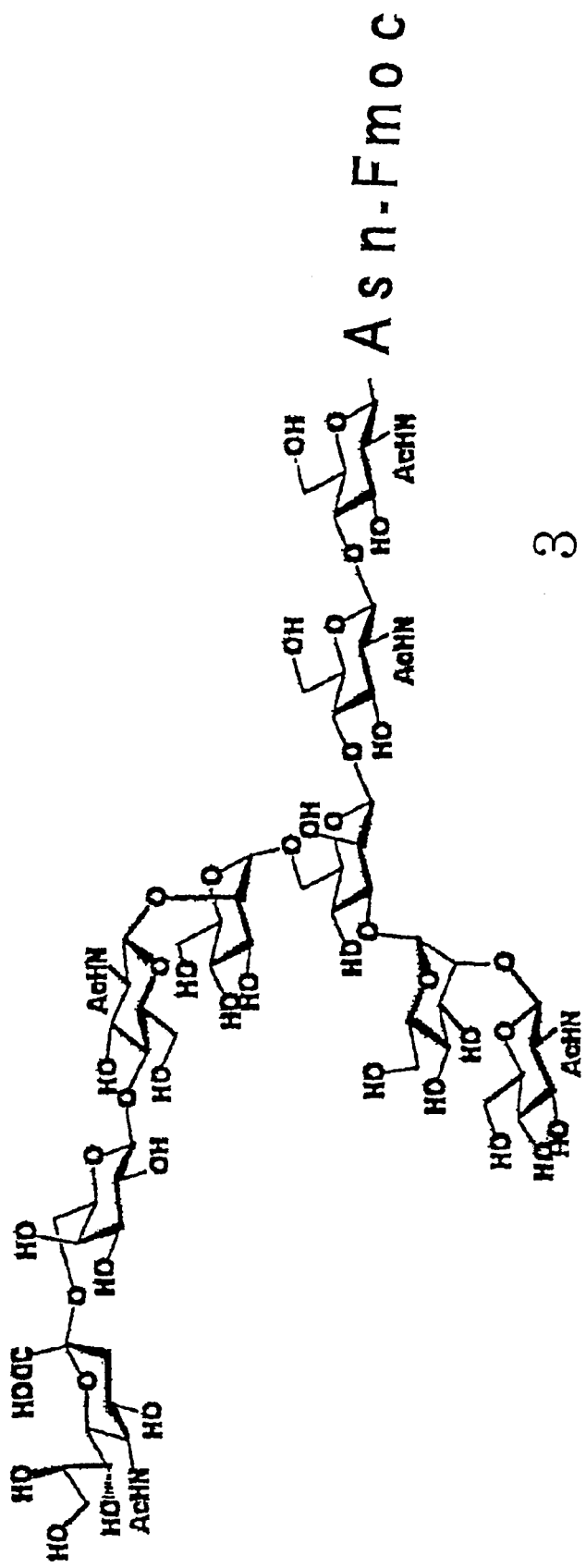
FIG. 10 shows an example of a conversion step of a sugar chain asparagine derivative with various glycosidases.
Figure 10B:
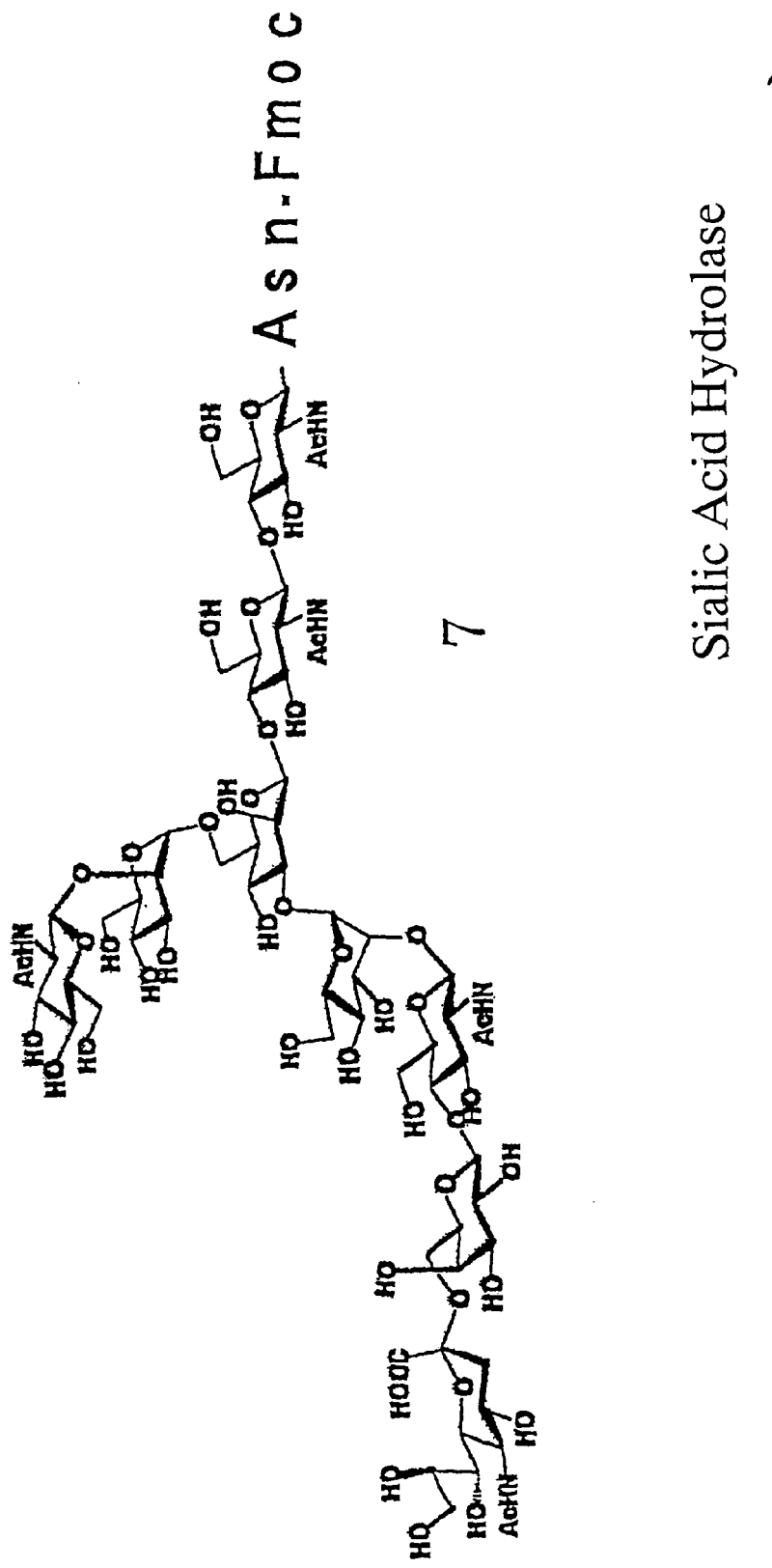
Figure 10C:
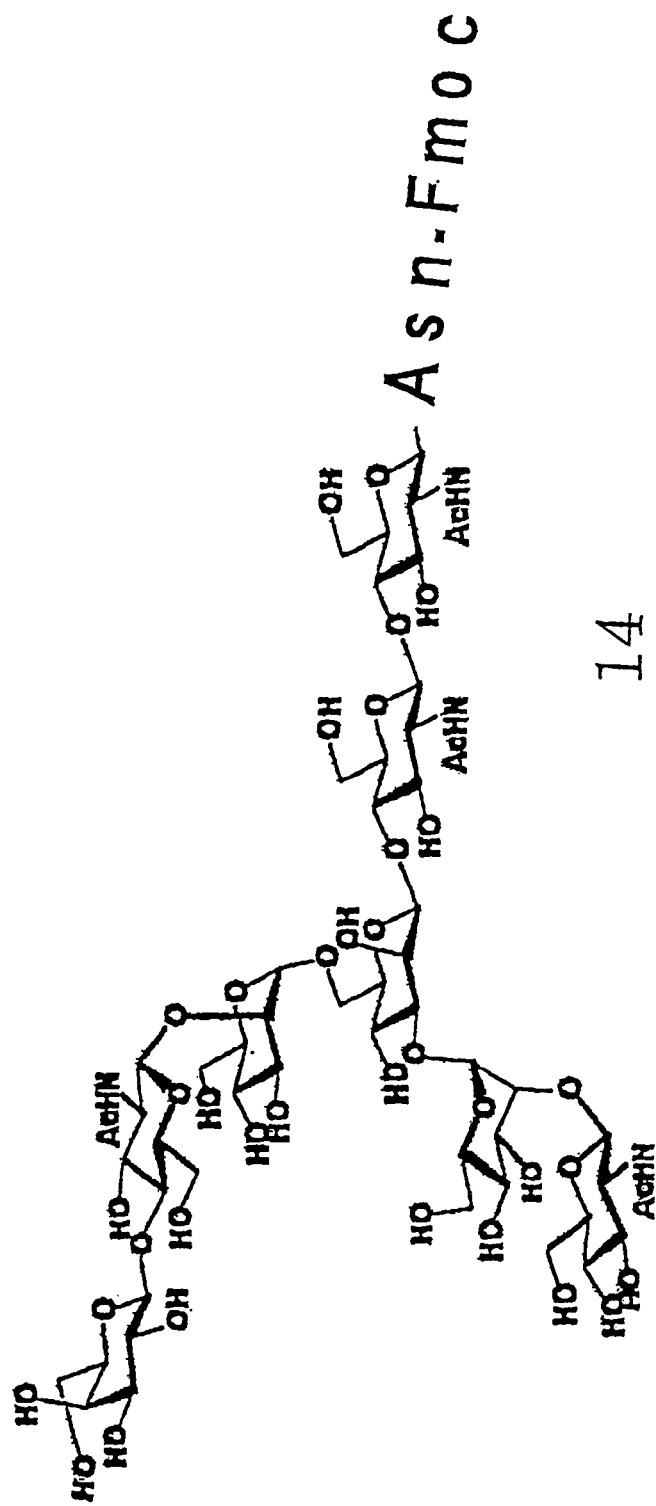
Figure 10D:
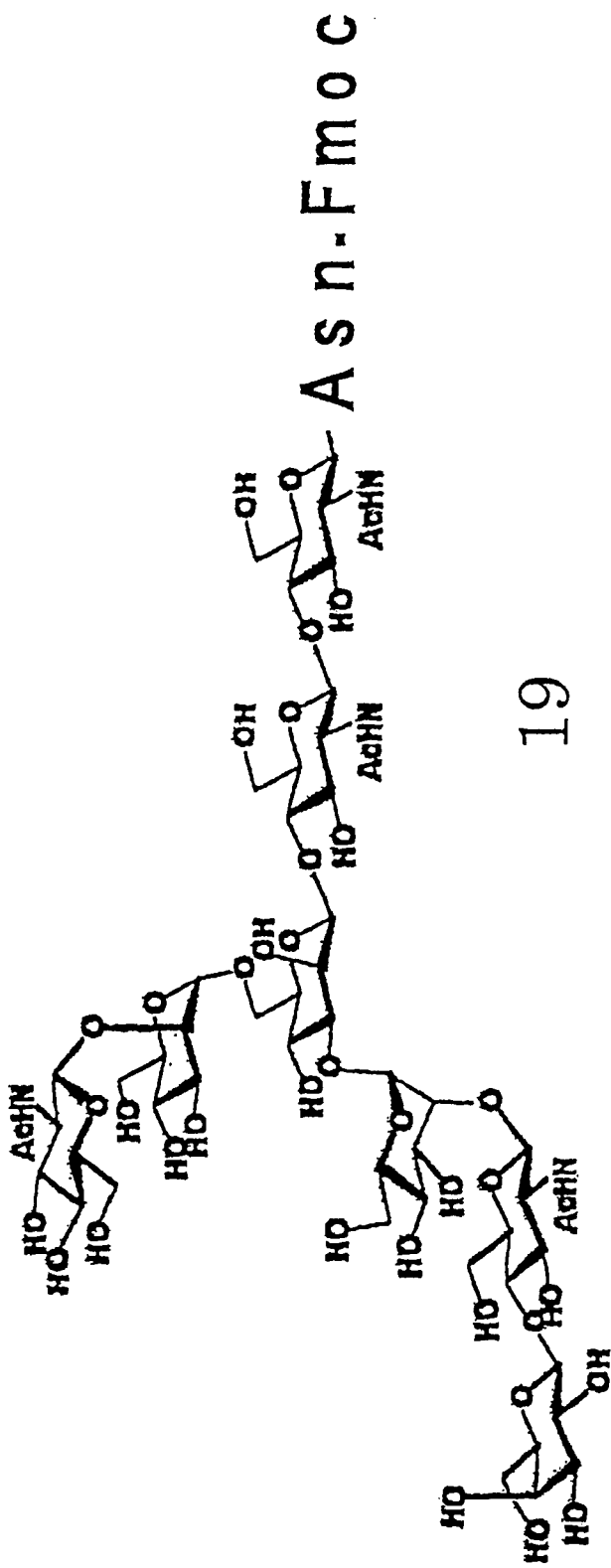
Figure 10E:
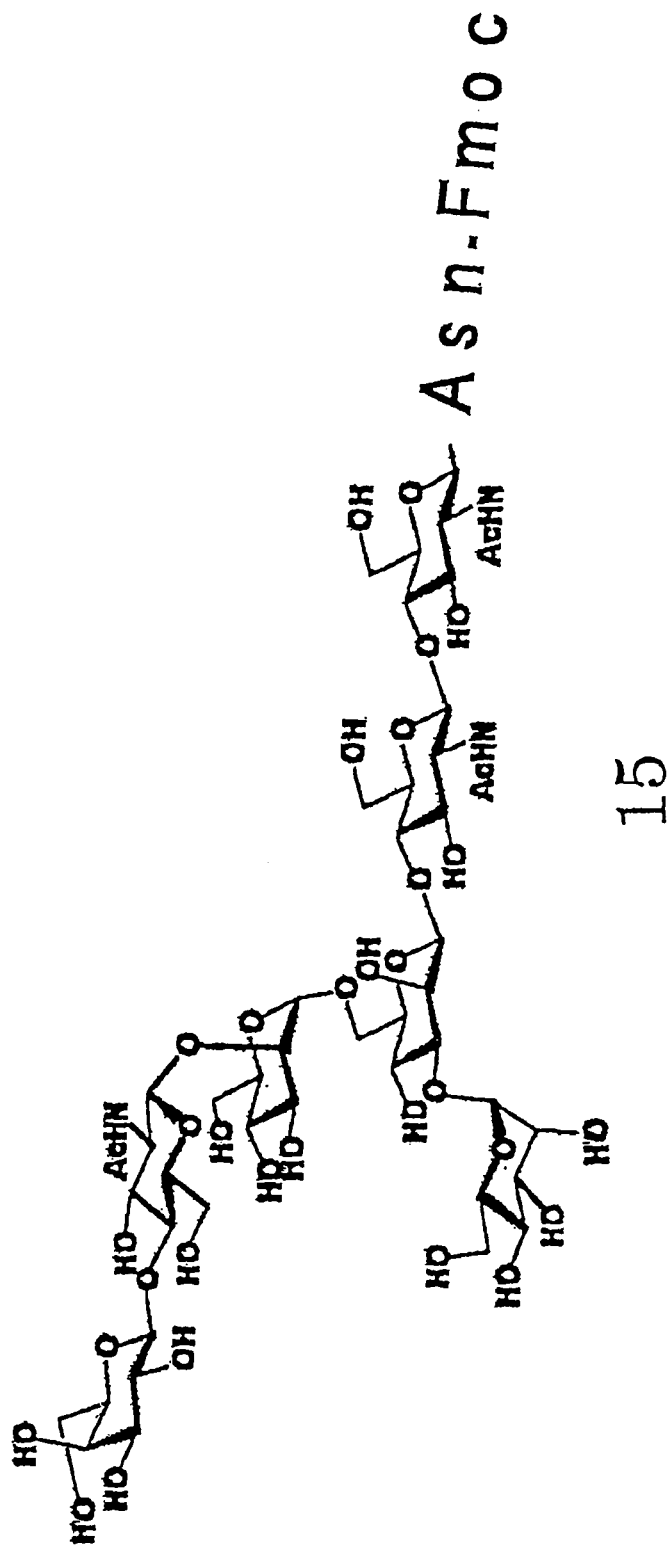
Figure 10F:
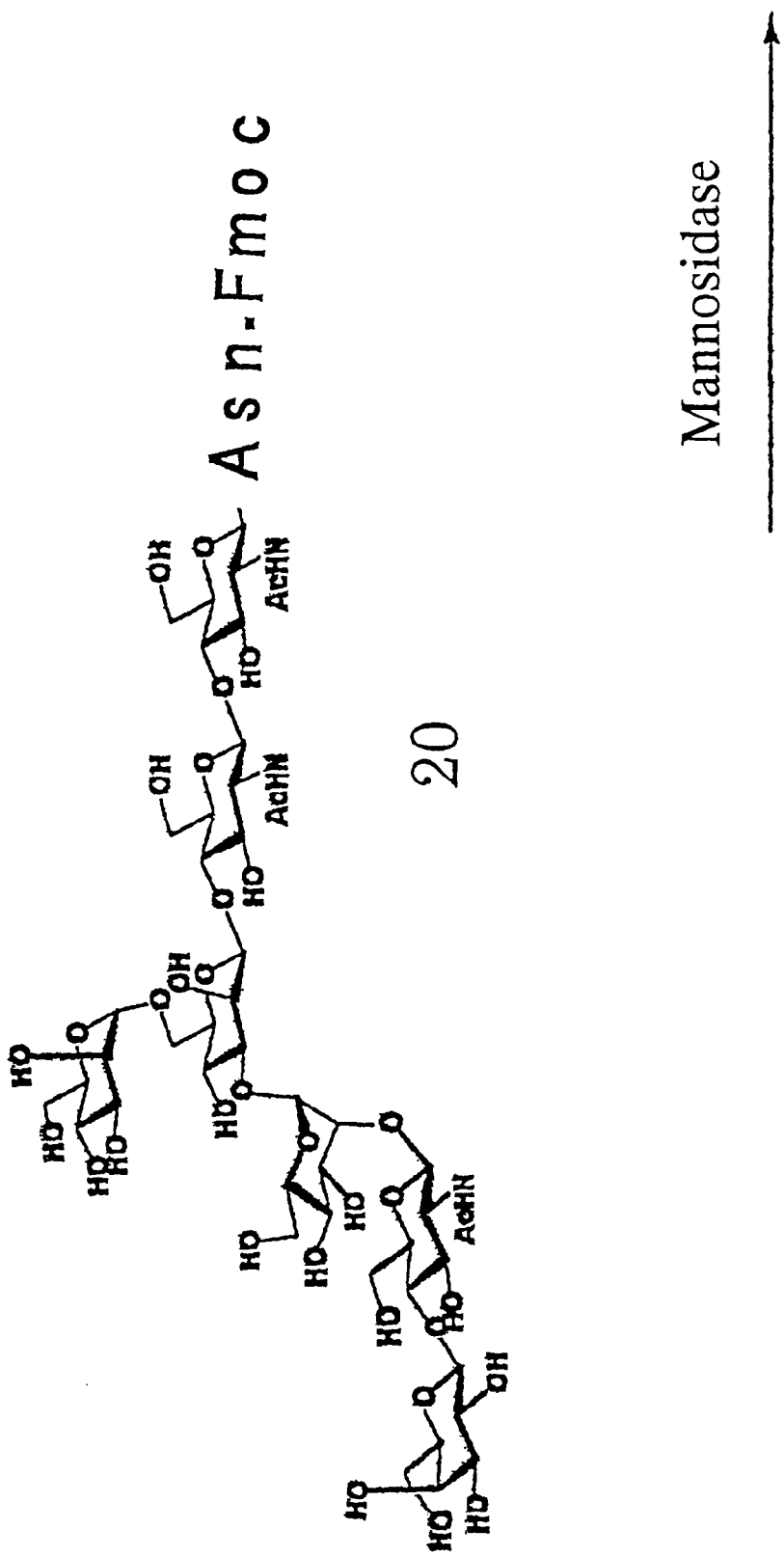
Figure 10G:
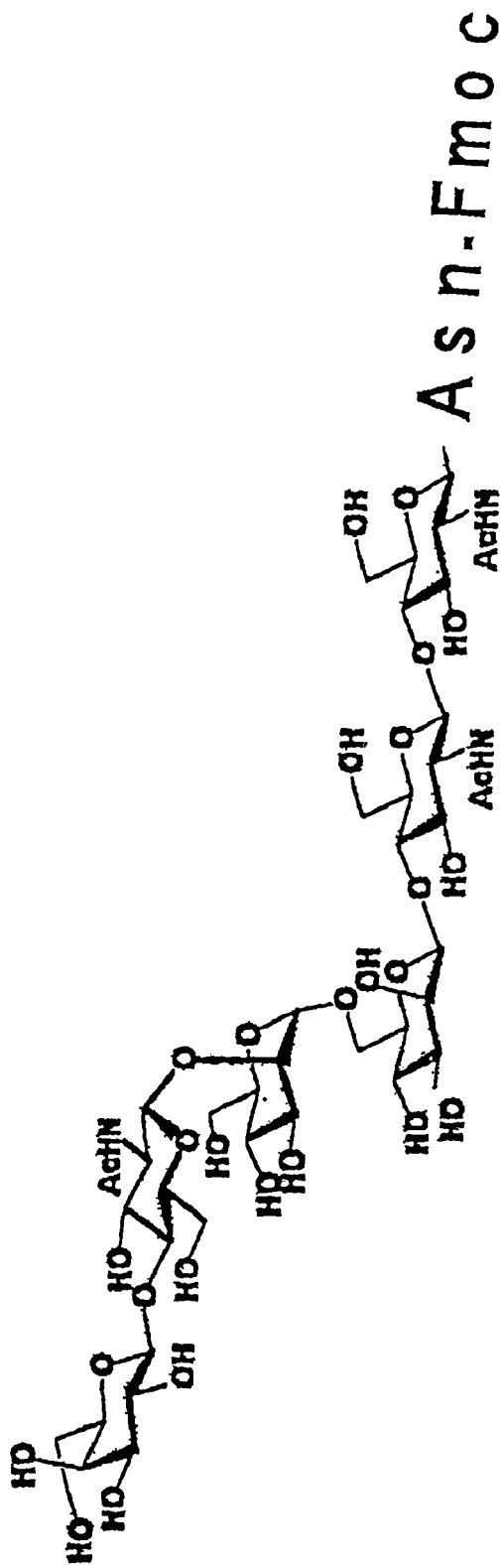
Figure 10H:
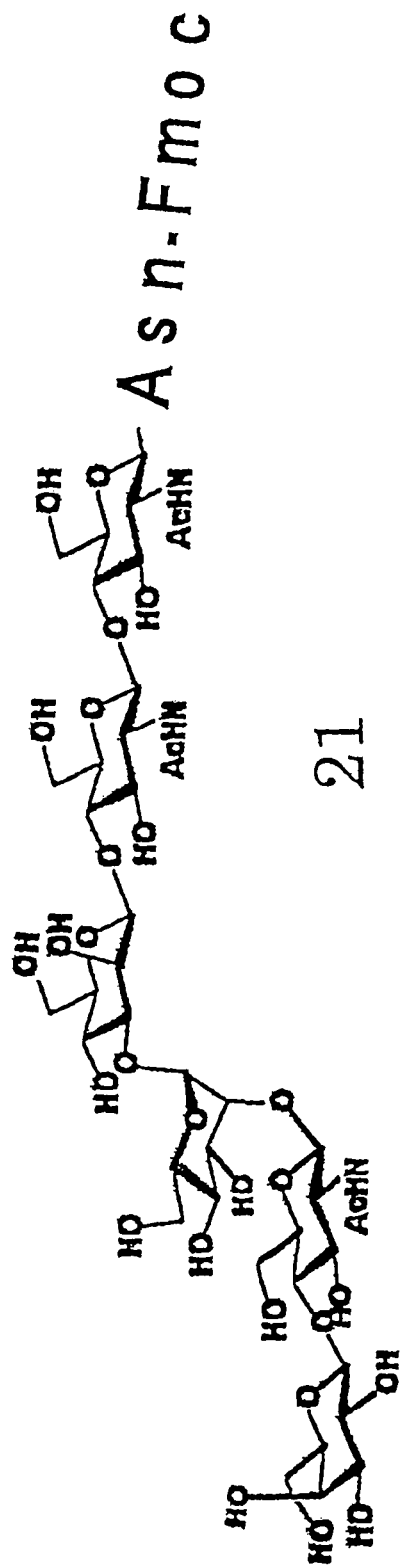
Figure 11A:
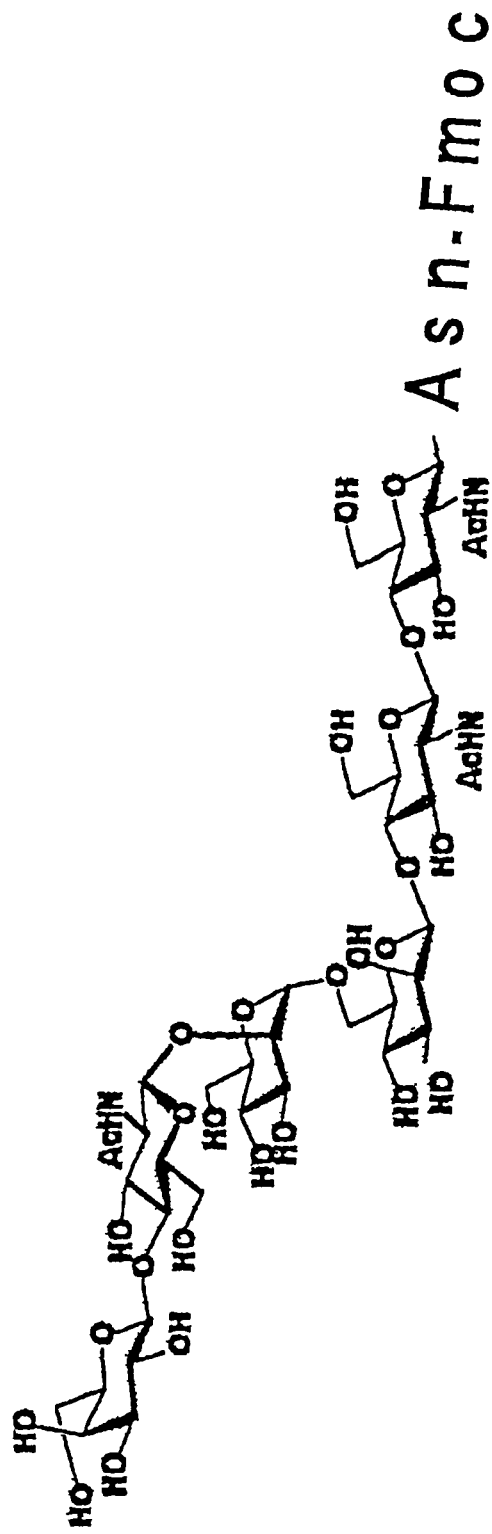
FIG. 11 shows an example of a conversion step of a sugar chain asparagine derivative with various glycosidases.
Figure 11B:
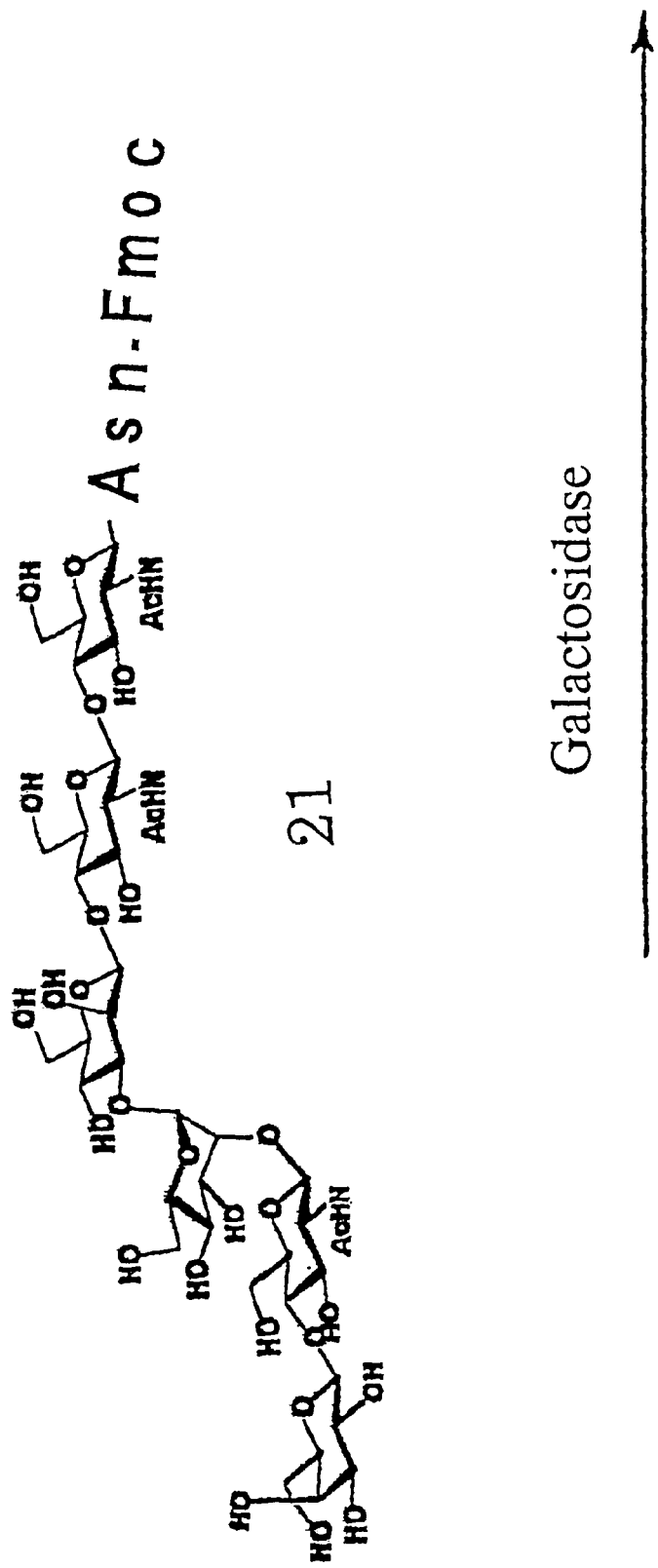
Figure 11C:
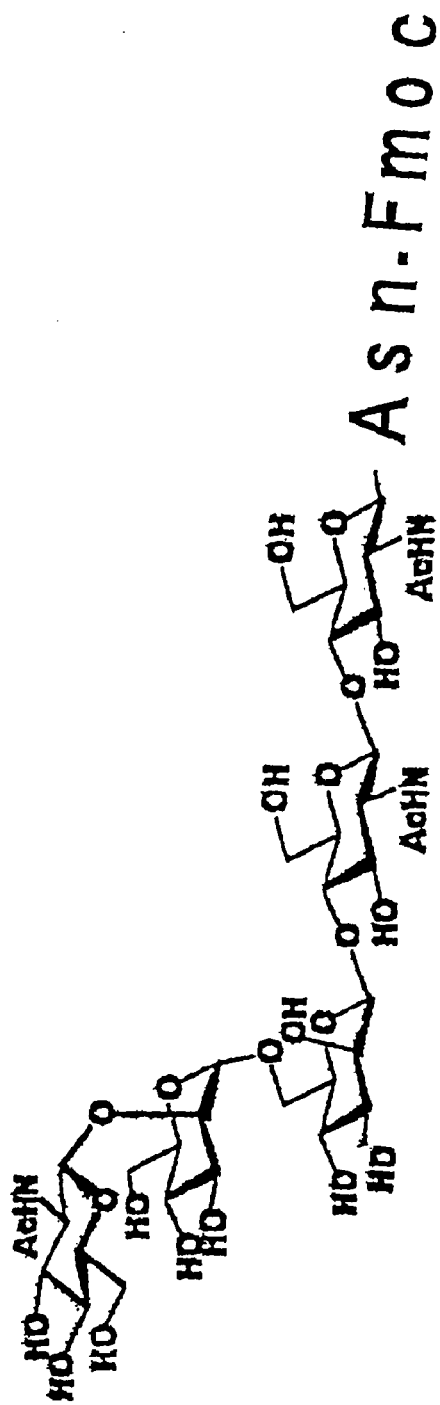
Figure 11D:
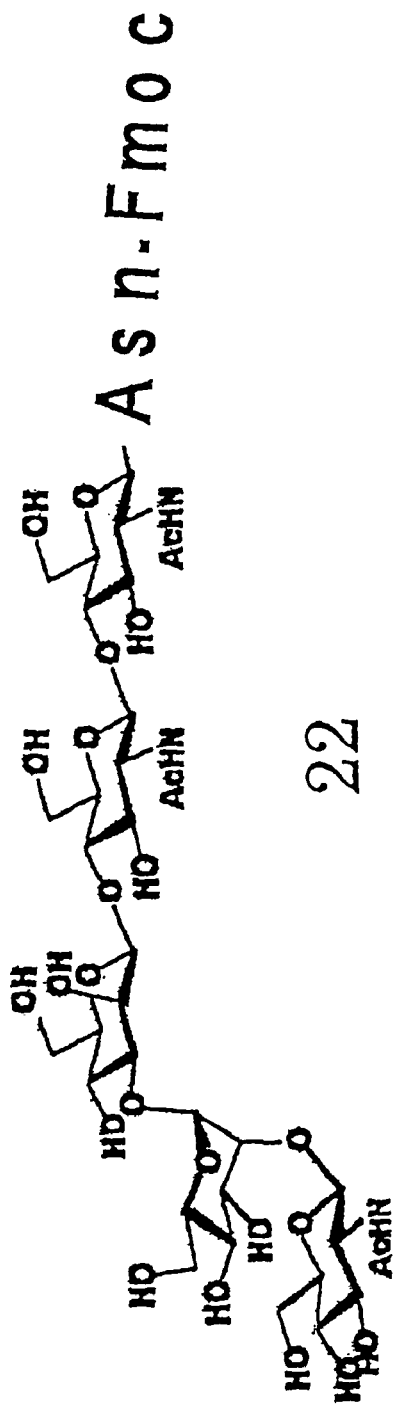
Figure 11E:
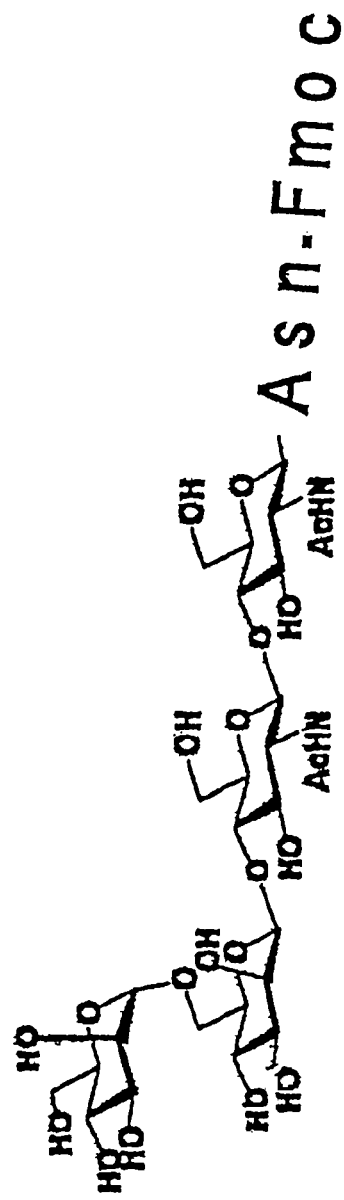
Figure 11F:
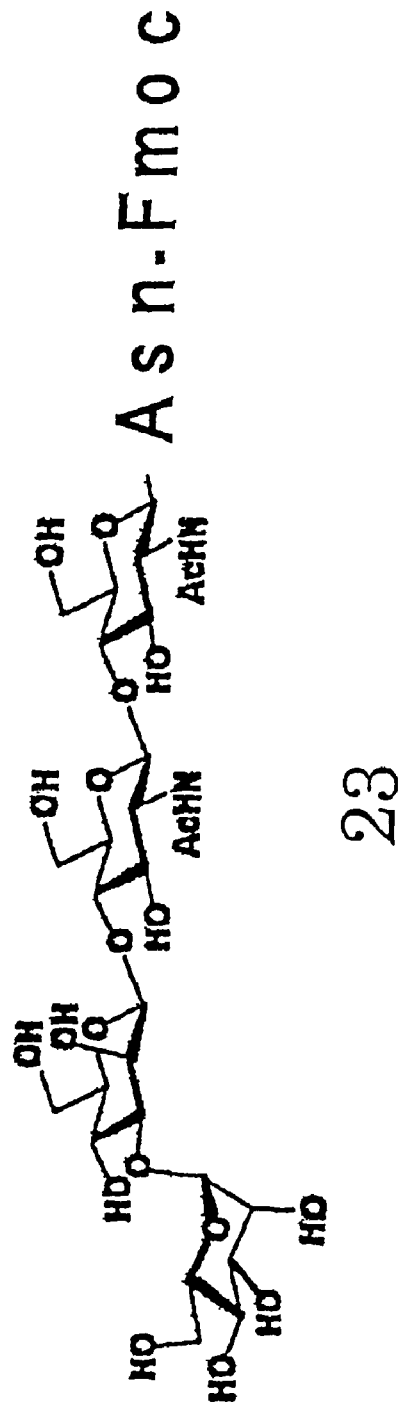

One of the features of the process for preparing a sugar chain asparagine derivative of the present invention resides in that the process comprises introducing (binding) a fat-soluble protecting group into (to) a sugar chain asparagine derived from, for instance, a naturally occurring glycoprotein, preferably a sugar chain asparagine contained in a mixture of sugar chain asparagines obtained from asparagine type sugar chains, to give a mixture of sugar chain asparagine derivatives, and thereafter separating the mixture into each of the sugar chain asparagine derivatives. The term "sugar chain asparagine" as used herein refers to a sugar chain having asparagine in a binding state. Also, the term "asparagine type sugar chain" refers to a group of sugar chains in each of which N-acetylglucosamine existing in a reducing terminal is bound by N-glycoside linkage to an acid amino group of asparagine (Asn) in a polypeptide of a protein, wherein the group of sugar chains have Man-β-(1-4)-GlcNAc-β-(1-4)-GlcNAc as a mother core. The term "sugar chain asparagine derivative" refers to a sugar chain asparagine having a fat-soluble protecting group in a state of binding to an asparagine residue. Also, in the structural formula of the compound, "AcHN" denotes acetamide group.

As mentioned above, the sugar chain derived from a naturally occurring glycoprotein is a mixture of sugar chains having random deletions of sugar residues at non-reducing terminals. The present inventors have surprisingly found that a fat-soluble protecting group is introduced into a sugar chain derived from a naturally occurring glycoprotein, concretely a sugar chain asparagine contained in a mixture of sugar chain asparagines, so that a mixture of the resulting sugar chain asparagine derivatives into which the protecting groups are introduced can be easily separated to individual sugar chain asparagine derivatives by means of a known chromatography. As a result, each of the sugar chain asparagine derivatives having a diversity of structures can be prepared in a large amount. For instance, the sugar chain asparagine derivatives having analogous structures, which had been conventionally difficult to separate, such as compounds 2 and 6 shown in FIG. 1 and compounds 3 and 7 shown in FIG. 2, can be separated, so that each of those compounds can be prepared easily in a large amount. In addition, many kinds of the sugar chain asparagine derivatives can be synthesized more by, for instance, removing the sugar residues from the resulting sugar chain asparagine derivative sequentially with glycosidases.

As described above, the individual sugar chain asparagine derivatives can be separated by introducing a fat-soluble protecting group into a sugar chain asparagine to derivatize the sugar chain asparagine. This is presumably due to the fact that a fat solubility of the overall sugar chain asparagine derivatives is increased by the introduction of the fat-soluble protecting group, so that an interaction with, for instance, a preferably employed reverse phase column is markedly improved, thereby resulting in even more sensitively separating individual sugar chain asparagine derivatives reflecting the difference in the sugar chain structures. For instance, the fat solubility of Fmoc group, which is a fat-soluble protecting group preferably used in the present invention, is very high. In other words, the fluorenyl backbone in Fmoc group has a very highly fat-soluble structure in which two benzene rings are bound to the 5-membered ring center. For instance, it is thought that a very strong interaction with octadecyl group in ODS column is generated, the ODS column being one of the reverse phase columns, whereby the sugar chain asparagine derivatives having analogous structures can be separated.

Further, according to the present invention, there can be obtained conveniently in a large amount various sugar chain asparagines by removing the protecting group of the resulting sugar chain asparagine derivatives, and also various sugar chains by removing the asparagine residues from the resulting sugar chain asparagines, as described below.

Concretely, the process for preparing a sugar chain asparagine derivative according to the present invention comprises the steps of:

(a) introducing a fat-soluble protecting group into the sugar chain asparagine contained in a mixture of one or more sugar chain asparagines, to give a mixture of sugar chain asparagine derivatives; and (b) subjecting the mixture of sugar chain asparagine derivatives or a mixture obtainable by hydrolyzing a sugar chain asparagine derivative contained in the mixture of sugar chain asparagine derivatives to chromatography, to separate each of the sugar chain asparagine derivatives therefrom.

The mixture of one or more sugar chain asparagines usable in the step (a) is not particularly limited, as long as the mixture is a mixture of one or more sugar chains each having asparagine in a binding state. For instance, the mixture may be a mixture of one or more sugar chains to which one or more asparagines are bound. Among them, the mixture of one or more sugar chains having asparagines bound at reducing terminals is preferred from the viewpoint of facilitation of availability. The term "sugar chain" as used herein refers to a sugar chain in which two or more monosaccharides are bound.

The mixture of the sugar chain asparagines can be obtained by a known process, preferably by obtaining a mixture of glycoproteins and/or glycopeptides from naturally occurring raw materials, such as milk, bovine-derived fetuin or egg, and adding to the mixture an enzyme such as protease, for instance, pronase (manufactured by Wako Pure Chemical Industries, Ltd.), Actinase-E (manufactured by Kaken Pharmaceutical Co., Ltd.) or a general carboxypeptidase or aminopeptidase to carry out a reaction under known reaction conditions to cleave a peptide moiety, thereby giving the mixture of the sugar chain asparagines as a reaction mixture after the reaction, or further removing the components other than the sugar chain asparagines from the reaction mixture by a known process, such as purification process using various chromatographic methods using gel filtration columns, ion exchange columns and the like and a high-performance liquid chromatography (HPLC), thereby giving the mixture of the sugar chain asparagines as a resulting product. From the viewpoint of the facilitation in the preparation, it is preferable that the above mixture is prepared by using a known egg-derived glycopeptide [*Biochimica et Biophysica Acta* 1335 (1997) p 23–32; crude SGP (a mixture containing proteins in egg yolk, an inorganic salt and the like, wherein the glycopeptide is contained in an amount of from about 10 to about 80% by weight)].

Also, it is more preferable that the sugar chain asparagines contained in the mixture are hydrolyzed to previously cleave a part of sugar residues thereof, from the viewpoint of efficiently obtaining the sugar chain asparagine derivatives having desired sugar chain structures. The degree of the cleavage is not particularly limited as long as the structure is retained within the scope of the term "sugar chain" as used herein. The mixture obtained as described above includes, for instance, a mixture containing a compound 24 shown in FIG. 3 and/or a compound having one or more deletions of sugar residues in the above compound. In this case, the upper limit of deletions of sugar residues from the compound is 9, from the viewpoint of retaining the structure of the "sugar chain" as used herein in the compound.

For instance, compounds 25 and 29 shown in FIG. 3 can be efficiently obtained in a mixture of the sugar chain asparagines containing the compound 24 (hereinafter referred to as a compound 24 mixture) by subjecting the mixture to an acid hydrolysis in the manner as described below, and furthermore the compounds 2 and 6 shown in FIG. 1, which are corresponding sugar chain asparagine derivatives, can be obtained efficiently.

For instance, an appropriate amount of an about 0.1 N aqueous acidic solution is added to the compound 24 mixture to carry out a reaction, for instance, at 4° to 100° C. During the reaction, with monitoring the progress of hydrolytic reaction by thin layer chromatography (for instance, silica gel 60F254 (manufactured by Merck), ethyl acetate: methanol:water=4:4:3 being used as an eluent), the reaction is stopped at a point where the compounds 25 and 29 can be obtained in the largest amount. For instance, the reaction may be stopped after about 5 to 10 hours under the condition of 25° C., or after about several minutes under the condition of 100° C. Preferably, the reaction is carried out at 70° C., the reaction is stopped 35 minutes after the beginning of the reaction, and the mixture is cooled on ice rapidly. The reaction can be stopped by neutralizing the reaction solution. In addition, the above acid is not particularly limited. For instance, there can be used inorganic acids and organic acids such as hydrochloric acid, sulfuric acid, nitric acid and trifluoroacetic acid, a cationic exchange resin, an insoluble solid reagent and the like.

Similarly, a compound 33 can be efficiently obtained from the compound 24 in the above mixture. For instance, an appropriate amount of the above aqueous acidic solution is added to the compound 24 mixture, the reaction is carried out preferably at 80° C., and the reaction is stopped at preferably 60 minutes after the beginning of the reaction.

The hydrolysis may also be carried out enzymatically. The enzyme used in the reaction is preferably a glycosidase, and an enzyme of either endo- or exo-reaction forms can be used. For instance, when the compounds 25 and 29 are obtained from the compound 24 in the same manner as described above, a sialic acid hydrolase having an activity of cleaving sialic acid at a terminal can be used. The enzyme is not particularly limited, and the enzyme may be any of commercially available enzymes, newly isolated enzymes, enzymes generated by means of genetic engineering and the like, as long as the enzyme has the above activity. The enzymatic reaction may be carried out in accordance with a known condition. During the reaction, the progress is monitored by thin layer chromatography in the same manner as described above, and the reaction may be appropriately stopped at a point where the compounds 25 and 29 are obtained in the largest amounts.

The fat-soluble protecting group is introduced into the sugar chain asparagine contained in the mixture of sugar chain asparagines using the mixture obtained as described above. The protecting group is not particularly limited, and there can be used, for instance, a carbonate-based or amide-based protecting group, such as Fmoc group, t-butyloxycarbonyl (Boc) group, benzyl group, allyl group, allyloxycarbonate group, or acetyl group. From the viewpoint that the resulting sugar chain asparagine derivative can be immediately used in the synthesis of a desired glycopeptide, the above protecting group is preferably Fmoc group, Boc group or the like, more preferably Fmoc group. The Fmoc group is especially effective when there exists in the sugar chain a sugar, such as sialic acid, which is relative unstable under acidic conditions. The introduction of the protecting group may be carried out according to a known process (for instance, *Protecting Groups in Organic Chemistry*, John Wiley & Sons INC., New York 1991, ISBN 0-471-62301-6).

For instance, when Fmoc group is used, an appropriate amount of acetone is added to the mixture containing sugar chain asparagines, 9-fluorenylmethyl-N-succinimidyl carbonate and sodium hydrogencarbonate are further added thereto and dissolved, and thereafter the resulting mixture is subjected to a binding reaction of Fmoc group to an asparagine residue at 25° C., whereby the Fmoc group can be introduced into the asparagine residue of the above sugar chain asparagine.

According to the procedures described above, a mixture of the sugar chain asparagine derivatives into each of which a fat-soluble protecting group is introduced is obtained.

Next, in the step (b), the mixture of the sugar chain asparagine derivatives is subjected to a known chromatography, especially a fractional chromatography, to separate each of the sugar chain asparagine derivatives therefrom. In this step, the mixture of sugar chain asparagine derivatives obtained in the above step (a) can be directly used. Alternatively, there may be used a mixture of the sugar chain asparagine derivatives obtained by further subjecting sugar chain asparagine derivatives contained in the above mixture to hydrolysis to previously cleave a part of the sugar residues thereof, from the viewpoint of efficiently obtaining sugar chain asparagine derivatives having the desired sugar chain structures. The degree of the cleavage of the sugar residues is the same as that described above. In addition, the hydrolysis may be carried out in the same manner as described above.

For instance, when compounds 3 and 7 are obtained, the mixture containing compounds 2 and 6 is subjected to hydrolytic treatment with a galactosidase, instead of separating the compounds 3 and 7 from the mixture, whereby the compounds 3 and 7 can be further easily separated from the resulting mixture by HPLC, and each of the compounds can be obtained as an isolated product in a large amount.

The separation of each of sugar chain asparagine derivatives by chromatography can be carried out by appropriately using known chromatographies, singly or in a combination of plural chromatographies.

For instance, the resulting mixture of sugar chain asparagine derivatives is purified by a gel filtration column chromatography, and then purified by using HPLC. The column which can be used in HPLC is preferably a reverse phase column, for instance, ODS, phenyl-based, nitrile-based, or anion exchange-based column, and concretely, a monoQ column manufactured by Pharmacia, Iatro-beads column manufactured by Iatron can be utilized. The separation conditions and the like may be adjusted by referring to a known condition. According to the above procedures, each of the desired sugar chain asparagine derivatives can be obtained from the mixture of sugar chain asparagine derivatives. FIG. 7 schematically shows an example of a step in the process for preparing a sugar chain asparagine derivative of the present invention.

Furthermore, the sugar chain asparagine derivative having a desired sugar chain structure can be efficiently obtained by hydrolyzing the sugar chain asparagine derivatives separated in the step (b) [step (b')]. For instance, in the stage of separating the sugar chain asparagine derivatives, the sugar chain asparagine derivatives can be roughly separated by limiting the kinds of the sugar chain asparagine derivatives contained in the mixture, and thereafter the sugar chain asparagine derivatives are subjected to hydrolysis, for instance, hydrolysis with a glycosidase, whereby the sugar chain asparagine derivatives having the desired sugar chain structures can be efficiently obtained. Here, the hydrolysis can be carried out in the same manner as described above. Especially, it is preferable that the hydrolysis is carried out with a glycosidase of which cleavage mode of the sugar residues is clear, from the viewpoint of more efficiently obtaining the sugar chain asparagine derivatives having the desired sugar chain structures.

For instance, the conversion of the compounds 2 and 6 to the compounds 3 and 7 by the removal of the galactose residues (FIG. 8) can be accomplished by dissolving the compounds 2 and 6 in a buffer (for instance, phosphate buffer, acetate buffer, Good's buffer or the like), and carrying out cleavage reaction of the galactose residues with a galactosidase in accordance with a known condition. The compounds 2 and 6 may be a mixture of these or individually isolated compounds. It is preferable that a commercially available known exo-form enzyme is utilized for the galactosidase used in this reaction. Also, the enzyme may be a newly isolated enzyme or an enzyme generated by genetic engineering, as long as the enzyme has a similar activity. Next, in the same manner as described above, the reaction solution obtained after the reaction (a mixture of sugar chain asparagine derivatives of which sugar residues are cleaved) may be subjected to chromatography to give each of sugar chain asparagine derivatives. For instance, it is preferable that the separation is carried out by HPLC (ODS column, eluent being a 50 mM aqueous ammonium acetate:acetonitrile=82:15).

The conversion of the compounds 3 and 7 to the compounds 4 and 8 by the removal of the N-acetylglucosamine residues (FIG. 8) can be accomplished by dissolving the compounds 3 and 7 in a buffer (for instance, phosphate buffer, acetate buffer, Good's buffer or the like), and carrying out cleavage reaction of the N-acetylglucosamine residues with an N-acetylglucosaminidase in accordance with a known condition. Also, an N-acetylhexosaminidase can be used. The compounds 3 and 7 may be mixtures of these or individually isolated compounds. It is preferable that a commercially available known exo-form enzyme is utilized for each enzyme used in this reaction. Also, the enzyme may be a newly isolated enzyme or an enzyme generated by genetic engineering, as long as the enzyme has a similar activity. Next, in the same manner as described above, the reaction solution obtained after the reaction (a mixture of sugar chain asparagine derivatives of which sugar residues are cleaved) is subjected to chromatography to give each of sugar chain asparagine derivatives. For instance, it is preferable that the separation is carried out by HPLC (ODS column, eluent being a 50 mM aqueous ammonium acetate:methanol=65:35 or a 50 mM aqueous ammonium acetate:acetonitrile=82:15).

The conversion of the compounds 4 and 8 to the compounds 5 and 9 by the removal of the mannose residues (FIG. 8) can be accomplished by dissolving the compounds 4 and 8 in a buffer (for instance, phosphate buffer, acetate buffer, Good's buffer or the like), and carrying out cleavage reaction of the mannose residues with a mannosidase under a known condition. The compounds 4 and 8 may be a mixture of these or individually isolated compounds. It is preferable that a commercially available known exo-form enzyme is utilized for the mannosidase used in this reaction. Also, the enzyme may be a newly isolated enzyme or an enzyme generated by genetic engineering, as long as the enzyme has a similar activity. Next, in the same manner as described above, the reaction solution obtained after the reaction (a mixture of sugar chain asparagine derivatives of which sugar residues are cleaved) is subjected to chromatography to give each of sugar chain asparagine derivatives. For instance, it is preferable that the separation is carried out by HPLC (ODS column, eluent: there can be used, for instance, a mixed solution of a buffer such as an about 10 to about 200 mM ammonium acetate and a water-soluble organic solvent with fat solubility such as acetonitrile, or ethanol, or methanol, or butanol, or propanol in appropriate amounts; when exemplified herein, it is preferable that the eluent is a 50 mM aqueous ammonium acetate:acetonitrile=82:18.).

The conversion of the compound 10 to the compound 11 by the removal of the galactose residues (FIG. 9) can be accomplished by dissolving a compound 10 in a buffer (for instance, phosphate buffer, acetate buffer, Good's buffer or the like), and carrying out cleavage reaction of the galactose residues with a galactosidase in accordance with a known condition in the same manner as described above. It is preferable that the separation of the sugar chain asparagine derivatives from the reaction solution obtained after the reaction (a mixture of sugar chain asparagine derivatives of which sugar residues are cleaved) is carried out by, for instance, HPLC (ODS column, eluent being a 50 mM aqueous ammonium acetate:acetonitrile=85:15).

Also, by further hydrolyzing the compound 11 with an arbitrary glycosidase, the compound can be converted into various sugar chain asparagine derivatives (for instance, compounds 11, 12, 13 and the like).

The conversion of the compound 11 to the compound 12 by the removal of the N-acetylglucosamine residues (FIG. 9) can be accomplished by dissolving the compound 11 in a buffer (for instance, phosphate buffer, acetate buffer, Good's buffer or the like), and carrying out cleavage reaction of the N-acetylglucosamine residues with an N-acetylglucosaminidase under a known condition in the same manner as described above. It is preferable that the separation of the sugar chain asparagine derivatives from the reaction solution obtained after the reaction (a mixture of sugar chain asparagine derivatives of which sugar residues are cleaved) is carried out by, for instance, HPLC (ODS column, eluent being a 50 mM aqueous ammonium acetate:acetonitrile=85:18).

The conversion of the compound 12 to the compound 13 by the removal of the mannose residues (FIG. 9) can be accomplished by dissolving the compound 12 in a buffer (for instance, phosphate buffer, acetate buffer, Good's buffer or the like), and carrying out cleavage reaction of the mannose residues with a mannosidase in accordance with a known condition in the same manner as described above. It is preferable that the separation of each of sugar chain asparagine derivatives from the reaction solution obtained after the reaction (a mixture of sugar chain asparagine derivatives of which sugar residues are cleaved) is carried out by, for instance, high-performance liquid column chromatography (ODS column, eluent being a 50 mM aqueous ammonium acetate:acetonitrile=82:18).

The conversion of the compounds 3 and 7 to the compounds 14 and 19 (FIG. 10) can be accomplished by dissolving the compounds 3 and 7 in a buffer (for instance, phosphate buffer, acetate buffer, Good's buffer or the like), and carrying out cleavage reaction of the sialic acid residues with a neuraminidase in accordance with a known condition. The compounds 3 and 7 may be a mixture of these or individually isolated compounds. It is preferable that a commercially available known exo-form enzyme is utilized for the sialic acid hydrolase used in this reaction. Also, the enzyme may be a newly isolated enzyme or an enzyme generated by genetic engineering, as long as the enzyme has a similar activity. Thereafter, in the same manner as described above, the reaction solution obtained after the reaction (a mixture of sugar chain asparagine derivatives of which sugar residues are cleaved) is subjected to chromatography to give each of sugar chain asparagine derivatives. For instance, it is preferable that the separation is carried out by high-performance liquid column chromatography (ODS column, eluent being a 50 mM aqueous ammonium acetate: acetonitrile=85:15).

The conversion of the compounds 14 and 19 to the compounds 15 and 20 by the removal of the N-acetylglucosamine residues (FIG. 10) can be accomplished by dissolving the compounds 14 and 19 in a buffer (for instance, phosphate buffer, acetate buffer, Good's buffer or the like), and carrying out cleavage reaction of the N-acetylglucosamine residues with an N-acetylglucosaminidase or the like in accordance with a known condition in the same manner as described above. It is preferable that the separation of each of sugar chain asparagine derivatives from the reaction solution obtained after the reaction (a mixture of sugar chain asparagine derivatives of which sugar residues are cleaved) is carried out by, for instance, high-performance liquid column chromatography (ODS column, eluent being a 50 mM aqueous ammonium acetate:acetonitrile=82:18).

The conversion of the compounds 15 and 20 to the compounds 16 and 21 by the removal of the mannose residues (FIG. 10) can be accomplished by dissolving the compounds 15 and 20 in a buffer (for instance, phosphate buffer, acetate buffer, Good's buffer or the like), and carrying out cleavage reaction of the mannose residues with a mannosidase in accordance with a known condition in the same manner as described above. It is preferable that the separation of each of sugar chain asparagine derivatives from the reaction solution obtained after the reaction (a mixture of sugar chain asparagine derivatives of which sugar residues are cleaved) is carried out by, for instance, high-performance liquid column chromatography (ODS column, eluent being a 50 mM aqueous ammonium acetate:acetonitrile=82:18).

The conversion of the compounds 16 and 21 to the compounds 17 and 22 by the removal of the galactose residues (FIG. 11) can be accomplished by dissolving the compounds 16 and 21 in a buffer (for instance, phosphate buffer, acetate buffer, Good's buffer or the like), and carrying out cleavage reaction of the galactose residues with a galactosidase in accordance with a known condition in the same manner as described above. It is preferable that the separation of each of sugar chain asparagine derivatives from the reaction solution obtained after the reaction (a mixture of sugar chain asparagine derivatives of which sugar residues are cleaved) is carried out by, for instance, high-performance liquid column chromatography (ODS column, eluent being a 50 mM aqueous ammonium acetate:acetonitrile=85:15).

The conversion of the compounds 17 and 22 to the compounds 18 and 23 by the removal of the N-acetylglucosamine residues (FIG. 11) can be accomplished by dissolving the compounds 17 and 22 in a buffer (for instance, phosphate buffer, acetate buffer, Good's buffer or the like), and carrying out cleavage reaction of the N-acetylglucosamine residues with an N-acetylglucosaminidase or the like in accordance with a known condition in the same manner as described above. It is preferable that the separation of each of sugar chain asparagine derivatives from the reaction solution obtained after the reaction (a mixture of sugar chain asparagine derivatives of which sugar residues are cleaved) is carried out by, for instance, high-performance liquid column chromatography (ODS column, eluent being a 50 mM aqueous ammonium acetate:acetonitrile=82:18).

As described above, each of the various sugar chain asparagine derivatives of which branching structures at the terminals of the sugar chains are not uniform, can be obtained as individual isolated compounds by further hydrolyzing the derivatives with various glycosidases and the like to remove the sugar residues at non-reducing terminals of the sugar chains after the obtainment of each of the sugar chain asparagine derivatives. Moreover, even a larger number of the kinds of the sugar chain asparagine derivatives can be prepared by changing the order or the kind of hydrolysis with various glycosidases.

According to a conventional process, enormous amounts of time and cost for obtaining the sugar chain asparagine derivatives having very limited sugar chain structures are required even on an analytical scale. On the contrary, according to the present invention, about 1 gram of the sugar chain asparagine derivatives having desired sugar chain structures can be prepared in an about 2-week period by using a conventional gel filtration column, HPLC column, and at least three kinds of glycosidases (for instance, galactosidase, mannosidase, and N-acetylglucosamidase) without necessitating any particular devices or reagents.

In accordance with the procedures described above, when the protecting group, for instance, is Fmoc group, there can be efficiently obtained a sugar chain asparagine derivative represented by the general formula:

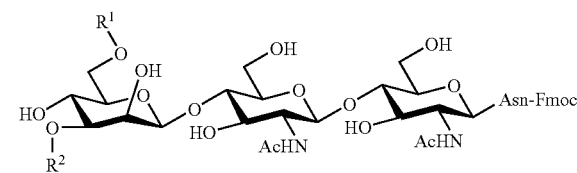

wherein $R^1$ and $R^2$, which may be identical or different, are H,

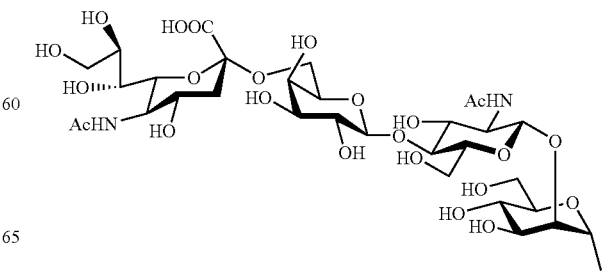

-continued

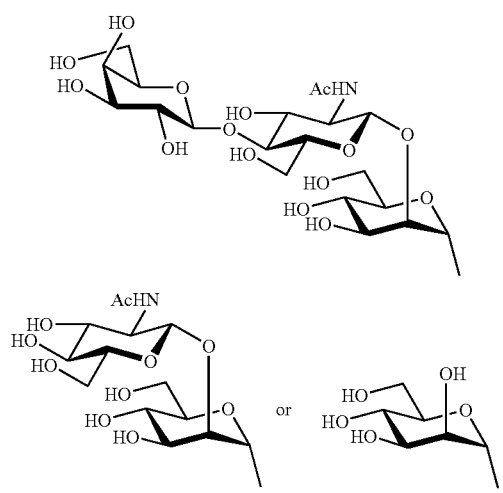

with proviso that a case where $R^1$ and $R^2$ are both is excluded.

Concretely, the above sugar chain asparagine derivative includes, for instance, each of the compounds shown in FIG. 1 and FIG. 2. Among them, the compound 1, the compounds 2 to 9, 11 to 23, 70 and 71 are compounds prepared for the first time in the present invention. The present invention encompasses the above compounds.

In addition, as a preferred embodiment of the process for preparing a sugar chain asparagine derivative of the present invention, there is provided a process for preparing a sugar chain asparagine derivative in which the step (a) is a step of providing a mixture of one or more sugar chain asparagines each having a sialic acid residue at a non-reducing terminal, introducing Fmoc group into the sugar chain asparagines contained in the above mixture, and introducing benzyl group into the sialic acid residue, to give a mixture of sugar chain asparagine derivatives. According to the above process, various forms of the sugar chain asparagine derivatives can be more efficiently obtained in a large amount. For instance, the separation efficiency of the compounds 2 and 6 shown in FIG. 1 can be increased, whereby the both compounds can be efficiently prepared. In other words, while there is a disadvantage in efficiently directly separating the compounds 2 and 6 definitely from a mixture of the both compounds, in this embodiment, the both compounds can be efficiently obtained from the mixture by introducing benzyl group into a sialic acid residue of the both compounds, and subjecting to the above step (b) first of all as a mixture of the following compounds 76 and 77:

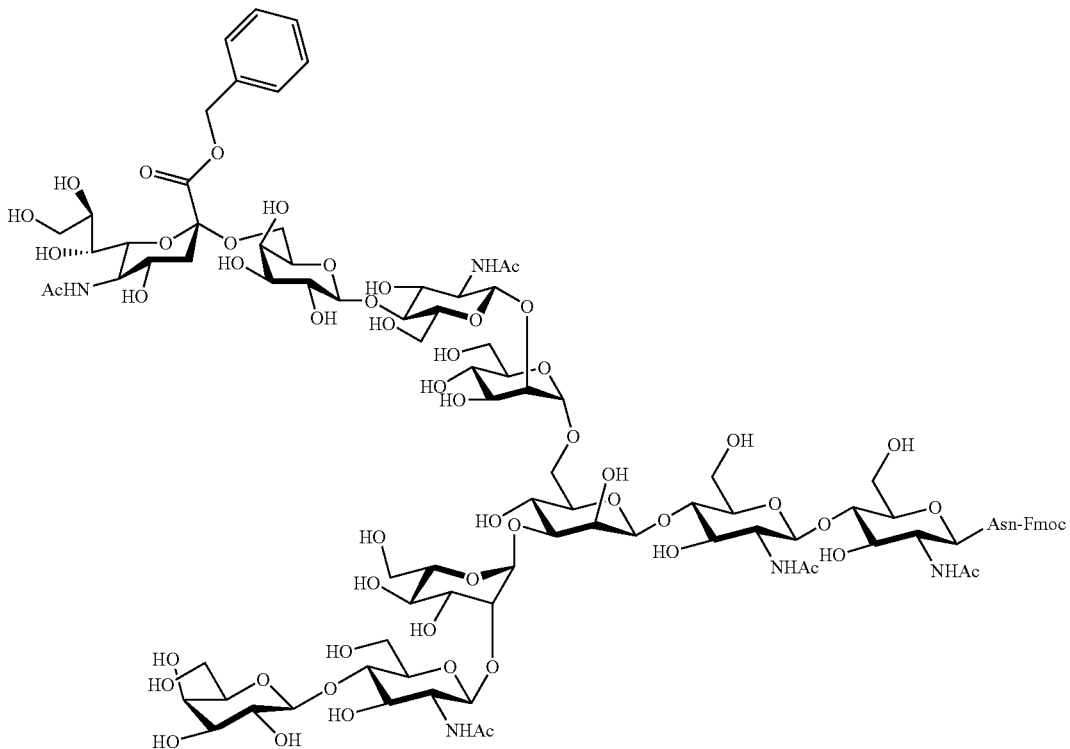

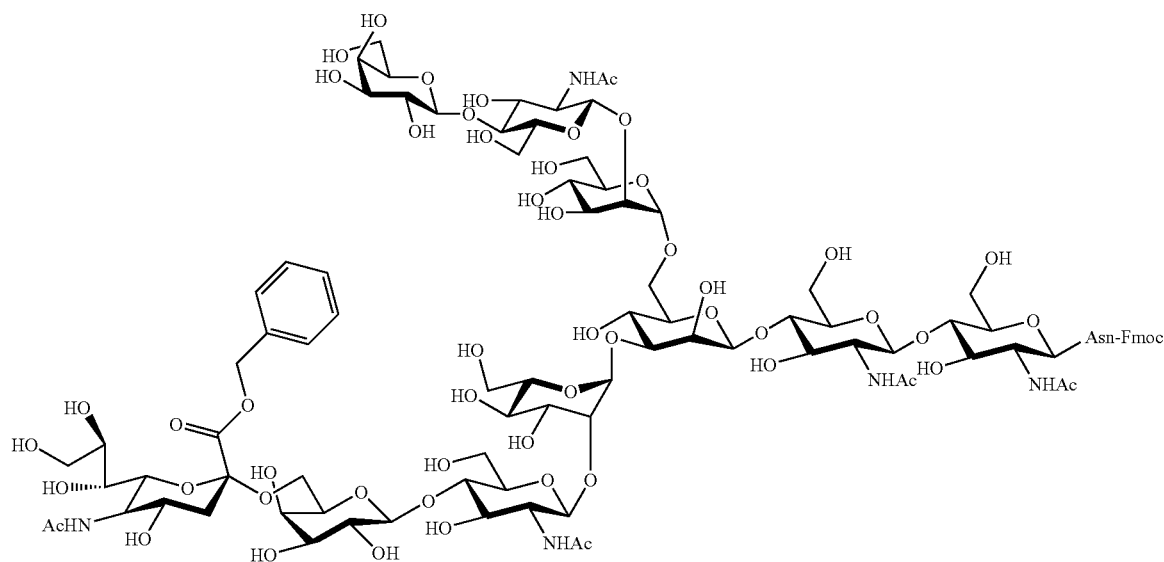

77

Therefore, since the compounds 76 and 77 can be relatively easily separated, the compounds can be separated, and thereafter removing the benzyl group from the compounds 76 and 77 by a process described below enable compounds 2 and 6 to be efficiently separated and obtained from the mixture of the compounds.

Contrary to the somewhat difficulty in separation of the compounds 2 and 6, it is thought that the reason why the separation of the compounds 76 and 77, which are obtained by introducing benzyl group into a sialic acid residue of the compounds 2 and 6, can be easily carried out is that a highly fat-soluble benzyl group is introduced into carboxyl group of the sialic acid residue, so that a hydrophobic interaction with a reverse phase column of HPLC (high-performance liquid chromatography) is further increased. Therefore, it is deduced that the interaction with the reverse phase column preferably employed in the separation step (b) may be markedly improved, whereby consequently the separation of the both compounds can be accomplished reflecting the difference in the sugar chain structure more sensitively.

The mixture of one or more sugar chain asparagines each having a sialic acid residue at a non-reducing terminal is not particularly limited, as long as the mixture is a mixture of one or more sugar chain asparagines having the above structure. A mixture of one or more sugar chains each having a sialic acid residue at a non-reducing terminal and also having asparagine bound at a reducing terminal is preferred from the viewpoint of easy availability. As the above mixture, a mixture containing the compound 24 shown in FIG. 3 and/or a compound having one or more deletions of sugar residues in the above compound is preferred.

It is preferable to carry out the above step (b'), from the viewpoint of further efficiently obtaining a sugar chain asparagine derivative having the desired sugar chain structure.

In this embodiment, as the sugar chain asparagine derivatives, there are obtained those prepared by introducing benzyl group and Fmoc group thereinto, and those prepared by introducing only Fmoc group thereinto.

The introduction of benzyl group into a sialic acid residue of the sugar chain asparagine may be carried out in accordance with a known process (for instance, see *Protecting Groups in Organic Chemistry*, John Wiley & Sons INC., New York 1991, ISBN 0-471-62301-6).

In accordance with the above procedures, for instance, there can be efficiently obtained a sugar chain asparagine derivative having benzyl group and Fmoc group introduced thereinto, respectively, which is represented by the general formula:

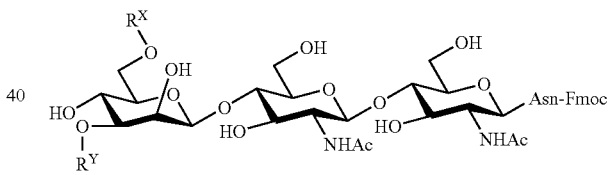

wherein one of $R^x$ and $R^y$ is

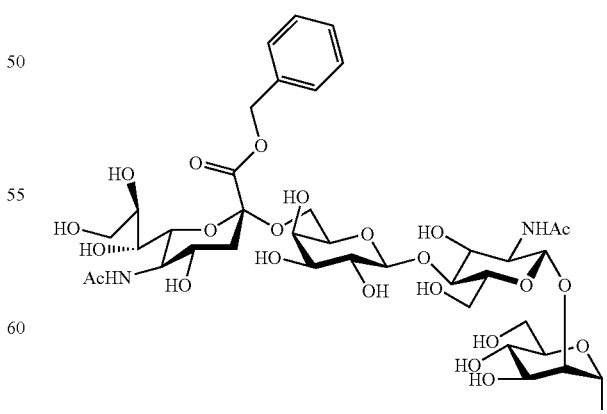

and the other is H,

25
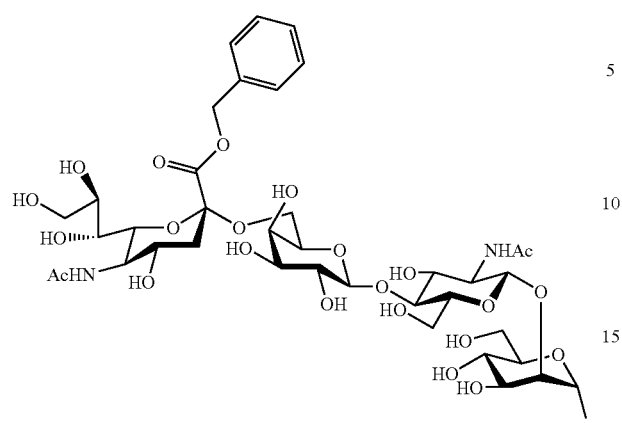
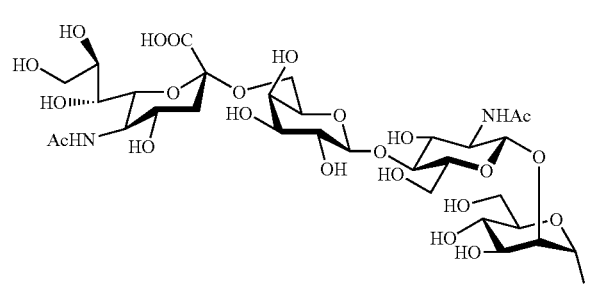
26
-continued
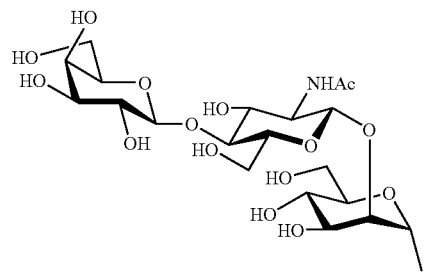
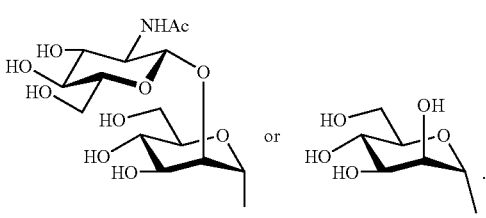
Concretely, the sugar chain asparagine derivative includes the above compounds 76 and 77, and the following compound 78:
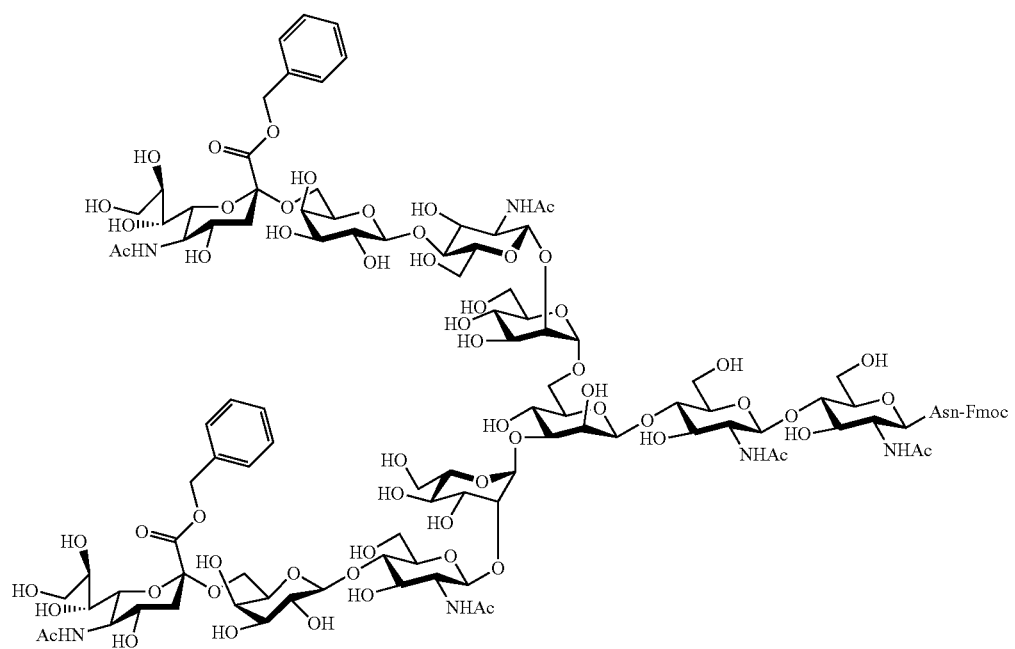

The sugar chain asparagine derivative obtained according to this embodiment can be directly used in solid phase synthesis of a glycopeptide. Since carboxyl group existing in a sialic acid residue of the sugar chain asparagine derivative is protected by benzyl group, there are some advantages that the desired sugar peptide can be efficiently obtained without causing side reactions involving the carboxyl group in the solid phase synthesis of the glycopeptide, as compared to the sugar chain asparagine derivative without introduction of benzyl group.

Also, the present invention provides a process for preparing a sugar chain asparagine capable of obtaining each of the various isolated sugar chain asparagines in a large amount. The above process further comprises, subsequent to the step of preparing a sugar chain asparagine derivative in accordance with the above process for preparing a sugar chain asparagine derivative, a step of removing the protecting group from the resulting sugar chain asparagine derivative.

In other words, the process for preparing a sugar chain asparagine according to the present invention comprises the steps of:

(a) introducing a fat-soluble protecting group into a sugar chain asparagine contained in a mixture of one or more sugar chain asparagines, to give a mixture of sugar chain asparagine derivatives;

(b) subjecting the mixture of sugar chain asparagine derivatives or a mixture obtainable by hydrolyzing a sugar chain asparagine derivative contained in the mixture of sugar chain asparagine derivatives to chromatography, to separate each of sugar chain asparagine derivatives therefrom; and (c) removing the protecting group from the sugar chain asparagine derivative separated in the step (b), to give a sugar chain asparagine.

The steps (a) and (b) are the same as those in the above process for preparing a sugar chain asparagine derivative, and the mixture of one or more sugar chain asparagines used and the fat-soluble protecting group used are also the same as those described above.

Figure 12A:
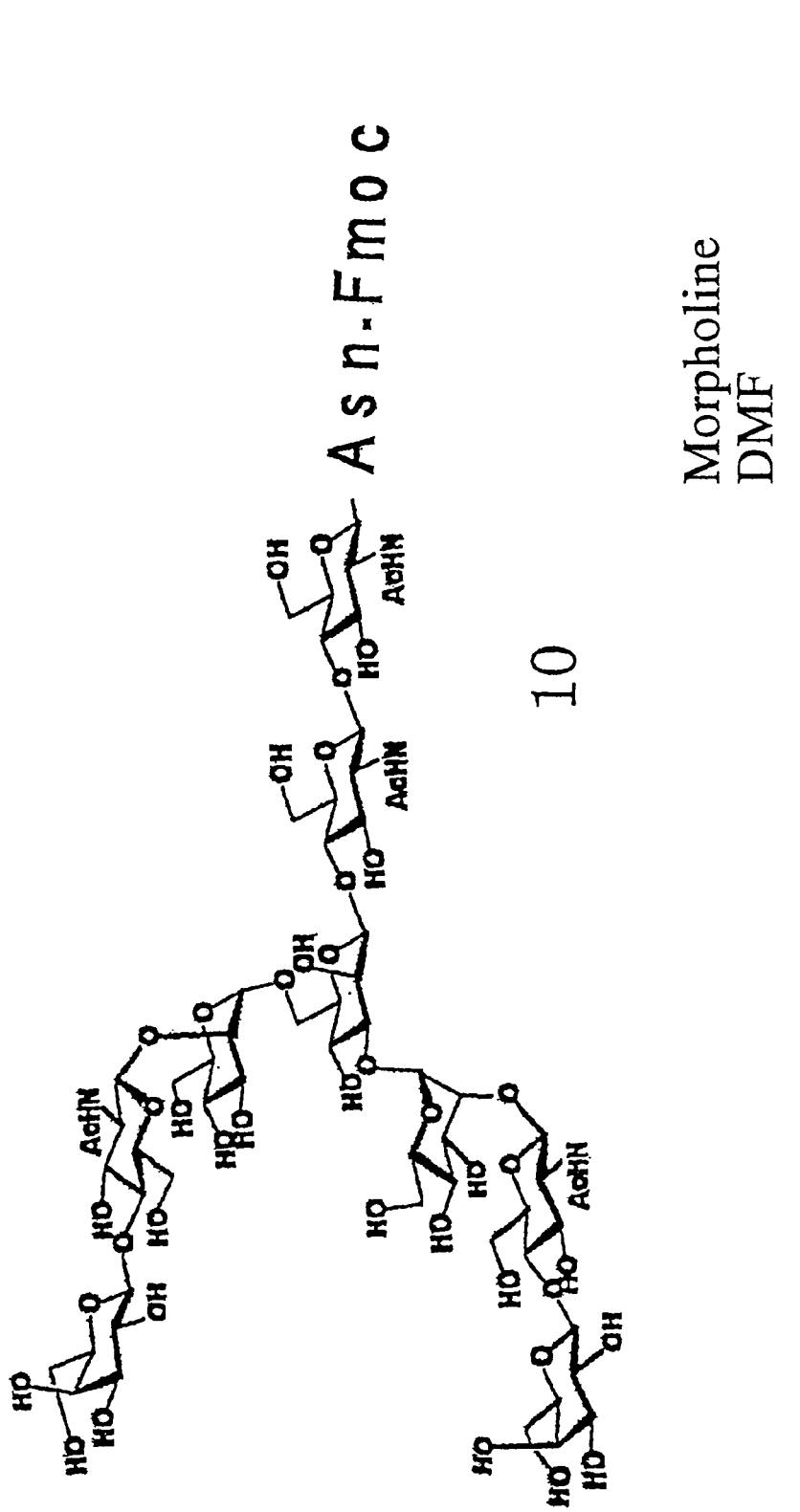
FIG. 12 shows an example of a step of removing a protecting group (Fmoc group) from a sugar chain asparagine derivative and an example of a step of removing an asparagine residue from a sugar chain asparagine.
Figure 12B:
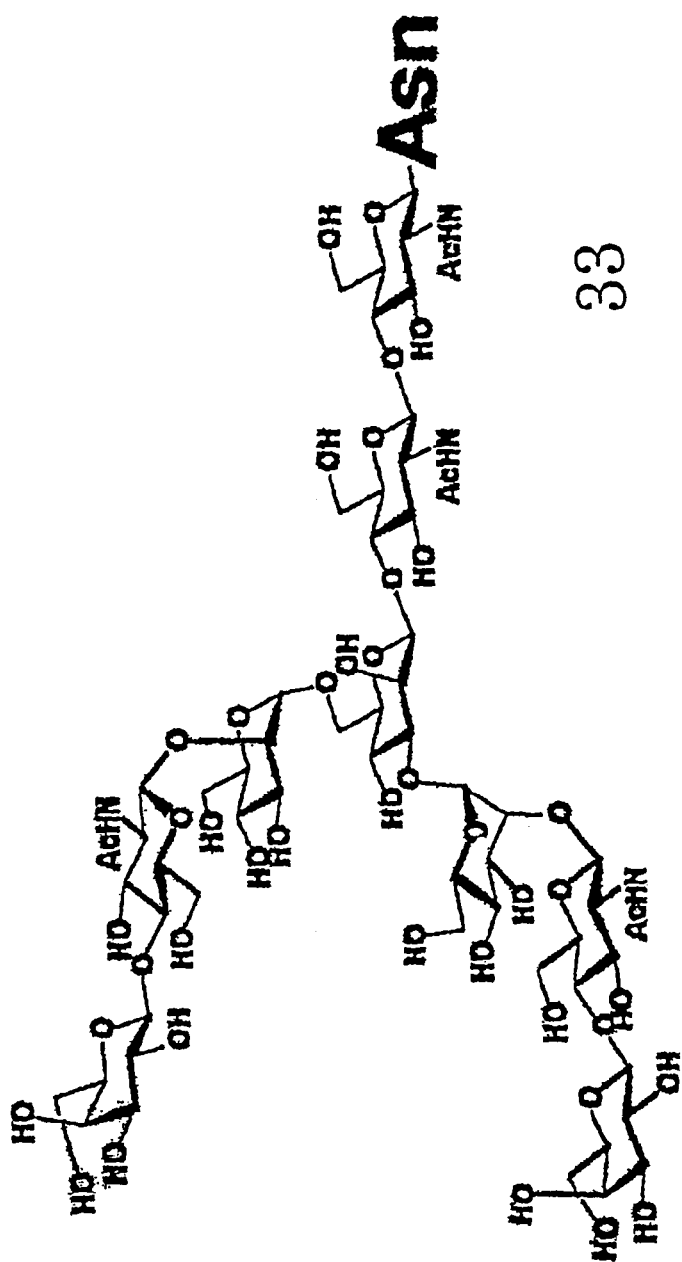
Figure 12C:
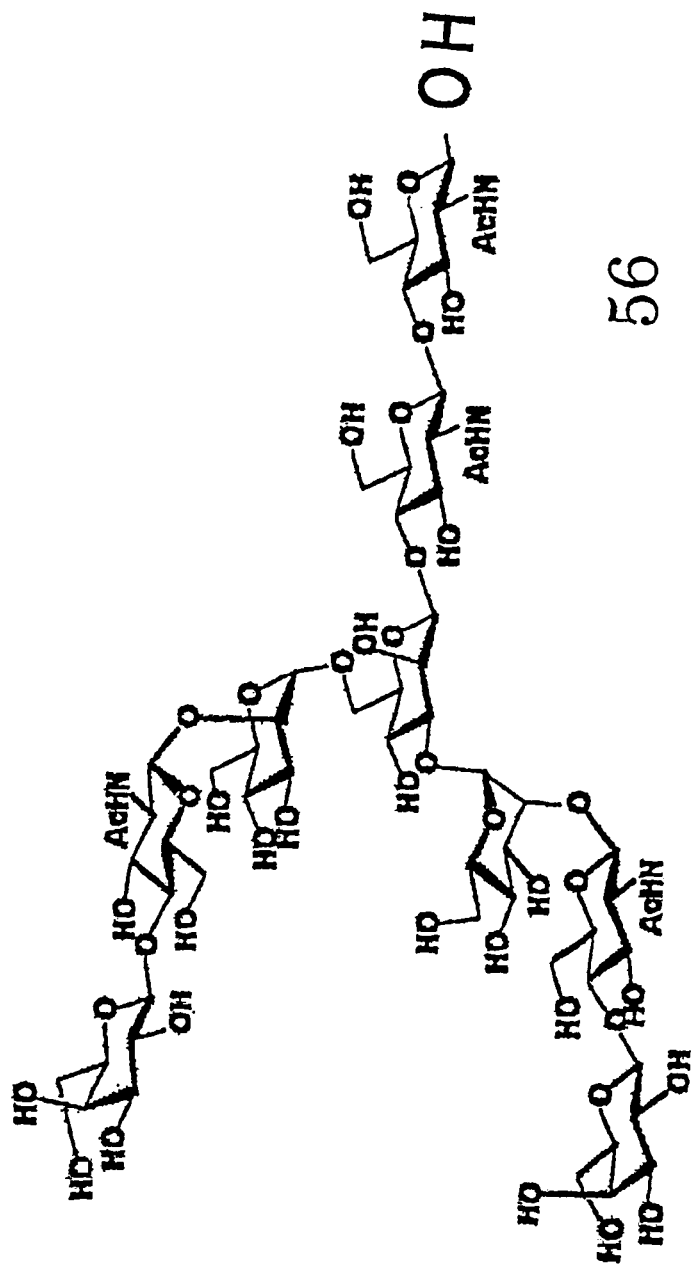

The removal of the protecting group from the sugar chain asparagine derivative in the step (c) can be carried out in accordance with a known process (for instance, see *Protecting Groups in Organic Chemistry*, John Wiley & Sons INC., New York 1991, ISBN 0-471-62301-6). For instance, when the protecting group is Fmoc group, the Fmoc group can be removed by adding morpholine to the sugar chain asparagine derivative in N,N-dimethylformamide (DMF) to carry out the reaction, as schematically shown in FIG. 12. On the other hand, Boc group can be removed by a reaction with a weak acid. After the removal of the protecting group, a sugar chain asparagine may be properly obtained by purifying a reaction mixture by a known process such as various chromatographies employing a gel filtration column, an ion exchange column or the like or a process of separation by HPLC as desired.

In addition, similarly to the above process for preparing a sugar chain asparagine derivative, as a preferred embodiment of the process for preparing a sugar chain asparagine of the present invention, there is provided a process for preparing a sugar chain asparagine, in which the step (a) is a step of providing a mixture of one or more sugar chain asparagines each having a sialic acid residue at a non-reducing terminal, introducing Fmoc group into the sugar chain asparagines contained in the above mixture, and introducing benzyl group into the sialic acid residue, to give a mixture of sugar chain asparagine derivatives. In this embodiment, in the step (c), the removal of benzyl group in addition to the removal of Fmoc group is carried out. The removal of benzyl group can be carried out in accordance with a known process (for instance, see *Protecting Groups in Organic Chemistry*, John Wiley & Sons INC., New York 1991, ISBN 0-471-62301-6).

Further, in the same manner as mentioned above, it is preferable to hydrolyze the sugar chain asparagine derivatives separated in the step (b) and/or hydrolyze the sugar chain asparagine obtained in the step (c), from the viewpoint of efficiently obtaining a sugar chain asparagine having a desired sugar chain structure. The hydrolysis can be carried out in the same manner as described above. It is more preferable to carry out the hydrolysis with a glycosidase [step (b') and/or step (c')], from the viewpoint of more efficiently obtaining a sugar chain asparagine having a desired sugar chain structure.

In accordance with the above procedures for instance, there can be efficiently obtained a sugar chain asparagine represented by the general formula:

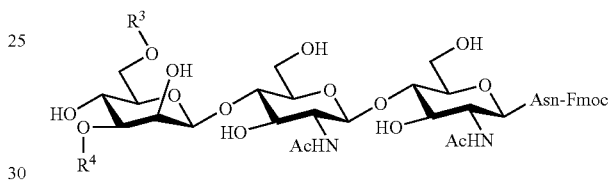

wherein $R^3$ and $R^4$, which may be identical or different, are H,

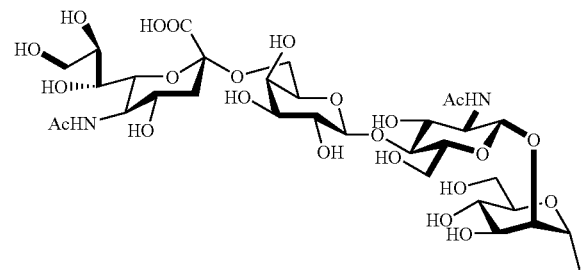

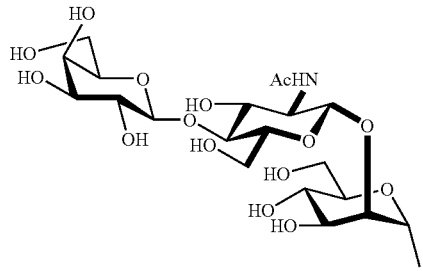

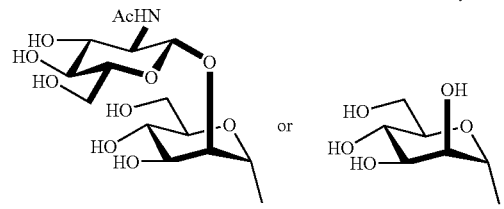

with proviso that a case where $R^3$ and $R^4$ are both

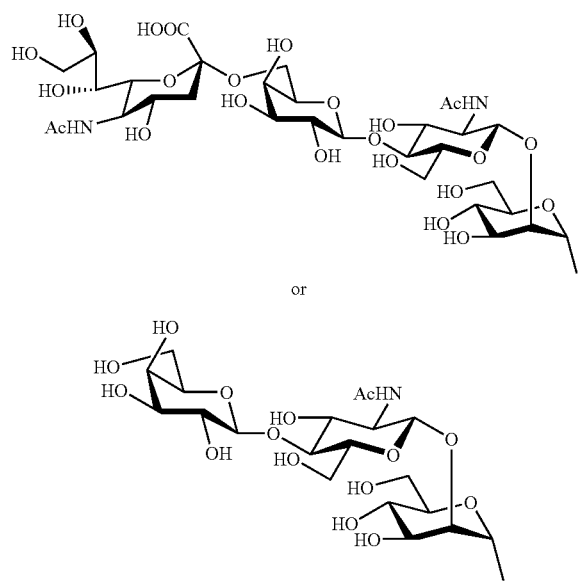

is excluded.

Concretely, the sugar chain asparagine includes, for instance, each of the compounds shown in FIG. 3 and FIG. 4. Among them, the compounds 25 to 32, 34 to 46, 72 and 73 are the compounds prepared for the first time in the present invention. The present invention encompasses the above compounds.

Further, the present invention provides a process for preparing a sugar chain capable of obtaining the various isolated sugar chains in a large amount. The above process further comprises, subsequent to the step of preparing a sugar chain asparagine in accordance with the above process for preparing a sugar chain asparagine, a step of removing an asparagine residue from the resulting sugar chain asparagine.

In other words, the process for preparing a sugar chain of the present invention comprises the step of:
(a) introducing a fat-soluble protecting group into a sugar chain asparagine contained in a mixture of one or more sugar chain asparagines, to give a mixture of sugar chain asparagine derivatives;
(b) subjecting the mixture of sugar chain asparagine derivatives or a mixture obtainable by hydrolyzing a sugar chain asparagine derivative contained in the mixture of sugar chain asparagine derivatives to chromatography, to separate each of sugar chain asparagine derivatives therefrom;
(c) removing the protecting group from the sugar chain asparagine derivative separated in the step (b), to give a sugar chain asparagine; and
(d) removing an asparagine residue from the sugar chain asparagine obtained in the step (c), to give the sugar chain.

The steps (a) to (c) are the same as those in the above process for preparing a sugar chain asparagine, and the mixture of one or more sugar chain asparagines used and the fat-soluble protecting group used are also the same as those mentioned above.

In addition, in the process for preparing a sugar chain of the present invention, as a preferred embodiment, there is provided a process for preparing a sugar chain asparagine, in which the step (a) is a step of providing a mixture of one or more sugar chain asparagines each having a sialic acid residue at a non-reducing terminal, introducing Fmoc group into the sugar chain asparagines contained in the above mixture, and introducing benzyl group into the sialic acid residue to give a mixture of sugar chain asparagine derivatives. In this embodiment, in the step (c), the removal of benzyl group in addition to the removal of Fmoc group is carried out. The removal of benzyl group can be carried out in accordance with the above process.

The removal of the asparagine residue from the sugar chain asparagine in the step (d) can be carried out in accordance with a known process. For instance, the sugar chain asparagine is reacted with anhydrous hydrazine and then acetylated to remove the asparagine residue, whereby a sugar chain can be obtained, as schematically shown in FIG. 12. Also, a sugar chain can be also obtained by refluxing the sugar chain asparagine with heating in a basic aqueous solution and thereafter acetylating the sugar chain asparagine to remove the asparagine residue. After the removal of the asparagine residue, the sugar chain may be purified appropriately by a known process such as various chromatographies employing a gel filtration column, an ion exchange column or the like, and a separation process by HPLC as desired.

Further, in the same manner as mentioned above, it is preferable to hydrolyze the sugar chain asparagine derivatives separated in the step (b) and/or hydrolyze the sugar chain asparagines obtained in the step (c), and/or hydrolyze the sugar chain obtained in the step (d), from the viewpoint of efficiently obtaining a sugar chain having a desired sugar chain structure. The hydrolysis may be carried out in the same manner as described above. It is more preferable to carry out the hydrolysis with a glycosidase [the step (b') and/or the step (c') and/or the step (d')], from the viewpoint of more efficiently obtaining a sugar chain having a desired sugar chain structure.

In accordance with the above procedures, for instance, there can be efficiently obtained a sugar chain represented by the general formula:

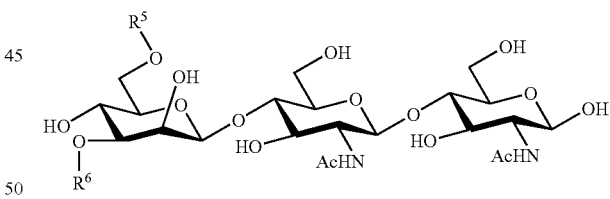

wherein $R^5$ and $R^6$, which may be identical or different, are H,

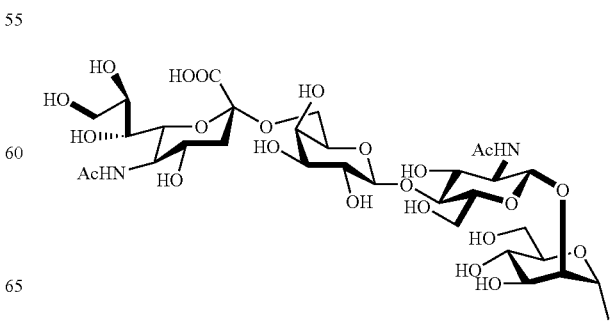

-continued

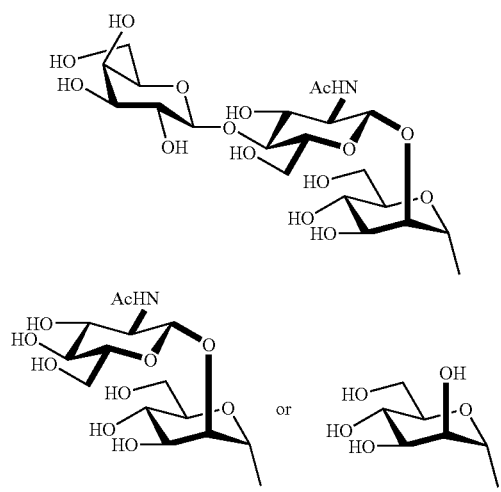

with proviso that a case where $R^5$ and $R^6$ are both

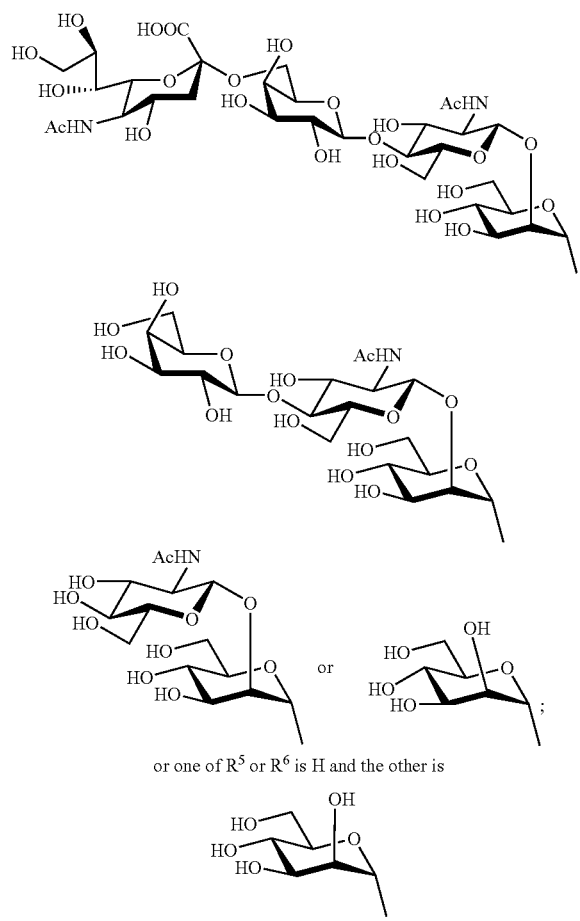

or one of $R^5$ or $R^6$ is H and the other is is excluded.

Concretely, the sugar chain includes, for instance, each of the compounds shown in FIG. 5 and FIG. 6. Among them, the compounds 48 to 55, 57 to 69, 74 and 75 are the compounds prepared for the first time in the present invention. The present invention encompasses the above compounds.

As described above, according to the present invention, the sugar chain asparagine derivative, the sugar chain asparagine and the sugar chain (hereinafter these three terms are collectively referred to as "sugar chain series" in some case) each having a desired sugar chain structure can be prepared at a low cost, efficiently and in a large amount.

The above sugar chain series are very useful in the field of the development of pharmaceuticals and the like. An application example in the development of the pharmaceuticals includes, for instance, a synthesis of cancer vaccine. It has been known that when the cell is cancerated, a sugar chain which is not initially existing in a body is expressed. It has been also known that when the sugar chain is synthesized chemically and administered to an individual as a vaccine, the cancer proliferation is suppressed. Therefore, if a desired sugar chain series can be prepared according to the present invention, a vaccine effective in the treatment of cancer can be synthesized. Also, a novel vaccine can be synthesized by derivatizing sugar chain series obtained according to the present invention by further bonding new sugar residues using a combination of a chemical reaction and a sugar transferase reaction and the like.

In addition, for instance, erythropoietin (EPO), a glycoprotein, has been used as a therapeutic agent for an anemia owing to its erythrocyte-proliferating ability, but it has been found that the EPO does not have any activity unless the EPO has a sugar chain bound thereto. As described above, some proteins exhibit their physiological effects only under the binding of sugar chains. Therefore, for instance, a novel glycoprotein having a novel physiological effect can be synthesized by preparing a protein itself in a large amount in an *E. coli* expression system without binding ability of a sugar chain to the protein, and subsequently introducing to the protein the sugar chain having a desired sugar chain structure, which is prepared according to the present invention, to give a novel physiological activity to the protein, or by introducing into a given protein the sugar chains having various sugar chain structures, which are prepared according to the present invention.

In addition, a novel physiological activity can be imparted by substituting a sugar chain existing in a naturally occurring glycoprotein with a sugar chain prepared according to the present invention. A technique of substituting a sugar chain owned by a glycoprotein with a sugar chain obtained according to the present invention includes, for instance, a process described in P. Sears and C. H. Wong, *Science*, 2001, vol. 291, p. 2344–2350. In other words, the process includes a process of treating a glycoprotein with a β-N-acetylglucosaminidase (Endo-H) to put the glycoprotein in a state in which only one N-acetylglucosamine residue is bound to the asparagine residue on the surface of the protein, and subsequently binding a desired sugar chain in the sugar chain asparagine obtained according to the present invention (for instance, each of the compounds shown in FIG. 3 and FIG. 4) to the N-acetylglucosamine residue described above with a β-N-acetylglucosaminidase (Endo-M). Alternatively, there can be carried out a process of providing an N-acetylglucosamine-bound tRNA, synthesizing a glycoprotein having an N-acetylglucosamine residue by utilizing, for instance, an *E. coli* expression system, and thereafter introducing a desired sugar chain in the sugar chain asparagine obtained according to the present invention into the glycoprotein with Endo-M.

In addition, the problem encountered currently when a glycoprotein is utilized as a therapeutic agent includes a rapid metabolic rate of the glycoprotein administered. This is due to the fact that the glycoprotein is metabolized by the liver immediately after the removal of the sialic acid existing in the sugar chain terminal of the glycoprotein in a living body. Therefore, it is necessary that the glycoprotein is administered at a certain dose. In view of the above, if a sugar chain is prepared according to the present invention, wherein sialic acid is newly introduced to a terminal of the sugar chain so as to be less removed, and the sugar chain is introduced into a target protein with Endo-M, the metabolic rate of the glycoprotein in a living body can be controlled, so that the amount of the glycoprotein to be administered can be lowered.

The present invention will be more specifically described by means of Examples, without intending to limit the present invention to these Examples. The structural formulas and the numbers for each of the compounds are shown in FIGS. 1 to 6. The data of $^1$H-NMR were obtained by the measurement with HOD at 4.8 ppm at 30° C. in Examples 1 to 7 and with a signal of methyl group of acetone as an internal standard at 2.225 ppm and HOD at 4.718 ppm at 30° C. in Examples 8 to 45. Also, the compounds from which Fmoc groups had been removed were measured in the co-existence of a 50 mM ammonium hydrogencarbonate in a measurement solvent.

EXAMPLE 1

Synthesis of Compound 24

In 100 ml of a tris-hydrochloric acid-calcium chloride buffer (TRIZMA BASE 0.05 mol/l, calcium chloride 0.01 mol/l, pH 7.5) was dissolved 2.6 g of an egg-derived crude SGP (sialyl glycopeptide). Fifty-eight milligrams (772 μmol) of sodium azide and 526 mg of Actinase-E (manufactured by Kaken Pharmaceutical Co., Ltd.) were added to this solution, and the mixture was allowed to stand at 37° C.

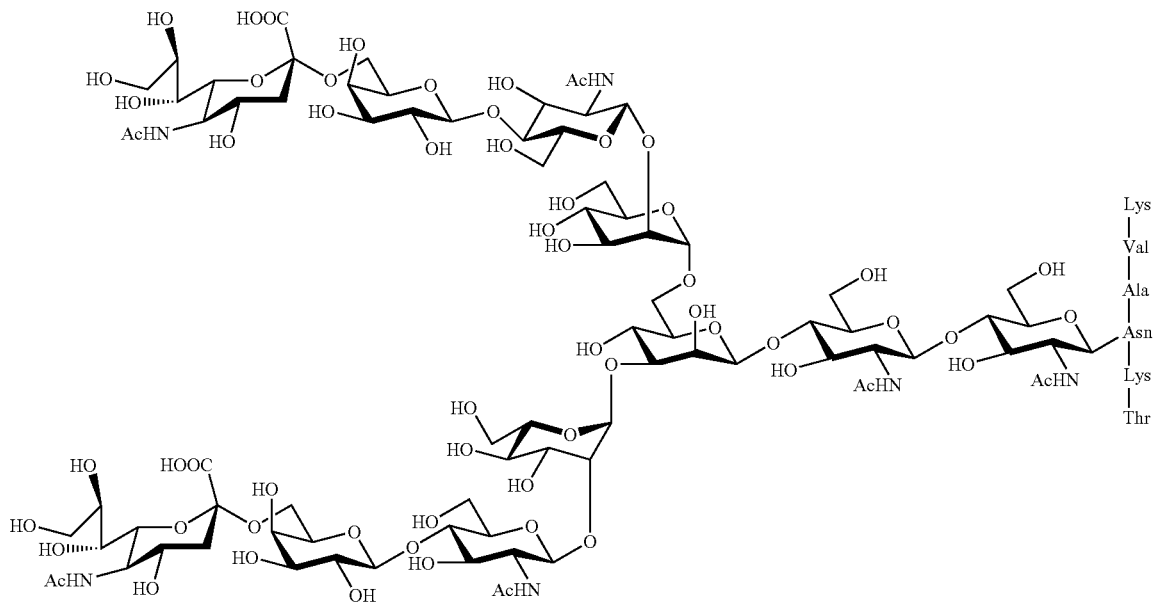

After 65 hours, 263 mg of Actinase-E was added again, and the mixture was allowed to stand at 37° C. for additional 24 hours. This solution was lyophilized, and thereafter the residue was purified twice by gel filtration column chromatography (Sephadex G-25, 2.5φ×1 m, eluent: water, flow rate: 1.0 ml/min), to give 1.3 g (555 μmol) of a desired compound 24 shown in FIG. 3. The structure of the sugar chain contained in SGP is shown as follows.

In addition, the physical data for the resulting compound 24 are as follows.

$^1$H-NMR (D$_2$O, 30° C.) 5.15 (1H, s, Man4-H$_1$), 5.06 (1H, d, GlcNAc1-H$_1$), 4.95 (1H, s, Man4'-H$_1$), 4.82 (1H, s, Man3-H$_1$), 4.69 (1H, d, GlcNAc2-H$_1$), 4.67 (2H, d, GlcNAc5,5'-H$_1$), 4.53 (2H, d, Gal6,6'-H$_1$), 4.34 (1H, d, Man3-H$_2$), 4.27 (1H, d, Man4'-H$_2$), 4.19 (1H, d, Man4-H$_2$) 3.03 (1H, dd, Asn-βCH), 3.00 (1H, dd, Asn-βCH), 2.76 (2H, dd, NeuAc7,7'-H$_{3eq}$), 2.15 (18H, s×6, —Ac), 1.79 (2H, dd, NeuAc7,7'-H$_{3ax}$)

EXAMPLE 2

Synthesis of Compounds 1, 2, 6 and 10

The compound 24 (609 mg, 261 μmol) obtained in Example 1 was dissolved in 20.7 ml of water, and 13.8 ml of 0.1 N hydrochloric acid was added thereto. Immediately after heating this solution at 70° C. for 35 minutes, the solution was cooled on ice, and a saturated aqueous sodium hydrogencarbonate was added thereto to adjust its pH to 7. The solution was lyophilized, and thereafter the residue was purified by gel filtration column chromatography (Sephadex G-25, 2.5φ×1 m, eluent: water, flow rate: 1.0 ml/min), to give 534 mg of a mixture of a compound 24, compounds 25 and 29, and a compound 33 each shown in FIG. 3. These four components were proceeded to the next step without being isolated from each other.

The physical data for the resulting sugar chain mixture are as follows.

$^1$H-NMR (D$_2$O, 30° C.) 5.13 (s, Man4-H$_1$), 5.12 (s, Man4-H$_1$), 5.01 (d, GlcNAc1-H$_1$), 4.94 (s, Man4'-H$_1$), 4.93 (s, Man4'-H$_1$), 4.82 (s, Man3-H$_1$), 4.60 (d, GlcNAc2-H$_1$), 4.58 (d, GlcNAc5,5'-H$_1$), 4.47 (dd, Gal6,6'-H$_1$), 4.44 (d, Gal6,6'-H$_1$), 4.24 (d, Man3-H$_2$), 4.19 (d, Man4'-H$_2$), 4.11 (d, Man4-H$_2$), 2.97 (bdd, Asn-βCH), 2.72 (dd, NeuAc7-H$_{3eq}$, NeuAc7-H$_{3eq}$), 2.64 (bdd, Asn-βCH), 2.15 (s×5, —Ac), 1.79 (dd, NeuAc7-H$_{3ax}$, NeuAc7'-H$_{3ax}$)

Four-hundred and twenty-nine milligrams of the mixture of the resulting sugar chain was dissolved in 16.3 ml of acetone and 11.2 ml of water. To this solution were added 9-fluorenyl methyl-N-succinimidyl carbonate (155.7 mg, 461.7 μmol) and sodium hydrogencarbonate (80.4 mg, 957 μmol), and the mixture was stirred at room temperature for 2 hours. This solution was applied to an evaporator to remove acetone, and the remaining solution was purified by gel filtration column chromatography (Sephadex G-25, 2.5φ×1 m, eluent: water, flow rate: 1.0 ml/min), to give 309 mg of a mixture of a compound 1, compounds 2 and 6, and a compound 10 each shown in FIG. 1. This mixture was purified by HPLC (ODS column, eluent: 50 mM aqueous ammonium acetate:methanol=65:35, 2.0φ×25 cm, flow rate: 3 ml/min). As a result, the compound 1 was eluted after 51 minutes, a mixture of the compounds 2 and 6 was eluted after 67 minutes, and the compound 10 was eluted after 93 minutes. Each of the fractions were collected and lyophilized, and thereafter desalted by gel filtration column chromatography (Sephadex G-25, 2.5φ×30 cm, eluent: water, flow rate: 1.0 ml/min), thereby giving 150 mg of a desired mixture of the compounds 2 and 6.

The physical data for the resulting compound 1 are as follows.

$^1$H-NMR (D$_2$O, 30° C.) 7.99 (2H, d, Fmoc), 7.79 (2H, d, Fmoc), 7.55 (4H, m, Fmoc), 5.15 (1H, s, Man4-H$_1$), 5.06 (1H, d, GlcNAc1-H$_1$), 4.95 (1H, s, Man4'-H$_1$), 4.82 (1H, s, Man3-H$_1$), 4.69 (1H, d, GlcNAc2-H$_1$), 4.67 (2H, d, GlcNAc5,5'-H$_1$), 4.53 (2H, d, Gal6,6'-H$_1$), 4.34 (1H, d, Man3-H$_2$), 4.27 (1H, d, Man4'-H$_2$), 4.19 (1H, d, Man4-H$_2$), 3.03 (1H, bdd, Asn-βCH), 3.00 (1H, bdd, Asn-βCH), 2.76 (2H, dd, NeuAc7,7'-H$_{3eq}$), 2.15 (18H, s×6, —Ac), 1.79 (2H, dd, NeuAc7,7'-H$_{3ax}$); HRMS Calcd for C$_{103}$H$_{154}$N$_8$NaO$_{66}$[M+Na$^+$] 2581.8838, found 2581.8821.

The physical data for the resulting mixture of the compounds 2 and 6 are as follows.

$^1$H-NMR (D$_2$O, 30° C.) 7.99 (d, Fmoc), 7.79 (d, Fmoc), 7.55 (m, Fmoc), 5.14 (s, Man4-H$_1$), 5.12 (s, Man4-H), 5.00 (d, GlcNAc1-H$_1$), 4.94 (s, Man4'-H$_1$), 4.93 (s, Man4'-H$_1$), 4.82 (s, Man3-H$_1$), 4.60 (d, GlcNAc2-H$_1$), 4.58 (d, GlcNAc5,5'-H$_1$), 4.46 (dd, Gal6,6'-H$_1$), 4.44 (d, Gal6,6'-H$_1$), 4.24 (d, Man3-H$_2$), 4.19 (d, Man4'-H$_2$), 4.11 (d, Man4-H$_2$), 2.97 (bdd, Asn-βCH), 2.72 (dd, NeuAc7-H$_{3eq}$, NeuAc7-H$_{3eq}$), 2.64 (bdd, Asn-βCH), 2.15 (s×5, —Ac), 1.79 (dd, NeuAc7-H$_{3ax}$, NeuAc7'-H$_{3ax}$)

The physical data for the resulting compound 10 are as follows.

$^1$H-NMR (D$_2$O, 30° C.) 7.99 (2H, d, Fmoc), 7.79 (2H, d, Fmoc), 7.55 (4H, m, Fmoc), 5.12 (1H, s, Man4-H$_1$), 5.06 (1H, d, GlcNAc1-H$_1$), 4.93 (1H, s, Man4'-H$_1$), 4.82 (1H, s, Man3-H$_1$), 4.69 (1H, d, GlcNAc2-H$_1$), 4.67 (2H, d, GlcNAc5,5'-H$_1$), 4.53 (2H, d, Gal6,6'-H$_1$), 4.34 (1H, d, Man3-H$_2$), 4.27 (1H, d, Man4'-H$_2$), 4.19 (1H, d, Man4-H$_2$), 3.03 (1H, bdd, Asn-βCH), 3.00 (1H, bdd, Asn-βCH), 2.15 (12H, s×4, —Ac); HRMS Calcd for C$_{81}$H$_{120}$N$_6$NaO$_{50}$[M+Na$^+$] 1999.6930, found 1999.6939.

EXAMPLE 3

Synthesis of Compounds 3 and 7

The mixture (224 mg, 97 μmol) of the compounds 2 and 6 obtained in Example 2 and 24 mg of bovine serum albumin were dissolved in 22 ml of HEPES buffer (50 mM, pH 6.0), and *Diplococcus pneumoniae*-derived β-galactosidase (1.35 U) was added thereto. This solution was allowed to stand at 37° C. for 15 hours, and thereafter lyophilized. The residue was purified by HPLC (ODS column, 2.0φ×25 cm, eluent: 50 mM aqueous ammonium acetate:acetonitrile=85:15, flow rate: 3 ml/min), and a compound 3 shown in FIG. 2 was eluted after 129 minutes, and a compound 7 was eluted after 134 minutes. Each of the fractions was collected and lyophilized. Subsequently, the fraction was desalted by HPLC (ODS column, 2.0φ×25 cm, eluent:water for a first 15 minutes, and applied to a gradient of water:acetonitrile of from 10:0 to 85:15 (volume ratio) for a period of from 16 to 30 minutes, and then to a gradient of water:acetonitrile from 85:15 to 80:20 for a period of from 31 to 45 minutes; flow rate: 3.0 ml/min), to give a desired compound 3 in an amount of 81 mg and a compound 7 in an amount of 75 mg.

The physical data for the resulting compound 3 are as follows.

$^1$H-NMR (D$_2$O, 30° C.) 7.99 (2H, d, Fmoc), 7.79 (2H, d, Fmoc), 7.55 (4H, m, Fmoc), 5.15 (1H, S, Man4-H$_1$), 5.06 (1H, d, GlcNAc1-H$_1$), 4.95 (1H, s, Man4'-H$_1$), 4.82 (1H, s, Man3-H$_1$), 4.69 (1H, d, GlcNAc2-H$_1$), 4.67 (2H, d, GlcNAc5,5'-H$_1$), 4.53 (1H, d, Gal6'-H$_1$), 4.34 (1H, d, Man3-H$_2$), 4.27 (1H, d, Man4'-H$_2$), 4.19 (1H, d, Man4-H$_2$), 2.97 (1H, bdd, Asn-βCH), 2.76 (1H, dd, NeuAc7'-H$_{3eq}$), 2.61 (1H, bdd, Asn-βCH), 2.15 (1SH, s×5, —Ac), 1.79 (1H, dd, NeuAc7'-H$_{3ax}$); HRMS Calcd for C$_{86}$H$_{127}$N$_7$NaO$_{53}$[M+Na$^+$] 2128.7356, found 2128.7363.

The physical data for the resulting compound 7 are as follows.

$^1$H-NMR(D$_2$O, 30° C.) 7.99 (2H, d, Fmoc), 7.79 (2H, d, Fmoc), 7.55 (4H, m, Fmoc), 5.15 (1H, S, Man4-H$_1$), 5.06 (1H, d, GlcNAc1-H$_1$), 4.95 (1H, s, Man4'-H$_1$), 4.82 (1H, s, Man3-H$_1$), 4.69 (1H, d, GlcNAc2-H$_1$), 4.67 (2H, d, GlcNAc5,5'-H$_1$), 4.53 (1H, d, Gal6-H$_1$), 4.34 (1H, d, Man3-H$_2$), 4.27 (1H, d, Man4'-H$_2$) 4.19 (1H, d, Man4-H$_2$), 2.97 (1H, bdd, Asn-βCH), 2.76 (1H, dd, NeuAc7-H$_{3eq}$), 2.60 (1H, b dd, Asn-βCH), 2.15 (15H, s×5, —Ac), 1.79 (1H, dd, NeuAc7-H$_{3ax}$); HRMS Calcd for C$_{86}$H$_{125}$N$_7$Na$_3$O$_{53}$[M+Na$^+$] 2172.6995, found 2172.7084.

EXAMPLE 4

Synthesis of Compounds 4 and 8

A mixture (90 mg, 47.3 μmol) of the compounds 3 and 7 obtained in Example 3 was dissolved in 8.1 ml of HEPES buffer (50 mM, pH 6.0) together with 8 mg of bovine serum albumin without separating the compounds from each other, and 2.88 U of a bovine kidney-derived β-glucosaminidase (manufactured by Sigma-Aldrich Corporation, from bovine kidney) was added thereto. This solution was allowed to stand at 37° C. for 18 hours, and thereafter lyophilized. The residue was purified by HPLC (ODS column, 2.0φ×25 cm, eluent: 50 mM aqueous ammonium acetate:methanol=65:35, flow rate: 3 ml/min), and a compound 4 shown in FIG. 2 was eluted after 117 minutes, and a compound 8 was eluted after 127 minutes. Each of the fractions was collected and lyophilized. Subsequently, the fraction was desalted by HPLC (ODS column, 2.0φ×25 cm, eluent: water for a first 15 minutes, and applied to a gradient of water:acetonitrile of from 10:0 to 85:15 for a period of from 16 to 30 minutes, and then to a gradient of water:acetonitrile of from 85:15 to 80:20 for a period of from 31 to 45 minutes; flow rate: 3.0 ml/min), to give a desired compound 4 in an amount of 40 mg and a compound 8 in an amount of 37 mg.

The physical data for the resulting compound 4 are as follows.

$^1$H-NMR (D$_2$O, 30° C.) 8.01 (2H, d, Fmoc), 7.80 (2H, d, Fmoc), 7.56 (4H, m, Fmoc), 5.22 (1H, s, Man4-H$_1$), 5.08 (1H, d, GlcNAc1-H$_1$), 4.94 (1H, s, Man4'-H$_1$), 4.84 (1H, s, Man3-H$_1$), 4.69 (1H, d, GlcNAc2-H$_1$), 4.67 (1H, d, GlcNAc5-H$_1$), 4.55 (1H, d, Gal6-H$_1$), 4.33 (1H, dd, Man3-H$_2$), 4.20 (1H, dd, Man4-H$_2$), 4.15 (1H, dd, Man4'-H$_2$), 2.97 (1H, bdd, Asn-βCH), 2.76 (2H, dd, NeuAc7,7'-H$_{3eq}$), 2.62 (1H, bdd, Asn-βCH), 2.15 (12H, s×4, —Ac), 1.79 (2H, dd, NeuAc7, 7'-H$_{3ax}$); HRMS Calcd for C$_{78}$H$_{114}$N$_6$NaO$_{48}$[M+Na$^+$] 1925.6562, found 1925.6539.

The physical data for the resulting compound 8 are as follows.

$^1$H-NMR (D$_2$O, 30° C.) 7.99 (2H, d, Fmoc), 7.79 (2H, d, Fmoc), 7.55 (4H, m, Fmoc), 5.15 (1H, S, Man4-H$_1$), 5.06 (1H, d, GlcNAc1-H$_1$), 4.95 (1H, s, Man4'-H$_1$), 4.82 (1H, s, Man3-H$_1$), 4.69 (1H, d, GlcNAc2-H$_1$), 4.67 (2H, d, GlcNAc5,5'-H$_1$), 4.53 (2H, d, Gal6,6'-H$_1$), 4.34 (1H, d, Man3-H$_2$), 4.27 (1H, d, Man4'-H$_2$), 2.97 (1H, bdd, Asn-βCH$_2$), 2.76 (1H, dd, NeuAc7'-H$_{3eq}$), 2.61 (1H, bdd, Asn-βCH$_2$), 2.15 (12H, s×4, —Ac), 1.79 (1H, dd, NeuAc7'-H$_{3ax}$); HRMS Calcd for C$_{78}$H$_{114}$N$_6$NaO$_{48}$[M+Na$^+$] 1925.6562, found 1925.6533.

EXAMPLE 5

Synthesis of Compound 5

The compound 4 (30 mg, 473 μmol) obtained in Example 4 and 3 mg of bovine serum albumin were dissolved in 6 ml of HEPES buffer (50 mM, pH 6.0), and 10 U of Jack Beans-derived a-mannosidase was added thereto. This solution was allowed to stand at 37° C. for 21 hours, and then lyophilized. Subsequently, the residue was purified by HPLC (ODS column, 2.0φ×25 cm, eluent:water for a first 15 minutes, and applied to a gradient of water:acetonitrile of from 10:0 to 85:15 for a period of from 16 to 30 minutes, and then to a gradient of water:acetonitrile of from 85:15 to 80:20 for a period of from 31 to 45 minutes; flow rate: 3.0 ml/min), to give 20 mg of a desired compound 5 shown in FIG. 1.

The physical data for the resulting compound 5 are as follows.

$^1$H-NMR (D$_2$O, 30° C.) 8.01 (2H, d, Fmoc), 7.80 (2H, d, Fmoc), 7.56 (4H, m, Fmoc), 5.00 (1H, d, GlcNAc1-H$_1$), 4.95 (1H, s, Man4'-H$_1$), 4.84 (1H, s, Man3-H$_1$), 4.67 (1H, d, GlcNAc2-H$_1$), 4.56 (1H, d, GlcNAc5-H$_1$), 4.44 (1H, d, Gal6-H$_1$), 4.11 (1H, dd, Man4'-H$_2$), 4.07 (1H, dd, Man3-H$_2$), 2.97 (1H, bdd, Asn-βCH), 2.76 (1H, dd, NeuAc7'-H$_{3eq}$), 2.62 (1H, bdd, Asn-βCH), 2.15 (12H, s×4, —Ac), 1.79 (2H, dd, NeuAc7'-H$_{3ax}$); HRMS Calcd for C$_{72}$H$_{104}$N$_6$NaO$_{43}$ [M+Na$^+$] 1763.6034, found 1763.6074.

EXAMPLE 6

Synthesis of Compound 9

The compound 8 (40 mg, 630 μmol) obtained in Example 4 and 5 mg of bovine serum albumin were dissolved in 7.8 ml of HEPES buffer (50 mM, pH 6.0), and 38 U of a Jack Beans-derived α-mannosidase was added thereto. This solution was allowed to stand at 37° C. for 63 hours, and then lyophilized. Subsequently, the residue was purified by HPLC (ODS column, 2.0φ×25 cm, eluent:water for a first 15 minutes, and applied to a gradient of water:acetonitrile of from 10:0 to 85:15 for a period of from 16 to 30 minutes, and then to a gradient of water:acetonitrile of from 85:15 to 80:20 for a period of from 31 to 45 minutes; flow rate: 3.0 ml/min), to give 30 mg of a desired compound 9.

The physical data for the resulting compound 9 are as follows.

$^1$H-NMR (D$_2$O, 30° C.) 8.01 (2H, d, Fmoc), 7.80 (2H, d, Fmoc), 7.56 (4H, m, Fmoc), 5.23 (1H, s, Man4-H$_1$), 5.08 (1H, d, GlcNAc1-H$_1$), 4.53 (1H, d, Gal6-H$_1$), 4.32 (1H, dd, Man3-H$_2$), 4.28 (1H, dd, Man4-H$_2$), 2.81 (1H, bdd, Asn-βCH), 2.76 (1H, dd, NeuAc7-H$_{3eq}$), 2.59 (1H, bdd, Asn-βCH), 2.13 (12H, s×4, —Ac), 1.80 (1H, dd, NeuAc7H$_{3ax}$); HRMS Calcd for C$_{72}$H$_{104}$N$_6$NaO$_{43}$[M+Na$^+$] 1763.6034, found 1763.6041.

EXAMPLE 7

Deprotection of Fmoc Group (Synthesis of Compound 33)

The compound 10 (10.5 mg, 5.27 μmol) obtained in Example 2 was dissolved in 1.4 ml of a 50% morpholine/N,N-dimethylformamide solution, and the solution was reacted for 2 hours under argon atmosphere at room temperature. Three milliliters of toluene was added to this solution, and the mixture was applied to an evaporator at 35° C. The procedures were repeated three times to remove the reaction solvent. The residue was purified by gel filtration column chromatography (Sephadex G-25, 2.5φ×30 cm, eluent: water, flow rate: 1.0 ml/min), to give 7 mg of a desired compound 33 shown in FIG. 3 (yield: 76%). The structure of the resulting compound was confirmed from the finding that its $^1$H-NMR spectrum was identical to that of the resulting compound 33 from Example 2.

The physical data for the resulting compound 33 are as follows.

$^1$H-NMR (30° C.) δ5.12 (s, 1H, Man4-H-1), 5.07 (d, 1H, J=9.7 Hz, GlcNAc1-H-1), 4.92 (s, 1H, Man4'-H-1), 4.76 (s, 1H, Man3-H-1), 4.62 (d, 1H, J=8.0 Hz, GlcNAc2-H-1), 4.58 (d, 2H, J=7.8 Hz, GlcNAc5,5'-H-1), 4.47 (d, 2H, J=7.9 Hz, Gal6,6'-H-1), 4.24 (bd, 1H, Man3-H-2), 4.19 (bdd, 1H, J=3.2 Hz, 1.4 Hz, Man4'-H-2), 4.12 (bdd, 1H, J=3.2 Hz, 1.4 Hz, Man4-H-2), 2.93 (dd, 1H, J=4.5 Hz, 17.0 Hz, Asn-βCH), 2.93 (dd, 1H, J=6.8 Hz, 17.0 Hz, Asn-βCH), 2.08 (s, 3H, Ac), 2.05 (s, 6H, Ac×2), 2.01 (s, 3H, Ac)

EXAMPLE 8

Synthesis of Compound 14

The compound 3 (28 mg, 21.3 μmol) and 1.0 mg of bovine serum albumin were dissolved in HEPES buffer (50 mM, pH 5.0, 454 μL), and neuraminidase (manufactured by Sigma-Aldrich Corporation, from *Viblio Cholerae*, 198 mU) was added thereto. This solution was allowed to stand at 37° C. for 20 hours, and thereafter the termination of the reaction was confirmed by HPLC analysis. The reaction solution was purified by HPLC (YMC Packed Column D-ODS-5 S-5 120A ODS No. 2020178, 20×250 mm, eluent: 50 mM aqueous ammonium acetate:acetonitrile=80:20, flow rate: 4 mL/min). Further, the residue was desalted on ODS column (Cosmosil 75C$_{18}$-OPN, 15×100 mm, eluted first with 50 mL of H₂O and then with 25% acetonitrile), to give a desired compound 14 (17 mg, yield: 70%). The physical data for the resulting compound are as follows.

$^1$H-NMR (30° C.) δ7.91 (d, 2H, J=7.5 Hz, Fmoc), 7.71 (d, 2H, J=7.5 Hz, Fmoc), 7.51 (dd, 2H, J=7.5 Hz, Fmoc), 7.43 (dd, 2H, J=7.5 Hz, Fmoc), 5.12 (s, 1H, Man4-H-1), 4.99 (d, 1H, J=9.5 Hz, GlcNAc1-H-1), 4.92 (s, 1H, Man4'-H-1), 4.76 (s, 1H, Man3-H-1), 4.58 (d, 1H, J=8.0 Hz, GlcNAc2-H-1), 4.55 (d, 1H, J=8.4 Hz, GlcNAc5'-H-1) 4.47 (d, 1H, J=7.8 Hz, Gal6'-H-1), 4.34 (t, 1H, Fmoc), 4.24 (bd, 1H, J=1.9 Hz Man3-H-2), 4.18 (bdd, 1H, J=1.4 Hz, 3.3 Hz, Man4-H-2), 4.11 (bdd, 1H, J=1.4 Hz, 3.5 Hz, Man4'-H-2), 2.72 (bdd, 1H, J=3.0 Hz, 15.7 Hz, Asn-βCH), 2.52 (bdd, 1H, J=8.7 Hz, 15.7 Hz, Asn-βCH), 2.06, 2.05, 2.04, 1.89 (each s, each 3H, Ac); HRMS Calcd for $C_{75}H_{110}N_6NaO_{45}[M+Na^+]$ 1837.6402, found 1837.6471.

EXAMPLE 9

Synthesis of Compound 19

The compound 7 (20 mg, 9.4 μmol) and 1.6 mg of bovine serum albumin were dissolved in HEPES buffer (50 mM, pH 5.0, 323 μL), and neuraminidase (manufactured by Sigma-Aldrich Corporation, from *Viblio Cholerae*, 141 mU) was added thereto. This solution was allowed to stand at 37° C. for 18 hours, and thereafter the termination of the reaction was confirmed by HPLC analysis. Subsequently, the reaction solution was purified by HPLC (YMC Packed Column D-ODS-5 S-5 120A ODS No. 2020178, 20×250 mm, eluent: 50 mM aqueous ammonium acetate:acetonitrile=80:20, flow rate: 4 mL/min). Further, the residue was desalted on an ODS column (Cosmosil 75$C_{18}$-OPN, 15×100 mm, eluted first with 50 mL of H₂O and then with 25% acetonitrile), to give a desired compound 19 (13 mg, yield: 76%). The structure of the resulting compound was confirmed from the finding that its $^1$H-NMR was identical to that of the preparation.

EXAMPLE 10

Synthesis of Compound 15

The compound 4 (45 mg, 24 μmol) and 1.7 mg of bovine serum albumin were dissolved in HEPES buffer (50 mM, pH 5.0, 820 μL), and neuraminidase (manufactured by Sigma-Aldrich Corporation, from *Viblio Cholerae*, 134 mU) was added thereto. This solution was allowed to stand at 37° C. for 14 hours, and thereafter the termination of the reaction was confirmed by HPLC analysis. Subsequently, the reaction solution was purified by HPLC (YMC Packed Column D-ODS-5 S-5 120A ODS No. 2020178, 20×250 mm, eluent: 50 mM aqueous ammonium acetate:acetonitrile=80:20, flow rate: 4 mL/min). Further, the residue was desalted on an ODS column (Cosmosil 75$C_{18}$-OPN, 15×100 mm, eluted first with 50 mL of H₂O and then with 25% acetonitrile), to give a desired compound 15 (28 mg, yield: 74%). The physical data for the resulting compound are as follows.

$^1$H-NMR (30° C.) δ7.92 (d, 2H, J=7.5 Hz, Fmoc), 7.71 (d, 2H, J=7.5 Hz, Fmoc), 7.51 (dd, 2H, J=7.5 Hz, Fmoc), 7.44 (dd, 2H, J=7.5 Hz, Fmoc), 5.10 (s, 1H, Man4-H-1), 4.99 (d, 1H, J=9.5 Hz, GlcNAc1-H-1), 4.92 (s, 1H, Man4'-H-1), 4.76 (s, 1H, Man3-H-1), 4.58 (d, 2H, GlcNAc2,5'-H-1), 4.47 (d, 1H, J=8.0 Hz, Gal6'-H-1), 4.35 (t, 1H, Fmoc), 4.24 (bd, 1H, J=1.9 Hz, Man3-H-2), 4.11 (bs, 1H, Man4'-H-2), 4.07 (bs, 1H, Man4-H-2), 2.72 (bd, 1H, J=15.5 Hz, Asn-βCH), 2.52 (bdd, 1H, J=8.7 Hz, 15.5 Hz, Asn-βCH), 2.06, 2.04, 1.89 (each s, each 3H, Ac); HRMS Calcd for $C_{67}H_{97}N_5NaO_{40}$ [M+Na⁺] 1634.5608, found 1634.5564.

EXAMPLE 11

Synthesis of Compound 70

The compound 15 (11 mg, 6.8 μmol) and 1.5 mg of bovine serum albumin were dissolved in HEPES buffer (50 mM, pH 5.0, 269 μL), and β-galactosidase (manufactured by Seikagaku Corporation, from Jack Beans, 11 μL, 275 mU) was added thereto. This solution was allowed to stand at 37° C. for 14 hours, and thereafter the termination of the reaction was confirmed by HPLC analysis. The reaction solution was purified by HPLC (YMC Packed Column D-ODS-5 S-5 120A ODS No. 2020178, 20×250 mm, eluent: 50 mM aqueous ammonium acetate:acetonitrile=80:20, flow rate: 4 mL/min). Further, the residue was desalted on an ODS column (Cosmosil 75$C_{18}$-OPN, 15×100 mm, eluted first with 50 mL of H₂O and then with 25% acetonitrile), to give a desired compound 70 (6.3 mg, yield: 64%). The physical data for the resulting compound are as follows.

$^1$H-NMR (30° C.) δ7.91 (d, 2H, J=7.5 Hz, Fmoc), 7.70 (d, 2H, J=7.5 Hz, Fmoc), 7.50 (dd, 2H, J=7.5 Hz, Fmoc), 7.43 (dd, 2H, J=7.5 Hz, Fmoc), 5.10 (s, 1H, Man4-H-1), 4.99 (d, 1H, J=9.5 Hz, GlcNAc1-H-1), 4.91 (s, 1H, Man4'-H-1), 4.76 (s, 1H, Man3-H-1), 4.55 (d, 2H, GlcNAc2,5'-H-1), 4.32 (t, 1H, Fmoc), 4.24 (bs, 1H, Man3-H-2), 4.10 (bs, 1H, Man4-H-2), 4.06 (bs, 1H, J=1.3 Hz, Man4'-H-2), 2.72 (bd, 1H, J=14.0 Hz, Asn-βCH), 2.52 (bdd, 1H, J=9.5 Hz, 14.8 Hz, Asn-βCH), 2.06, 2.05, 1.89 (each s, each 3H, Ac); MS(Fab) Calcd for $C_{61}H_{88}N_5O_{35}$[M+H⁺] 1450.5, found 1450.4.

EXAMPLE 12

Synthesis of Compound 20

The compound 8 (47 mg, 25 μmol) and 1.9 mg of bovine serum albumin were dissolved in HEPES buffer (50 mM, pH 5.0, 840 μL), and neuraminidase (manufactured by Sigma-Aldrich Corporation, from *Viblio Cholerae*, 369 mU) was added thereto. This solution was allowed to stand at 37° C. for 37 hours, and thereafter the termination of the reaction was confirmed by HPLC analysis. The reaction solution was lyophilized, and the lyophilized product was subsequently purified by HPLC (YMC Packed Column D-ODS-5 S-5 120A ODS No. 2020178, 20×250 mm, eluent: 50 mM aqueous ammonium acetate:acetonitrile=80:20, flow rate: 4 mL/min). Further, the residue was desalted on an ODS column (Cosmosil 75$C_{18}$-OPN, 15×100 mm, eluted first with 50 mL of H₂O and then with 25% acetonitrile), to give a desired compound 20 (26 mg, yield: 65%). The physical data for the resulting compound are as follows.

$^1$H-NMR (30° C.) δ7.92 (d, 2H, J=7.5 Hz, Fmoc), 7.71 (d, 2H, J=7.5 Hz, Fmoc), 7.51 (dd, 2H, J=7.5 Hz, Fmoc), 7.43 (dd, 2H, J=7.5 Hz, Fmoc), 5.12 (s, 1H, Man4-H-1), 4.99 (d, 1H, J=9.4 Hz, GlcNAc1-H-1), 4.91 (s, 1H, Man4'-H-1), 4.77 (s, 1H, Man3-H-1), 4.57 (bd, 2H, GlcNAc2,5'-H-1), 4.46 (d, 1H, J=7.5 Hz, Gal6'-H-1), 4.34 (t, 3H, Fmoc), 4.24 (bs, 1H, Man4'-H-2), 4.19 (bs, 1H, Man4-H-2), 2.72 (bd, 1H, J=15.5 Hz, Asn-βCH), 2.52 (bdd, 1H, J=9.2 Hz, 15.5 Hz, Asn-βCH), 2.06, 2.05, 1.89 (each s, each 3H, Ac); HRMS Calcd for $C_{67}H_{97}N_5NaO_{40}$[M+Na⁺] 1634.5608, found 1634.5644.

EXAMPLE 13

Synthesis of Compound 71

The compound 20 (12 mg, 7.4 µmol) and 1.0 mg of bovine serum albumin were dissolved in HEPES buffer (50 mM, pH 5.0, 330 µL), and β-galactosidase (manufactured by Seikagaku Corporation, from Jack Beans, 12 µL, 297 mU) was added thereto. This solution was allowed to stand at 37° C. for 46 hours, and thereafter the termination of the reaction was confirmed by HPLC analysis. The reaction solution was purified by HPLC (YMC Packed Column D-ODS-5 S-5 120A ODS No. 2020178, 20×250 mm, eluent: 50 mM aqueous ammonium acetate:acetonitrile=80:20, flow rate: 4 mL/min). Further, the residue was desalted on an ODS column (Cosmosil 75$C_{18}$-OPN, 15×100 mm, eluted first with 50 mL of $H_2O$ and then with 25% acetonitrile), to give a desired compound 71 (6.6 mg, yield: 61%). The physical data for the resulting compound are as follows.

$^1$H-NMR (30° C.) δ7.90 (d, 2H, J=7.5 Hz, Fmoc), 7.70 (d, 2H, J=7.5 Hz, Fmoc), 7.49 (dd, 2H, J=7.5 Hz, Fmoc), 7.42 (dd, 2H, J=7.5 Hz, Fmoc), 5.11 (s, 1H, Man4-H-1), 4.99 (d, 1H, J=9.4 Hz, GlcNAc1-H-1), 4.91 (s, 1H, Man4'-H-1), 4.76 (s, 1H, Man3-H-1), 4.55 (d, 2H, GlcNAc2,5-H-1), 4.31 (b, 1H, Fmoc), 4.24 (bs, 1H, Man3-H-2), 4.18 (bs, 1H, Man4-H-2), 3.97 (dd, 1H, J=1.8 Hz, 3.3 Hz, Man4'-H-2), 2.72 (bd, 1H, J=15.5 Hz, Asn-βCH), 2.52 (bdd, 1H, J=8.0 Hz, 15.5 Hz, Asn-βCH), 2.06, 2.05, 1.88 (each s, each 3H, Ac); MS(Fab) Calcd for $C_{61}H_{88}N_5O_{35}[M+H^+]$ 1450.5, found 1450.3.

EXAMPLE 14

Synthesis of Compound 16

The compound 5 (32 mg, 18.4 µmol) and 2.5 mg of bovine serum albumin were dissolved in HEPES buffer (50 mM, pH 5.0, 713 µL), and neuraminidase (manufactured by Sigma-Aldrich Corporation, from *Viblio Cholerae*, 134 mU) was added thereto. This solution was allowed to stand at 37° C. for 17 hours, and thereafter the termination of the reaction was confirmed by HPLC analysis. Subsequently, the reaction solution was purified by HPLC (YMC Packed Column D-ODS-5 S-5 120A ODS No. 2020178, 20×250 mm, eluent: 50 mM aqueous ammonium acetate:acetonitrile=80:20, flow rate: 4 mL/min). Further, the residue was desalted on an ODS column (Cosmosil 75$C_{18}$-OPN, 15×100 mm, eluted first with 50 mL of $H_2O$ and then with 25% acetonitrile), to give a desired compound 16 (13 mg, yield: 52%). The physical data for the resulting compound are as follows.

$^1$H-NMR (30° C.) δ7.92 (d, 2H, J=7.5 Hz, Fmoc), 7.71 (d, 2H, J=7.5 Hz, Fmoc), 7.51 (dd, 2H, J=7.5 Hz, Fmoc), 7.44 (dd, 2H, J=7.5 Hz, Fmoc), 5.00 (d, 1H, J=9.9 Hz, GlcNAc1-H-1), 4.92 (s, 1H, Man4'-H-1), 4.75 (s, 1H, Man3-H-1), 4.58 (d, 2H, J=7.5 Hz, GlcNAc2,5-H-1), 4.47 (d, 1H, J=7.8 Hz, Gal6'-H-1), 4.34 (t, 1H, Fmoc), 4.10 (bd, 1H, Man3-H-2), 4.07 (bs, 1H, Man4'-H-2), 2.72 (bdd, 1H, J=15.5 Hz, Asn-βCH), 2.52 (bdd, 1H, J=9.2 Hz, 15.5 Hz, Asn-βCH), 2.07, 2.05, 1.89 (each s, each 3H, Ac); MS(Fab) Calcd for $C_{61}H_{88}N_5O_{35}[M+H^+]$ 1450.5, found 1450.3.

EXAMPLE 15

Synthesis of Compound 17

The compound 16 (9 mg, 6.2 µmol) and 1.6 mg of bovine serum albumin were dissolved in HEPES buffer (50 mM, pH 5.0, 613 µL), and β-galactosidase (manufactured by Seikagaku Corporation, from Jack Beans, 186 mU) was added thereto. This solution was allowed to stand at 37° C. for 32 hours, and thereafter the termination of the reaction was confirmed by HPLC analysis. The reaction solution was purified by HPLC (YMC Packed Column D-ODS-5 S-5 120A ODS No. 2020178, 20×250 mm, eluent: 50 mM aqueous ammonium acetate:acetonitrile=80:20, flow rate: 4 mL/min). Further, the residue was desalted on an ODS column (Cosmosil 75$C_{18}$-OPN, 15×100 mm, eluted first with 50 mL of $H_2O$ and then with 25% acetonitrile), to give a desired compound 17 (5.4 mg, yield: 68%). The physical data for the resulting compound are as follows.

$^1$H-NMR (30° C.) δ7.89 (d, 2H, J=7.5 Hz, Fmoc), 7.68 (d, 2H, J=7.5 Hz, Fmoc), 7.49 (dd, 2H, J=7.5 Hz, Fmoc), 7.42 (dd, 2H, J=7.5 Hz, Fmoc), 4.99 (d, 1H, J=9.7 Hz, GlcNAc1-H-1), 4.91 (s, 1H, Man4'-H-1), 4.55 (d, 1H, J=8.1 Hz, GlcNAc2,5'-H-1), 4.09, 4.07 (s, 1H, Man4'-H-2, Man3-H-2), 2.72 (bd, 1H, J=15.5 Hz Asn-βCH), 2.56 (bdd, 1H, J=8.1 Hz, 15.5 Hz, Asn-βCH), 2.07, 2.05, 1.89 (each s, each 3H, Ac); MS(Fab) Calcd for $C_{55}H_{77}N_5NaO_{30}[M+Na^+]$ 1310.5, found 1310.2.

EXAMPLE 16

Synthesis of Compound 18

The compound 17 (3.4 mg, 2.6 µmol) and 1.1 mg of bovine serum albumin were dissolved in HEPES buffer (50 mM, pH 5.0, 257 µL), and N-acetyl-β-D-glucosaminidase (Sigma-Aldrich Corporation, from Jack Beans, 144 mU) was added thereto. This solution was allowed to stand at 37° C. for 24 hours, and thereafter the termination of the reaction was confirmed by HPLC analysis. The reaction solution was purified by HPLC (YMC Packed Column D-ODS-5 S-5 120A ODS No. 2020178, 20×250 mm, eluent: 50 mM aqueous ammonium acetate:acetonitrile=80:20, flow rate: 4 mL/min). Further, the residue was desalted on an ODS column (Cosmosil 75$C_{18}$-OPN, 15×100 mm, eluted first with 50 mL of $H_2O$ and then with 25% acetonitrile), to give a desired compound 18 (2.1 mg, yield: 75%). The physical data for the resulting compound are as follows.

$^1$H-NMR (30° C.) δ7.91 (d, 2H, J=7.5 Hz, Fmoc), 7.71 (d, 2H, J=7.5 Hz, Fmoc), 7.51 (dd, 2H, J=7.5 Hz, 7.5 Hz, Fmoc), 7.43 (dd, 2H, J=7.5 Hz, 7.5 Hz, Fmoc), 5.00 (d, 1H, J=9.7 Hz, GlcNAc1-H-1), 4.91 (d, 1H, J=1.6 Hz, Man4'-H-1), 4.76 (s, 1H, Man3-H-1), 4.58 (d, 1H, J=7.8 Hz, GlcNAc2-H-1), 4.34 (t, 1H, Fmoc), 4.07 (d, 1H, J=2.7 Hz, Man4'-H-2), 3.97 (dd, 1H, J=1.6 Hz, 3.7 Hz, Man3-H-2), 2.72 (bdd, 1H, J=3.2 Hz, 15.1 Hz, Asn-βCH), 2.52 (bdd, 1H, J=8.9 Hz, 15.1 Hz, Asn-βCH), 2.07, 1.89 (each s, each 3H, Ac); MS(Fab) Calcd for $C_{47}H_{65}N_4O_{25}[M+Na^+]$ 1085.4, found 1085.3.

EXAMPLE 17

Synthesis of Compound 21

The compound 9 (28 mg, 16 µmol) and 1.7 mg of bovine serum albumin were dissolved in HEPES buffer (50 mM, pH 5.0, 624 µL), and neuraminidase (manufactured by Sigma-Aldrich Corporation, from *Viblio Cholerae*, 117 mU) was added thereto. This solution was allowed to stand at 37° C. for 17 hours, and thereafter the termination of the reaction was confirmed by HPLC analysis. Subsequently, the reaction solution was purified by HPLC (YMC Packed Column D-ODS-5 S-5 120A ODS No. 2020178, 20×250 mm, eluent:

50 mM aqueous ammonium acetate:acetonitrile=80:20, flow rate: 4 mL/min). Further, the residue was desalted on an ODS column (Cosmosil 75$C_{18}$-OPN, 15×100 mm, eluted first with 50 mL of $H_2O$ and then with 25% acetonitrile), to give a desired compound 21 (14.6 mg, yield: 68%). The physical data for the resulting compound are as follows.

$^1$H-NMR (30° C.) δ7.92 (d, 2H, J=7.5 Hz, Fmoc), 7.71 (d, 2H, J=7.5 Hz, Fmoc), 7.50 (dd, 2H, J=7.5 Hz, Fmoc), 7.43 (dd, 2H, J=7.5 Hz, Fmoc), 5.12 (s, 1H, Man4-H-1), 4.99 (d, 1H, J=9.5 Hz, GlcNAc1-H-1), 4.77 (s, 1H, Man3-H-1), 4.57 (d, 2H, J=7.2 Hz, GlcNAc2-H-1), 4.46 (d, 1H, J=7.8 Hz, Gal6-H-1), 4.34 (t, 1H Fmoc), 4.22 (bd, 1H, J=2.7 Hz, Man3-H-2), 4.19 (b, 1H, Man4-H-2), 2.72 (bdd, 1H, J=15.5 Hz, Asn-βCH), 2.52 (bdd, 1H, J=9.8 Hz, 15.5 Hz, Asn-βCH), 2.05 (s, 6H, Ac×2), 1.89 (s, 3H, Ac); MS(Fab) Calcd for $C_{61}H_{88}N_5O_{35}[M+H^+]$ 1450.5, found 1450.3.

EXAMPLE 18

Synthesis of Compound 22

The compound 21 (10 mg, 6.9 μmol) and 1.6 mg of bovine serum albumin were dissolved in HEPES buffer (50 mM, pH 5.0, 672 μL), and β-galactosidase (manufactured by Seikagaku Corporation, from Jack Beans, 205 mU) was added thereto. This solution was allowed to stand at 37° C. for 20 hours, and thereafter the termination of the reaction was confirmed by HPLC analysis. The reaction solution was purified by HPLC (YMC Packed Column D-ODS-5 S-5 120A ODS No. 2020178, 20×250 mm, eluent: 50 mM aqueous ammonium acetate:acetonitrile=80:20, flow rate: 4 mL/min). Further, the residue was desalted on an ODS column (Cosmosil 75$C_{18}$-OPN, 15×100 mm, eluted first with 50 mL of $H_2O$ and then with 25% acetonitrile), to give a desired compound 22 (5.6 mg, yield: 64%). The physical data for the resulting compound are as follows.

$^1$H-NMR (30° C.) δ7.87 (d, 2H, J=7.5 Hz, Fmoc), 7.67 (d, 2H, J=7.5 Hz, Fmoc), 7.48 (dd, 2H, J=7.5 Hz, Fmoc), 7.41 (dd, 2H, J=7.5 Hz, Fmoc), 5.12 (s, 1H, Man4-H-1), 4.99 (d, 1H, J=9.7 Hz, GlcNAc1-H-1), 4.76 (s, 1H, Man3-H-1), 4.55 (d, 2H, J=8.6 Hz, GlcNAc2,5-H-1), 4.26 (t, 1H, Fmoc), 4.22 (d, 1H, J=2.2 Hz, Man3-H-2), 4.18 (bdd, 1H, J=1.3 Hz, 3.3 Hz, Man4-H-2), 2.72 (bd, 1H, J=15.5 Hz, Asn-βCH), 2.54 (bdd, 1H, J=9.5 Hz, 15.5 Hz, Asn-βCH), 2.05 (s, 6H, Ac×2), 1.88 (s, 3H, Ac); MS(Fab) Calcd for $C_{55}H_{78}N_5O_{30}[M+H^+]$ 1288.5, found 1288.3.

EXAMPLE 19

Synthesis of Compound 23

The compound 22 (3.6 mg, 2.8 μmol) and 1.2 mg of bovine serum albumin were dissolved in HEPES buffer (50 mM, pH 5.0, 277 μL), and N-acetyl-β-D-glucosaminidase (Sigma-Aldrich Corporation, from Jack Beans, 195 mU) was added thereto. This solution was allowed to stand at 37° C. for 24 hours, and thereafter the termination of the reaction was confirmed by HPLC analysis. The reaction solution was purified by HPLC (YMC Packed Column D-ODS-5 S-5 120A ODS No. 2020178, 20×250 mm, eluent: 50 mM aqueous ammonium acetate:acetonitrile=80:20, flow rate: 4 mL/min). Further, the residue was desalted on an ODS column (Cosmosil 75$C_{18}$-OPN, 15×100 mm, eluted first with 50 mL of $H_2O$ and then with 25% acetonitrile), to give a desired compound 23 (2.3 mg, yield: 77%). The physical data for the resulting compound are as follows.

$^1$H-NMR (30° C.) δ7.91 (d, 2H, J=7.5 Hz, Fmoc), 7.70 (d, 2H, J=7.5 Hz, Fmoc), 7.50 (dd, 2H, J=7.5 Hz, Fmoc), 7.43 (dd, 2H, J=7.5 Hz, Fmoc), 5.11 (s, 1H, Man4-H-1), 4.99 (d, 1H,J=9.7 Hz, GlcNAc1-H-1), 4.77 (s, 1H, Man3-H-1), 4.57 (d, 1H, J=6.5 Hz, GlcNAc-H-1), 4.33 (t, 1H, Fmoc), 4.22 (d, 1H, J=3.0 Hz, Man3-H-2), 4.07 (bdd, 1H, J=2.1 Hz, Man4-H-2), 2.72 (bdd, 1H, J=15.5 Hz, Asn-βCH), 2.52 (bdd, 1H, J=8.9 Hz, 15.5 Hz, Asn-βCH), 2.05, 1.89 (each s, each 3H, Ac); MS(Fab) Calcd for $C_{47}H_{65}N_4O_{25}[M+H^+]$ 1085.4, found 1085.3.

EXAMPLE 20

Synthesis of Compound 11

The compound 10 (123 mg, 62 μmol) and bovine serum albumin (1.1 mg) were dissolved in HEPES buffer (50 mM, pH 5.0, 2.5 mL), and β-galactosidase (manufactured by Seikagaku Corporation, from Jack Beans, 24 μL, 612 mU) was added thereto. This solution was allowed to stand at 37° C. for 61 hours, and thereafter the termination of the reaction was confirmed by HPLC analysis. The reaction solution was lyophilized, and subsequently purified by HPLC (YMC Packed Column D-ODS-5 S-5 120A ODS No. 2020178, 20×250 mm, eluent: 50 mM aqueous ammonium acetate: acetonitrile=80:20, flow rate: 3.5 mL/min). Further, the residue was desalted on an ODS column (Cosmosil 75$C_{18}$-OPN, 15×100 mm, eluted first with 50 mL of $H_2O$ and then with 25% acetonitrile), to give a desired compound 11 (71 mg, yield: 70%). The physical data for the resulting compound are as follows.

$^1$H-NMR (30° C.) δ7.91 (d, 2H, J=7.5 Hz, Fmoc), 7.71 (d, 2H, J=7.5 Hz, Fmoc), 7.50 (dd, 2H, J=7.5 Hz, Fmoc), 7.43 (dd, 2H, J=7.5 Hz, Fmoc), 5.11 (s, 1H, Man4-H-1), 4.99 (1H, d, J=9.9 Hz, GlcNAc1-H-1), 4.91 (s, 1H, Man4'-H-1), 4.76 (s, 1H, Man3-H-1), 4.55 (d, 2H, J=8.6 Hz, GlcNAc2, 5-H-1), 4.34 (t, 1H, Fmoc), 4.24 (s, 1H, Man3-H-2), 4.18 (s, 1H, Man4-H-2), 4.10 (s, 1H, Man4'-H-2) 2.72 (bd, 1H, J=15.5 Hz, Asn-βCH), 2.51 (bdd, 1H, J=9.0 Hz, 15.5 Hz, Asn-βCH), 2.06 (s, 3H, Ac), 2.05 (s, 6H, Ac×2), 1.88 (s, 3H, Ac); HRMS Calcd for $C_{69}H_{100}N_6NaO_{40}[M+Na^+]$ 1675.5873, found 1675.5841.

EXAMPLE 21

Synthesis of Compound 12

The compound 11 (50 mg, 30 μmol) and 2.0 mg of bovine serum albumin were dissolved in HEPES buffer (50 mM, pH 5.0, 920 μL), and N-acetyl-β-D-glucosaminidase (manufactured by Sigma-Aldrich Corporation, from Jack Beans, 2.1 U) was added thereto. This solution was allowed to stand at 37° C. for 48 hours, and thereafter the termination of the reaction was confirmed by HPLC analysis. The reaction solution was purified by HPLC (YMC Packed Column D-ODS-5 S-5 120A ODS No. 2020178, 20×250 mm, eluent: 50 mM aqueous ammonium acetate:acetonitrile=80:20, flow rate: 4 mL/min), and lyophilized. This residue was desalted on an ODS column (Cosmosil 75$C_{18}$-OPN, 15×100 mm, eluted first with 50 mL of $H_2O$ and then with 25% acetonitrile), to give a desired compound 12 (25 mg, yield: 66%). The physical data for the resulting compound are as follows.

$^1$H-NMR (30° C.) δ7.91 (d, 2H, J=7.5 Hz, Fmoc), 7.70 (d, 2H, J=7.5 Hz, Fmoc), 7.50 (dd, 2H, J=7.5 Hz, Fmoc), 7.43 (dd, 2H, J=7.5 Hz, Fmoc), 5.10 (s, 1H, Man4-H-1), 4.99 (d, 1H, J=9.7 Hz, GlcNAc1-H-1), 4.91 (bd, 1H, J=1.6 Hz, Man4'-H-1), 4.77 (s, 1H, Man3-H-1), 4.58–4.52 (b, 1H, GlcNAc2-H-1), 4.33 (t, 1H, Fmoc), 4.24 (bs, 1H, Man3-H-2), 4.06 (dd, 1H, J=1.6 Hz, 3.2 Hz, Man4-H-2), 3.97 (dd, 1H, J=1.6 Hz, 3.5 Hz, Man4'-H-2), 2.72 (bd, 1H, J=15.5 Hz, Asn-βCH), 2.53 (bdd, 1H, J=9.0 Hz, 15.5 Hz, Asn-βCH), 2.05, 1.88 (each s, each 3H, Ac).

EXAMPLE 22

Synthesis of Compound 13

The compound 12 (10 mg, 11 μmol) and 0.9 mg of bovine serum albumin were dissolved in HEPES buffer (50 mM, pH 5.0, 440 μL), and α-mannosidase (manufactured by Sigma-Aldrich Corporation, from Jack Beans, 30 μL, 3.2 U) was added thereto. This solution was allowed to stand at 37° C. for 21 hours, and thereafter the termination of the reaction was confirmed by HPLC analysis. Subsequently, the reaction solution was purified by HPLC (YMC Packed Column D-ODS-5 S-5 120A ODS No. 2020178, 20×250 mm, eluent: 50 mM aqueous ammonium acetate:acetonitrile=80:20, flow rate: 4 mL/min). Further, the residue was desalted on an ODS column (Cosmosil 75$C_{18}$-OPN, 15×100 mm, eluted first with 50 ml of $H_2O$ and then with 25% acetonitrile), to give a desired compound 13 (3 mg, yield: 43%). The physical data for the resulting compound are as follows.

$^1$H-NMR (30° C.) δ7.92 (d, 2H, J=7.5 Hz, Fmoc), 7.71 (d, 2H, J=7.5 Hz, Fmoc), 7.51 (dd, 2H, J=7.5 Hz, Fmoc), 7.43 (dd, 2H, J=7.5 Hz, Fmoc), 4.99 (d, 1H, J=9.5 Hz, GlcNAc1-H-1), 4.76 (s, 1H, Man3-H-1), 4.57 (1H, GlcNAc2-H-1), 4.06 (d, 1H, J=3.2 Hz, Man3-H-2), 2.72 (bd, 1H, J=15.5 Hz, Asn-βCH), 2.52 (bdd, 1H, J=8.3 Hz, 15.5 Hz, Asn-βCH), 2.05, 1.89 (each s, each 3H, Ac).

(Deprotection of Fmoc Group of Sugar Chain Asparagine Derivative)

All of the sugar chain asparagine derivatives were subjected to the deprotection of the Fmoc group in accordance with the following procedures. First, 240 μL of N,N-dimethylformamide and 160 μL of morpholine were added per 1 μmol of the Fmoc form of the sugar chain asparagine, and the resulting mixture was subjected to reaction at room temperature under argon atmosphere. The termination of the reaction was confirmed by TLC (eluent: 1M ammonium acetate:isopropanol=8:5), and thereafter the mixture was cooled with ice water. To this mixture was added diethyl ether in an amount of 10 times that of the reaction solution, with stirring the mixture for 15 minutes, and thereafter the precipitates formed were filtered. The residue obtained was dissolved in water, and evaporated at 35° C. Further, a procedure of adding 3 mL of toluene thereto and evaporating the mixture was repeated three times. The residue was purified by reverse phase column chromatography (Cosmosil 75$C_{18}$-OPN, 15×100 mm, eluent: water).

EXAMPLE 23

Synthesis of Compound 33

The compound 10 (10.5 mg, 5.3 μmol) was reacted for 7 hours in accordance with the above procedures, to give a desired compound 33 (7 mg, yield: 76%). The resulting compound was confirmed from the finding that its $^1$H-NMR was identical to that of the preparation.

EXAMPLE 24

Synthesis of Compound 26

The compound 3 (8.0 mg, 3.8 μmol) was subjected to the reaction for 21 hours in accordance with the above procedures, to give a desired compound 26 (6.3 mg, yield: 88%). The physical data for the resulting compound are as follows.

$^1$H-NMR (30° C.) δ5.13 (s, 1H, Man4-H-1), 5.07 (d, 1H, J=9.9 Hz, GlcNAc1-H-1), 4.95 (s, 1H, Man4'-H-1), 4.78 (s, 1H, Man3-H-1), 4.62 (2H, GlcNAc2,5'-H-1), 4.56 (d, 1H, J=8.1 Hz, GlcNAc5-H-1), 4.52 (d, 1H, J=7.8 Hz, Gal6'-H-1), 4.25 (bs, 1H, Man3-H-2), 4.19 (bs, 1H, Man4'-H-2), 4.12 (bs, 1H, Man4-H-2), 2.94 (dd, 1H, J=4.5 Hz, 17.0 Hz, Asn-βCH), 2.85 (dd, 1H, J=6.8 Hz, 17.0 Hz, Asn-βCH), 2.68 (dd, 1H, J=4.6 Hz, 12.4 Hz, NeuAc7'-H-3$_{eq}$), 2.08, 2.07, 2.06, 2.04, 2.02 (each s, each 3H, Ac), 1.72 (dd, 1H, J=12.1 Hz, 12.1 Hz, NeuAc7'-H-3$_{ax}$); MS(Fab) Calcd for $C_{71}H_{118}N_7O_{51}[M+H^+]$ 1884.7, found 1884.5.

EXAMPLE 25

Synthesis of Compound 27

The compound 4 (11.0 mg, 5.8 μmol) was subjected to the reaction for 23 hours in accordance with the above procedures, to give a desired compound 27 (8.5 mg, yield: 88%). The physical data for the resulting compound are as follows.

$^1$H-NMR (30° C.) δ5.11 (s, 1H, Man4-H-1), 5.08 (d, 1H, J=9.7 Hz, GlcNAc1-H-1), 4.95 (s, 1H, Man4'-H-1), 4.78 (s, 1H, Man3-H-1), 4.62 (d, 2H, GlcNAc2,5'-H-1), 4.45 (d, 1H, J=7.6 Hz, Gal6'-H-1), 4.26 (bd, 1H, Man3-H-2), 4.12 (bd, 1H, Man4'-H-2), 4.08 (bdd, 1H, J=1.6 Hz, 3.3 Hz, Man4-H-2), 2.94 (dd, 1H, J=4.0 Hz, 17.2 Hz, Asn-βCH), 2.85 (dd, 1H, J=7.2 Hz, 17.2 Hz, Asn-βCH), 2.68 (dd, 1H, J=4.1 Hz, 12.1 Hz, NeuAc7'-H-3$_{eq}$), 2.09, 2.07, 2.04, 2.02 (each s, each 3H, Ac), 1.72 (dd, 1H, J=12.1 Hz, 12.1 Hz, NeuAc7'-H-3$_{ax}$); MS(Fab) Calcd for $C_{63}H_{104}N_6NaO_{46}[M+Na^+]$ 1703.6, found 1703.1.

EXAMPLE 26

Synthesis of Compound 28

The compound 5 (7.0 mg, 4.0 μmol) was subjected to the reaction for 21 hours in accordance with the above procedures, to give a desired compound 28 (5.3 mg, yield: 87%). The physical data for the resulting compound are as follows.

$^1$H-NMR (30° C.) δ5.07 (d, 1H, J=9.4 Hz, GlcNAc1-H-1), 4.94 (s, 1H, Man4'-H-1), 4.76 (s, 1H, Man3-H-1), 4.61, 4.59 (each d, each 1H, GlcNAc2,5'-H-1), 4.44 (d, 1H, J=7.8 Hz, Gal6'-H-1), 4.10, 4.07 (each 1H, Man4',3-H-2), 2.93 (dd, 1H, J=4.6 Hz, 17.5 Hz, Asn-βCH), 2.85 (dd, 1H, J=7.0 Hz, 17.5 Hz, Asn-βCH), 2.67 (dd, 1H, J=4.6 Hz, 12.2 Hz, NeuAc7'-H-3$_{eq}$), 2.08, 2.06, 2.02, 2.01 (each s, each 3H, Ac), 1.71 (2H, dd, J=12.2 Hz, 12.2 Hz, NeuAc7'-H-3$_{ax}$); MS(Fab) Calcd for $C_{57}H_{94}N_6NaO_{41}[M+Na^+]$ 1541.5, found 1541.3.

EXAMPLE 27

Synthesis of Compound 30

The compound 7 (13.9 mg, 6.6 μmol) was subjected to the reaction for 7 hours in accordance with the above procedures, to give a desired compound 30 (8.0 mg, yield: 64%). The physical data for the resulting compound are as follows.

$^1$H-NMR (30° C.) δ5.13 (s, 1H, Man4-H-1), 5.06 (d, 1H, J=9.9 Hz, GlcNAc1-H-1), 4.91 (s, 1H, Man4'-H-1), 4.77 (s, 1H, Man3-H-1), 4.61, 4.60 (each d, each 1H, J=8.0 Hz, GlcNAc2,5-H-1), 4.55 (d, 1H, J=8.4 Hz, GlcNAc5'-H-1), 4.44 (d, 1H, J=8.0 Hz, Gal6-H-1), 4.24 (bd, 1H, Man3-H-2), 4.19 (bdd, 1H, J=1.3 Hz, 3.2 Hz, Man4'-H-2), 4.10 (bdd, 1H, J=1.4 Hz, 3.2 Hz, Man4-H-2), 2.90 (dd, 1H, J=4.5 Hz, 16.7 Hz, Asn-βCH), 2.80 (dd, 1H, J=7.5 Hz, 16.7 Hz, Asn-βCH), 2.66 (dd, 1H, J=4.6 Hz, 12.4 Hz, NeuAc7-H-3$_{eq}$), 2.07, 2.06, 2.05, 2.02, 2.01 (each s, each 3H, Ac), 1.71 (dd, 1H, J=12.4 Hz, 12.4 Hz, NeuAc7-H-3$_{ax}$); MS(Fab) Calcd for $C_{71}H_{117}N_7NaO_{51}$[M+Na$^+$] 1906.7, found 1906.1.

EXAMPLE 28

Synthesis of Compound 31

The compound 8 (8.0 mg, 4.2 μmol) was subjected to the reaction for 12 hours in accordance with the above procedures, to give a desired compound 31 (6.0 mg, yield: 86%). The physical data for the resulting compound are as follows.

$^1$H-NMR (30° C.) δ5.12 (s, 1H, Man4-H-1), 5.06 (d, 1H, J=9.5 Hz, GlcNAc1-H-1), 4.91 (s, 1H, Man4'-H-1), 4.77 (s, 1H, Man3-H-1), 4.61, 4.59 (each d, each 1H, GlcNAc2,5-H-1), 4.43 (d, 1H, J=8.0 Hz, Gal6-H-1), 4.24 (bd, 1H, Man3-H-2), 4.18 (bdd, 1H, Man4'-H-2), 2.91 (bd, 1H, J=17.0 Hz, Asn-βCH), 2.81 (dd, 1H, J=6.5 Hz, 17.0 Hz, Asn-βCH), 2.66 (dd, 1H, J=4.6 Hz, 12.6 Hz, NeuAc7-H-3$_{eq}$), 2.06, 2.06, 2.02, 2.00 (each s, each 3H, Ac), 1.70 (dd, 1H, J=12.6 Hz, 12.6 Hz, NeuAc7-H-3$_{ax}$); MS(Fab) Calcd for $C_{63}H_{104}N_6NaO_{46}$[M+Na$^+$] 1703.6, found 1703.0.

EXAMPLE 29

Synthesis of Compound 32

The compound 9 (7.7 mg, 4.4 μmol) was subjected to the reaction for 23 hours in accordance with the above procedures, to give a desired compound 32 (5.2 mg, yield: 78%). The physical data for the resulting compound are as follows.

$^1$H-NMR (30° C.) δ5.14 (s, 1H, Man4-H-1), 5.07 (d, 1H, J=9.4 Hz, GlcNAc1-H-1), 4.78 (s, 1H, Man3-H-1), 4.61, 4,60 (each d, each 1H, GlcNAc2,5-H-1), 4.44 (d, 1H, J=8.0 Hz, Gal6-H-1), 4.23 (d, 1H, J=3.0 Hz, Man3-H-2), 4.19 (bdd, 1H, J=1.3 Hz, 2.9 Hz, Man4-H-2), 2.92 (dd, 1H, J=4.1 Hz, 17.2 Hz, Asn-βCH), 2.83 (dd, 1H, J=7.5 Hz, 12.7 Hz, Asn-βCH), 2.67 (dd, 1H, J=4.6 Hz, 12.7 Hz, NeuAc7-H-3$_{eq}$), 2.06 (s, 6H, Ac×2), 2.03, 2.01 (each s, each 3H, Ac), 1.71 (dd, 1H, J=12.7 Hz, 12.7 Hz, NeuAc7-H-3$_{ax}$); MS(Fab) Calcd for $C_{57}H_{94}N_6NaO_{41}$[M+Na$^+$] 1541.5, found 1541.2.

EXAMPLE 30

Synthesis of Compound 37

The compound 14 (9.1 mg, 5.0 μmol) was subjected to the reaction for 13 hours in accordance with the above procedures, to give a desired compound 37 (6.5 mg, yield: 77%). The physical data for the resulting compound are as follows.

$^1$H-NMR (30° C.) δ5.11 (s, 1H, Man4-H-1), 5.06 (d, 1H, J=9.5 Hz, GlcNAc1-H-1), 4.92 (s, 1H, Man4'-H-1), 4.75 (s, 1H, Man3-H-1), 4.61, 4.57, 4.55 (each d, each 1H, J=7.5 Hz, GlcNAc2,5,5'-H-1), 4.46 (d, 1H, J=7.3 Hz, Gal6'-H-1), 4.23 (bs, 1H, Man3-H-2), 4.18 (bs, 1H, Man4'-H-2), 4.10 (bs, 1H, Man4-H-2), 2.87 (dd, 1H, J=4.8 Hz, 17.0 Hz, Asn-βCH), 2.76 (dd, 1H, J=7.2 Hz, 17.0 Hz, Asn-βCH), 2.07 (s, 3H, Ac), 2.04 (s, 6H, Ac×2), 2.00 (s, 3H, Ac); MS(Fab) Calcd for $C_{60}H_{100}N_6NaO_{43}$[M+Na$^+$] 1615.6, found 1615.0.

EXAMPLE 31

Synthesis of Compound 42

The compound 19 (9.8 mg, 5.4 μmol) was subjected to the reaction for 13 hours in accordance with the above procedures, to give a desired compound 42 (8.0 mg, yield: 88%). The physical data for the resulting compound are as follows.

$^1$H-NMR (30° C.) δ5.11 (s, 1H, Man4-H-1), 5.06 (d, 1H, J=9.5 Hz, GlcNAc1-H-1), 4.91 (s, 1H, Man4'-H-1), 4.76 (s, 1H, Man3-H-1), 4.60, 4.57, 4.55 (each d, each 1H, GlcNAc2,5,5'-H-1), 4.46 (d, 1H, J=7.8 Hz, Gal6-H-1), 4.28 (s, 1H, Man3-H-2), 4.18 (s, 1H, Man4'-H-2), 4.10 (s, 1H, Man4-H-2), 2.88 (dd, 1H, J=4.0 Hz, 16.6 Hz, Asn-βCH), 2.77 (dd, 1H, J=7.5 Hz, 16.6 Hz, Asn-βCH), 2.07 (s, 3H, Ac), 2.04 (s, 6H, Ac×2), 2.00 (s, 3H, Ac); MS(Fab) Calcd for $C_{60}H_{101}N_6O_{43}$[M+H$^+$] 1593.6, found 1593.8.

EXAMPLE 32

Synthesis of Compound 38

The compound 15 (5.1 mg, 3.2 μmol) was subjected to the reaction for 11 hours in accordance with the above procedures, to give a desired compound 38 (4.0 mg, yield: 91%). The physical data for the resulting compound are as follows.

$^1$H-NMR (30° C.) δ5.10 (s, 1H, Man4-H-1), 5.07 (d, 1H, J=9.4 Hz, GlcNAc1-H-1), 4.92 (s, 1H, Man4'-H-1), 4.76 (s, 1H, Man3-H-1), 4.61, 4.57 (each d, each 1H, J=7.8 Hz, GlcNAc2,5'-H-1), 4.47 (d, 1H, J=7.8 Hz, Gal6'-H-1), 4.24 (d, 1H, J=2.3 Hz, Man3-H-2), 4.10, 4.06 (each bd, each 1H, Man4',4-H-2), 2.90 (dd, 1H, J=4.2 Hz, 16.8 Hz, Asn-βCH), 2.81 (dd, 1H, J=7.3 Hz, 16.8 Hz, Asn-βCH), 2.07, 2.04, 2.01 (each s, each 3H, Ac); MS(Fab) Calcd for $C_{52}H_{88}N_5O_{38}$[M+H$^+$] 1390.5, found 1390.1.

EXAMPLE 33

Synthesis of Compound 72

The compound 70 (4.0 mg, 2.8 μmol) was subjected to the reaction for 13 hours in accordance with the above procedures, to give a desired compound 72 (2.9 mg, yield: 85%). The physical data for the resulting compound are as follows.

$^1$H-NMR (30° C.) δ5.09 (s, 1H, Man4-H-1), 5.06 (d, 1H, J=9.8 Hz, GlcNAc1-H-1), 4.91 (s, 1H, Man4'-H-1), 4.76 (s, 1H, Man3-H-1), 4.61, 4.54 (each d, each 1H, GlcNAc2,5-H-1), 4.24 (s, 1H, Man3-H-2), 4.10, 4.06 (each bs, each 1H, Man4,4'-H-2), 2.87 (dd, 1H, J=17.2 Hz, Asn-βCH), 2.76 (dd, 1H, J=6.5 Hz, 17.2 Hz, Asn-βCH), 2.07, 2.04, 2.00 (each s, each 3H, Ac); MS(Fab) Calcd for $C_{46}H_{78}N_5O_{33}$[M+H$^+$] 1228.5, found 1228.3.

EXAMPLE 34

Synthesis of Compound 43

The compound 20 (5.4 mg, 3.3 μmol) was subjected to the reaction for 11 hours in accordance with the above procedures, to give a desired compound 43 (4.1 mg, yield: 87%). The physical data for the resulting compound are as follows.

$^1$H-NMR (30° C.) δ5.11 (s, 1H, Man4-H-1), 5.07 (d, 1H, J=9.5 Hz, GlcNAc1-H-1), 4.91 (s, 1H, Man4'-H-1), 4.77 (s, 1H, Man3-H-1), 4.61, 4.57 (each d, each 1H, GlcNAc2,5-H-1), 4.46 (d, 1H, Gal6-H-1), 4.24 (s, 1H, Man3-H-2), 4.18 (bs, 1H, Man4-H-2), 2.90 (dd, 1H, J=4.0 Hz, 17.0 Hz, Asn-βCH), 2.80 (dd, 1H, J=7.3 Hz, 17.0 Hz, Asn-βCH), 2.07, 2.04, 2.01 (each s, each 3H, Ac); MS(Fab) Calcd for $C_{52}H_{88}N_5O_{38}$[M+H$^+$] 1390.5, found 1390.2.

EXAMPLE 35

Synthesis of Compound 73

The compound 71 (4.0 mg, 2.8 μmol) was subjected to the reaction for 13 hours in accordance with the above procedures, to give a desired compound 73 (2.9 mg, yield: 85%). The physical data for the resulting compound are as follows.

$^1$H-NMR (30° C.) δ5.11 (s, 1H, Man4-H-1), 5.06 (d, 1H,J=9.9 Hz, GlcNAc1-H-1), 4.91 (s, 1H, Man4'-H-1), 4.77 (s, 1H, Man3-H-1), 4.60, 4.54 (each d, each 1H, J=7.9 Hz, GlcNAc2,5-H-1), 4.24 (s, 1H, Man3-H-2), 4.18 (dd, 1H, J=1.6 Hz, 1.6 Hz, Man4-H-2), 3.96 (1H, dd, J=1.6 Hz, 1.6 Hz, Man4-H-2), 2.88 (dd, 1H, J=4.3 Hz, 16.8 Hz, Asn-βCH), 2.77 (dd, 1H, J=7.2 Hz, 16.8 Hz, Asn-βCH), 2.06, 2.04, 2.00 (each s, each 3H, Ac); MS(Fab) Calcd for $C_{46}H_{78}N_5O_{33}[M+H^+]$ 1228.5, found 1228.3.

EXAMPLE 36

Synthesis of Compound 39

The compound 16 (2.2 mg, 1.5 μmol) was subjected to the reaction for 7 hours in accordance with the above procedures, to give a desired compound 39 (1.6 mg, yield: 84%). The physical data for the resulting compound are as follows.

$^1$H-NMR (30° C.) δ5.07 (d, 1H, J=9.7 Hz, GlcNAc1-H-1), 4.92 (s, 1H, Man4'-H-1), 4.75 (s, 1H, Man3-H-1), 4.62, 4.58 (each d, each 1H, GlcNAc2,5-H-1), 4.09, 4.08 (each s, each 1H, Man3,4'-H-2), 2.91 (dd, 1H, J=4.1 Hz, 16.9 Hz, Asn-βCH), 2.81 (dd, 1H, J=6.8 Hz, 16.9 Hz, Asn-βCH), 2.08, 2.04, 2.01 (each s, each 3H, Ac); MS(Fab) Calcd for $C_{46}H_{77}N_5NaO_{33}[M+Na^+]$ 1250.4, found 1250.3.

EXAMPLE 37

Synthesis of Compound 40

The compound 17 (1.5 mg, 1.2 μmol) was subjected to the reaction for 14 hours in accordance with the above procedures, to give a desired compound 40 (1.1 mg, yield: 89%). The physical data for the resulting compound are as follows.

$^1$H-NMR (30° C.) δ5.07 (d, 1H, J=9.5 Hz, GlcNAc1-H-1), 4.91 (s, 1H, Man4'-H-1), 4.76 (s, 1H, Man3-H-1), 4.62, 4.55 (each d, each 1H, GlcNAc2,5-H-1), 4.10, 4.07 (each s, each 1H, Man4',3-H-2), 2.89 (dd, 1H, J=3.7 Hz, 17.0 Hz, Asn-βCH), 2.79 (dd, 1H, J=7.0 Hz, 17.0 Hz, Asn-βCH), 2.07, 2.05, 2.01 (each s, each 3H, Ac); MS(Fab) Calcd for $C_{40}H_{67}N_5NaO_{28}[M+Na^+]$ 1088.4, found 1088.2.

EXAMPLE 38

Synthesis of Compound 41

The compound 18 (1.3 mg, 1.2 μmol) was subjected to the reaction for 14 hours in accordance with the above procedures, to give a desired compound 41 (0.8 mg, yield: 80%). The physical data for the resulting compound are as follows.

$^1$H-NMR (30° C.) δ5.07 (d, 1H, J=9.5 Hz, GlcNAc1-H-1), 4.91 (s, 1H, Man4'-H-1), 4.76 (s, 1H, Man3-H-1), 4.62 (d, 1H, J=7.8 Hz, GlcNAc2-H-1), 4.08 (d, 1H, J=2.9 Hz, Man3-H-2), 2.92 (dd, 1H, J=3.9 Hz, 17.3 Hz, Asn-βCH), 2.83 (dd, 1H, J=7.0 Hz, 17.3 Hz, Asn-βCH), 2.07, 2.01 (each s, each 3H, Ac); MS(Fab) Calcd for $C_{32}H_{55}N_4O_{27}[M+H^+]$ 863.3, found 863.2.

EXAMPLE 39

Synthesis of Compound 44

The compound 21 (2.3 mg, 1.6 μmol) was subjected to the reaction for 7 hours in accordance with the above procedures, to give a desired compound 44 (1.6 mg, yield: 84%). The physical data for the resulting compound are as follows.

$^1$H-NMR (30° C.) δ5.11 (s, 1H, Man4-H-1), 5.06 (d, 1H,J=9.8 Hz, GlcNAc1-H-1), 4.77 (s, 1H, Man3-H-1), 4.61, 4.57 (each d, each 1H, GlcNAc2,5-H-1), 4.46 (d, 1H, J=7.8 Hz, Gal-H-1), 4.22, 4.18 (each bs, each 1H, Man3,4-H-2), 2.91 (dd, 1H,J=4.1 Hz, 17.3 Hz, Asn-βCH), 2.82 (dd, 1H, J=7.0 Hz, 17.3 Hz, Asn-βCH), 2.05, 2.04, 2.01 (each s, each 3H, Ac); MS(Fab) Calcd for $C_{46}H_{78}N_5O_{33}[M+H^+]$ 1228.5, found 1228.3.

EXAMPLE 40

Synthesis of Compound 45

The compound 22 (1.6 mg, 1.3 μmol) was subjected to the reaction for 14 hours in accordance with the above procedures, to give a desired compound 45 (1.1 mg, yield: 85%). The physical data for the resulting compound are as follows.

$^1$H-NMR (30° C.) δ5.12 (s, 1H, Man4-H-1), 5.07 (d, 1H, J=9.7 Hz, GlcNAc1-H-1), 4.77 (s, 1H, Man3-H-1), 4.61, 4.54 (each d, each 1H, GlcNAc2,5-H-1), 4.22 (d, 1H,J=2.5 Hz, Man3-H-2), 4.18 (dd, 1H,J=1.4 Hz, 3.0 Hz, Man4'-H-2), 2.89 (dd, 1H, J=4.3 Hz, 16.9 Hz, Asn-βCH), 2.78 (dd, 1H, J=7.5 Hz, 16.9 Hz, Asn-βCH), 2.06, 2.05, 2.01 (each s, each 3H, Ac); MS(Fab) Calcd for $C_{40}H_{67}N_5NaO_{28}[M+Na^+]$ 1088.4, found 1088.3.

EXAMPLE 41

Synthesis of Compound 46

The compound 23 (1.6 mg, 1.5 μmol) was subjected to the reaction for 14 hours in accordance with the above procedures, to give a desired compound 46 (1.1 mg, 6.4 μmol, yield: 85%). The physical data for the resulting compound are as follows.

$^1$H-NMR (30° C.) δ5.10 (s, 1H, Man4-H-1), 5.06 (d, 1H, J=9.5 Hz, GlcNAc1-H-1), 4.77 (s, 1H, Man3-H-1), 4.61 (d, 1H, J=7.3 Hz, GlcNAc2-H-1), 4.22 (d, 1H, J=2.4 Hz, Man3-H-2), 4.07 (dd, 1H, J=1.6 Hz, 3.0 Hz, Man4'-H-2), 2.90 (dd, 1H, J=4.3 Hz, 17.0 Hz, Asn-βCH), 2.80 (dd, 1H, J=7.0 Hz, 17.2 Hz, Asn-βCH), 2.05, 2.01 (each s, each 3H, Ac); MS(Fab) Calcd for $C_{32}H_{55}N_4O_{23}[M+H^+]$ 863.3, found 863.3.

EXAMPLE 42

Synthesis of Compound 34

The compound 11 (12.4 mg, 7.5 μmol) was subjected to the reaction for 11 hours in accordance with the above procedures, to give a desired compound 34 (9.2 mg, yield: 86%). The physical data for the resulting compound are as follows.

$^1$H-NMR (30° C.) δ5.11 (s, 1H, Man4-H-1), 5.07 (d, 1H, J=10.0 Hz, GlcNAc1-H-1), 4.91 (s, 1H, Man4'-H-1), 4.77 (s, 1H, Man3-H-1), 4.61 (d, 1H, J=6.8 Hz, GlcNAc2-H-1), 4.55 (d, 2H, GlcNAc5,5'-H-1), 4.24 (bs, 1H, Man3-H-2), 4.18 (bs, 1H, Man4'-H-2), 4.10 (bs, 1H, Man4-H-2), 2.80 (dd, 1H, J=3.8 Hz, 15.6 Hz, Asn-βCH), 2.63 (dd, 1H, J=8.2 Hz, 15.6 Hz, Asn-βCH), 2.07 (s, 3H, Ac), 2.05 (s, 6H, Ac×2), 2.01 (s, 3H, Ac); MS(Fab) Calcd for $C_{54}H_{90}N_6NaO_{38}[M+Na^+]$ 1453.5, found 1453.2.

EXAMPLE 43

Synthesis of Compound 35

The compound 12 (12.0 mg, 8.4 μmol) was subjected to the reaction for 11 hours in accordance with the above procedures, to give a desired compound 35 (7.0 mg, yield: 81%). The physical data for the resulting compound are as follows.

$^1$H-NMR (30° C.) δ5.10 (s, 1H, Man4-H-1), 5.07 (d, 1H, J=9.7 Hz, GlcNAc1-H-1), 4.91 (s, 1H, Man4'-H-1), 4.78 (s, 1H, Man3-H-1), 4.61 (d, 1H, J=8.0 Hz, GlcNAc2-H-1), 4.25 (bs, 1H, Man3-H-2), 4.06 (bs, 1H, Man4'-H-2), 3.97 (bs, 1H, Man4-H-2), 2.79 (dd, 1H, J=5.0 Hz, 17.0 Hz, Asn-βCH), 2.61 (dd, 1H, J=7.3 Hz, 17.0 Hz, Asn-βCH), 2.07, 2.01 (each s, each 3H, Ac); MS(Fab) Calcd for $C_{38}H_{65}N_4O_{28}[M+H^+]$ 1025.4, found 1025.2.

EXAMPLE 44

Synthesis and Isolation of Compounds 76 and 77

The compounds 2 and 6 (5.0 mg, 2.2 μmol) were dissolved in 220 μL of water, and 100 μL of a 22 mM aqueous cesium carbonate was added thereto to adjust its pH to 7.0. This solution was lyophilized. Four-hundred and thirty microliters of N,N-dimethylformamide was added to the solid obtained after drying, and further 20 μL of a 6.6 μmol benzyl bromide/N,N-dimethylformamide solution was added thereto. This solution was stirred under argon atmosphere. After 48 hours, the disappearance of the starting material was confirmed by TLC (eluent: 1M NH$_4$OAc: isopropanol=2:1), and thereafter 4.4 mL of diethyl ether was added to the solution to allow the compound to precipitate therefrom. The precipitated sugar chains were filtered, and the residual sugar chain was dissolved in water and lyophilized. The residue after the lyophilization was purified by fractional HPLC (YMC Packed Column D-ODS-5 S-5 120A ODS No. 2020178, 20×250 mm, eluent: 50 mM aqueous ammonium acetate:acetonitrile=78:22, flow rate: 4 mL/min), and a compound 77 was eluted after 88 minutes and a compound 76 was eluted after 91 minutes. The fractions were collected, and further desalted on an ODS column (Cosmosil 75C$_{18}$-OPN, 15×100 mm, eluted first with 50 mL of H$_2$O and then with 25% acetonitrile), to give a desired compound 76 in an amount of 1.6 mg and a desired compound 77 in an amount of 1.8 mg. The physical data for the resulting compound are as follows.

Data for Compound 76

$^1$H-NMR (30° C.) δ7.92 (d, 2H, J=7.5 Hz, Fmoc), 7.71 (d, 2H, J=7.5 Hz, Fmoc), 7.53–7.40 (m, 9H, Fmoc, —CH$_2$-Ph), 5.38 (d, 1H, J=12.1 Hz, —CH$_2$-Ph), 5.31 (d, 1H, J=12.1 Hz, —CH$_2$-Ph), 5.12 (s, 1H, Man4-H-1), 4.99 (d, 1H, J=9.5 Hz, GlcNAc1-H-1), 4.92 (s, 1H, Man4'-H-1), 4.76 (s, 1H, Man3-H-1), 4.58 (m, 3H, GlcNAc2,5,5'-H-1), 4.47 (d, 1H, J=7.9 Hz, Gal6'-H-1), 4.33 (d, 1H, J=7.9 Hz, Gal6-H-1), 4.24 (bs, 1H, Man3-H-2), 4.19 (bs, 1H, Man4'-H-2), 4.11 (bs, 1H, Man4-H-2), 2.72 (bd, 1H, Asn-βCH), 2.68 (dd, 1H, J=4.6 Hz, 12.7 Hz, NeuAc7-H-3$_{eq}$), 2.52 (dd, 1H, J=8.7 Hz, 15.0 Hz, Asn-βCH), 2.07, 2.04, 2.03, 2.02, 1.89 (each s, each 3H, Ac), 1.84 (dd, 1H, J=12.7 Hz, 12.7 Hz, NeuAc7-H3$_{ax}$); MS(Fab) Calcd for $C_{99}H_{143}N_{17}NaO_{58}[M+H^+]$ 2380.8, found 2380.0.

Data for Compound 77

$^1$H-NMR (30° C.) δ7.91 (d, 2H, J=7.5 Hz, Fmoc), 7.71 (d, 2H, J=7.5 Hz, Fmoc), 7.53–7.41 (m, 9H, Fmoc, —CH$_2$-Ph), 5.37 (d, 1H, J=12.1 Hz, —CH$_2$-Ph), 5.31 (d, 1H, J=12.1 Hz, —CH$_2$-Ph), 5.12 (s, 1H, Man4-H-1), 4.99 (d, 1H, J=9.8 Hz, GlcNAc1-H-1), 4.93 (s, 1H, Man4'-H-1), 4.76 (s, 1H, Man3-H-1), 4.58 (m, 3H, GlcNAc2,5,5'-H-1), 4.46 (1H, d, J=7.8 Hz, Gal6-H-1), 4.33 (d, 1H, J=7.8 Hz, Gal6'-H-1), 4.24 (bs, 1H, Man3-H-2), 4.19 (bs, 1H, Man4'-H-2), 4.11 (bs, 1H, Man4-H-2), 2.72 (bd, 1H, Asn-βCH), 2.68 (dd, 1H, J=4.8 Hz, 13.0 Hz, NeuAc7-H-3$_{eq}$), 2.52 (bdd, 1H, J=9.7 Hz, 14.1 Hz, Asn-βCH), 2.06, 2.05, 2.04, 2.02, 1.89 (each s, each 3H, Ac), 1.84 (dd, 1H, J=13.0 Hz, 13.0 Hz, NeuAc7-H-3$_{ax}$); MS(Fab) Calcd for $C_{99}H_{143}N_7NaO_{58}[M+H^+]$ 2380.8, found 2380.5.

EXAMPLE 45

Synthesis of Compound 78

A cooled aqueous solution of the compound 1 (20 mg) was applied onto a Dowex-50 W×8 (H$^+$) column (φ 0.5 cm×5 cm) chilled at 4° C., and the eluted aqueous solution was lyophilized. The resulting lyophilized product was dissolved in a chilled water at 4° C., an aqueous Cs$_2$CO$_3$ (2.5 mg/1 ml) was added thereto to adjust a pH of the aqueous solution to 5 to 6, and the aqueous solution was then lyophilized. The Fmoc-disialo-sugar chain sample after the lyophilization was dissolved in a dry DMF (1.3 ml), and benzyl bromide (5.1 μl) was added thereto with stirring the mixture at room temperature for 45 minutes under argon gas stream. The termination of the reaction was confirmed by TLC, thereafter the reaction solution was cooled to 0° C., and 10 ml of diethyl ether was added to the reaction solution to precipitate the desired product. This substance was filtered with a filter paper. Distilled water was added to the residual desired product, and eluted as a filtrate, and subsequently concentrated under a reduced pressure. The resulting residue was purified by applying to an ODS column (φ 1.6 cm×14 cm, eluent: H$_2$O→40% aqueous MeOH), to give a compound 78 (18.2 mg, yield: 85%). The physical data for the resulting compound 78 are as follows.

$^1$H-NMR (30° C.) 7.90 (d, 2H, Fmoc), 7.70 (d, 2H, Fmoc), 7.53–7.40 (m, 9H, Bn, Fmoc), 5.36 (d, 2H, J=11.6 Hz, CH$_2$), 5.30 (d, 2H, J=11.6 Hz, CH$_2$), 5.12 (s, 1H, Man4-H$_1$), 4.99 (d, 1H, J=9.7 Hz, GlcNAc1-H$_1$), 4.93 (s, 1H, Man4'-H$_1$), 4.75 (s, 1H, Man3-H$_1$), 4.57 (m, 3H, GlcNAc2-H$_1$, GlcNAc5,5'-H$_1$), 4.32 (d, 2H, Gal6,6'-H$_1$), 4.24 (d, 1H, Man3-H$_2$), 4.18 (d, 1H, Man4'-H$_2$), 4.10 (1H, d, Man4-H$_2$) 2.72 (bd, 1H, Asn-βCH), 2.67 (dd, 2H, NeuAc7,7'-H$_{3eq}$), 2.51 (bdd, 1H, Asn-βCH), 2.06 (s, 3H, Ac), 2.03, 2.01 (each s, each 6H, Ac×2), 1.89 (s, 3H, Ac), 1.83 (2H, dd, J=12.2, 12.2 Hz, NeuAc7,7'-H$_{3ax}$); HRMS Calcd for $C_{117}H_{165}N_8Na_2O_{66}[M+Na^+]$ 2783.9597, found 2783.9501.

INDUSTRIAL APPLICABILITY

According to the present invention, various sugar chains having desired sugar chain structures can be obtained in large amounts very conveniently. Therefore, there is expected to be utilized for therapeutic agents against cancer, inflammation, influenza and the like. Especially, the sugar chain asparagine derivative and sugar chain asparagine which can be obtained in the present invention are excellent in safety without any risks such as admixing of toxic substances during the preparation processes.

The invention claimed is:

1. A process for preparing a sugar chain asparagine derivative derived from a sugar chain asparagine, comprising the steps of:
   (a) introducing a fat-soluble protecting group selected from the group consisting of Fmoc and Boc groups into the sugar chain aspargine contained in a mixture of one or more sugar chain asparagines, to give a mixture of sugar chain asparagine derivatives; and
   (b) subjecting the mixture of sugar chain asparagine derivatives or a mixture obtainable by hydrolyzing a sugar chain asparagine derivative contained in the mixture of sugar chain asparagine derivatives to chromatography, to separate each of the sugar chain asparagine derivatives therefrom.

2. The process according to claim 1, further comprising the step of (b'): hydrolyzing the sugar chain asparagine derivative separated in step (b) with a glycosidase.

3. The process according to claim 1 or 2, wherein the mixture of one or more sugar chain asparagines comprises a compound of the following formula, in which Asn denotes asparagine:

5. The process according to any one of claims 1 to 3, wherein the step (a) is a step of introducing Fmoc group into the sugar chain aspargine contained in a mixture of one or more sugar chain asparagines having a sialic acid residue at a non-reducing terminal, and introducing benzyl group into the sialic acid residue, to give a mixture of sugar chain asparagine derivatives.

6. A process for isolating a sugar chain aspargine from a mixture, comprising the steps of:
   (a) introducing a fat-soluble protecting group selected from the group consisting of Fmoc and Boc groups into a sugar chain aspargine contained in a mixture of one or more sugar chain asparagines, to give a mixture of sugar chain asparagine derivatives;
   (b) subjecting the mixture of sugar chain asparagine derivatives or a mixture obtainable by hydrolyzing a sugar chain asparagine derivative contained in the mixture of sugar chain asparagine derivatives to chromatography, to separate each of the sugar chain asparagine derivatives therefrom; and
   (c) removing the protecting group from the sugar chain asparagine derivative separated in the step (b), to give the sugar chain asparagine.

7. The process according to claim 6, further comprising the step of:
   (b') hydrolyzing the sugar chain asparagine derivative separated in step (b) with a glycosidase; and/or

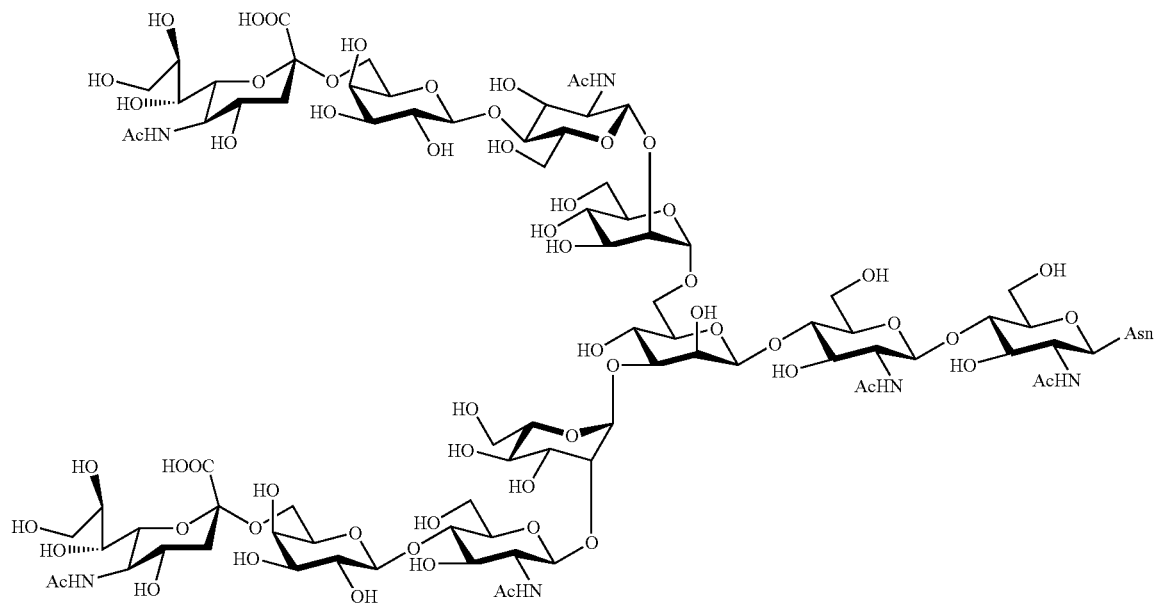

and/or a compound having one or more deletions of sugar residues in the above compound.

4. The process according to any one of claims 1 to 3, wherein the fat-soluble protecting group is fluorenylmethoxycarbonyl (Fmoc) group.

(c') hydrolyzing the sugar chain asparagine obtained in step (c) with a glycosidase.

8. The process according to claim 6 or 7, wherein the mixture of one or more sugar chain asparagines comprises a compound of the following formula, in which Asn denotes asparagine:

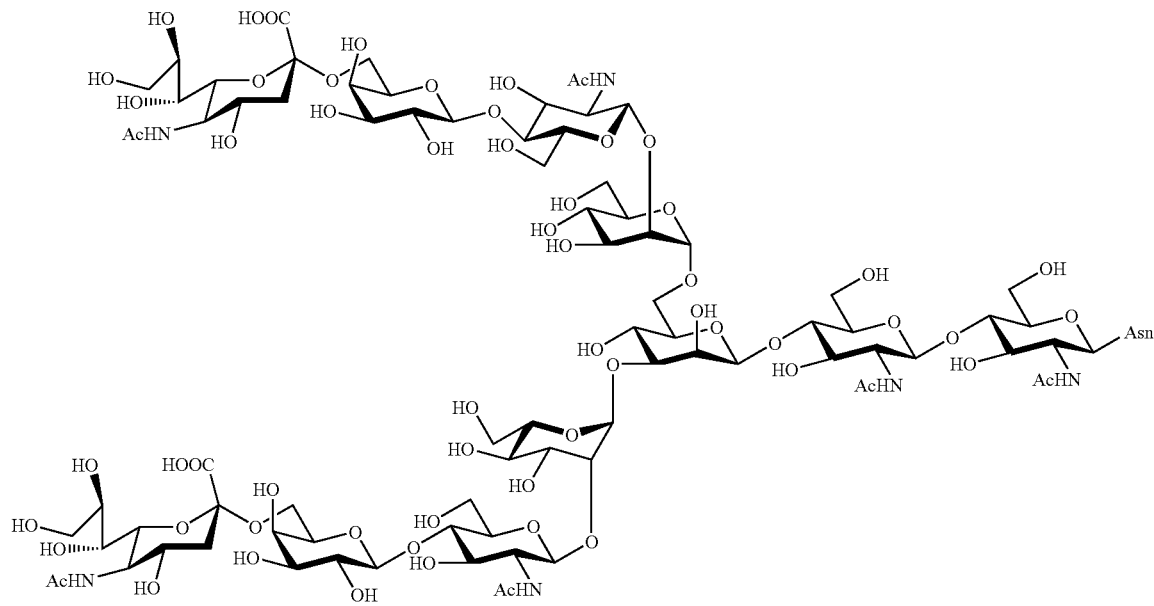

and/or a compound having one or more deletions of sugar residues in the above compound.

9. The process according to any one of claims 6 to 8, wherein the fat-soluble protecting group is Fmoc group.

10. The process according to any one of claims 6 to 8, wherein the step (a) is a step of introducing Fmoc group into the sugar chain aspargine contained in a mixture of one or more sugar chain asparagines having a sialic acid residue at a non-reducing terminal, and introducing benzyl group into the sialic acid residue, to give a mixture of sugar chain asparagine derivatives.

11. A process for preparing a sugar chain from a mixture of sugar chain asparagines, comprising the steps of:
 (a) introducing a fat-soluble protecting group selected from the group consisting of Fmoc and Boc groups into a sugar chain aspargine contained in a mixture of one or more sugar chain asparagines, to give a mixture of sugar chain asparagine derivatives;
 (b) subjecting the mixture of sugar chain asparagine derivatives or a mixture obtainable by hydrolyzing a sugar chain asparagine derivative contained in the mixture of sugar chain asparagine derivatives to chromatography, to separate each of the sugar chain asparagine derivatives therefrom;
 (c) removing the protecting group from the sugar chain asparagine derivative separated in the step (b), to give a sugar chain asparagine; and
 (d) removing an asparagine residue from the sugar chain asparagine obtained in the step (c), to give the sugar chain.

12. The process claim 11, further comprising the step of:
 (b') hydrolyzing the sugar chain asparagine derivative separated in step (b) with a glycosidase; and/or
 (c') hydrolyzing the sugar chain asparagine obtained in step (c) with a glycosidase; and/or
 (d') hydrolyzing the sugar chain obtained in step (d) with a glycosidase.

13. The process according to claim 11 or 12, wherein the mixture of one or more sugar chain asparagines comprises a compound of the following formula, in which Asn denotes asparagine:

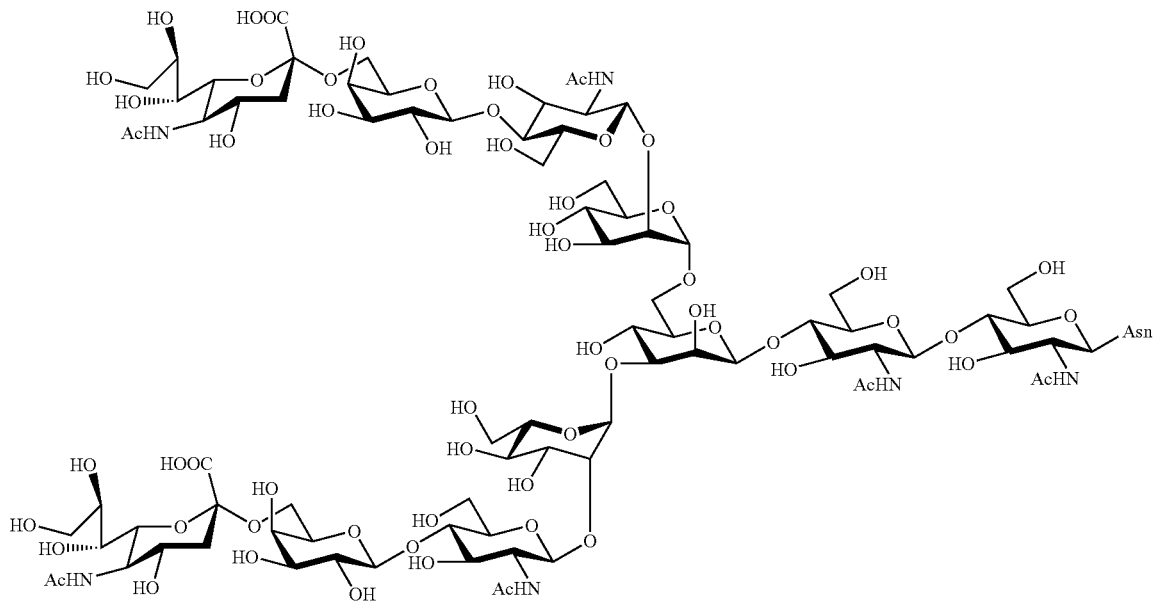

and/or a compound having one or more deletions of sugar residues in the above compound.

14. The process according to any one of claims 11 to 13, wherein the fat-soluble protecting group is Fmoc group.

15. The process according to any one of claims 11 to 13, wherein the step (a) is a step of introducing Fmoc group into the sugar chain aspargine contained in a mixture of one or more sugar chain asparagines having a sialic acid residue at a non-reducing terminal, and introducing benzyl group into the sialic acid residue, to give a mixture of sugar chain asparagine derivatives.

16. A sugar chain asparagine derivative having the general formula:

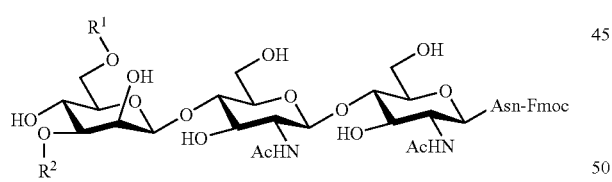

wherein Asn is asparagine, $R^1$ and $R^2$, which may be identical or different, are H,

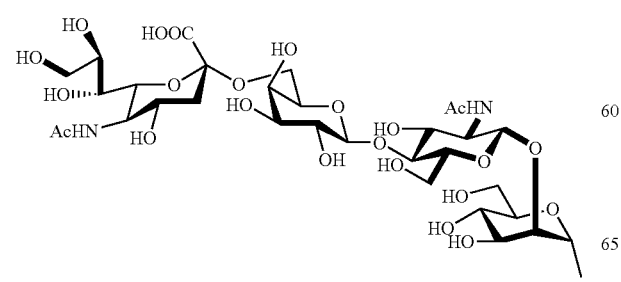

-continued

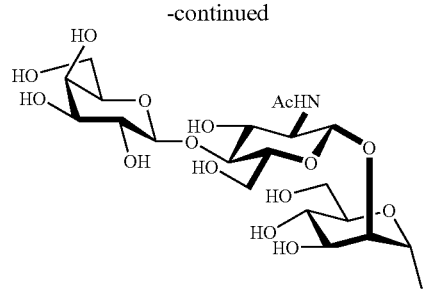

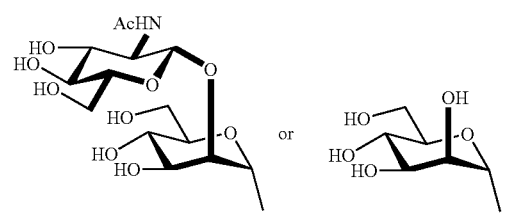

with proviso that a case where $R^1$ and $R^2$ are both H,

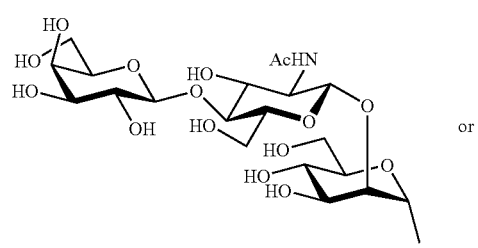

-continued
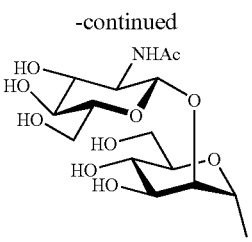
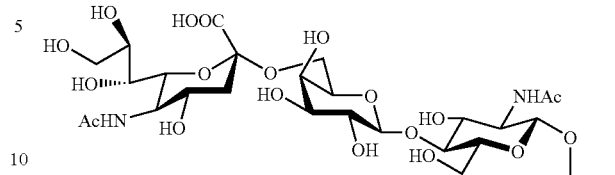
is excluded.
17. A sugar chain asparagine derivative having the general formula:
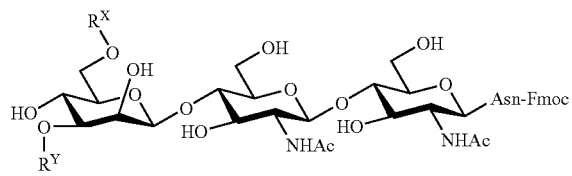
wherein one of $R^x$ and $R^y$ is
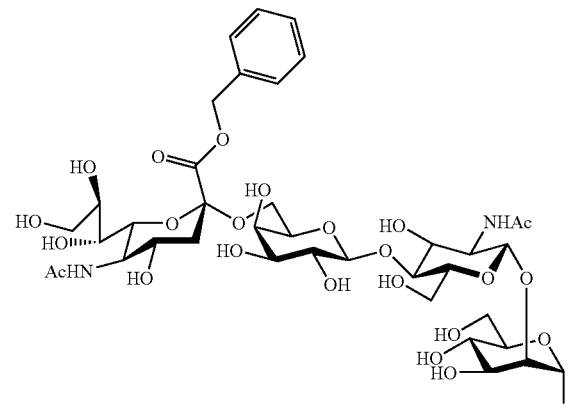
and the other is H,
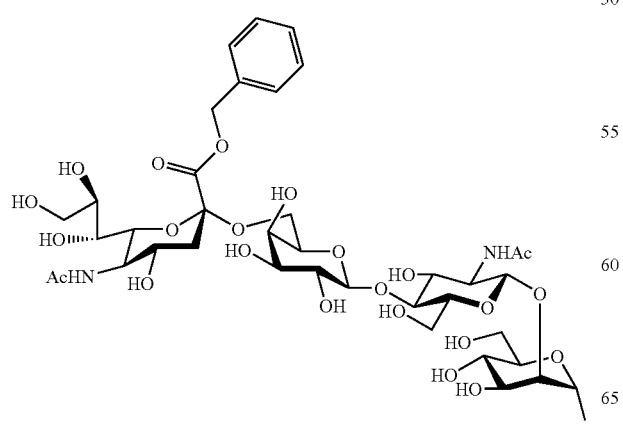
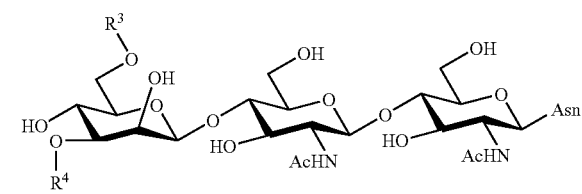
18. A sugar chain asparagine having the general formula:
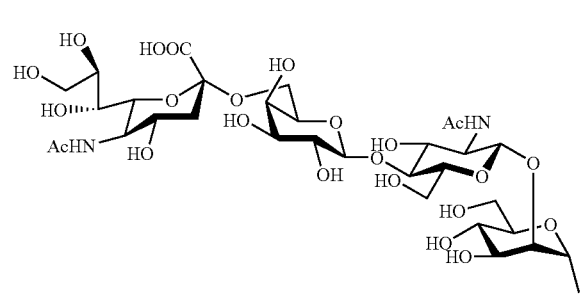
wherein Asn is asparagine, $R^3$ and $R^4$, which may be identical or different, are H, -continued

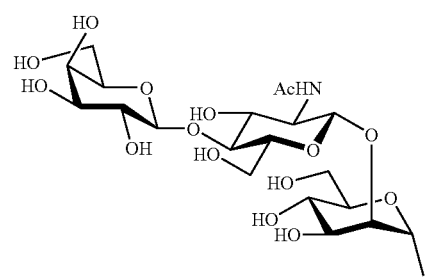

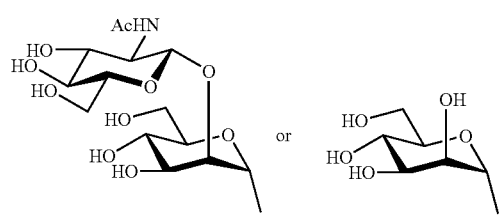

with proviso that (i) a case where $R^3$ and $R^4$ are the same, (ii) a case where R3 is

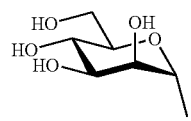

and $R^4$ is H or

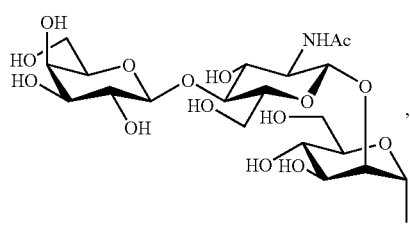

and
(iii) a case where $R^3$ is H and $R^4$ is

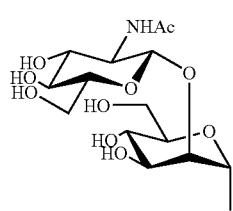

are excluded.

19. A sugar chain having the general formula:

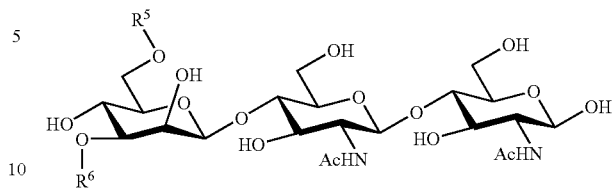

wherein $R^5$ and $R^6$, which may be identical or different, are H,

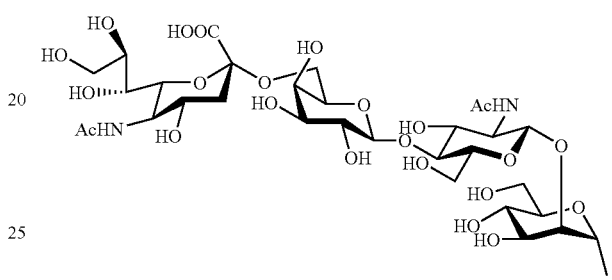

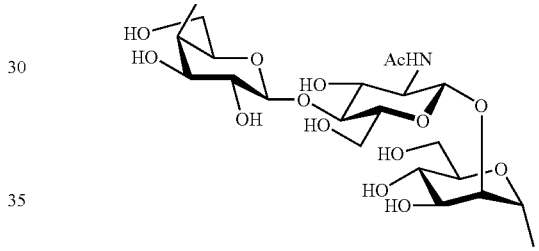

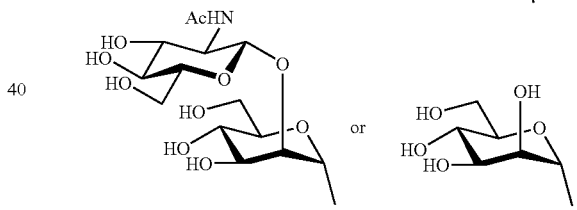

with proviso that (i) a case where $R^5$ and $R^6$ are the same, (ii) a case where one of $R^5$ and $R^6$ is

and the other is H or

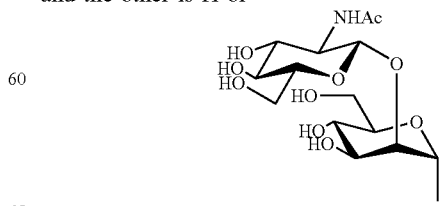

and (iii) a case where $R^5$ is

63
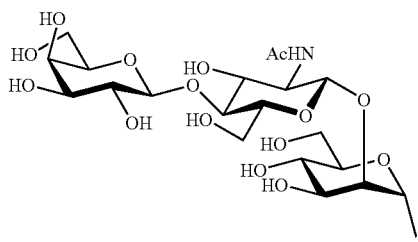
and R⁶ is
64
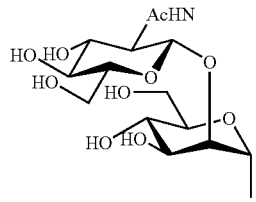
are excluded.
* * * * *